US009322066B2

(12) United States Patent
Ricci et al.

(10) Patent No.: US 9,322,066 B2
(45) Date of Patent: Apr. 26, 2016

(54) PREDICTORS FOR CANCER TREATMENT

(75) Inventors: Deborah Ricci, Ringoes, NJ (US); Weimin Li, Radnor, PA (US); Erin DeVay Henitz, Flemington, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 4 days.

(21) Appl. No.: 13/569,517

(22) Filed: Aug. 8, 2012

(65) Prior Publication Data

US 2013/0216524 A1 Aug. 22, 2013

Related U.S. Application Data

(60) Provisional application No. 61/522,596, filed on Aug. 11, 2011, provisional application No. 61/560,555, filed on Nov. 16, 2011.

(51) Int. Cl.

| | |
|---|---|
| *G01N 33/574* | (2006.01) |
| *A61K 39/395* | (2006.01) |
| *C12Q 1/68* | (2006.01) |
| *A61K 31/196* | (2006.01) |
| *A61K 31/573* | (2006.01) |
| *A61K 31/69* | (2006.01) |
| *G01N 33/92* | (2006.01) |
| *A61K 31/19* | (2006.01) |
| *A61K 31/198* | (2006.01) |

(52) U.S. Cl.
CPC .............. *C12Q 1/6886* (2013.01); *A61K 31/19* (2013.01); *A61K 31/196* (2013.01); *A61K 31/198* (2013.01); *A61K 31/573* (2013.01); *A61K 31/69* (2013.01); *A61K 39/39558* (2013.01); *G01N 33/57407* (2013.01); *G01N 33/92* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,693,617 | A | 12/1997 | Stein et al. |
| 5,756,764 | A | 5/1998 | Fenteany et al. |
| 5,780,454 | A | 7/1998 | Adams et al. |
| 6,018,020 | A | 1/2000 | Attwood et al. |
| 6,066,730 | A | 5/2000 | Adams et al. |
| 6,075,150 | A | 6/2000 | Wang et al. |
| 6,083,903 | A | 7/2000 | Adams et al. |
| 6,096,778 | A | 8/2000 | Chatterjee et al. |
| 6,297,217 | B1 | 10/2001 | Adams et al. |
| 6,465,433 | B1 | 10/2002 | Adams et al. |
| 6,548,668 | B2 | 4/2003 | Adams et al. |
| 6,617,317 | B1 | 9/2003 | Adams et al. |
| 6,713,446 | B2 | 3/2004 | Gupta |
| 6,747,150 | B2 | 6/2004 | Adams et al. |
| 6,831,099 | B1 | 12/2004 | Crews et al. |
| 6,958,319 | B2 | 10/2005 | Gupta |
| 7,109,323 | B2 | 9/2006 | Plamondon et al. |
| 7,119,080 | B2 | 10/2006 | Adams et al. |
| 7,422,830 | B2 | 9/2008 | Nam et al. |

FOREIGN PATENT DOCUMENTS

| | | |
|---|---|---|
| WO | WO 2004/053066 A2 | 6/2004 |
| WO | WO 2006/133420 A2 | 12/2006 |
| WO | WO 2008/021183 A2 | 2/2008 |
| WO | WO 2009/148528 A2 | 12/2009 |

OTHER PUBLICATIONS

Lichter et al, Blood, 2012, 120:4513-4516.*
Coiffier et al, Blood, ASH Annual Meeting Abstracts 2011;118:Abstract 265.*
Ricci et al, Blood, ASH Annual Meeting Abstracts, 2009 114: Abstract 3875.*
Michiels et al, Lancet, 2005, 365:488-492.*
de Jong et al, Haematologica, 2009, 94:70-77.*
Canioni et al, J Clin Oncol, 2008, 26:440-446.*
International Search Report relating to International Patent Application No. PCT/US2012/049941, filed Aug. 8, 2012. Date of Mailing of International Search Report: Jan. 28, 2013.
Written Opinion of the International Search Authority relating to International Patent Applcation No. PCT/US2012/049941, filed Aug. 8, 2012. Date of Mailing of Written Opinion: Jan. 28, 2013.
Arif et al, "Frequency of bcl-2 gene rearrangement in B-Cell Non-Hodgkin's lymphoma.", *Asian Pacific J Cancer Prev,* 2009; pp. 237-240, vol. 10(2).
Binstadt et al, "IgG Fc receptor polymorphisms in human disease: Implications for intravenous immunoglobulin therapy." *J Allergy Clin Immunol,* 2003, pp. 697-703, vol. 111(4).
Blum, K.A., "Upcoming Diagnostic and Therapeutic Developments in Classical Hodgkin1s Lymphoma II.", *Hematology* Dec. 1, 2010, pp. 93-100, vol. 2010(1), XP55049366, ISSN: 1520-4391, DOI:10. 1182/asheducation-2010.1.93/p. 94; table 2.
Catron et al, "Therapeutic activity of humanized anti-CD20 monoclonal antibody and polymorphism in IgG Fc receptor FcgammaRIIIa gene.", *Blood* 2002, pp. 757-758, vol. 99(3).
Chen et al, "Autocatalytic subunit processing couples active site formation in the 20S proteasome to completion of assembly.", *Cell,* 1996, pp. 961-972, vol. 86.
Chen et al, "Genome-wide siRNA screen for modulators of cell death induced by proteasome inhibitor bortezomib.", *Cancer Res.,* 2010, pp. 4318-4326, vol. 70(11).
Dave et al, "Prediction of survival in follicular lymphoma based on molecular features of tumor-infiltrating immune cells.", *NEJM* 2004, pp. 2159-2169, vol. 351(21).
Ding et al, "Bortezomib in combination with IGEV chemotherapy regimen for a primary refractory Hodgkin's lymphoma of bone.", *Leukemia Research,* Sep. 1, 2009, pp. e170-e172, vol. 33(9), New York, NY, US XP026222057, ISSN: 0145-2126, 001: 10.1016/J. LEUKRES.2009.03.036 [retrieved on Apr. 28, 2009 Jp. 170-p. e171].
Farinha, P., "Analysis of multiple biomarkers shows that lymphoma-associated macrophage (LAM) content is an independent predictor of survival in follicular lymphoma (FL).", *Blood,* Sep. 15, 2005, pp. 2169-2174, vol. 106(6), XP55041472., ISSN: 0006-4971. 001:10. 1182/blood-2005-04-1565, Abstract.
Fischer et al, "New approaches and therapeutics targeting apoptosis in disease.", *Pharmacol Rev,* 2005, pp. 187-215, vol. 57(2).
Goy et al, "Potential biomarkers of bortezomib activity in mantle cell lymphoma from the phase 2 PINNACLE trial.", *Leukemia & Lymphoma,* 2010, pp. 1269-1277, vol. 51(7).
Kamper et al,"Tumor-infiltrating macrophages correlate with adverse prognosis and Epstein-Barr virus status in classical Hodgkin's lymphoma.", *Haematologica,* Nov. 11, 2010, pp. 269-276, vol. 96(2), XP55041465, ISSN: 0390-6078, 001:10.3324/haematol.2010.031542, Abstract.

(Continued)

*Primary Examiner* — Mark Halvorson

(57) ABSTRACT

The present invention provides methods of predicting a response to a cancer treatment by determining CD68 level or PSMB1 (P11A) polymorphism in a biological sample and the presence or quantity of a second biomarker in the patient. The invention also provides kits and methods for treating cancer.

3 Claims, 8 Drawing Sheets

(56) References Cited

OTHER PUBLICATIONS

Karin et al, "NF-kB in cancer: From innocent bystander to major culprit.", *Nature Rev Cancer*, 2002, pp. 301-310, vol. 2(4).
Keats et al, "Promiscuous mutations activate the noncanonical NF-kappaB pathway in multiple myeloma." *Cancer Cell*, 2007, pp. 131-144, vol. 12(2).
Lichter, D. I., "Sequence analysis of the 20S proteasome β-subunit genes in tumor tissue and cell lines.", *A Thesis in the Field of Biotechnology for the Degree of Master of Liberal Arts in Extension Studies.*, Nov. 2008, Harvard University.
Lichter, D. I., "Sequence analysis of the 20S proteasome β-subunit genes in tumor tissue and cell lines.", *A Thesis in the Field of Biotechnology for the Degree of Master Liberal Arts in Extension Studies.*, Nov. 2008, Harvard University; Bibliographical information, downloaded from internet Dec. 16, 2013.
Lichter et al, Supplemental Material, 2012.
Mitsiades et al, "Molecular sequelae of proteasome inhibition in human multiple myeloma cells.", *Proc Natl Acad Sci*, 2002, pp. 14374-14379, vol. 99(22).
Mulligan et al, "Gene expression profiling and correlation with clinical outcome in clinical trials of the proteasome inhibitor bortezomib.", *Blood*, 2007, pp. 3177-3188, vol. 109(8).
San Miguel et al, "Bortezomib plus Melphalan and Prednisone for Initial Treatment of Multiple Myeloma.", *N. Engl. J. Med.*, Aug. 28, 2008, pp. 906-917, vol. 359(9).
Schmidt et al, "Sequence information within proteasomal prosequences mediates efficient integration of β-subunits into the 20S proteasome complex.", *J Mol Biol*, 1999, pp. 117-128, vol. 288(1).
Shin et al, "Notch1 augments NF-kappaB activity by facilitating its nuclear retention.", *EMBO*, 2006, pp. 129-138, vol. 25(1).
Steensma et al, "Splenic histopathological patterns in chronic myelomonocytic leukemia with clinical correlations: reinforcement of the heterogeneity of the syndrome.", *Leukemia Research*, Sep. 1, 2003, pp. 775-782, vol. 27(9), XP55041467, ISSN: 0145-2126, 001:10.1016/S0145-2126(03)00006-7, Abstract.
Steidl et al, "Macrophages predict treatment outcome in Hodgkin's lymphoma.", *Haematologica*, Jan. 31, 2011, pp. 186-189, vol. 96(2), XP55041473, ISSN: 0390-6078, 001: 10.3324/haematol.2010.033316, p. 188.
Steidl et al, "Tumor-Associated Macrophages and Survival in Classic Hodgkin's Lymphoma.", New England Journal of Medicine, Mar. 11, 2010, pp. 875-885, vol. 362(10), XP55041466., ISSN: 0028-4793. 001:10.1056/NEJMoa0905680, Abstract.
Taskinen et al, "A high tumor-associated macrophage content predicts favorable outcome in follicular lymphoma patients treated with rituximab and cyclophosphamide-doxorubicin-vincristine-prednisone." *Clin Cancer Res*, 2007, pp. 5784-5789, vol. 13(19).
Wojcik, C., "Regulation of apoptosis by the ubiquitin and proteasome pathway.", *J Cell Mol Med*, 2002, pp. 25-48, vol. 6(1).
Wu et al, "A novel polymorphism of FcgammaRIIIa (CD16) alters receptor function and predisposes to autoimmune disease.", *J Clin Invest*, 1997, pp. 1059-1070, vol. 100(5).
Yeung et al, "PS-341 (bortezomib) induces lysosomal cathepsin b release and a caspase-2 dependent mitochondrial permeabilization and apoptosis in human pancreatic cancer cells.", *J Biol Chem*, 2006, pp. 11923-11932, vol. 281(17).
Yin et al, "Proteasome inhibitor PS-341 causes cell growth arrest and apoptosis in human gliobastoma multiforme (GBM).", *Oncogene*, 2005, pp. 344-354, vol. 24(3): 344-354.
Barton, Mary Kay, "Predictive biomarkers may help individualize treatment for patients with follicular lymphoma", CA: A Cancer Journal for Clinicians, vol. 63, No. 5, Jul. 10, 2013, pp. 293-294, XP055174933, ISSN: 0007-9235, DOI: 10.3322/caac.21197.
Coiffier, B., et al., "Prespecified Candidate Biomarkers Identify Follicular Lymphoma Patients Who Achieved Longer Progression-Free Survival with Bortezomib-Rituximab Versus Rituximab", Clinical Cancer Research, vol. 19, No. 9, Apr. 2, 2013, pp. 2551-2561, XP055174935, ISSN: 1078-0432, DOI: 10.1158/1078-0432.CCR-12-3069.

\* cited by examiner

US 9,322,066 B2

PREDICTORS FOR CANCER TREATMENT

CROSS REFERENCE TO RELATED APPLICATIONS

This application claims priority to provisional application Ser. No. 61/522,596, filed Aug. 11, 2011 and provisional application Ser. No. 61/560,555, filed Nov. 16, 2011, both of which are incorporated herein by reference in their entirety.

FIELD OF THE INVENTION

The invention is related to treatment of cancer patients.

BACKGROUND OF THE INVENTION

While advances in development of successful cancer therapies progress, only a subset of patients respond to any particular therapy. With the narrow therapeutic index and the toxic potential of many available cancer therapies, such differential responses potentially contribute to patients undergoing unnecessary, ineffective and even potentially harmful therapy regimens.

One way to optimize therapy to treat individual patients is to determine whether the patient one or more predictors that correlate with a particular outcome in response to therapy. See, e.g., WO2004/053066; WO2006/133420; WO2008/021183; and WO2009/148528. The ability to predict drug sensitivity in patients is particularly challenging because drug responses reflect both the properties intrinsic to the target cells and also a host's metabolic properties.

There is a need to identify further predictive markers to identify particular cancer patients who are expected to have a favorable outcome when administered particular cancer therapies.

SUMMARY OF THE INVENTION

The invention provides a method for identifying whether a patient has an increased chance for a favorable outcome in response to a cancer treatment, comprising: determining the presence, absence or quantity of one or more predictors in the patient, wherein the presence, absence or quantity of the predictor correlates with at least one favorable outcome.

The presence of predictors may be determined by obtaining a biological sample from said patient. The cancer treatment may comprise administration of a proteasome inhibitor, such as bortezomib. The predictors may be one or more of low CD68, PSMB1 (P11A), PSMB5 (R24C), P65, time since last cancer treatment, one prior treatment, low FLIPI score, age (65 or younger), and low tumor burden.

Also provided are diagnostic kits for identifying patients likely to have a positive outcome in response to a cancer treatment.

The invention also provides methods for treating cancer patients by determining the presence, absence or quantity of one or more predictors in the patient, and selecting a method of treatment dependent on whether the patient is likely to respond to the treatment.

Also provided are uses for proteasome inhibitors for the treatment of cancer, wherein the patients are characterized by one or more of: low CD68, PSMB1 (P11A), PSMB5 (R24C), P65, time since last cancer treatment, one prior treatment, low FLIPI score, age, and low tumor burden.

DETAILED DESCRIPTION OF THE INVENTION

Figure 1:
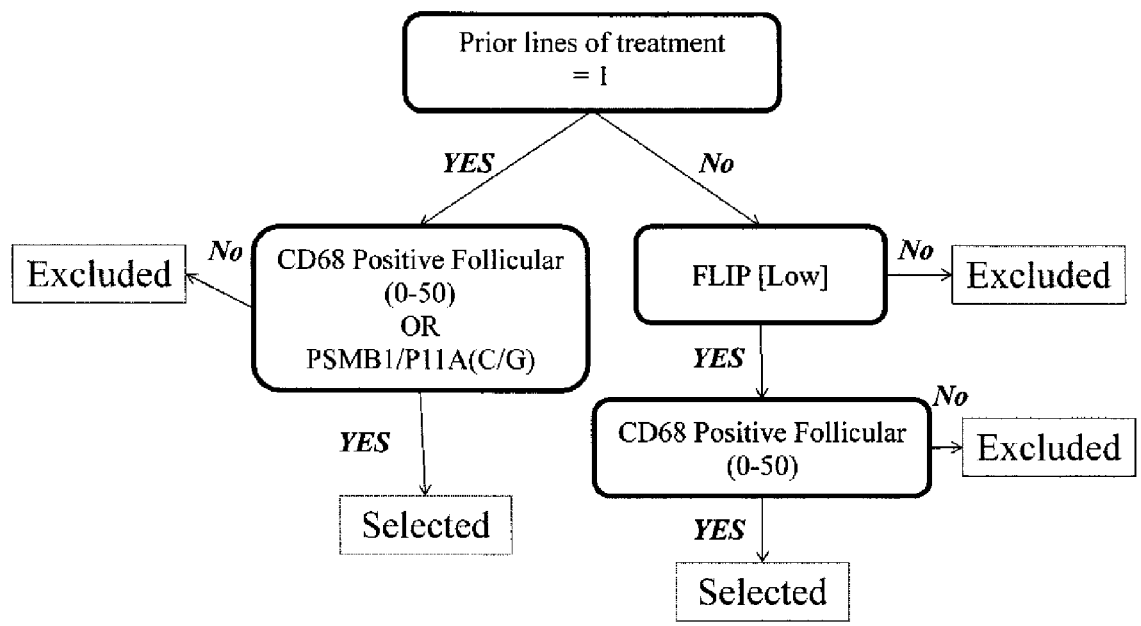
FIGS. 1-8 show decision trees for determining whether a particular patient will have an increased chance for favorable outcome in response to treatment. "Selected" means that the patient will have an increased chance for favorable outcome in response to treatment.
Figure 2:
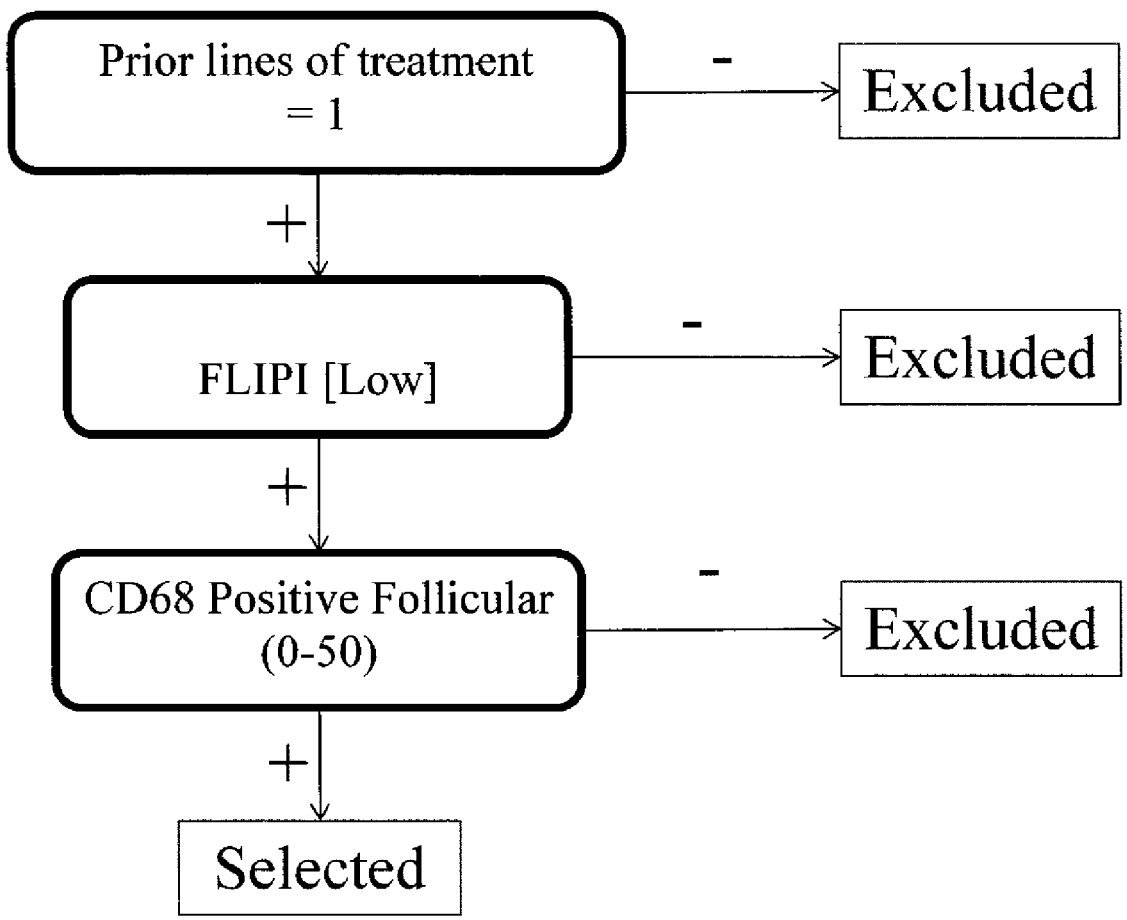
Figure 3:
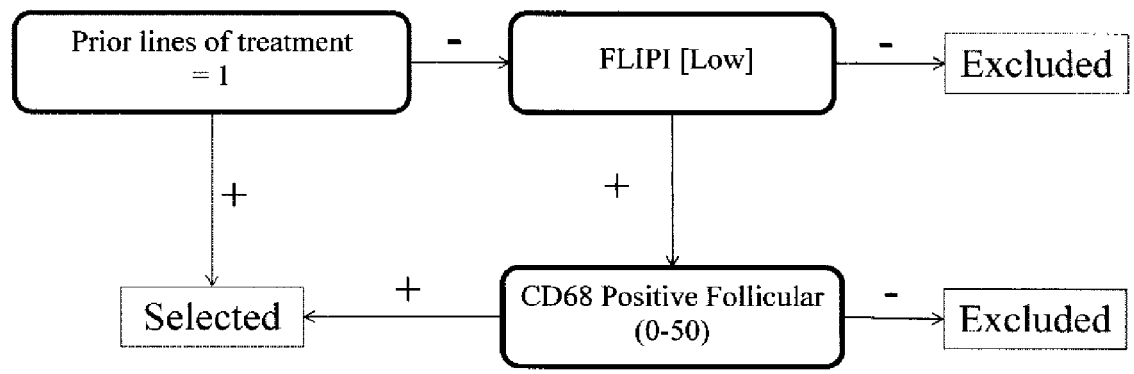
Figure 4:
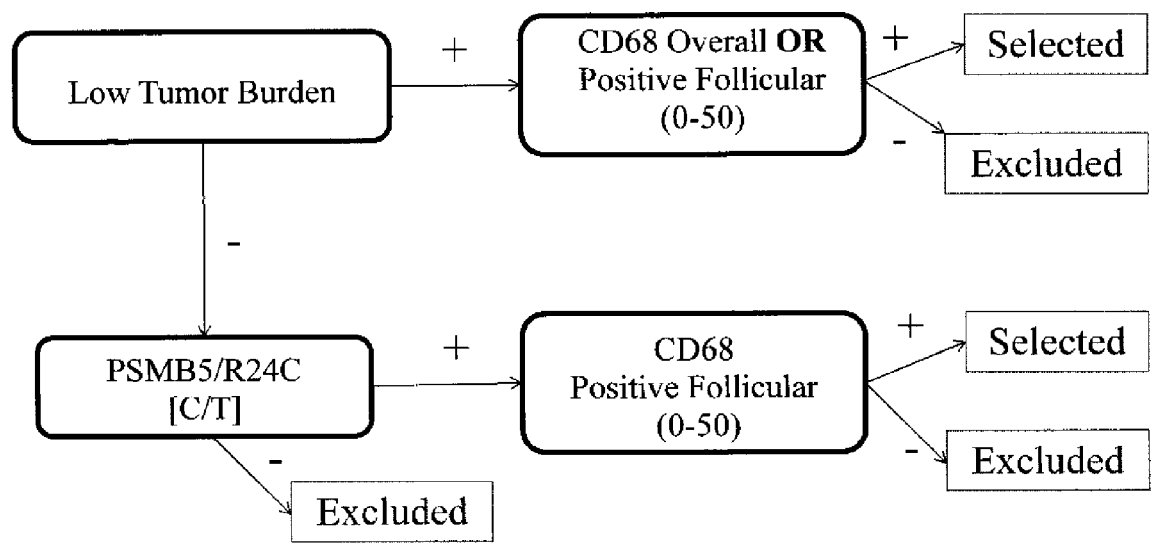
Figure 5:
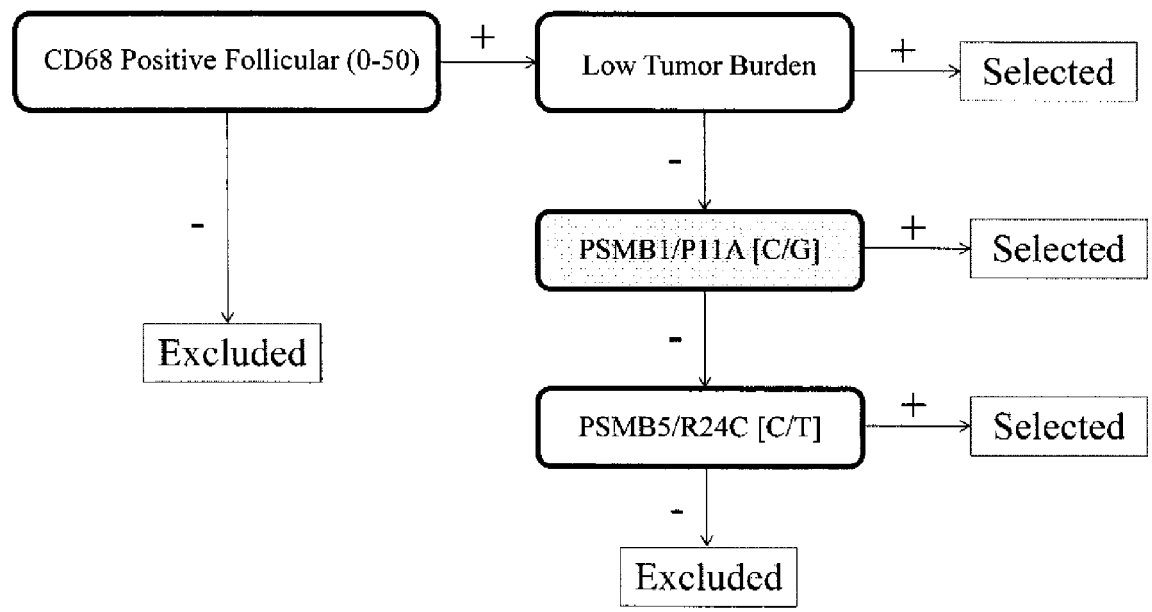
Figure 6:
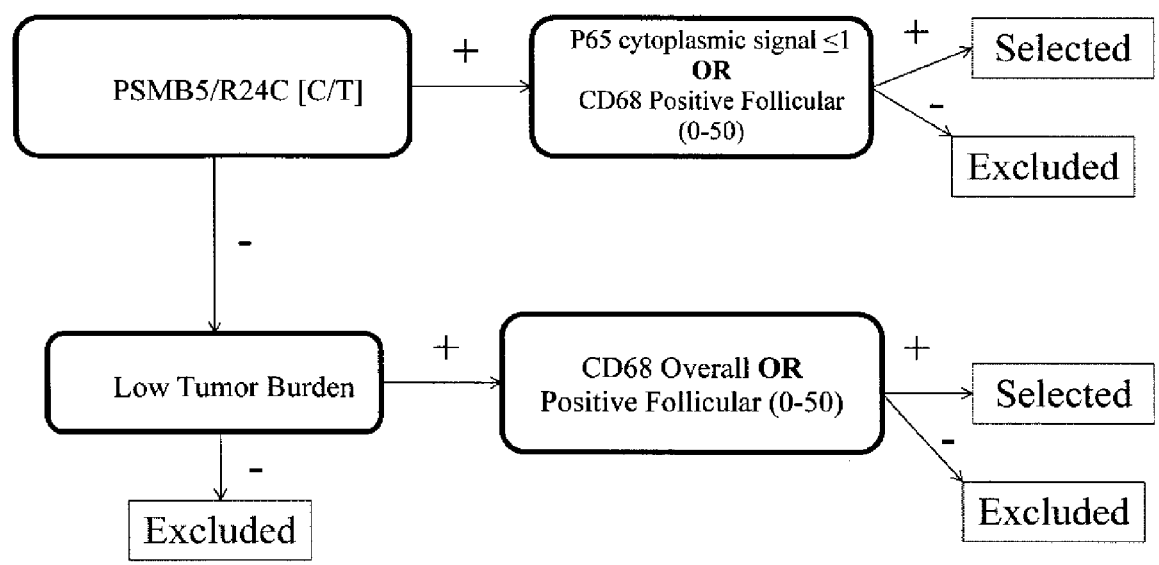
Figure 7:
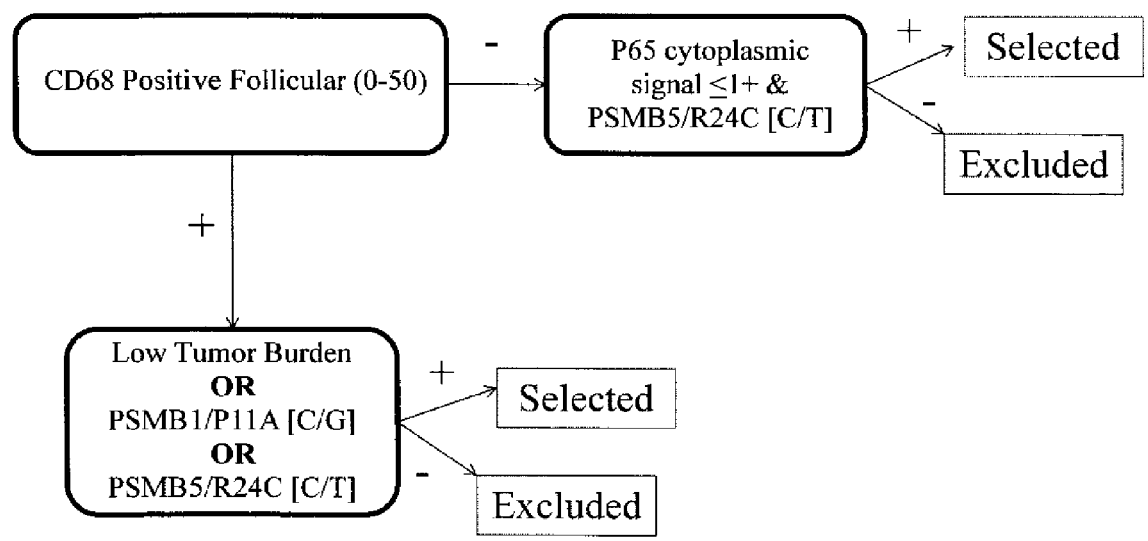
Figure 8:
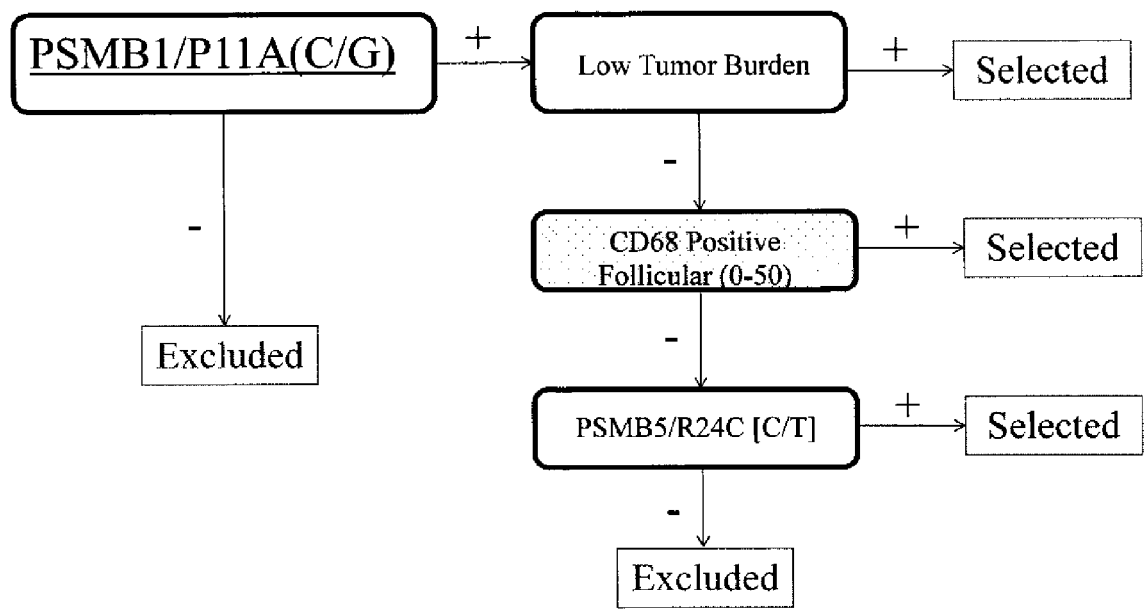

The present invention describes predictors that serve as useful tools for the prognosis and planning for the treatment of cancer. The predictors are predictive of whether there will be a favorable outcome in response to a particular treatment, for example, treatment with a proteasome inhibitor.

Without limitation, the present invention provides (a) methods for a predicting response to a treatment in a cancer patient by determining presence or quantity of one or more predictors, (b) kits useful in determination of the presence or quantity of the one or more predictors, (c) methods for treating cancer by selecting patients based on presence or quantity of one or more predictors and (d) treating cancer in patients with one or more predictors.

In certain embodiments, a method is provided for predicting response to a cancer treatment (for example, treatment with a proteasome inhibitor such as bortezomib) in a cancer patient comprising determining the presence or quantity of a predictor in a patient or a biological sample from the patient; and wherein the presence or quantity of the predictor is correlated with at least one positive outcome. Certain embodiments comprise determining the presence or quantity of a second predictor in the patient or a biological sample from the patient, wherein the presence or quantity of the second predictor is correlated with at least one positive outcome.

The present invention involves the identification of predictors also referred to herein as "variants", "markers" "biomarkers" and/or "factors", that correlate with an increased probability of favorable response to a cancer treatment. The association of patient response to a cancer treatment with these predictors can increase of higher confidence in the safety and/or efficacy with the particular treatment. The predictors may be a gene, protein, patient characteristic, or aspect of the patient history.

Predictors according to this invention which correlate with at least one favorable outcome include low CD68, PSMB1 (P11A) polymorphism, PSMB5 (R24C) polymorphism, P65, age (under 65), one prior treatment, low Follicular Lymphoma International Prognostic Index (FLIPI) score, time since last anti-cancer treatment and low tumor burden. Preferably, the patient has low CD68 or PSMB1 (P11A) and the presence of at least one other predictor. In one embodiment, the patient has low CD68 and PSMB1 (P11A) polymorphism. Predictor pairs according to this invention which correlate with at least one favorable outcome include those shown in Tables 6 and 7.

By "low CD68" is meant that the subject or biological sample from the patient shows less CD68 quantity than the average patient or biological samples from an average patient who has the same disease. In certain embodiments, low CD68 means that 25% or less of the cells in a biological sample express CD68; 50% or less of the cells in a biological sample express CD68; 25% or less of the follicular cells in a biological sample express CD68; 50% or less of the follicular cells in a biological sample express CD68; 25% or less of the perifollicular cells in a biological sample express CD68; or 50% or less of the perifollicular cells in a biological sample express CD68.

By "low FLIPI" score is meant a score of 0 or 1 factor on the Follicular Lymphoma International Prognostic Index (FLIPI score). To determine FLIPI score, one point is assigned to each of: age greater than 60 years, Stage III or IV disease, greater than 4 lymph node groups involved, serum hemoglobin less than 12 g/dL and elevated serum LDH.

As used herein, the terms "comprising", "containing", "having" and "including" are used in their open, non-limiting sense.

"Quantity" may mean the value, intensity, concentration, amount, degree, or expression level. For example, quantity of a gene may be the number of times a gene or portion thereof is present in a subject's genome or in the cells of the subject. Quantity may also mean the number of cells in a biological sample expressing a marker, or the overall expression level or intensity of the marker in a biological sample. Quantity may also refer to the number of types or lines of therapy the patient to which the patient may previously been exposed. The quantity may be in comparison to an absolute number, in comparison to a reference sample from a healthy patient, in comparison to an average number from healthy patients, or in comparison to an average number from patients with similar disease.

The cancer treatment may include administration of a single drug or treatment, or a combination treatment comprising administration of more than one drug or treatment. The cancer treatment may be administration of chemotherapy, radiotherapy, or immunotherapy; or the cancer treatment may be a bone marrow transplant.

In certain embodiments, the cancer treatment comprises administering a proteasome inhibitor to a patient. A proteasome inhibitor is any substance which inhibits enzymatic activity of the 20S or 26S proteasome in vitro or in vivo. In some embodiments, the proteasome inhibitor is a peptidyl boronic acid. Peptidyl boronic acids include bortezomib. Proteasome inhibitors include those compounds disclosed in U.S. Pat. Nos. 5,756,764; 5,693,617; 6,831,099; 6,096,778; 6,075,150; 6,018,020; 7,119,080; 6,747,150; 6,617,317; 6,548,668; 6,465,433; 6,297,217; 6,083,903; 6,066,730; 5,780,454; 7,422,830; 7,109,323; 6,958,319; 6,713,446; and 6,699,835. The proteasome inhibitor may be bortezomib.

In certain embodiments, the cancer treatment comprises treatment with anti-cancer agents, including but not limited to, acemannan, aclarubicin, aldesleukin, alemtuzumab, alitretinoin, altretamine, amifostine, aminoglutethimide, amsacrine, anagrelide, anastrozole, ancestim, asparaginase, bevacizumab, bexarotene, broxuridine, capecitabine, celmoleukin, cetrorelix, cetuximab, cladribine, clofarabine, clotrimazole, daclizumab, dexrazoxane, dilazep, docosanol, doxifluridine, bromocriptine, carmustine, cyclophosphamide, cytarabine, diclofenac, edelfosine, edrecolomab, eflornithine, emitefur, exemestane, exisulind, fadrozole, filgrastim, finasteride, fludarabine phosphate, formestane, fotemustine, gallium nitrate, gemcitabine, glycopine, heptaplatin, hydroxyurea, ibandronic acid, imiquimod, iobenguane, irinotecan, irsogladine, lanreotide, leflunomide, lenograstim, lentinan sulfate, letrozole, liarozole, lobaplatin, lonidamine, masoprocol, melarsoprol, melphalan, mercaptopurine, methotrexate, metoclopramide, mifepristone, miltefosine, mirimostim, mitoguazone, mitolactol, mitomycin, mitoxantrone, molgramostim, nafarelin, nartograstim, nedaplatin, nilutamide, noscapine, oprelvekin, osaterone, oxaliplatin, pamidronic acid, pegaspargase, pentosan polysulfate sodium, pentostatin, picibanil, pirarubicin, porfimer sodium, prednisone, raloxifene, raltitrexed, rasburicase, rituximab, romurtide, sargramostim, sizofuran, sobuzoxane, sonermin, steroids, suramin, tasonermin, tazarotene, tegafur, temoporfin, temozolomide, teniposide, tetrachlorodecaoxide, thalidomide, thymalfasin, thyrotropin alfa, topotecan, toremifene, trastuzumab, treosulfan, tretinoin, trilostane, trimetrexate, ubenimex, valrubicin, verteporfin, vincristine, vinblastine, vindesine, and vinorelbine. In a preferred embodiment, the cancer treatment comprises rituximab. In other preferred embodiments, the cancer treatment comprises melphalin or prednisone, or a combination of melphalin and prednisone.

In certain embodiments, the cancer treatment is a combination treatment. The combination treatment may comprise treatment with a proteasome inhibitor and another cancer treatment or anti-cancer agent. In certain embodiments, the other anti-cancer agent is a monoclonal antibody, e.g., rituximab. In other embodiments, the other anti-cancer agent is melphalin, prednisone, or a combination of melphalin and prednisone.

The favorable outcome may be an overall response rate, overall survival rate, overall complete response rate, duration of response, longer time to next therapy, treatment free interval, positive response to treatment, a longer time-to-progression, longer term survival and/or longer progression-free survival. The favorable outcome may be dose-dependent or dose-independent. The favorable outcome may favorable be in comparison to no treatment, or in comparison to another cancer treatment or cancer treatment(s).

"Cancer" or "tumor" is intended to include any neoplastic growth in a patient, including an initial tumor and any metastases. The cancer can be of the hematological or solid tumor type. Hematologic cancers include such as myelomas e.g., multiple myeloma), leukemias (e.g., Waldenstrom's syndrome, acute myelogenous leukemia, chronic lymphocytic leukemia, granulocytic leukemia, monocytic leukemia, lymphocytic leukemia), and lymphomas (e.g., follicular lymphoma, mantle cell lymphoma, diffuse large B cell lymphoma, malignant lymphoma, plasmocytoma, reticulum cell sarcoma, Hodgkin's disease, non-Hodgkin's lymphoma or follicular B-cell non-Hodgkin's lymphoma). Solid tumors can originate in organs, and include cancers such as brain, skin, lung, breast, prostate, ovary, colon, kidney, and liver. The cancer may be at the primary site, a metastasis, refractory (e.g. refractory to one or more lines of treatment) and/or recurring. In certain embodiments, the cancer is follicular B-cell non-Hodgkin's lymphoma or multiple myeloma.

When the predictor is present within the patient's body, the presence, absence or quantity of the predictor may be assessed by obtaining a biological sample from a patient and determining whether said biological sample contains the predictor or in what amounts the biological sample contains the predictor. A "biological sample" as used herein refers to a sample containing or consisting of tissues, cells, biological fluids and isolates thereof, isolated from a subject, as well as tissues, cells and fluids present within a subject. Examples of biological samples include, for example, sputum, blood, blood cells (e.g., white blood cells), amniotic fluid, plasma, serum, semen, saliva, bone marrow, tissue or fine-needle biopsy samples, urine, peritoneal fluid, pleural fluid, and cell cultures. Biological samples may also include sections of tissues such as frozen sections taken for histological purposes. In certain embodiments, the biological sample may be or include tumor cells. Biological samples from a hematological tumor may include bone marrow and/or peripheral blood.

Detection of predictor in a biological sample may be performed by any conventional method for detecting the type of predictor, e.g., direct measurement, immunohistochemistry, immunoblotting, immunoflourescence, immunoabsorbence, immunoprecipitations, protein array, flourescence in situ hybridization, FACS analysis, hybridization, in situ hybridization, Northern blots, Southern blots, Western blots, ELISA, radioimmunoassay, gene array/chip, PCR, RT-PCR, or cytogenetic analysis.

When the predictor is based on a particular genotype or polymorphism, the biological sample may be analyzed by genotyping. The term "genotype" refers to the alleles present in DNA from a subject or patient, where an allele can be defined by the particular nucleotide(s) present in a nucleic acid sequence at a particular site(s). Often a genotype is the nucleotide(s) present at a single polymorphic site known to vary in the human population. "Genotyping" refers to the process of determining the genotype of an individual by the use of biological assays. Current methods of doing this include PCR, DNA sequencing, antisense oligonucleotide probes, and hybridization to DNA microarrays or beads.

A "single nucleotide polymorphism" (SNP, pronounced snip) is a DNA sequence variation occurring when a single nucleotide—A, T, C, or G—in the genome (or other shared sequence) differs between members of a species (or between paired chromosomes in an individual). For example, two sequenced DNA fragments from different individuals, AAGCCTA to AAGCTTA, contain a difference in a single nucleotide. In this case it is said that there are two alleles: C and T. Almost all common SNPs have only two alleles.

The detection of the presence or absence of at least one genotype variance involves contacting a nucleic acid sequence corresponding to one of the genes identified herein or a product of such a gene with a probe. The probe is able to distinguish a particular form of the gene or gene product or the presence or a particular variance or variances, e.g., by differential binding or hybridization.

When the predictor is the presence or quantity (including the expression level) of a particular gene or protein, the presence or quantity (including the expression level) may be determined by immunohistochemistry of a biological sample.

In certain embodiments, a kit is provided for identifying patients who are candidates for a cancer treatment comprising a first reagent for detecting the presence or quantity of one of the predictors of the invention in a biological sample and a second reagent for detecting the presence or quantity of a second predictor of the invention in a biological sample, and instructions for employing the predictors to identify patients who are candidates for the treatment. In certain embodiments, the first reagent detects CD68 quantity and the second reagent detects PSMB1 (P11A) polymorphism or PSMB5 (R24C) polymorphism. The reagents may be antibodies (for example, when testing CD68) or they may be probes or arrays of probes (for example, when detecting gene polymorphism)

In certain embodiments, a method for treating a patient for cancer comprising: determining the presence or quantity of a first predictor in patient or a biological sample from said patient; and determining the presence or quantity of a second predictor in said patient or a biological sample from said patient; and selecting a method of treatment dependent on whether said patient is likely to respond to said treatment.

The invention also provides uses of proteasome inhibitors for the treatment of cancer in a patient, where the patient is characterized by the presence, absence, or quantity of at least one predictor correlated with at least one positive outcome in response to the proteasome inhibitor.

All publications cited herein are hereby incorporated by reference. Unless defined otherwise, all technical and scientific terms used herein have the same meaning as commonly understood to one of ordinary skill in the art to which this invention pertains.

EXAMPLE 1

Non-Hodgkin lymphoma (NHL) encompasses several unique malignant lymphoid disease entities that vary in clinical behavior, morphologic appearance, immunologic, and molecular phenotype. Follicular lymphoma (FL), the most common indolent NHL, exhibits similar variability with some patients exhibiting very slow disease course while others progress and die within only 5 year (Dave 2004). A randomized, open-label, active-controlled, multicenter, multinational, prospective study to compare the efficacy and safety of the combination of bortezomib and rituximab (Vc-R) to single-agent rituximab in subjects who have relapsed or refractory, rituximab-naive or -sensitive follicular B-cell NHL was performed.

Subjects were centrally randomized to Treatment Groups A (Vc-R) or B (rituximab) in a 1:1 ratio taking into account the following stratification factors:

Follicular Lymphoma International Prognostic Index (FLIPI) score (low [0 or 1 factor], intermediate [2 factors], high [≥3 factors]);
Prior rituximab therapy (yes, no);
Time since last dose of anti-lymphoma therapy (≤1 year, >1 year);
Region (United States/Canada, European Union, Rest of World).

Tumor samples for DNA and protein analysis and a blood sample for DNA analysis were collected.

Protein candidates selected were NF-κB (RELA/p65), PSMA5, p27, and CD68. These proteins are attenuated by bortezomib treatment (NF-κB (RELA/p65); PSMA5, p27), regulated by the ubiquitin proteasome pathway (p27), or associated with poor prognosis in lymphoma (CD68). Elevated expression levels of NF-κB (RELA/p65) were associated with longer time-to-progression (TTP) in mantle cell lymphoma (MCL) and in multiple myeloma (Goy 2010, Mulligan 2007, and Keats 2007). Low level expression of PSMA5 was associated with longer TTP in MCL (Goy 2010). Survival analysis in the MCL study also showed that high levels of p27 correlated with better overall survival (OS) (Goy 2010). CD68 was also prespecified and has recently been reported to be a prognostic marker for poor outcome in lymphoma and is also associated with response to rituximab. Candidate genes selected for somatic mutation analysis were Bcl-2 and Notch-1. Other candidates were considered, but were not included because the frequency of the known mutations was less then 10% in the lymphoma setting. Additionally, small amounts of DNA were recovered from collected samples, so the analyses were limited to these two candidates. Bcl-2 has mutation frequencies of 23% in B-cell lymphoma and 50% in follicular lymphoma (Arif 2009) and Notch-1 has a mutation frequency of 24%. Bcl-2 is an important anti-apoptotic protein frequently over expressed in aggressive lymphomas and previous reports have suggested that bortezomib overcomes Bcl-2-mediated protection (Fischer 2005, Yin 2005, Yeung 2006, Mitsiades 2002 and Wojcik 2002). Notch-1 has been shown to increase the residence time of NF-κB (RELA/p65) in the nucleus (Shin 2006). This acts in direct opposition to bortezomib, which prevents NF-κB from reaching the nucleus by inhibiting proteasomal degradation of I-kappa-B proteins, whose role is to retain NF-κB in the cytoplasm. Notch 1-mediated increased residence time of NF-κB in the nucleus activates the transcription of the cell cycle regulators, eg, cyclins D1 and D2, which may contribute to the up-regulation of genes involved in immune and inflammatory processes (Karin 2002). Mutations found in functional sequences of these two genes were hypothesized to contribute to inter-individual responses to treatment with bortezomib.

Drug target candidate genes were included for both bortezomib (PSMB1, 2, 5, 6, 8, 9) and rituximab (FCGR2A, FCGR3A). The chemical structure of bortezomib interacts with PSMB subunits 1, 2, and 5 and there is documented evidence of polymorphisms in these subunits as well as in PSMB6, 7, and 8. Polymorphisms within the subunits may affect the ability of the drug to bind effectively or may prevent autocatalytic processing of pro-sequences that could lead to variability in levels of proteasomes and/or response to bortezomib in individual patients. For rituximab, the presence of single nucleotide polymorphisms (SNPs) corresponding to phenotypic expression of valine (V) or phenylalanine (F) at amino acid 158 of FCGR3A and of histidine (H) or arginine (A) at amino acid 131 of FCG2A greatly influences the affinity of IgG for the Fcγ receptor (Binstadt 2003, Wu 1997). Expression of the high-affinity V allele at 158 results in tighter binding of FCG3A to IgG1 and IgG3, whereas the low-affinity F allele is associated with decreased binding of FCG3A to IgG. Similarly, the high-affinity H allele at 131 results in greater affinity of FCGR2A for IgG2, whereas the low-affinity A allele correlates with decreased binding. Correlation of these low-affinity polymorphisms has been associated with worse clinical response and progression-free survival (PFS) after rituximab therapy in studies of NHL (Cartron 2002). Therefore, we examined whether subjects with these polymorphisms were responsive to treatment with Vc-R as this may be an alternative therapy for patients with limited treatment options.

The exploratory objectives in this study were to identify patient populations who were more or less likely to respond to Vc-R or rituximab alone by:
  Performing association analyses of CD68, NF-κB (RELA/p65), PSMA5, and p27 protein expression levels with selected clinical study endpoints
  Performing association analyses of Notch-1 and Bcl-2 somatic mutations (single and in combination) with selected clinical study endpoints
  Performing association analyses of FCGR2A and FCGR3A polymorphisms (SNPs) with selected clinical study endpoints
  PSMB1, PSMB2, PSMB5, PSMB6, PSMB8, and PSMB9 polymorphisms (SNPs) with selected clinical study endpoints
  Performing combinations of biomarkers with selected clinical study endpoints.

Multiple testing corrections were done using the false discovery rate (FDR) method for pair-wise comparisons and by forward selection when multiple biomarker combinations were compared. In practical terms, the FDR is the expected proportion of false positives; for example, if 1000 observations were predicted to be different, and the FDR for these observations was 0.10, then 100 of these observations would be expected to be false positives. Over-fitting is controlled by cross validation and independent validation within the analysis.

Genes with sufficient variation include:
FCGR2A (H166R, Q62R, Q62X)
FCGR3A (V212F)
PSMB1 (P11A)
PSMB5 (R24C)
PSMB8 (G8R)
PSMB9 (R60H, V32I)
PSMA (positive nuclear and cytoplasmic staining)
CD68 (overall positive, positive follicular, positive peri-follicular)
P27 (nuclei positive, intensity score)
RELA/p65 (positive nuclear and cytoplasmic staining, intensity score).

The intent-to-treat (ITT) population was defined as all subjects who were randomized. Subjects in this population were analyzed according to the treatment to which they were randomized. Biomarker evaluations were done on this population when biomarker data was generated for the clinical study endpoints.

Protein marker expression levels (CD68, NF-κB (P65), PSMA5, P27) were determined by immunohistochemistry (IHC). The expression level cut-points for single-marker analyses were:
  CD68:
% positive follicular (0-25, 26-50, 51-75, >75),
% positive peri-follicular (0-25, 26-50, 51-75, >75),
overall % positive (0-25, 26-50, 51-75, >75)
  NF-κB (p65):
% positive cytoplasmic signal (<90%, >91% cutoffs),
% positive nuclear signal (0, <5%, >5%)
Nuclear staining intensity (<1+, >2+)
  PSMA5:
% positive cytoplasmic signal (0-20, 30-50, 60-70, 80-90)
% positive nuclear signal (0-20, 30-50, 60-70, 80-90)
Cytoplasmic staining intensity (<2+, 3+)
Nuclear positive vs. all other
  P27:
% positive nuclear staining (0-20, 30-50, 60-70, 80-100)
Nuclear signal intensity (<1+, >2+)

Cut-points selected for pair-wise comparisons were chosen to reduce the total number of comparisons that would be done. The selected cut-points are found in Table 1:

TABLE 1

Cut-Points for Protein Markers Included in the Pair-Wise Comparisons

| Protein Marker | Cutoff |
| --- | --- |
| 20S (PSMA5) % nuclear staining | ≤20 vs. >20 |
| 20S (PSMA5) % positive cytoplasmic signal | ≤90 vs. >90 |
| 20S intensity cytoplasmic signal | ≤2+ vs. >2 |
| CD68 overall positive | ≤50 vs. >50 |
| CD68 positive follicular | ≤50 vs. >50 |
| CD68 positive perifollicular | ≤50 vs. >50 |
| P27 % nuclei positive | ≤70 vs. >70 |
| P27 signal intensity | ≤1+ vs. >1 |
| P65 (NF-κB) % nuclear staining | 0 vs. >0 |
| P65 (NF-κB) % positive cytoplasmic signal | ≤90% vs. >90% |
| P65 (NF-κB) intensity cytoplasmic signal | ≤1+ vs. >1 |

Germline SNP data for PSMB subunits and FCGR2A and FCGR3A genes were generated by standard polymerase chain reaction (PCR) methodologies. Alleles detected in these assays are found in Table 2:

TABLE 2

Alleles for PSMB Subunits and FCGR2A and FCGR3A Genes

| FCGR2A | FCGR3A | PSMB1 | PSMB2 | PSMB5 | PSMB6 | PSMB8 | PSMB9 |
| --- | --- | --- | --- | --- | --- | --- | --- |
| H166R (aka H131R) | D118N | A171S | E49X | L206M | A234D | G8R | G9E |

TABLE 2-continued

Alleles for PSMB Subunits and FCGR2A and FCGR3A Genes

| FCGR2A | FCGR3A | PSMB1 | PSMB2 | PSMB5 | PSMB6 | PSMB8 | PSMB9 |
|---|---|---|---|---|---|---|---|
| P273L | D183G | I208N | G187V | R24C | P107A | R141C | R60H |
| Q62R | E63V | P11A | L159F | — | — | V182M | V32I |
| Q62X | H194Y | P193L | — | — | — | — | — |
| V217I | L102R | — | — | — | — | — | — |
| — | L281F | — | — | — | — | — | — |
| — | R270X | — | — | — | — | — | — |
| — | S231A | — | — | — | — | — | — |
| — | S72R | — | — | — | — | — | — |
| — | V142I | — | — | — | — | — | — |
| — | V212F (aka V158F) | — | — | — | — | — | — |

The following clinical endpoints were included in the analysis within each treatment group and an overall comparison was made with the biomarker-related endpoints: Progression-free survival, defined as the interval between the date of randomization and the date of progressive disease (PD) or death, whichever is first reported in the ITT population; overall survival; overall response rate (complete response [CR]+CR unconfirmed [CRu]+partial response [PR]); overall CR rate (CR+CRu); duration of response; time to next anti-lymphoma therapy; and treatment free interval.

Subjects from who met all of the following criteria were included in the analysis: subjects in the ITT population; subjects with evaluable biomarker data determined by IHC- or PCR-based methodologies; and subjects with clinical data for at least one of the clinical endpoints listed above.

The primary biomarker analysis was aimed at identification of differentially expressed proteins, mutations, or genotypes that were associated with clinical study endpoints. Covariates included in the analysis were: FLIPI score (low [0 or 1 factor], intermediate [2 factors], high [≥3 factors]); prior rituximab therapy (yes, no); time since last dose of anti-lymphoma therapy (≤1 year, >1 year); region (United States/Canada, European Union, Rest of World), age, sex, race, Ann Arbor stage (I, II, III, IV), Number of prior lines of therapy (1, 2 and more), and high tumor burden (yes, no).

For single-marker association analyses and pair-wise comparisons, a log rank test and Cox proportional hazard model was utilized for assessments of PFS, TTP, and OS between the treatment groups. Kaplan-Meier curves were utilized to estimate the distribution differences between groups in the time-to-event analyses. Comparison of the response rates between the treatment groups was conducted using the Fishers exact test. Single-marker association analyses were stratified by the covariates.

For pair-wise comparison analysis, biomarker pairs were formed by combinations of two markers. A log rank test was utilized for assessments of PFS, TTP, and OS between the treatment groups in the subpopulation defined by biomarker pairs. Kaplan-Meier curves were utilized to estimate the distribution differences between groups in the time-to-event analyses. Comparison of the response rates between the treatment groups was conducted using the Fishers exact test. Methods of Analysis for the multiple biomarker comparison models can be found in section 4.6.

For each analysis, demographic and baseline characteristic variables were to be summarized for the biomarker population as follows. Descriptive statistics (mean, standard deviation, median, and range) were calculated for baseline demographic data (including: age (year), age category (>65 years and ≤65 years), sex (male, female), race (White, Asian/Pacific Islander, and Black/Other), FLIPI score (low [0 or 1 factor], intermediate [2 factors], high [≥3 factors]); prior rituximab therapy (yes, no); time since last dose of anti-lymphoma therapy (≤1 year, >1 year); Ann Arbor stage (I, II, III, IV), number of prior lines of therapy (1, 2 and more), high tumor burden (yes, no), and region (United States/Canada, European Union, Rest of World) and were compared with summary statistics from the clinical trial data sets.

The stratified log rank test and Cox proportional hazard model was utilized for assessments of PFS between the treatment groups. The Kaplan-Meier method was to be used to estimate the distribution of overall PFS for each treatment group in the biomarker population, and overall; stratified by expression level, SNP, or mutation (or covariate groups as noted above). The hazard ratio and 95% confidence interval was based on a stratified Cox's proportion hazard model with treatment as the explanatory variable. Analyses were done for the population overall and by treatment group, and each of these analyses were also stratified by the following factors if sufficient sample size existed:

FLIPI score (low [0 or 1 factor], intermediate [2 factors], high [≥3 factors])
Prior rituximab therapy (yes, no)
Time since last dose of anti-lymphoma therapy (≤1 year, >1 year)
Region (United States/Canada, European Union (Belgium, Czech Republic, Finland, France, Germany, Great Britain, Greece, Hungary, Italy, Poland, Portugal, Slovakia, Spain, and Sweden), Rest of World (Argentina, Australia, Brazil, India, Israel, Mexico, China, Korea, Romania, Russia, South Africa, Thailand, and Ukraine))
Age (<65, >65)
Sex
Race
Ann Arbor stage (I, II, III, IV)
Number of prior lines of therapy (1, 2 and more)
High tumor burden (yes, no)

Overall Survival was measured from the date of randomization to the date of the subject's death. If the subject was alive or the vital status was unknown, it was censored at the date that the subject was last known to be alive. Similar to PFS and TTP, the Cox proportional hazard model was used to evaluate the association between biomarker endpoints and OS. Kaplan-Meier survival curves were presented. Analyses were done for the population overall and by treatment group, and each of these analyses was stratified by the covariates used for PFS.

Comparison of the response rates between the treatment groups was conducted using the Fishers Exact Test. Duration of response, time to response, and time to clinical relapse were analyzed descriptively, where appropriate, and the biomarker subset was compared (if appropriate, determined as per the initial analysis) to the overall clinical cohort, by treatment group and overall. An exploratory estimate of the response rates in each treatment group was presented with 2-sided 95% confidence intervals. The number and percentage of subjects falling into each response category was descriptively tabulated.

Analyses were done for the population overall and by treatment group. Each of these analyses were stratified by the same covariates utilized for PFS assessment.

Further analyses were planned because of the number of pair-wise comparisons that were significant prior to FDR corrections and because these pairs selected unique individuals with longer PFS and a trend for longer survival. These analyses sought to identify a single biomarker classifier that selected for a large PFS benefit and an OS benefit (or trend) with a high population frequency. The dataset was utilized whereby discovery and confirmation test sets within the same population were defined. The study was conducted as follows:

Subjects with no missing biomarker values (n=354) were assigned in a ratio of 7:3 into a discovery and confirmation set using simple randomization. The balance demographic factors and clinical covariates listed previously were confirmed using either the t-test or Mann-Whitney test. The discovery set (67%) was used for identification of biomarkers with significant association with PFS; subjects included had no missing biomarker data. The confirmation set (33%) was used for independent validation. Subjects with missing data were included in the confirmation dataset provided that significant biomarker data identified in the discovery phase was available. Additionally, evaluable sample from China were also included in the confirmation set.

As in the initial analyses, if all subjects have the same protein expression level for a particular biomarker, that biomarker was removed from the analysis. If all subjects had the same mutation, no mutation, or 1 mutation level represented 90% of the samples, then either that mutation or that gene was removed from the analysis.

In the discovery phase of biomarker combination analysis, all subjects that had missing values for any biomarker specified in Section 2 were excluded. Samples with missing data were included in the confirmation set provided that the missing data was not part of the associated dataset. Samples with missing biomarker data were considered "unevaluable" and were excluded from the confirmation set, all other samples not used in the discovery set were included in the confirmation set.

Biomarker outliers were not removed from the analysis.

Demographic and baseline covariates were to be compared using the t-test or Mann-Whitney test to ensure that there were no statistically significant differences between the discovery and confirmation sets. Demographic and baseline characteristics were to be summarized for the discovery and confirmation sets and overall. Subjects excluded in the final analysis were not to be evaluated in this data comparison. Descriptive statistics (mean, standard deviation, median, and range) were to be calculated for the baseline demographic data and comparison between the demographic and test set were to be made to ensure there were no significant differences between them.

Covariates included in the analysis were: FLIPI score (low [0 or 1 factor], intermediate [2 factors], [≥3 high factors]); prior rituximab therapy (yes, no); time since last dose of anti-lymphoma therapy (≤1 year, >1 year), age, Ann Arbor stage (I, II, III, IV), Number of prior lines of therapy (1, 2 and more), high tumor burden (yes, no), region (United States/Canada, European Union, Rest of World), sex, and race.

All markers and covariates were to be treated as categorical variables in the analysis. Protein biomarkers were to be dichotomized. The cut-points for protein markers were to be optimized based on enrichment of responders vs. non-responders and reasonable population size. Specifically, for each biomarker, number of responders and non-responders (based on overall response) and their percentages in the evaluable population were to be determined using every potential cut-point listed in the Table 3. Summary tables with potential cut-points, number of responders, number of non-responders, and their percentages were to be generated for each biomarker.

TABLE 3

Response by Cut-Point (Evaluable Population)

| Protein Marker | Cutoff |
|---|---|
| 20S (PSMA5) % nuclear staining | 20%, 50%, 70%, 90% |
| 20S (PSMA5) % positive cytoplasmic signal | 20%, 50%, 70%, 90% |
| 20S intensity cytoplasmic signal | 0, 1, 2 |
| CD68 overall positive | 25, 50, 75, 90 |
| CD68 positive follicular | 25, 50, 75, 90 |
| CD68 positive perifollicular | 25, 50, 75, 90 |
| P27 % nuclei positive | 20%, 50%, 70%, 90% |
| P27 signal intensity | 0, 1, 2 |
| P65 (NF-κB) % nuclear staining | 0, 1, 5, 10, 20 |
| P65 (NF-κB) % positive cytoplasmic signal | 20%, 50%, 70%, 90% |
| P65 (NF-κB) intensity cytoplasmic signal | 0, 1, 2 |

All genotypes were to be considered separately in the analysis (eg, C/C, C/T, T/T):
FCGR2A (H166R, Q62R, Q62X)
FCGR3A (V212F)
PSMB1 (P11A)
PSMB5 (R24C)
PSMB8 (G8R)
PSMB9 (R60H, V32I).

Evaluation and Ranking of Single-Marker Associations with PFS (Discovery set)

The initial step of the analysis was selection and ranking of markers that were to be used in subsequent multiple comparison analysis. All protein, SNPs with greater than 10% genotype variability, and clinical covariates listed were to be included as categorical variables. The evaluation was to include the following steps:

Biomarkers (including clinical covariates) that showed improvement of PFS from prior single-marker association analysis (p<0.2) were reported. Only analyses that were done using IRC review were used.

Each biomarker and clinical covariate was evaluated by Cox regression to assess the importance of biomarkers with respect to PFS. The P-values and weights/odds ratios of all markers in the Cox model were reported.

To evaluate correlation among biomarkers, a pairwise correlation matrix was generated using Spearman correlation method. Biomarkers that showed high correlation (p<0.05 and correlation coefficient >0.7) were highlighted. Markers that had high correlation were re-analyzed in a Cox regression model with their interaction terms.

An interim summary of this analysis was generated for selecting markers that were used in multiple comparison analysis. The markers that were selected were based on the following criteria:

Relatively lower P-values in Cox regression for marker effect on PFS.

PFS benefit in Vc-R arm compared to R arm that were based on interaction with treatment in Cox regression or single marker logrank tests.

If multiple markers are highly correlated and have high ranks from Cox regression, representative marker(s) that have the highest rank from Cox regression with interaction terms were used. Subpopulations of samples showing a large PFS benefit in Vc-R arm compared to the R arm were to be identified by an exhaustive search of "AND" combination of biomarkers. Specifically, subpopulations of patients were formed from "AND" combinations of any two or three biomarkers selected in section 4.6.1. The difference of PFS for the patient subsets defined by the markers was evaluated using the log-rank test with PFS as response variable and 5-fold cross-validation as described below.

The discovery set was randomly split into 5 subsets with 20% of subjects in each subset. An 80% subset was formed by combining 4 of the 5 subsets. Using the 80% subset, subpopulations of patients were formed from "AND" combinations of biomarkers. If the number of samples (N) in either Vc-R or R is <5 for the subpopulation, the subpopulation was skipped. For subpopulations with N≥5 in both arms, the difference in PFS for the patient subsets defined by the two markers was evaluated using the log-rank test. A looser P-value cutoff was applied because of the exploratory nature of this analysis. The PFS benefit was subsequently tested on the remaining 20% subset.

The remaining 4 cross validation sets were tested similarly (P value cutoff was not applied due to small sample size). Specifically, a different 20% subset from above and a new 80% subset formed with remaining subjects was used to repeat logrank tests until all 5 20% subsets were tested. The proportion of iterations with large PFS benefit in both 90% subset and 10% subset were reported.

Biomarker combinations were merged and evaluated again for PFS benefit and statistical significance with cross validation. For subpopulations formed from merging of marker combinations, if the size of the subpopulation is ≤10% of the discovery set, no statistical test will be performed. Exhaustive merging of marker pairs and assessment of PFS benefit was performed. Only marker combinations or merging of marker combinations that were significant were reported to save computational time. Results were saved after each iteration.

For top ranked marker combinations, decision rules for defining selected patient subpopulations were established using Classification and Regression Tree. Association of the selected patient subpopulations for other clinical endpoints was also evaluated. Performance of PFS and OS in the confirmation set was evaluated by testing the association of biomarkers identified in the discovery set using the decision rules defined. The PFS of both biomarker positive and negative subgroups was reported for both study arms in the confirmation set. P-value cutoff was not applicable due to a small sample size, but was still reported.

Samples included in the independent confirmation set may have missing values for biomarkers not found to associate with PFS, however, subjects who could not be classified due to missing values of the selected biomarkers were regarded as "unevaluable" and were excluded.

Initial analyses focused on single-marker associations stratified by covariates. Significant associations were found in the single marker association analysis including CD68, PSMB1 (P11A), P65 and PSMB5 (R24C). Subsequent pairwise analysis identified a biomarker pair with significantly longer PFS and a trend for an OS benefit. Because there were no data sets available for independent confirmation of this finding, dataset was split into the Discovery and Confirmation sets described above. As part of that analysis, multiple biomarker combinations were compared and other significant combinations were identified. The association deemed to be most clinically appropriate from all analyses was the PSMB P11A heterozygote in combination with CD68 Low (0-50%) expression. Sub-populations of clinical interest are subjects with high tumor burden, prior rituximab and one or two prior lines of therapy.

Pair-wise combinations of markers were conducted using the stratified log rank test for each potential pair to determine differences in PFS between the Vc-R and rituximab only treatment groups. One-hundred and two biomarker pairs had a log rank p<0.05. Of these, 97 pairs had a >1% population frequency. Fourteen pairs also showed a PFS improvement of ≥6 months. In this analysis, 1,140 pair-wise comparisons were made (covariates were paired with each individual marker to supplement the analyses). Following FDR correction, 1 pair was significant (FDR=0.051). This biomarker pair identified 33% of the biomarker evaluable population that had a 7.5 month PFS advantage when treated with Vc-R compared with rituximab alone (Table 4) and a trend for better OS (p=0.055, HR: 0.426 [0.174, 1.046] This pair is composed of PSMB1 P11A (C/G heterozygote) and CD68 Low expression defined as 0-50 positively stained cells. Following, this pair will be referred to as the biomarker positive subgroup. The biomarker negative subgroup does not have this biomarker pair and has a different PSMB1 genotype and CD68 expression level.

TABLE 4

Comparison of Biomarker Positive Population With Biomarker Negative Population for PFS and OS

| | | Biomarker Positive (N = 118) | | Biomarker Negative (N = 238) | | Total (N = 356) | |
|---|---|---|---|---|---|---|---|
| | | Vc – R | Rituximab | Vc – R | Rituximab | Vc – R | Rituximab |
| PFS | N | 57 | 61 | 118 | 120 | 175 | 181 |
| | Median (months) | 16.6 | 9.1 | 12.5 | 12.5 | 13.6 | 11.3 |
| | 95% CI | (0.26-0.639) | | (0.759-1.425) | | (0.621-1.032) | |
| | p-value | 0.0001 | | 0.8097 | | 0.0855 | |
| | HR | 0.407 | | 1.04 | | 0.801 | |

TABLE 4-continued

Comparison of Biomarker Positive Population With Biomarker Negative Population for PFS and OS

| | | Biomarker Positive (N = 118) | | Biomarker Negative (N = 238) | | Total (N = 356) | |
|---|---|---|---|---|---|---|---|
| | | Vc – R | Rituximab | Vc – R | Rituximab | Vc – R | Rituximab |
| OS | N | 57 | 61 | 118 | 120 | 175 | 181 |
| | Median (months) | NA | NA | NA | NA | NA | NA |
| | 95% CI | (0.174-1.046) | | (0.617-1.658) | | (0.527-1.239) | |
| | p-value | 0.0550 | | 0.9645 | | 0.3270 | |
| | HR | 0.426 | | 1.011 | | 0.808 | |

Biomarker positive = PSMB P11A heterozygote and CD68 "Low" biomarker pair,
Biomarker negative = all subjects without this pair,
Vc – R = Bortezomib + Rituximab,
PFS = progression free survival,
OS = overall survival,
CI = confidence interval,
HR = hazard ratio Importantly, biomarker positive subgroup (PSMB1 P11A heterozygote and CD68 Low expression) also had a significantly better overall response rate 73.7% for those treated with Vc-R compared to 47.5% with R alone (p=0.0077), and a longer time to next treatment (p=0.0013) and duration of treatment free interval (p=0.0017).

Similar AE profiles were observed in the biomarker positive and biomarker negative populations. Similar treatment exposure was observed in the biomarker positive and biomarker negative populations. Subjects treated with rituximab in the biomarker positive population had a median dose of 2941 mg/m$^2$ compared to 2940 mg/m$^2$ in the biomarker negative population. Subjects treated with Vc-R in the biomarker positive population had a median dose of 31.1 mg/m$^2$ compared to 30 mg/m$^2$ in the biomarker negative population. Total number of doses, duration of exposure, dose intensity, relative dose intensity and maximum number of cycles received also showed very similar differences.

Subjects treated with Bortezomib+rituximab maintained longer PFS when biomarker positive and stratified by any FLIPI score, by tumor burden, by Ann Arbor score, by age, by region, by sex, and by race. In patients with higher risk and poor prognosis, e.g. high tumor burden, medium or high FLIPI, older than 65, or with prior rituximab treatment, greater PFS improvement were observed in patients when biomarker positive comparing to when biomarker negative. Longer PFS was maintained regardless of time from last treatment or number of previous treatments by prior rituximab or by number of rituximab treatments less than or equal to 2.

Subjects treated with Bortezomib+rituximab maintained longer overall survival when biomarker positive and stratified by FLIPI score, by tumor burden, by Ann Arbor score, by age, by region, by sex, and by race. Subjects treated with Velcade+rituximab maintained longer PFS when positive for CD68 low (0-50) and stratified by any FLIPI score, by tumor burden, by Ann Arbor score, by age, by region, by sex, and by race. When CD68 high, they did better on rituximab alone as expected. Subjects treated with Velcade+rituximab maintained longer PFS when positive for PSMB P11A heterozygote and stratified by any FLIPI score, by tumor burden, by Ann Arbor score, by age, by region, by sex, and by race. When CD68 high, they did better on rituximab alone as expected.

A trend for a longer OS was found for biomarker positive subjects (p=0.055, HR 0.426. When the biomarker contributions are examined individually, this trend is less distinguishable. For subjects that are PSMB1 P11A C/G heterogygotes, the significance is p=0.2525 and HR=0.673 while subjects that are CD68 positive (0-50), the significance is p=0.0714 and HR=0.615.

Subjects treated with Velcade+rituximab had a trend for better OS when positive for CD68 low (0-50) and stratified by any FLIPI score, by tumor burden, by Ann Arbor score, by age, by region, by sex, and by race. Subjects treated with Velcade+rituximab had a trend for better OS when positive for PSMB1 P11A heterozygote and stratified by any FLIPI score, by tumor burden, by Ann Arbor score, by age, by region, by sex, and by race.

Following cross validation, the pair previously described (CD68 Low and PSMB P11A) was found to be significant in the smaller discovery cohort (p=0.0003, 14.2 months for Vc-R vs 8.5 months for R, HR=0.4 (0.24, 0.67)). There was still a trend for longer OS in the biomarker positive population (p=0.1291), HR=0.47(0.17, 1.27). Although the number of subjects in the confirmation cohorts is small, the positive trend in both PFS and OS was found to be maintained. In confirmation cohort 1 (n=106), subjects treated with Vc-R had approximately 18.2 mo PFS while those treated with R alone had 9.5 months PFS (p=0.0817, HR=0.44). In confirmation cohort 2 (n=426), subjects treated with Vc-R had 13.9 months median PFS while those treated with R had 9.5 months median PFS (p=0.0878, HR=0.49). The trend in OS was also maintained It was of interest to determine the individual contributions of each biomarker to the PFS benefit found in subjects with both biomarkers (PSMB1 P11A heterozygote and CD68 Low). Within the biomarker positive population, subjects with PSMB1 P11A (C/G) had 16.6 months median PFS when treated with Vc-R compared to 9.5 months median PFS when treated with R alone, showing a 7.1 month PFS advantage when the combination was used. This benefit was not seen in biomarker negative subjects with Vc-R. Consistent with prior publication on CD68 and rituxan, this study shows that subjects with higher CD68 expression do better on rituximab alone (16.2 months median PFS) than those with lower CD68 expression (9.3 months median PFS). However, these subjects with low CD68 (0-50) had significantly longer PFS (14 months median) when treated with the combination compared to similar patients treated with R alone (9.3 months median); this is a 4.7 month PFS advantage (HR=0.64 (95% CI: 0.475-0.864).

These results suggest that patient subgroups can be identified prior to therapy that have significantly longer PFS and a trend for better OS when treated with combination Vc-R compared to R alone. One biomarker pair that maintains significance after multiple comparison corrections (FDR=0.051) includes a proteasomal subunit SNP [PSMB1 P11A heterozygote] and CD68 with low (0-50) expression. Three hundred fifty six subjects were evaluable for both of these biomarkers within this study. Additionally, this biomarker pair had a high population frequency with approximately one third of the evaluable subjects having both of these biomarkers. Subjects with this biomarker pair had a longer PFS interval when treated with Vc-R (16.6 months) compared to rituximab alone (9.1 months) demonstrating a PFS benefit of approximately 7.5 months with the combination. This group also appears to have an OS benefit with Vc-R that clearly trends toward significance (HR: 0.426 (0.174-1.046) P=0.0550), a higher ORR (73.7% on Vc-R vs 47.5% on rituximab alone, p=0.0077), a longer time to next treatment interval (33.1 mo on Vc-R vs 14.8 mo on rituximab alone, p=0.0013) and a longer duration of treatment free interval (27.8 mo vs 10.1 mo, p=0.0017).

Importantly, the CD68/PSMB P11A biomarker positive cohort was representative of the overall trial population with regard to demographics and clinical characteristics. Of note, approximately half of this cohort was represented by subjects with high risk disease and poor prognostic features. In patients with higher tumor burden (~54%), medium or high FLIPI (~76%), older age (>65) (~25%), with prior Rituximab treatment (~46%), or with two (~26%) or more than two (~30%) lines of prior therapy the PFS benefit of the CD68/PSMB P11A biomarker positive cohort appears to be maintained. These patients are generally regarded as "high risk" with limited treatment options and these preliminary findings suggest that biomarker positive subjects with high risk features may benefit from Vc-R.

Polymorphisms in PSMB1 and PSMB5 were found to have significant associations with clinical endpoints as single markers. The combination of PSMB1 [P11A] with CD68 was found to be synergistic and present in a high proportion of the study cohort. PSMB1 P11A is a polymorphism found in the leader sequence of the proteasome PSMB1 gene (Chen 1996). The leader sequence is responsible for appropriate subunit assembly and it has been reported that alterations of charged amino acids reduces the efficiency of subunit assembly (Schmidt 1999). Once assembled autocatalysis allows removes the leader sequence. The second biomarker in the pair is CD68 expressing tumor infiltrating macrophages. Previous reports have shown that high levels of CD68 associate with better response to rituximab (Taskinen 2007).

Importantly, this study has shown that subjects with low levels of CD68 expression have longer PFS and better overall response to Vc-R compared to R alone especially when present with PSMB1 P11A heterozygote as discussed above. Following cross validation, the pair previously described (CD68 Low and PSMB P11A) was found to be significant in the smaller discovery cohort (p=0.0003, 14.2 months for Vc-R vs 8.5 months for rituximab alone, HR=0.4 (0.24, 0.67)). There was still a trend for longer OS in the biomarker positive population (p=0.1291), HR=0.47(0.17, 1.27). Although the number of subjects in the confirmation cohorts was small, the positive trend in both PFS and OS was found to be maintained. In confirmation cohort 1 (which excludes subjects from China; n=106), subjects treated with Vc-R had approximately 18.2 mo PFS while those treated with R alone had 9.5 months PFS (p=0.0817, HR=0.44). In confirmation cohort 2 (which includes China subjects and subjects with missing data; n=126), subjects treated with Vc-R had 13.9 months median PFS while those treated with R had 9.5 months median PFS (p=0.0878, HR=0.49). The trend in OS was also maintained.

EXAMPLE 2

Single predictors which correlated with a positive response are shown in Table 5.

TABLE 5

| | | Single predictors. | | | |
|---|---|---|---|---|---|
| Marker A | Marker Subtype | PFS Vc + R vs. R median days | N Vc + R vs. R | Logrank P-value | % N in ITT |
| CD68 OVERALL POSITIVE | 0-25 | 11.5 mo vs 10.6 mo 0.9 mo PFS improvement | 40 vs 44 | 0.422 | 12.4 |
| CD68 OVERALL POSITIVE | 26-50 | 12.1 mo vs 9.3 mo 2.8 mo PFS improvement | 114 vs 108 | 0.0588 | 32.9 |
| CD68 POSITIVE FOLLICULAR | 0-25 | 14.1 mo vs 9.3 mo 4.8 mo PFS improvement | 50 vs 60 | 0.0934 | 16.3 |
| CD68 POSITIVE FOLLICULAR | 26-50 | 13.4 mo vs 9.1 mo 4.3 mo PFS improvement | 84 vs 91 | 0.0289 | 25.9 |
| P65 INTENSITY CYTOPLASMIC SIGNAL | <=1+ | 11.6 mo vs 9.3 mo 2.3 mo PFS improvement | 41 vs 43 | 0.2455 | 12.4 |
| PSMB1/P11A | C/G | 14 mo vs 9.3 mo 4.7 mo improvement | 115 vs 127 | 0.0218 | 35.9 |
| PSMB5/R24C | C/T | 17.6 mo vs 9.3 mo 8.3 mo improvement | 41 vs 41 | 0.4016 | 12.1 |

EXAMPLE 3

Predictor pairs which correlated with a positive response are shown in Tables 6 and 7.

TABLE 6

Significant marker pairs.

| Marker A | Marker B | PFS Vc – R vs. R median month | N Vc – R vs. R | Logrank P-value | FDR |
|---|---|---|---|---|---|
| PSMB5/R24C C/T | P65 INTENSITY CYTOPLASMIC SIGNAL <=1+ | 27 mo vs. 10.4 mo 16.6 mo improvement | 5 vs. 7 | 0.0439 | 0.489 |
| PSMB1/P11A C/G | 20S % POSITIVE CYTOPLASMIC SIGNAL: >90 | 18.9 mo vs. 9.5 mo 9.4 improvement | 50 vs 50 | 0.0145 | 0.447 |
| PSMB1/P11A C/G | CD68 POSITIVE FOLLICULAR: 0-50 | 16.6 mo vs. 9.1 mo 7.5 mo improvement | 57 vs 61 | 0.0001 | 0.051 |
| PSMB1/P11A C/G | CD68 POSITIVE PERIFOLLICULAR: >50 | 16.6 mo vs. 9.2 mo 7.4 improvement | 24 vs 28 | 0.0365 | 0.471 |
| PSMB9/R60H G/G | P65 % NUCLEAR STAINING: >0 | 16.2 mo vs. 9.5 mo 6.7 improvement | 35 vs 28 | 0.0303 | 0.455 |
| PSMB5/R24C C/T | CD68 POSITIVE FOLLICULAR: 0-50 | 13.7 mo vs. 7.2 mo 6.5 mo improvement | 18 vs 21 | 0.0220 | 0.447 |
| HI Tumor BD NO | CD68 OVERALL POSITIVE: 0-50 | 22.8 mo vs. 16 mo 6.8 mo improvement | 64 vs 68 | 0.0177 | 0.447 |
| HI Tumor BD NO | CD68 POSITIVE FOLLICULAR: 0-50 | 20.5 mo vs. 13.8 mo 6.7 improvement | 64 vs 66 | 0.0310 | 0.455 |
| Prior RX: 1 | CD68 POSITIVE FOLLICULAR: 0-50 | 18.2 mo vs. 9.3 mo 8.9 mo improvement | 63 vs 69 | 0.0129 | 0.447 |
| PSMB1/P11A C/G | Time since last Rx: >1 year | 18.2 mo vs. 10.7 mo 7.5 mo improvement | 72 vs 74 | 0.0198 | 0.447 |
| Prior Ritutux NO | CD68 POSITIVE FOLLICULAR: 0-50 | 15.9 mo vs. 9.2 mo 6.7 mo improvement | 73 vs 86 | 0.0066 | 0.437 |
| PSMB1/P11A C/G | Age group: <=65 | 15.3 mo vs. 9.2 mo 6.1 mo improvement | 86 vs 96 | 0.0071 | 0.437 |
| Sex MALE | 20S % NUCLEAR STAINING: >20 | 13.7 mo vs. 7.7 mo 6 mo improvement | 63 vs 48 | 0.0050 | 0.437 |
| Race Group OTHER | 20S % NUCLEAR STAINING: >20 | 11.4 mo vs. 3.8 mo 7.6 mo improvement | 11 vs 7 | 0.0320 | 0.455 |
| PSMB1/P11A C/G | PSMB5/R24C C/T | 13.7 mo vs. 7.8 mo 5.9 mo improvement | 7 vs. 7 | 0.0221 | 0.4468 |

TABLE 7

Significant marker pairs

| Combination | PFS Vc – R vs. R median month | Logrank P-value |
|---|---|---|
| P65 Cytoplasmic signal >90% & | 23.6 vs. 10.6 mo (13 mo) | 0.0132 |
| 1 prior treatment* | 16 vs. 8.9 mo (7.1 mo) | n.s. |
| CD68 Pos Follic (0-50) & | 14.2 vs 8.5 mo (5.7 mo) | 0.0025 |
| P11A[C/G]** | 14.4 vs 9.2 mo (5.2 mo) | n.s. |

Arif A (2009), Jamal S, Mushtaq S, Ahmed S, Mubarik A. Frequency of bcl-2 gene rearrangement in B-Cell Non-Hodgkin's lymphoma. Asian Pacific J Cancer Prev 2009; 10(2): 237-240.

Binstadt B A (2003), Geha R S, Bonilla F A. IgG Fc receptor polymorphisms in human disease: Implications for intravenous immunoglobulin therapy. J Allergy Clin Immunol 2003; 111(4): 697-703.

Cartron G (2002), Dacheux L, Salles G, Solal-Celigny P, Bardos P, Colombat P, Watier H. Therapeutic activity of humanized anti-CD20 monoclonal antibody and polymorphism in IgG Fc receptor FcgammaRIIIa gene. Blood 2002; 99(3): 754-758.

Chen P (1996), Hochstrasser M. Autocatalytic subunit processing couples active site formation in the 20S proteasome to completion of assembly. Cell 1996; 86: 961-972.

Chen S (2010), Blank J L, Peters T, Liu X J, Rappoli D M, Pickard M D, Menon S, Driscoll D L, Lingaraj T, Burkhardt A L, Chen W, Garcia K, Sappal D S, Gray J, Hales P, Leroy P J, Ringeling J, Rabino C, Spelman J J, Morganstem J P, Lightcap E S. Genome-wide siRNA screen for modulators of cell death induced by proteasome inhibitor bortezomib. Cancer Res 2010; 70(11): 4318-4326.

Clinical Study Protocol 26866138-LYM3001. A randomized, open-label, multicenter study of VELCADE with rituximab or rituximab alone in subjects with relapsed or refractory, rituximab naïve or sensitive follicular B-cell non-Hodgkin's lymphoma. Document No. EDMS-PSDB-4649082:4.0; Johnson & Johnson Pharmaceutical Research & Development (19 May 2006).

Clinical Study Report 26866138-LYM3001. A randomized, open-label, multicenter study of VELCADE with rituximab or rituximab alone in subjects with relapsed or refractory, rituximab naïve or sensitive follicular B-cell non-Hodgkin's lymphoma. Document No. EDMS-ERI-16225335:1.0; Johnson & Johnson Pharmaceutical Research & Development (9 Feb. 2011).

Dave S S (2004), Wright G, Tan B, Rosenwald A, Gascoyne R D, Chan W C, Fisher R I, Braziel R M, Rimsza L M, Grogan T M, Miller T P, Leblanc M, Greiner T C, Weisenburger D D, Lynch J C, Vose J, Armitage J O, Smeland E B, Kvaloy S, Holte H, Delabie J, Connors J M, Lansdorp P M, Ouyang Q, Lister T A, Davies A J, Norton A J, Muller-Hermelink H K, Ott G, Campo E, Montserrat E, Wilson W H, Jaffe E S, Simon R, Yang L, Powell J, Zhao H, Goldschmidt N, Chiorazzi M, Staudt L M. Prediction of survival in follicular lymphoma based on molecular features of tumor-infiltrating immune cells. NEJM 2004; 351(21): 2159-2169.

Fischer U (2005), Schulze-Osthoff K. New approaches and therapeutics targeting apoptosis in disease. Pharmacol Rev 2005; 57(2): 187-215.

Goy A (2010), Bernstein S, McDonald A, Pickard M, Shi H, Fleming M, Bryant B, Trepicchio W, Fisher R, Boral A, Mulligan G. Potential biomarkers of bortezomib activity in mantle cell lymphoma from the phase 2 PINNACLE trial. Leukemia & Lymphoma 2010; 51(7): 1269-1277.

Karin M (2002), Cao Y, Florian G R, Li Z W. NF-kB in cancer: From innocent bystander to major culprit. Nature Rev Cancer 2002; 2(4): 301-310.

Keats J J (2007), Fonseca R, Chesi M, Schop R, Baker A, Chng Wj, Van Wier S, Tiedemann R, Shi C X, Sebag M, Braggio E, Henry T, Zhu Y X, Fogle H, Price-Troska T, Altmann G, Mancini C, Brents L A, Kumar S, Greipp P, Dispenzieri A, Bryant B, Mulligan G, Bruhn L, Barrett M, Valdez R, Trent J, Stewart A K, Carpten J, Bergsagel P L. Promiscuous mutations activate the noncanonical NF-kappaB pathway in multiple myeloma. Cancer Cell 2007; 12(2): 131-144.

Mitsiades N (2002), Mitsiades C S, Poulaki V, Chauhan D, Fanourakis G, Gu X, Bailey C, Joseph M, Libermann T A, Treon S P, Munshi N C, Richardson P G, Hideshima T, Anderson K C. Molecular sequelae of proteasome inhibition in human multiple myeloma cells. Proc Natl Acad Sci USA 2002; 99(22): 14374-14379.

Mulligan G (2007), Mitsiades C, Bryant B, Zhan F, Chng W J, Roels S, Koenig E, Fergus A, Huang Y, Richardson P, Trepicchio W L, Broyl A, Sonnveld P, Shaghnessy J D, Bergsagel P L, Schenkein D, Esseltine D L, Boral A, Anderson K C. Gene expression profiling and correlation with clinical outcome in clinical trials of the proteasome inhibitor bortezomib. Blood 2007; 109(8): 3177-3188.

Schmidt M (1999), Zantopf D, Kraft R, Kostka S, Preissner R, Kloetzel P M. Sequence information within proteasomal prosequences mediates efficient integration of β-subunits into the 20S proteasome complex. J Mol Biol 1999; 288(1): 117-128.

Shin H M (2006), Minter L M, Cho O H, Gottipati S, Fauq A H, Golde T E, Sonenshein G E, Osborne B A. Notch1 augments NF-kappaB activity by facilitating its nuclear retention. EMBO 2006; 25(1): 129-138.

Taskinen M (2007), Karjalainen-Lindsberg M L, Nyman H, Eerola L M, Leppa S. A high tumor-associated macrophage content predicts favorable outcome in follicular lymphoma patients treated with rituximab and cyclophosphamide-doxorubicin-vincristine-prednisone. Clin Cancer Res 2007; 13(19): 5784-5789.

Wojcik C (2002). Regulation of apoptosis by the ubiquitin and proteasome pathway. J Cell Mol Med 2002; 6(1): 25-48.

Wu J (1997), Edberg J C, Redecha P B, Bansal V, Guyre P M, Coleman K, Salmon J E, Kimberly R P. A novel polymorphism of FcgammaRIIIa (CD16) alters receptor function and predisposes to autoimmune disease. J Clin Invest 1997; 100(5): 1059-1070.

Yeung B H (2006), Huang D C, Sinicrope F A. PS-341 (bortezomib) induces lysosomal cathepsin b release and a caspase-2 dependent mitochondrial permeabilization and apoptosis in human pancreatic cancer cells. J Biol Chem 2006; 281(17): 11923-11932.

Yin D (2005), Zhou H, Kumagai T, Liu G, Ong J M, Black K L, Koeffler H P. Proteasome inhibitor PS-341 causes cell growth arrest and apoptosis in human glioblastoma multiforme (GBM). Oncogene 2005; 24(3): 344-354.

EXAMPLE 4

Appendix 2 presents an overall summary of the single-marker associations with clinical endpoint other than PFS and stratified by clinical covariates from the previous examples.

Appendix 3 outlines the data for all significant pair-wise combinations from the previous examples. Note: Selected=Biomarker positive, Not Selected=Biomarker negative.

EXAMPLE 5

The VISTA study was an open-label, randomized study of VELCADE/Melphalan/Prednisone versus Melphalan/Prednisone in subjects with previously untreated multiple myeloma. San Miguel, *N. Engl. J. Med.* 2008 Aug. 28; 359 (9):906-17. The primary efficacy objective of this study was to determine whether the addition of VELCADE (Bortezomib for Injection) to standard melphalan/prednisone (MP) therapy improves the time to disease progression (TTP) in subjects with previously untreated multiple myeloma.

The exploratory objectives in biomarker analysis from the VISTA study were to identify patient populations that are more or less likely to respond to VELCADE/Melphalan/Prednisone versus Melphalan/Prednisone alone by:
Confirming the finding (from lymphoma studies) of a single marker association of PSMB1 P11A and PSMB5 R24C with PFS and OS.
Association with other clinical endpoints including: time to progression (TTP), complete response (CR), Overall response rate, time to response and duration of response.

Association of PSMB1 P11A and PSMB5 R24C individually or in combination with TTP, PFS, and OS were estimated using the log rank test between treatment groups for biomarker positive and negative populations. The overall biomarker population by treatment arm had similar associations made. Medians of TTP, PFS, and OS, difference in median TTP, PFS, and OS between treatment groups, log rank P-value, hazard ratio and its 95% confidence intervals and frequencies of events were reported. Kaplan-Meier plots were presented for each biomarker. When positive associations were found for TTP, OS or PFS, then the other clinical endpoints were tested with similar methods and output. For ORR, Fishers exact test was used. The number and percentage of subjects falling into each response category were descriptively tabulated.

Table 8 shows the progression free survival benefit of 5.3 months with VELCADE-MP vs. MP alone in patients with PSMB1 P11A (C/G) marker.

| Statistic | Biomarker Positive | | Biomarker Negative | | Total | |
|---|---|---|---|---|---|---|
| | Vmp | mp | Vmp | mp | Vmp | mp |
| Event/Total (%) | 39/82 (47.6) | 61/89 (68.5) | 47/87 (54.0) | 68/94 (72.3) | 86/169 (50.9) | 129/183 (70.5) |
| Median (95% CI) | 20.3 mo (556, 873) | 15 mo (253, 511) | 17.7 mo (459, 610) | 11.2 mo (254, 436) | 19 mo (533, 662) | 12.6 mo (279, 463) |
| HR (Vmp vs mp) | 0.44 (0.29, 0.67) | | 0.62 (0.43, 0.90) | | 0.54 (0.41, 0.71) | |

| | Biomarker Positive | | Biomarker Negative | | Total | |
|---|---|---|---|---|---|---|
| Statistic | Vmp | mp | Vmp | mp | Vmp | mp |
| HR p-Value (Vmp vs mp) | <.0001 | | 0.0117 | | <.0001 | |

Table 9 shows the overall survival benefit of 6 months with VELCADE-MP vs. MP alone in patients with PSMB1 P11A (C/G) marker.

| | Biomarker Positive | | Biomarker Negative | | Total | |
|---|---|---|---|---|---|---|
| Statistic | Vmp | mp | Vmp | mp | Vmp | mp |
| Event/Total (%) | 47/82 (57.3) | 65/89 (73.0) | 42/87 (48.3) | 55/94 (58.5) | 89/169 (52.7) | 120/183 (65.6) |
| Median (95% CI) | 52 (1322, 1845) | 39 (893, 1412) | 58 (1318, —) | 46 (965, 1745) | 56 (1372, 1845) | 42 (1014, 1470) |
| HR Vmp vs mp | 0.63 (0.44, 0.92) | | 0.81 (0.54, 1.22) | | 0.72 (0.55, 0.95) | |
| HR p-Value (Vmp vs mp) | 0.0167 | | 0.3153 | | 0.0179 | |

APPENDIX 2, TABLE 2.1

Overall survival (OS) by Protein Expression and by Covariate, IRC Review (Significant [p ≤ 0.05], Frequency of ≥10% or Higher)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| 20S % POSITIVE CYTOPLASMIC SIGNAL: 0-20 | 2 Prior Lines of Therapy | 8.28 (0.85, 80.83) | | 1/10 | — | 3/4 | 809 | 122 |
| 20S % POSITIVE CYTOPLASMIC SIGNAL: 95-100 | 2 Prior Lines of Therapy | 0.42 (0.17, 1.00) | | 14/35 | 1205 | 9/40 | — | 122 |
| CD68 OVERALL POSITIVE: 26-50 | 2 Prior Lines of Therapy | 0.33 (0.12, 0.87) | | 13/26 | 1205 | 7/30 | — | 111 |
| CD68 POSITIVE PERIFOLLICULAR: 26-50 | 2 Prior Lines of Therapy | 0.30 (0.09, 1.04) | | 7/16 | 1205 | 5/27 | — | 98 |
| P65 % POSITIVE CYTOPLASMIC SIGNAL: >90% | 2 Prior Lines of Therapy | 0.42 (0.19, 0.97) | | 19/52 | — | 9/44 | — | 125 |
| P65 INTENSITY CYTOPLASMIC SIGNAL: ≥2+ | 2 Prior Lines of Therapy | 0.35 (0.14, 0.88) | | 19/55 | — | 7/43 | — | 125 |
| CD68 OVERALL POSITIVE: 26-50 | No High Tumor Burden | 0.21 (0.06, 0.72) | | 14/54 | — | 3/46 | — | 204 |
| CD68 POSITIVE PERIFOLLICULAR: 26-50 | No High Tumor Burden | 0.11 (0.01, 0.82) | | 10/41 | — | 1/33 | — | 182 |
| P27 % NUCLEI POSITIVE: 0-20 | No High Tumor Burden | 3.91 (0.98, 15.69) | | 3/29 | — | 6/17 | — | 215 |
| 20S INTENSITY CYTOPLASMIC SIGNAL: ≤2+ | Intermediate FLIPI Score | 5.43 (1.17, 25.14) | | 2/48 | — | 9/41 | — | 168 |
| P65 INTENSITY CYTOPLASMIC SIGNAL: ≤1+ | Intermediate FLIPI Score | 6.84 (0.80, 58.74) | | 1/17 | — | 5/13 | — | 170 |
| CD68 POSITIVE FOLLICULAR: 0-25 | No Prior Rituximab Therapy | 0.21 (0.05, 0.97) | | 11/36 | — | 3/25 | 1343 | 210 |
| CD68 POSITIVE FOLLICULAR: 0-25 | ≤65 years old | 0.29 (0.10, 0.83) | | 14/46 | — | 5/41 | — | 292 |
| 20S INTENSITY CYTOPLASMIC SIGNAL: ≥3+ | Male | 0.30 (0.12, 0.77) | | 10/27 | — | 8/62 | — | 204 |

APPENDIX 2, TABLE 2.1-continued

Overall survival (OS) by Protein Expression and by Covariate, IRC Review (Significant [p ≤ 0.05], Frequency of ≥10% or Higher)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| CD68 POSITIVE PERIFOLLICULAR: 26-50 | Male | 0.29 (0.10, 0.83) | | 11/30 | — | 5/39 | — | 169 |
| P27 % NUCLEI POSITIVE: 60-70 | Male | 0.09 (0.01, 0.93) | | 4/12 | — | 1/14 | — | 202 |
| CD68 OVERALL POSITIVE: 51-75 | Ann Arbor Stage III | 6.24 (1.25, 31.02) | | 2/21 | — | 6/13 | 1078 | 144 |
| 20S % POSITIVE CYTOPLASMIC SIGNAL: 0-20 | Ann Arbor Stage IV | 7.22 (0.80, 65.02) | | 1/15 | — | 4/11 | 1103 | 236 |
| 20S % POSITIVE CYTOPLASMIC SIGNAL: 95-100 | Ann Arbor Stage IV | 0.50 (0.27, 0.91) | | 25/56 | 1205 | 19/75 | 1343 | 236 |

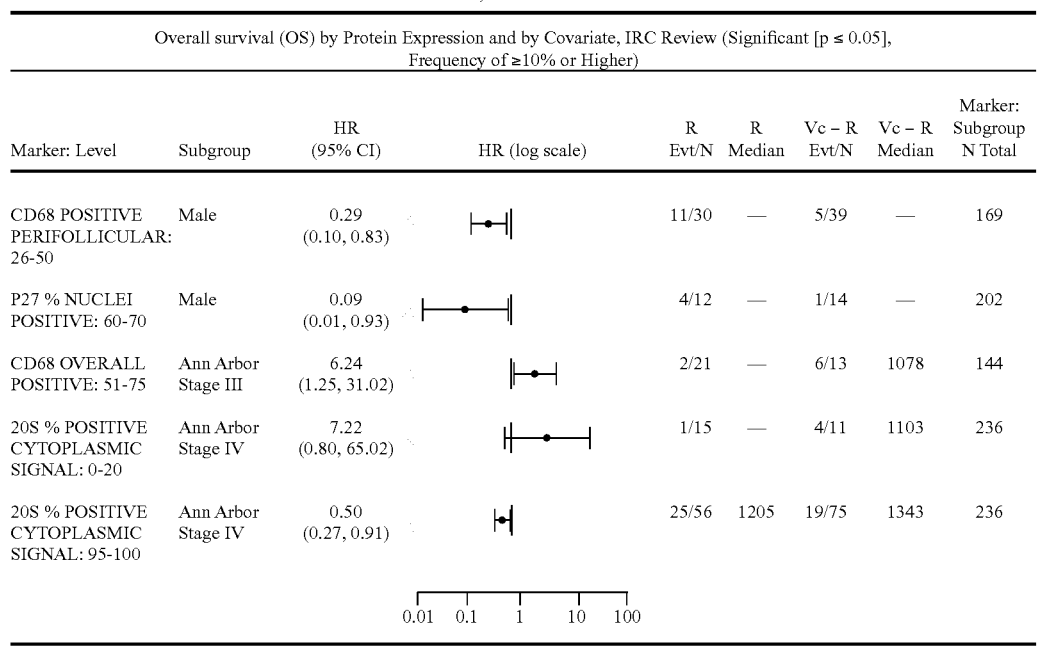

APPENDIX 2, TABLE 2.2

OS by Germline Genetic Variant nd by Covariate, IRC Review (Significant [p ≤ 0.05], Frequency of ≥10% or Higher)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| PSMB9/R60H: A/A | 3 Prior Lines of Therapy | 6.92 (0.79, 60.79) | | 1/6 | — | 5/7 | 846 | 85 |
| PSMB5/R24C: C/T | Intermediate FLIPI Score | 0.10 (0.01, 0.97) | | 4/10 | 971 | 1/16 | — | 186 |
| PSMB5/R24C: C/T | Ann Arbor Stage IV | 0.22 (0.07, 0.66) | | 9/15 | 717 | 5/28 | — | 270 |

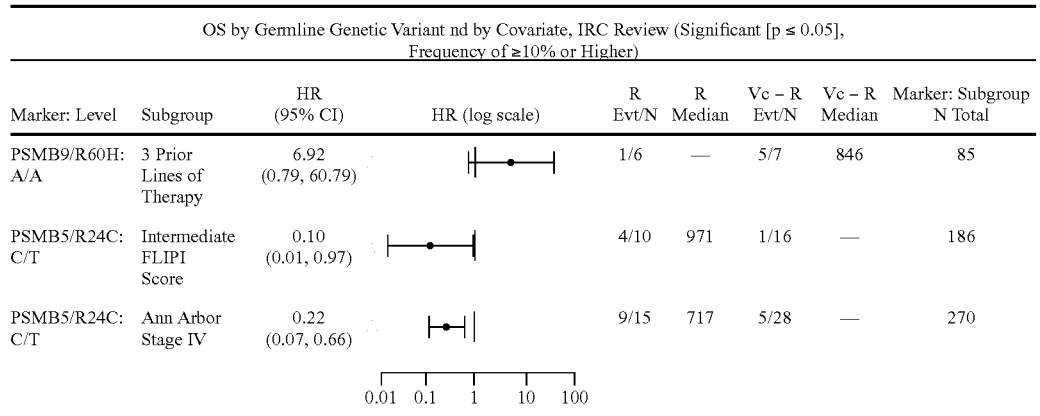

APPENDIX 2, TABLE 2.3

OS by Somatic Mutation and by Covariate, IRC Review (Significant [p ≤ 0.05], Frequency of ≥10% or Higher)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| NOTCH/X28DEL: MND | 2 Prior Lines of Therapy | 0.44 (0.20, 0.97) | | 20/56 | — | 10/48 | — | 109 |
| NOTCH/P2513L: MD | No High Tumor Burden | 0.14 (0.02, 1.15) | | 7/26 | — | 1/21 | — | 163 |
| BCL2/P59L: MD | High Tumor Burden | 0.17 (0.04, 0.65) | | 5/6 | 282 | 4/14 | — | 172 |
| BCL2/P59L: MD | High FLIPI Score | 0.21 (0.05, 0.86) | | 6/6 | 282 | 4/7 | 843 | 125 |

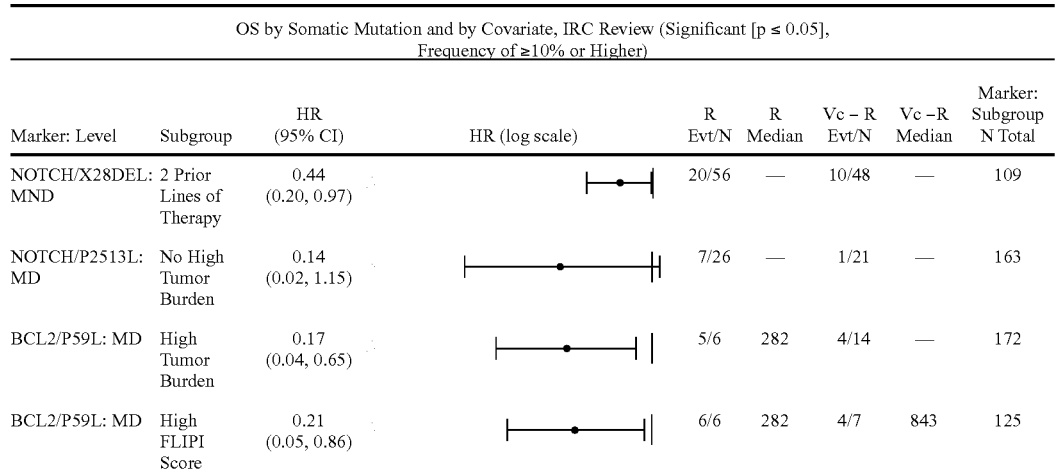

APPENDIX 2, TABLE 2.3-continued

OS by Somatic Mutation and by Covariate, IRC Review (Significant [p ≤ 0.05], Frequency of ≥10% or Higher)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| BCL2/P59L: MD | No Prior Rituximab Therapy | 0.12 (0.03, 0.48) | | 5/5 | 174 | 4/13 | — | 178 |
| BCL2/P59L: MD | Rest of World | 0.22 (0.06, 0.84) | | 4/5 | 174 | 5/12 | — | 152 |
| NOTCH/P2513L: MD | >65 years old | 0.30 (0.09, 1.03) | | 8/13 | 795 | 4/13 | — | 92 |
| BCL2/P59L: MD | Female | 0.26 (0.07, 0.92) | | 6/8 | 536 | 4/14 | — | 180 |
| BCL2/R106H: MD | Male | 0.25 (0.07, 0.84) | | 8/10 | 318 | 4/12 | — | 169 |
| NOTCH/Q2460X: MD | Male | 0.11 (0.02, 0.70) | | 3/3 | 595 | 5/12 | — | 142 |
| NOTCH/X28DEL: MND | Male | 0.57 (0.32, 1.00) | | 26/75 | — | 22/97 | — | 180 |
| BCL2/P59L: MD | Ann Arbor Stage IV | 0.12 (0.03, 0.50) | | 5/5 | 174 | 4/12 | — | 149 |

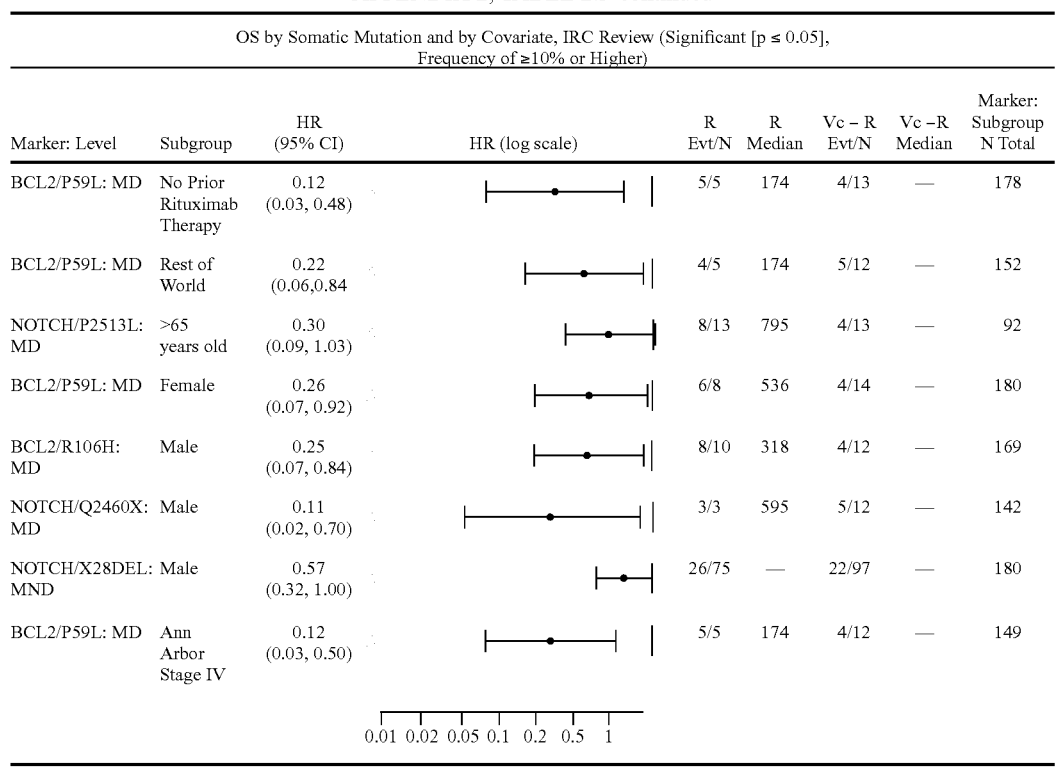

0.01 0.02 0.05 0.1 0.2 0.5 1

APPENDIX 2, TABLE 2.4

Time to Progression (TTP), by Protein Expression and by Covariate, IRC Review (Significant [p ≤ 0.05], Frequency of ≥10% or Higher)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| CD68 POSITIVE FOLLICULAR: 26-50 | No Subgroup | 0.66 (0.45, 0.96) | | 65/91 | 277 | 48/84 | 414 | 387 |
| P65 % POSITIVE CYTOPLASMIC SIGNAL: >90% | No Subgroup | 0.75 (0.59, 0.96) | | 139/204 | 334 | 116/186 | 414 | 470 |
| CD68 POSITIVE FOLLICULAR: 26-50 | 1 Prior Line of Therapy | 0.51 (0.27, 0.94) | | 26/39 | 349 | 18/40 | 881 | 176 |
| CD68 POSITIVE PERIFOLLICULAR: >75 | 1 Prior Line of Therapy | 0.24 (0.09, 0.65) | | 13/18 | 275 | 7/16 | 716 | 174 |
| P65 % POSITIVE CYTOPLASMIC SIGNAL: >90% | 1 Prior Line of Therapy | 0.67 (0.45, 0.98) | | 56/89 | 349 | 48/88 | 506 | 203 |
| 20S % NUCLEAR STAINING: 30-50 | 2 Prior Lines of Therapy | 0 41 (0.18, 0.95) | | 11/13 | 239 | 13/22 | 431 | 122 |
| CD68 OVERALL POSITIVE: 0-25 | 2 Prior Lines of Therapy | 0.22 (0.05, 0.90) | | 6/8 | 142 | 4/7 | 771 | 111 |
| CD68 POSITIVE PERIFOLLICULAR: 0-25 | 2 Prior Lines of Therapy | 0.13 (0.03, 0.64) | | 7/8 | 70 | 4/7 | 771 | 98 |
| CD68 POSITIVE FOLLICULAR: 51-75 | 3 Prior Lines of Therapy | 9.40 (1.13, 78.09) | | 1/4 | — | 8/8 | 276 | 60 |

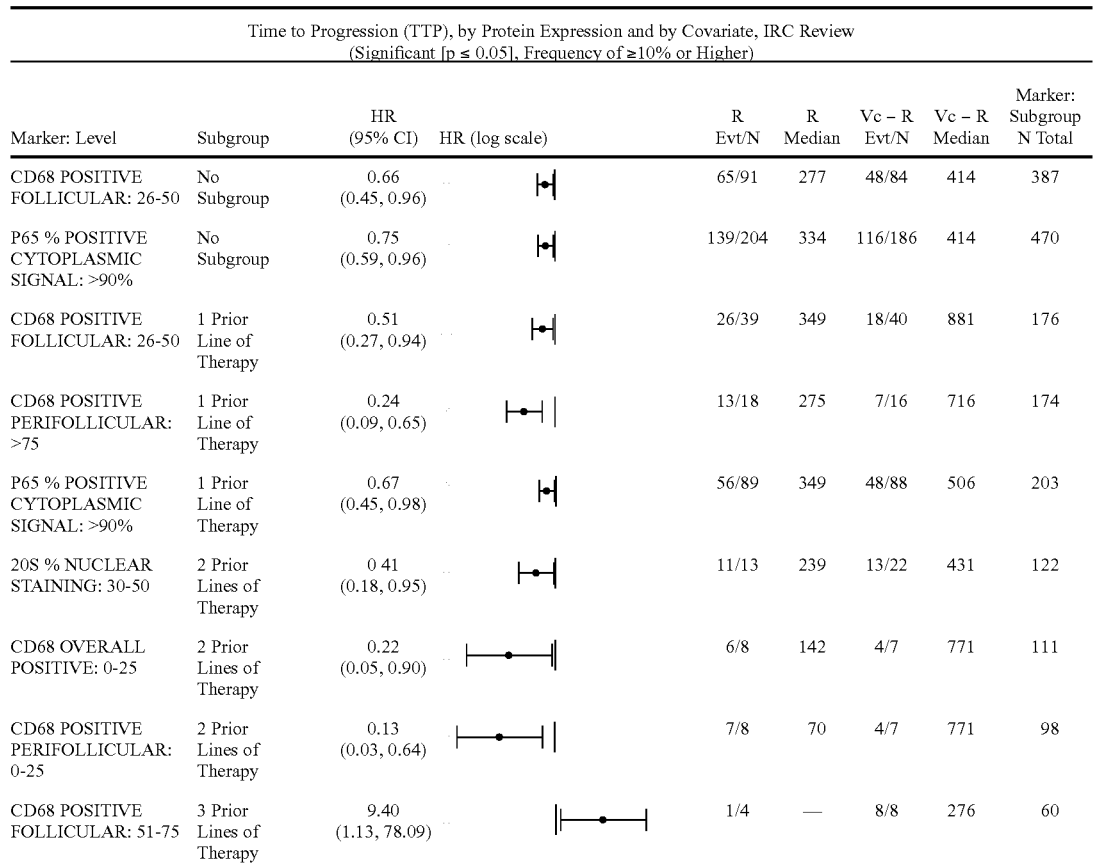

APPENDIX 2, TABLE 2.4-continued

Time to Progression (TTP), by Protein Expression and by Covariate, IRC Review
(Significant [p ≤ 0.05], Frequency of ≥10% or Higher)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| P27 SIGNAL INTENSITY: ≥2+ | 4 Prior Lines of Therapy | 3.02 (1.09, 8.34) | | 9/15 | 348 | 8/10 | 144 | 32 |
| CD68 OVERALL POSITIVE: 26-50 | No High Tumor Burden | 0.50 (0.29, 0.86) | | 37/54 | 357 | 22/46 | 881 | 204 |
| CD68 POSITIVE FOLLICULAR: 26-50 | No High Tumor Burden | 0.50 (0.27, 0.93) | | 29/44 | 351 | 17/39 | 881 | 182 |
| CD68 OVERALL POSITIVE: 26-50 | High FLIPI Score | 0.58 (0.36, 0.94) | | 36/45 | 277 | 35/52 | 366 | 181 |
| CD68 POSITIVE FOLLICULAR: 26-50 | High FLIPI Score | 0.57 (0.33, 0.97) | | 31/37 | 205 | 25/36 | 347 | 156 |
| P65 % POSITIVE CYTOPLASMIC SIGNAL: >90% | High FLIPI Score | 0.65 (0.45, 0.94) | | 61/83 | 239 | 53/77 | 358 | 193 |
| P65 INTENSITY CYTOPLASMIC SIGNAL: ≥2+ | High FLIPI Score | 0.67 (0.46, 0.98) | | 60/80 | 275 | 51/76 | 358 | 193 |
| P27 % NUCLEI POSITIVE: 60-70 | Intermediate FLIPI Score | 3.34 (1.20, 9.30) | | 6/13 | 513 | 10/11 | 215 | 165 |
| P65 % POSITIVE CYTOPLASMIC SIGNAL: ≤90% | Intermediate FLIPI Score | 2.77 (1.00, 7.64) | | 5/16 | 567 | 15/19 | 351 | 170 |
| P65 % NUCLEAR STAINING: 0 | No Prior Rituximab Therapy | 0.69 (0.49, 0.97) | | 77/102 | 322 | 55/92 | 426 | 255 |
| P65 % POSITIVE CYTOPLASMIC SIGNAL: >90% | No Prior Rituximab Therapy | 0.68 (0.49, 0.95) | | 80/112 | 345 | 61/105 | 463 | 255 |
| CD68 OVERALL POSITIVE: 0-25 | ≤1 year since last anti-lymphoma treatment | 2.66 (1.02, 6.96) | | 11/18 | 424 | 11/13 | 202 | 173 |
| CD68 POSITIVE FOLLICULAR: 0-25 | >1 year since last anti-lymphoma treatment | 0.49 (0.26, 0.91) | | 23/34 | 357 | 20/33 | 519 | 235 |
| P65 % POSITIVE CYTOPLASMIC SIGNAL: >90% | >1 year since last anti-lymphoma treatment | 0.69 (0.49, 0.96) | | 77/117 | 357 | 61/112 | 519 | 288 |
| CD68 OVERALL POSITIVE: 26-50 | Rest of World | 0.63 (0.40, 1.00) | | 40/51 | 277 | 34/52 | 367 | 198 |
| CD68 OVERALL POSITIVE: 26-50 | ≤65 years old | 0.65 (0.44, 0.95) | | 57/77 | 278 | 50/84 | 414 | 329 |
| CD68 POSITIVE FOLLICULAR: 26-50 | ≤65 years old | 0.55 (0.36, 0.86) | | 52/67 | 270 | 34/62 | 406 | 292 |
| CD68 POSITIVE PERIFOLLICULAR: >75 | ≤65 years old | 0.46 (0.22, 0.98) | | 17/23 | 275 | 12/23 | 506 | 289 |

APPENDIX 2, TABLE 2.4-continued

Time to Progression (TTP), by Protein Expression and by Covariate, IRC Review
(Significant [p ≤ 0.05], Frequency of ≥10% or Higher)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| P27 SIGNAL INTENSITY: ≥2+ | ≤65 years old | 0.73 (0.55, 0.97) | | 104/153 | 281 | 91/149 | 406 | 344 |
| P65 % NUCLEAR STAINING: 0 | ≤65 years old | 0.72 (0.53, 0.98) | | 97/138 | 287 | 71/118 | 414 | 349 |
| P65 % POSITIVE CYTOPLASMIC SIGNAL: >90% | ≤65 years old | 0.66 (0.50, 0.89) | | 108/154 | 278 | 83/142 | 422 | 349 |
| P65 INTENSITY CYTOPLASMIC SIGNAL: ≥2+ | ≤65 years old | 0.74 (0.55, 0.98) | | 105/152 | 287 | 85/139 | 406 | 349 |
| 20S % POSITIVE CYTOPLASMIC SIGNAL: 0-20 | >65 years old | 0.14 (0.02, 1.21) | | 5/6 | 278 | 4/7 | 738 | 118 |
| CD68 POSITIVE FOLLICULAR: 51-75 | Female | 2.38 (1.11, 5.13) | | 14/26 | 708 | 13/14 | 324 | 217 |
| 20S % NUCLEAR STAINING: 60-70 | Male | 0.37 (0.17, 0.84) | | 13/16 | 212 | 15/20 | 358 | 204 |
| 20S INTENSITY CYTOPLASMIC SIGNAL: ≥3+ | Male | 0.58 (0.34, 1.00) | | 20/27 | 280 | 39/62 | 422 | 204 |
| CD68 POSITIVE PERIFOLLICULAR: 26-50 | Male | 0.48 (0.27, 0.86) | | 22/30 | 239 | 26/39 | 429 | 169 |
| P27 SIGNAL INTENSITY: ≥2+ | Male | 0.70 (0.48, 1.00) | | 52/72 | 280 | 69/101 | 360 | 202 |
| P65 % NUCLEAR STAINING: 0 | Male | 0.67 (0.46, 0.98) | | 56/74 | 280 | 56/84 | 358 | 207 |
| P65 % POSITIVE CYTOPLASMIC SIGNAL: >90% | Male | 0.61 (0.42, 0.87) | | 54/72 | 271 | 65/97 | 414 | 207 |
| CD68 POSITIVE PERIFOLLICULAR: 26-50 | Other | 0.14 (0.01, 1.31) | | 4/4 | 128 | 4/5 | 346 | 22 |
| CD68 POSITIVE FOLLICULAR: 26-50 | White | 0.59 (0.39, 0.89) | | 53/77 | 334 | 39/73 | 463 | 335 |
| P65 % POSITIVE CYTOPLASMIC SIGNAL: >90% | White | 0.72 (0.55, 0.94) | | 119/179 | 345 | 99/162 | 426 | 406 |
| P65 INTENSITY CYTOPLASMIC SIGNAL: ≤1+ | Ann Arbor Stage III | 0.26 (0.08, 0.90) | | 7/11 | 204 | 7/11 | 464 | 151 |
| 20S % POSITIVE CYTOPLASMIC SIGNAL: 95-100 | Ann Arbor Stage IV | 0.66 (0.43, 1.00) | | 43/56 | 278 | 47/75 | 414 | 236 |
| CD68 OVERALL POSITIVE: 26-50 | Ann Arbor Stage IV | 0.65 (0.42, 0.99) | | 44/56 | 277 | 45/68 | 366 | 222 |
| P27 % NUCLEI POSITIVE: 30-50 | Ann Arbor Stage IV | 0.43 (0.20, 0.92) | | 15/19 | 278 | 13/23 | 485 | 237 |
| P27 SIGNAL INTENSITY: ≥2+ | Ann Arbor Stage IV | 0.70 (0.50, 0.99) | | 64/85 | 283 | 73/113 | 358 | 237 |

APPENDIX 2, TABLE 2.4-continued

Time to Progression (TTP), by Protein Expression and by Covariate, IRC Review
(Significant [p ≤ 0.05], Frequency of ≥10% or Higher)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| P65 % POSITIVE CYTOPLASMIC SIGNAL: >90% | Ann Arbor Stage IV | 0.65 (0.46, 0.91) | | 67/87 | 275 | 66/104 | 366 | 240 |

0.01  0.1  1  10  100

APPENDIX 2, TABLE 2.5

TTP by Germline Genetic Variant and by Covariate, IRC review
(Significant [p ≤ 0.05], Frequency of ≥10% or Higher)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| PSMB1/P11A: C/G | No Subgroup | 0.70 (0.51, 0.96) | | 82/127 | 288 | 74/115 | 426 | 542 |
| PSMB9/V32I: C/C | No Subgroup | 0.80 (0.65, 0.99) | | 177/266 | 345 | 157/254 | 417 | 542 |
| PSMB5/R24C: C/T | 2 Prior Lines of Therapy | 0.32 (0.11, 0.95) | | 8/10 | 280 | 6/12 | 534 | 142 |
| PSMB1/A171S: G/G | High Tumor Burden | 0.74 (0.57, 0.97) | | 110/147 | 273 | 107/149 | 344 | 296 |
| PSMB1/I208N: T/T | High Tumor Burden | 0.74 (0.57, 0.97) | | 110/147 | 273 | 107/149 | 344 | 296 |
| PSMB1/P11A: C/G | High Tumor Burden | 0.66 (0.44, 0.99) | | 52/72 | 253 | 44/65 | 358 | 296 |
| PSMB1/P193L: C/C | High Tumor Burden | 0.74 (0.57, 0.97) | | 110/147 | 273 | 107/149 | 344 | 296 |
| PSMB2/E49X: G/G | High Tumor Burden | 0.74 (0.57, 0.97) | | 110/147 | 273 | 107/149 | 344 | 296 |
| PSMB2/G187V: G/G | High Tumor Burden | 0.74 (0.57, 0.97) | | 110/147 | 273 | 107/149 | 344 | 296 |
| PSMB2/L159F: C/C | High Tumor Burden | 0.74 (0.57, 0.97) | | 110/147 | 273 | 107/149 | 344 | 296 |
| PSMB5/L206M: C/C | High Tumor Burden | 0.74 (0.57, 0.97) | | 110/147 | 273 | 107/149 | 344 | 296 |
| PSMB5/R24C: C/T | High Tumor Burden | 0.39 (0.19, 0.77) | | 17/21 | 275 | 18/24 | 352 | 296 |
| PSMB6/A234D: C/C | High Tumor Burden | 0.74 (0.57, 0.97) | | 110/147 | 273 | 107/149 | 344 | 296 |
| PSMB8/G8R: G/G | High Tumor Burden | 0.73 (0.56, 0.96) | | 104/140 | 271 | 105/145 | 344 | 296 |

APPENDIX 2, TABLE 2.5-continued

TTP by Germline Genetic Variant and by Covariate, IRC review
(Significant [p ≤ 0.05], Frequency of ≥10% or Higher)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| PSMB8/R141C: C/C | High Tumor Burden | 0.74 (0.57, 0.97) | | 110/147 | 273 | 107/149 | 344 | 296 |
| PSMB8/V182M: G/G | High Tumor Burden | 0.74 (0.57, 0.97) | | 110/147 | 273 | 107/149 | 344 | 296 |
| PSMB9/G9E: G/G | High Tumor Burden | 0.74 (0.56, 0.96) | | 110/145 | 271 | 107/148 | 344 | 296 |
| PSMB9/V32I: C/C | High Tumor Burden | 0.73 (0.56, 0.96) | | 108/142 | 273 | 101/142 | 331 | 296 |
| PSMB1/A171S: G/G | High FLIPI Score | 0.68 (0.49, 0.92) | | 84/112 | 273 | 75/110 | 350 | 222 |
| PSMB1/I208N: T/T | High FLIPI Score | 0.68 (0.49, 0.92) | | 84/112 | 273 | 75/110 | 350 | 222 |
| PSMB1/P193L: C/C | High FLIPI Score | 0.68 (0.49, 0.92) | | 84/112 | 273 | 75/110 | 350 | 222 |
| PSMB2/E49X: G/G | High FLIPI Score | 0.68 (0.49, 0.92) | | 84/112 | 273 | 75/110 | 350 | 222 |
| PSMB2/G187V: G/G | High FLIPI Score | 0.68 (0.49, 0.92) | | 84/112 | 273 | 75/110 | 350 | 222 |
| PSMB2/L159F: C/C | High FLIPI Score | 0.68 (0.49, 0.92) | | 84/112 | 273 | 75/110 | 350 | 222 |
| PSMB5/L206M: C/C | High FLIPI Score | 0.68 (0.49, 0.92) | | 84/112 | 273 | 75/110 | 350 | 222 |
| PSMB6/A234D: C/C | High FLIPI Score | 0.68 (0.49, 0.92) | | 84/112 | 273 | 75/110 | 350 | 222 |
| PSMB6/P107A: C/C | High FLIPI Score | 0.68 (0.49, 0.93) | | 81/107 | 275 | 74/108 | 350 | 222 |
| PSMB8/G8R: G/G | High FLIPI Score | 0.69 (0.50, 0.95) | | 77/105 | 273 | 73/107 | 350 | 222 |
| PSMB8/R141C: C/C | High FLIPI Score | 0.68 (0.49, 0.92) | | 84/112 | 273 | 75/110 | 350 | 222 |
| PSMB8/V182M: G/G | High FLIPI Score | 0.68 (0.49, 0.92) | | 84/112 | 273 | 75/110 | 350 | 222 |
| PSMB9/G9E: G/G | High FLIPI Score | 0.69 (0.50, 0.94) | | 84/111 | 273 | 75/109 | 348 | 222 |
| PSMB9/V32I: C/C | High FLIPI Score | 0.65 (0.47, 0.89) | | 80/105 | 239 | 71/105 | 348 | 222 |
| PSMB1/P11A: C/G | No Prior Rituximab Therapy | 0.64 (0.43, 0.98) | | 49/68 | 330 | 43/70 | 464 | 287 |

APPENDIX 2, TABLE 2.5-continued

TTP by Germline Genetic Variant and by Covariate, IRC review
(Significant [p ≤ 0.05], Frequency of ≥10% or Higher)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| PSMB9/V32I: C/C | No Prior Rituximab Therapy | 0.73 (0.55, 0.99) | | 98/138 | 351 | 79/136 | 483 | 287 |
| PSMB1/A171S: G/G | >1 year since last anti-lymphoma treatment | 0.71 (0.54, 0.94) | | 104/165 | 381 | 91/166 | 529 | 331 |
| PSMB1/I208N: T/T | >1 year since last anti-lymphoma treatment | 0.71 (0.54, 0.94) | | 104/165 | 381 | 91/166 | 529 | 331 |
| PSMB1/P11A: C/G | >1 year since last anti-lymphoma treatment | 0.60 (0.39, 0.91) | | 47/74 | 338 | 42/72 | 576 | 331 |
| PSMB1/P193L: C/C | >1 year since last anti-lymphoma treatment | 0.71 (0.54, 0.94) | | 104/165 | 381 | 91/166 | 529 | 331 |
| PSMB2/E49X: G/G | >1 year since last anti-lymphoma treatment | 0.71 (0.54, 0.94) | | 104/165 | 381 | 91/166 | 529 | 331 |
| PSMB2/G187V: G/G | >1 year since last anti-lymphoma treatment | 0.71 (0.54, 0.94) | | 104/165 | 381 | 91/166 | 529 | 331 |
| PSMB2/L159F: C/C | >1 year since last anti-lymphoma treatment | 0.71 (0.54, 0.94) | | 104/165 | 381 | 91/166 | 529 | 331 |
| PSMB5/L206M: C/C | >1 year since last anti-lymphoma treatment | 0.71 (0.54, 0.94) | | 104/165 | 381 | 91/166 | 529 | 331 |
| PSMB6/A234D: C/C | >1 year since last anti-lymphoma treatment | 0.71 (0.54, 0.94) | | 104/165 | 381 | 91/166 | 529 | 331 |
| PSMB6/P107A: C/C | >1 year since last anti-lymphoma treatment | 0.71 (0.53, 0.94) | | 103/159 | 381 | 90/162 | 519 | 331 |
| PSMB8/G8R: G/G | >1 year since last anti-lymphoma treatment | 0.73 (0.55, 0.98) | | 96/155 | 414 | 86/159 | 519 | 331 |
| PSMB8/R141C: C/C | >1 year since last anti-lymphoma treatment | 0.71 (0.54, 0.94) | | 104/165 | 381 | 91/166 | 529 | 331 |
| PSMB8/V182M: G/G | >1 year since last anti-lymphoma treatment | 0.71 (0.54, 0.94) | | 104/165 | 381 | 91/166 | 529 | 331 |
| PSMB9/G9E: G/G | >1 year since last anti-lymphoma treatment | 0.70 (0.53, 0.93) | | 104/163 | 381 | 91/165 | 519 | 331 |

APPENDIX 2, TABLE 2.5-continued

TTP by Germline Genetic Variant and by Covariate, IRC review
(Significant [p ≤ 0.05], Frequency of ≥10% or Higher)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| PSMB9/V32I: C/C | >1 year since last anti-lymphoma treatment | 0.69 (0.51, 0.92) | | 102/160 | 379 | 86/158 | 529 | 331 |
| PSMB1/A171S: G/G | ≤65 years old | 0.71 (0.55, 0.91) | | 131/198 | 326 | 115/194 | 435 | 392 |
| PSMB1/I208N: T/T | ≤65 years old | 0.71 (0.55, 0.91) | | 131/198 | 326 | 115/194 | 435 | 392 |
| PSMB1/P11A: C/G | ≤65 years old | 0.58 (0.40, 0.85) | | 62/96 | 288 | 50/86 | 506 | 392 |
| PSMB1/P193L: C/C | ≤65 years old | 0.71 (0.55, 0.91) | | 131/198 | 326 | 115/194 | 435 | 392 |
| PSMB2/E49X: G/G | ≤65 years old | 0.71 (0.55, 0.91) | | 131/198 | 326 | 115/194 | 435 | 392 |
| PSMB2/G187V: G/G | ≤65 years old | 0.71 (0.55, 0.91) | | 131/198 | 326 | 115/194 | 435 | 392 |
| PSMB2/L159F: C/C | ≤65 years old | 0.71 (0.55, 0.91) | | 131/198 | 326 | 115/194 | 435 | 392 |
| PSMB5/L206M: C/C | ≤65 years old | 0.71 (0.55, 0.91) | | 131/198 | 326 | 115/194 | 435 | 392 |
| PSMB5/R24C: C/C | ≤65 years old | 0.71 (0.55, 0.93) | | 115/170 | 334 | 103/167 | 429 | 392 |
| PSMB6/A234D: C/C | ≤65 years old | 0.71 (0.55, 0.91) | | 131/198 | 326 | 115/194 | 435 | 392 |
| PSMB6/P107A: C/C | ≤65 years old | 0.71 (0.55, 0.92) | | 126/189 | 330 | 113/190 | 435 | 392 |
| PSMB8/G8R: G/G | ≤65 years old | 0.72 (0.56, 0.93) | | 124/189 | 330 | 111/186 | 422 | 392 |
| PSMB8/R141C: C/C | ≤65 years old | 0.71 (0.55, 0.91) | | 131/198 | 326 | 115/194 | 435 | 392 |
| PSMB8/V182M: G/G | ≤65 years old | 0.71 (0.55, 0.91) | | 131/198 | 326 | 115/194 | 435 | 392 |
| PSMB9/G9E: G/G | ≤65 years old | 0.70 (0.55, 0.90) | | 131/196 | 326 | 115/193 | 431 | 392 |
| PSMB9/R60H: G/G | ≤65 years old | 0.69 (0.50, 0.96) | | 79/119 | 330 | 68/113 | 487 | 392 |
| PSMB9/V32I: C/C | ≤65 years old | 0.69 (0.53, 0.89) | | 129/192 | 326 | 108/186 | 435 | 392 |
| PSMB9/R60H: A/G | Male | 0.54 (0.31, 0.94) | | 22/28 | 273 | 34/48 | 351 | 241 |
| PSMB1/A171S: G/G | Ann Arbor Stage IV | 0.72 (0.54, 0.95) | | 95/127 | 278 | 93/143 | 360 | 270 |
| PSMB1/I208N: T/T | Ann Arbor Stage IV | 0.72 (0.54, 0.95) | | 95/127 | 278 | 93/143 | 360 | 270 |

APPENDIX 2, TABLE 2.5-continued

TTP by Germline Genetic Variant and by Covariate, IRC review
(Significant [p ≤ 0.05], Frequency of ≥10% or Higher)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| PSMB1/P11A: C/G | Ann Arbor Stage IV | 0.64 (0.42, 0.96) | | 46/59 | 235 | 48/68 | 351 | 270 |
| PSMB1/P193L: C/C | Ann Arbor Stage IV | 0.72 (0.54, 0.95) | | 95/127 | 278 | 93/143 | 360 | 270 |
| PSMB2/E49X: G/G | Ann Arbor Stage IV | 0.72 (0.54, 0.95) | | 95/127 | 278 | 93/143 | 360 | 270 |
| PSMB2/G187V: G/G | Ann Arbor Stage IV | 0.72 (0.54, 0.95) | | 95/127 | 278 | 93/143 | 360 | 270 |
| PSMB2/L159F: C/C | Ann Arbor Stage IV | 0.72 (0.54, 0.95) | | 95/127 | 278 | 93/143 | 360 | 270 |
| PSMB5/L206M: C/C | Ann Arbor Stage IV | 0.72 (0.54, 0.95) | | 95/127 | 278 | 93/143 | 360 | 270 |
| PSMB6/A234D: C/C | Ann Arbor Stage IV | 0.72 (0.54, 0.95) | | 95/127 | 278 | 93/143 | 360 | 270 |
| PSMB6/P107A: C/C | Ann Arbor Stage IV | 0.74 (0.55, 0.99) | | 92/124 | 279 | 92/140 | 358 | 270 |
| PSMB8/G8R: G/G | Ann Arbor Stage IV | 0.73 (0.54, 0.98) | | 88/120 | 279 | 88/138 | 352 | 270 |
| PSMB8/R141C: C/C | Ann Arbor Stage IV | 0.72 (0.54, 0.95) | | 95/127 | 278 | 93/143 | 360 | 270 |
| PSMB8/V182M: G/G | Ann Arbor Stage IV | 0.72 (0.54, 0.95) | | 95/127 | 278 | 93/143 | 360 | 270 |
| PSMB9/G9E: G/G | Ann Arbor Stage IV | 0.71 (0.53, 0.94) | | 95/126 | 278 | 93/142 | 358 | 270 |
| PSMB9/V32I: C/C | Ann Arbor Stage IV | 0.69 (0.51, 0.93) | | 93/123 | 277 | 89/138 | 363 | 270 |

0.05  0.1  0.2  0.5  1

APPENDIX 2, TABLE 2.6

TTP by somatic mutation and by covariate, IRC review
(Significant [p ≤ 0.05], Frequency of ≥10% and Higher)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| BCL2/A43G: MND | No Subgroup | 0.73 (0.55, 0.95) | | 110/161 | 334 | 96/154 | 435 | 315 |
| BCL2/C.-11C>T: MND | No Subgroup | 0.77 (0.60, 1.00) | | 130/192 | 334 | 113/179 | 422 | 390 |
| BCL2/E29K: MND | No Subgroup | 0.71 (0.53, 0.95) | | 102/150 | 326 | 87/139 | 435 | 318 |
| BCL2/P46S: MND | No Subgroup | 0.73 (0.55, 0.97) | | 100/147 | 287 | 92/147 | 429 | 310 |
| BCL2/P59S: MND | No Subgroup | 0.73 (0.55, 0.97) | | 100/145 | 288 | 94/147 | 429 | 309 |
| BCL2/Q52P: MND | No Subgroup | 0.73 (0.55, 0.96) | | 105/153 | 288 | 97/154 | 429 | 307 |
| BCL2/R106H: MND | No Subgroup | 0.72 (0.55, 0.95) | | 112/162 | 338 | 94/151 | 422 | 372 |
| NOTCH/X28DEL: MND | No Subgroup | 0.78 (0.61, 1.00) | | 133/194 | 334 | 120/189 | 414 | 400 |
| NOTCH/X28INS: MND | No Subgroup | 0.75 (0.59, 0.96) | | 138/198 | 334 | 123/195 | 414 | 401 |
| BCL2/A43G: MND | 1 Prior Line of Therapy | 0.62 (0.40, 0.97) | | 45/72 | 349 | 35/67 | 624 | 139 |
| BCL2/P59L: MD | 1 Prior Line of Therapy | 0.14 (0.02, 0.83) | | 3/3 | 398 | 6/11 | 553 | 139 |
| NOTCH/X28INS: MND | 1 Prior Line of Therapy | 0.65 (0.44, 0.97) | | 53/84 | 365 | 47/88 | 553 | 178 |
| BCL2/P46L: MD | 2 Prior Lines of Therapy | 0.14 (0.02, 1.28) | | 5/5 | 226 | 2/4 | — | 83 |
| BCL2/R106H: MND | 6 or More Prior Lines of Therapy | 0.11 (0.01, 1.04) | | 4/4 | 50 | 4/5 | 305 | 11 |
| NOTCH/G_A1702P: MND | 6 or More Prior Lines of Therapy | 0.13 (0.01, 1.19) | | 5/6 | 70 | 4/5 | 305 | 11 |
| NOTCH/I168:N: MND | 6 or More Prior Lines of Therapy | 0.13 (0.01, 1.19) | | 5/6 | 70 | 4/5 | 305 | 11 |

APPENDIX 2, TABLE 2.6-continued

TTP by somatic mutation and by covariate, IRC review
(Significant [p ≤ 0.05], Frequency of ≥10% and Higher)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| NOTCH/L1679P: MND | 6 or More Prior Lines of Therapy | 0.13 (0.01, 1.19) | | 5/6 | 70 | 4/5 | 305 | 11 |
| NOTCH/L1679Q: MND | 6 or More Prior Lines of Therapy | 0.13 (0.01, 1.19) | | 5/6 | 70 | 4/5 | 305 | 11 |
| NOTCH/P2515FS4: MND | 6 or More Prior Lines of Therapy | 0.13 (0.01, 1.19) | | 5/6 | 70 | 4/5 | 305 | 11 |
| NOTCH/X26DEL: MND | 6 or More Prior Lines of Therapy | 0.14 (0.01, 1.31) | | 4/5 | 130 | 4/5 | 305 | 10 |
| NOTCH/X26INS: MND | 6 or More Prior Lines of Therapy | 0.14 (0.01, 1.31) | | 4/5 | 130 | 4/5 | 305 | 10 |
| NOTCH/X28DEL: MND | 6 or More Prior Lines of Therapy | 0.13 (0.01, 1.25) | | 4/5 | 70 | 4/5 | 305 | 11 |
| NOTCH/X28INS: MND | 6 or More Prior Lines of Therapy | 0.12 (0.01, 1.10) | | 5/6 | 70 | 4/5 | 305 | 11 |
| NOTCH/X26DEL: MND | No High Tumor Burden | 0.65 (0.43, 1.00) | | 56/87 | 422 | 36/71 | 630 | 163 |
| NOTCH/X28INS: MND | No High Tumor Burden | 0.62 (0.42, 0.93) | | 62/98 | 422 | 41/82 | 630 | 184 |
| BCL2/A43G: MND | High Tumor Burden | 0.65 (0.46, 0.92) | | 63/83 | 241 | 64/90 | 352 | 173 |
| BCL2/E29K: MND | High Tumor Burden | 0.63 (0.43, 0.90) | | 59/79 | 239 | 57/82 | 358 | 174 |
| BCL2/P46L: MND | High Tumor Burden | 0.61 (0.42, 0.90) | | 50/67 | 241 | 59/83 | 352 | 173 |
| BCL2/P46S: MND | High Tumor Burden | 0.61 (0.42, 0.88) | | 55/73 | 239 | 63/89 | 348 | 170 |
| BCL2/P59L: MD | High Tumor Burden | 0.21 (0.05, 0.86) | | 4/6 | 137 | 11/14 | 506 | 172 |
| BCL2/P59L: MND | High Tumor Burden | 0.64 (0.44, 0.94) | | 54/72 | 241 | 56/80 | 344 | 172 |
| BCL2/P59S: MND | High Tumor Burden | 0.60 (0.42, 0.87) | | 56/73 | 241 | 62/87 | 358 | 170 |
| BCL2/Q52P: MND | High Tumor Burden | 0.60 (0.42, 0.85) | | 58/76 | 239 | 65/92 | 352 | 168 |

APPENDIX 2, TABLE 2.6-continued

TTP by somatic mutation and by covariate, IRC review
(Significant [p ≤ 0.05], Frequency of ≥10% and Higher)

| Marker: Level | Subgroup | HR (log scale) | HR (95% CI) | R Evt/N | R Median | Vc – R Evt/N | Vc – R Median | Marker: Subgroup N Total |
|---|---|---|---|---|---|---|---|---|
| BCL2/R106H: MND | High Tumor Burden | | 0.66 (0.46, 0.93) | 63/83 | 241 | 64/93 | 352 | 209 |
| NOTCH/F1593S: MND | High Tumor Burden | | 0.68 (0.48, 0.98) | 57/77 | 253 | 64/91 | 358 | 168 |
| NOTCH/G_A1702P: MND | High Tumor Burden | | 0.68 (0.49, 0.95) | 68/90 | 241 | 69/96 | 348 | 187 |
| NOTCH/I1681N: MND | High Tumor Burden | | 0.69 (0.49, 0.96) | 68/90 | 241 | 70/97 | 348 | 187 |
| NOTCH/L1575P: MND | High Tumor Burden | | 0.69 (0.48, 0.99) | 56/76 | 253 | 64/91 | 358 | 168 |
| NOTCH/L1586P: MND | High Tumor Burden | | 0.68 (0.48, 0.98) | 57/77 | 253 | 64/91 | 358 | 168 |
| NOTCH/L1586Q: MND | High Tumor Burden | | 0.68 (0.48, 0.96) | 58/78 | 241 | 67/94 | 352 | 172 |
| NOTCH/L1594P: MND | High Tumor Burden | | 0.68 (0.48, 0.98) | 57/77 | 253 | 64/91 | 358 | 168 |
| NOTCH/L1597H: MND | High Tumor Burden | | 0.68 (0.48, 0.96) | 58/78 | 241 | 67/94 | 352 | 172 |
| NOTCH/L1597_S1598INSG: MND | High Tumor Burden | | 0.68 (0.48, 0.98) | 57/77 | 253 | 64/91 | 358 | 168 |
| NOTCH/L1601P: MND | High Tumor Burden | | 0.67 (0.47, 0.96) | 57/77 | 253 | 63/90 | 358 | 168 |
| NOTCH/L1679P: MND | High Tumor Burden | | 0.69 (0.49, 0.96) | 68/90 | 241 | 70/97 | 348 | 187 |
| NOTCH/L1679Q: MND | High Tumor Burden | | 0.69 (0.49, 0.96) | 68/90 | 241 | 70/97 | 348 | 187 |
| NOTCH/L2458V: MND | High Tumor Burden | | 0.70 (0.49, 0.99) | 61/83 | 253 | 68/95 | 352 | 178 |
| NOTCH/P2513L: MND | High Tumor Burden | | 0.66 (0.45, 0.96) | 57/76 | 253 | 51/71 | 358 | 198 |
| NOTCH/P2515FS4: MND | High Tumor Burden | | 0.69 (0.49, 0.96) | 68/90 | 241 | 70/98 | 352 | 189 |
| NOTCH/Q2441X: MND | High Tumor Burden | | 0.70 (0.49, 0.99) | 61/83 | 253 | 68/95 | 352 | 178 |

APPENDIX 2, TABLE 2.6-continued

TTP by somatic mutation and by covariate, IRC review
(Significant [p ≤ 0.05], Frequency of ≥10% and Higher)

| Marker: Level | Subgroup | HR (log scale) | HR (95% CI) | R Evt/N | R Median | Vc – R Evt/N | Vc – R Median | Marker: Subgroup N Total |
|---|---|---|---|---|---|---|---|---|
| NOTCH/Q2460X: MND | High Tumor Burden | | 0.69 (0.48, 1.00) | 57/79 | 270 | 60/87 | 360 | 181 |
| NOTCH/R1599 > QS: MND | High Tumor Burden | | 0.68 (0.48, 0.98) | 57/77 | 253 | 64/91 | 358 | 168 |
| NOTCH/R1599P: MND | High Tumor Burden | | 0.68 (0.48, 0.96) | 58/78 | 241 | 67/94 | 352 | 172 |
| NOTCH/V1579DEL: MND | High Tumor Burden | | 0.68 (0.48, 0.98) | 57/77 | 253 | 64/91 | 358 | 168 |
| NOTCH/V1579E: MND | High Tumor Burden | | 0.68 (0.48, 0.96) | 58/78 | 241 | 67/94 | 352 | 172 |
| NOTCH/V1579G: MND | High Tumor Burden | | 0.68 (0.48, 0.98) | 57/77 | 253 | 64/91 | 358 | 168 |
| NOTCH/X28INS: MND | High Tumor Burden | | 0.73 (0.53, 0.99) | 76/100 | 253 | 82/113 | 324 | 217 |
| BCL2/A43G: MND | High FLIPI Score | | 0.63 (0.41, 0.95) | 47/66 | 239 | 43/61 | 358 | 127 |
| BCL2/E29K: MND | High FLIPI Score | | 0.64 (0.41, 0.99) | 43/62 | 239 | 39/55 | 366 | 128 |
| BCL2/P46L: MND | High FLIPI Score | | 0.60 (0.38, 0.95) | 37/53 | 210 | 40/55 | 352 | 124 |
| BCL2/P59L: MND | High FLIPI Score | | 0.64 (0.41, 1.00) | 40/57 | 239 | 39/55 | 358 | 125 |
| BCL2/P59S: MND | High FLIPI Score | | 0.63 (0.41, 0.97) | 42/59 | 224 | 41/57 | 352 | 123 |
| BCL2/Q52P: MND | High FLIPI Score | | 0.62 (0.41, 0.95) | 44/61 | 224 | 43/60 | 352 | 121 |
| BCL2/R106H: MND | High FLIPI Score | | 0.60 (0.39, 0.92) | 50/68 | 239 | 38/57 | 366 | 151 |
| NOTCH/G_A1702P: MND | High FLIPI Score | | 0.67 (0.45, 0.99) | 52/72 | 212 | 49/67 | 346 | 139 |
| NOTCH/I1681N: MND | High FLIPI Score | | 0.67 (0.45, 0.99) | 52/72 | 212 | 49/67 | 346 | 139 |
| NOTCH/L1679P: MND | High FLIPI Score | | 0.67 (0.45, 0.99) | 52/72 | 212 | 49/67 | 346 | 139 |

APPENDIX 2, TABLE 2.6-continued

TTP by somatic mutation and by covariate, IRC review
(Significant [p ≤ 0.05], Frequency of ≥10% and Higher)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| NOTCH/L1679Q: MND | High FLIPI Score | 0.67 (0.45, 0.99) | | 52/72 | 212 | 49/67 | 346 | 139 |
| NOTCH/P2515FS4: MND | High FLIPI Score | 0.66 (0.45, 0.99) | | 52/72 | 239 | 47/67 | 358 | 141 |
| NOTCH/X28DEL: MND | High FLIPI Score | 0.66 (0.45, 0.96) | | 60/81 | 239 | 50/73 | 352 | 159 |
| NOTCH/X28INS: MND | High FLIPI Score | 0.61 (0.42, 0.89) | | 61/81 | 239 | 52/76 | 352 | 160 |
| BCL2/R106H: MD | Intermediate FLIPI Score | 3.47 (1.07, 11.29) | | 4/10 | 924 | 10/11 | 281 | 130 |
| BCL2/P46S: MND | Low FLIPI Score | 0.51 (0.27, 1.00) | | 24/38 | 349 | 14/38 | — | 83 |
| BCL2/Q52P: MND | Low FLIPI Score | 0.53 (0.28, 1.00) | | 26/41 | 349 | 15/40 | 508 | 81 |
| NOTCH/G_A1702P: MND | Low FLIPI Score | 0.52 (0.28, 0.97) | | 28/43 | 381 | 15/41 | — | 84 |
| NOTCH/I1681N: MND | Low FLIPI Score | 0.52 (0.28, 0.97) | | 28/43 | 381 | 15/41 | — | 84 |
| NOTCH/L1679P: MND | Low FLIPI Score | 0.52 (0.28, 0.97) | | 28/43 | 381 | 15/41 | — | 84 |
| NOTCH/L1679Q: MND | Low FLIPI Score | 0.52 (0.28, 0.97) | | 28/43 | 381 | 15/41 | 771 | 84 |
| NOTCH/X28INS: MND | Low FLIPI Score | 0.56 (0.32, 1.00) | | 30/48 | 349 | 19/48 | 771 | 98 |
| BCL2/A43G: MND | No Prior Rituximab Therapy | 0.69 (0.48, 0.99) | | 69/98 | 345 | 52/85 | 485 | 183 |
| BCL2/E29K: MND | No Prior Rituximab Therapy | 0.65 (0.45, 0.96) | | 65/93 | 345 | 46/76 | 508 | 186 |
| BCL2/P46S: MND | No Prior Rituximab Therapy | 0.66 (0.45, 0.97) | | 60/87 | 287 | 48/79 | 508 | 175 |
| BCL2/Q52P: MND | No Prior Rituximab Therapy | 0.68 (0.47, 0.99) | | 63/91 | 287 | 51/83 | 485 | 174 |
| BCL2/R106H: MND | No Prior Rituximab Therapy | 0.67 (0.46, 0.98) | | 66/95 | 351 | 46/79 | 483 | 213 |

APPENDIX 2, TABLE 2.6-continued

TTP by somatic mutation and by covariate, IRC review
(Significant [p ≤ 0.05], Frequency of ≥10% and Higher)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| NOTCH/X28INS: MND | No Prior Rituximab Therapy | 0.71 (0.51, 1.00) | | 79/112 | 357 | 64/107 | 463 | 226 |
| BCL2/P46L: MD | >1 year since last anti-lymphoma treatment | 0.20 (0.05, 0.72) | | 10/10 | 408 | 4/10 | 637 | 180 |
| NOTCH/X28IN8: MND | >1 year since last anti-lymphoma treatment | 0.72 (0.51, 1.00) | | 75/113 | 379 | 67/119 | 506 | 237 |
| BCL2/E29K: MND | Rest of World | 0.65 (0.43, 0.98) | | 55/75 | 241 | 41/63 | 415 | 154 |
| BCL2/R106H: MND | Rest of World | 0.66 (0.44, 0.97) | | 60/83 | 275 | 42/69 | 422 | 184 |
| NOTCH/X28INS: MND | Rest of World | 0.68 (0.48, 0.96) | | 72/97 | 275 | 59/92 | 406 | 194 |
| BCL2/A43G: MND | ≤65 years old | 0.63 (0.46, 0.87) | | 89/124 | 277 | 67/115 | 483 | 239 |
| BCL2/C.-11C > T: MND | ≤65 years old | 0.69 (0.52, 0.93) | | 102/147 | 278 | 81/135 | 429 | 296 |
| BCL2/E29K: MND | ≤65 years old | 0.60 (0.43, 0.84) | | 83/117 | 275 | 59/103 | 485 | 241 |
| BCL2/P46L: MD | ≤65 years old | 0.40 (0.16, 0.99) | | 13/14 | 226 | 8/15 | 485 | 238 |
| BCL2/P46L: MND | ≤65 years old | 0.66 (0.47, 0.93) | | 74/105 | 277 | 62/104 | 429 | 238 |
| BCL2/P46S: MND | ≤65 years old | 0.62 (0.45, 0.87) | | 80/111 | 275 | 66/113 | 456 | 236 |
| BCL2/P59L: MND | ≤65 years old | 0.64 (0.45, 0.89) | | 80/112 | 277 | 59/103 | 431 | 237 |
| BCL2/P59S: MND | ≤65 years old | 0.63 (0.45, 0.87) | | 81/110 | 275 | 69/114 | 435 | 235 |
| BCL2/Q52P: MND | ≤65 years old | 0.63 (0.46, 0.86) | | 85/117 | 275 | 69/117 | 435 | 234 |
| BCL2/R106H: MND | ≤65 years old | 0.60 (0.44, 0.83) | | 89/124 | 275 | 64/112 | 483 | 281 |

APPENDIX 2, TABLE 2.6-continued

TTP by somatic mutation and by covariate, IRC review
(Significant [p ≤ 0.05], Frequency of ≥10% and Higher)

| Marker: Level | Subgroup | HR (log scale) | HR (95% CI) | R Evt/N | R Median | Vc – R Evt/N | Vc – R Median | Marker: Subgroup N Total |
|---|---|---|---|---|---|---|---|---|
| NOTCH/F1593S: MND | ≤65 years old | | 0.69 (0.50, 0.95) | 84/117 | 277 | 66/110 | 429 | 227 |
| NOTCH/G_A1702P: MND | ≤65 years old | | 0.66 (0.48, 0.89) | 96/133 | 277 | 72/121 | 429 | 255 |
| NOTCH/I168IN: MND | ≤65 years old | | 0.66 (0.49, 0.90) | 96/133 | 277 | 73/122 | 422 | 255 |
| NOTCH/L1575P: MND | ≤65 years old | | 0.70 (0.50, 0.96) | 83/116 | 277 | 66/110 | 429 | 227 |
| NOTCH/L1586P: MND | ≤65 years old | | 0.69 (0.50, 0.95) | 84/117 | 277 | 66/110 | 429 | 227 |
| NOTCH/L1586Q: MND | ≤65 years old | | 0.69 (0.50, 0.95) | 86/120 | 277 | 69/114 | 422 | 234 |
| NOTCH/L1594P: MND | ≤65 years old | | 0.69 (0.50, 0.95) | 84/117 | 277 | 66/110 | 429 | 227 |
| NOTCH/L1597H: MND | ≤65 years old | | 0.69 (0.50, 0.95) | 86/120 | 277 | 69/114 | 422 | 234 |
| NOTCH/L1597_S1598INSG: MND | ≤65 years old | | 0.69 (0.50, 0.95) | 84/117 | 277 | 66/110 | 429 | 227 |
| NOTCH/L1601P: MND | ≤65 years old | | 0.68 (0.49, 0.94) | 84/117 | 277 | 65/109 | 431 | 227 |
| NOTCH/L1679P: MND | ≤65 years old | | 0.66 (0.49, 0.90) | 96/133 | 277 | 73/122 | 422 | 255 |
| NOTCH/L1679Q: MND | ≤65 years old | | 0.66 (0.49, 0.90) | 96/133 | 277 | 73/122 | 422 | 255 |
| NOTCH/L2458V: MND | ≤65 years old | | 0.67 (0.49, 0.92) | 86/120 | 277 | 71/117 | 422 | 237 |
| NOTCH/P2513L: MND | ≤65 years old | | 0.59 (0.41, 0.84) | 77/107 | 275 | 51/90 | 429 | 269 |
| NOTCH/P2515FS4: MND | ≤65 years old | | 0.67 (0.49, 0.90) | 96/134 | 278 | 74/123 | 431 | 259 |
| NOTCH/Q2441X: MND | ≤65 years old | | 0.67 (0.49, 0.92) | 86/120 | 275 | 71/115 | 422 | 237 |
| NOTCH/Q2460X: MND | ≤65 years old | | 0.64 (0.45, 0.90) | 78/110 | 275 | 60/104 | 422 | 239 |

APPENDIX 2, TABLE 2.6-continued

TTP by somatic mutation and by covariate, IRC review
(Significant [p ≤ 0.05], Frequency of ≥10% and Higher)

| Marker: Level | Subgroup | HR (log scale) | HR (95% CI) | R Evt/N | R Median | Vc – R Evt/N | Vc – R Median | Marker: Subgroup N Total |
|---|---|---|---|---|---|---|---|---|
| NOTCH/R1599 > QS: MND | ≤65 years old | | 0.69 (0.50, 0.95) | 84/117 | 277 | 66/110 | 429 | 227 |
| NOTCH/R1599P: MND | ≤65 years old | | 0.69 (0.50, 0.95) | 86/120 | 277 | 69/114 | 422 | 234 |
| NOTCH/V1579DEL: MND | ≤65 years old | | 0.69 (0.50, 0.95) | 84/117 | 277 | 66/110 | 429 | 227 |
| NOTCH/V1579E: MND | ≤65 years old | | 0.69 (0.50, 0.95) | 86/120 | 277 | 69/114 | 422 | 234 |
| NOTCH/V1579G: MND | ≤65 years old | | 0.69 (0.50, 0.95) | 84/117 | 277 | 66/110 | 429 | 227 |
| NOTCH/X26DEL: MND | ≤65 years old | | 0.70 (0.52, 0.94) | 96/137 | 281 | 78/132 | 431 | 273 |
| NOTCH/X26INS: MND | ≤65 years old | | 0.68 (0.51, 0.92) | 97/138 | 281 | 78/133 | 435 | 273 |
| NOTCH/X28DEL: MND | ≤65 years old | | 0.66 (0.50, 0.89) | 106/149 | 278 | 83/140 | 422 | 298 |
| NOTCH/X28INS: MND | ≤65 years old | | 0.64 (0.48, 0.85) | 109/149 | 277 | 85/143 | 429 | 298 |
| NOTCH/P2513L: MND | >65 years old | | 1.96 (1.03, 3.75) | 16/33 | 616 | 24/33 | 414 | 92 |
| BCL2/P59L: MD | Female | | 0.28 (0.08, 0.95) | 6/8 | 398 | 9/14 | 512 | 180 |
| BCL2/P59S: MND | Female | | 0.66 (0.44, 0.97) | 66/97 | 348 | 42/73 | 512 | 178 |
| BCL2/Q52P: MND | Female | | 0.68 (0.46, 1.00) | 67/100 | 348 | 43/76 | 553 | 176 |
| BCL2/R106H: MND | Female | | 0.65 (0.44, 0.98) | 65/96 | 357 | 38/70 | 506 | 203 |
| BCL2/A43G: MND | Male | | 0.60 (0.40, 0.91) | 43/59 | 273 | 51/76 | 414 | 135 |
| BCL2/E29K: MND | Male | | 0.60 (0.39, 0.93) | 40/55 | 271 | 46/68 | 414 | 138 |
| BCL2/P46S: MND | Male | | 0.64 (0.42, 0.98) | 37/52 | 241 | 52/75 | 360 | 133 |

APPENDIX 2, TABLE 2.6-continued

TTP by somatic mutation and by covariate, IRC review
(Significant [p ≤ 0.05], Frequency of ≥10% and Higher)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| BCL2/Q52P: MND | Male | 0.64 (0.42, 0.97) | | 38/53 | 271 | 54/78 | 360 | 131 |
| NOTCH/G_A1702P: MND | Male | 0.66 (0.44, 0.98) | | 44/63 | 241 | 56/81 | 360 | 145 |
| NOTCH/I1681N: MND | Male | 0.67 (0.45, 1.00) | | 44/63 | 241 | 57/82 | 360 | 145 |
| NOTCH/L1679P: MND | Male | 0.67 (0.45, 1.00) | | 44/63 | 241 | 57/82 | 360 | 145 |
| NOTCH/L1679Q: MND | Male | 0.67 (0.45, 1.00) | | 44/63 | 241 | 57/82 | 360 | 145 |
| NOTCH/L2458V: MND | Male | 0.63 (0.42, 0.95) | | 42/59 | 241 | 56/80 | 360 | 139 |
| NOTCH/P2513L: MND | Male | 0.58 (0.38, 0.91) | | 39/54 | 239 | 42/63 | 414 | 155 |
| NOTCH/P2515FS4: MND | Male | 0.65 (0.43, 0.96) | | 44/62 | 273 | 57/84 | 406 | 148 |
| NOTCH/Q2441X: MND | Male | 0.64 (0.42, 0.95) | | 42/59 | 241 | 56/79 | 360 | 139 |
| NOTCH/Q2460X: MND | Male | 0.61 (0.40, 0.94) | | 41/57 | 241 | 47/70 | 414 | 142 |
| NOTCH/X28DEL: MND | Male | 0.69 (0.48, 1.00) | | 54/75 | 275 | 65/97 | 352 | 180 |
| NOTCH/X28INS: MND | Male | 0.68 (0.47, 0.97) | | 57/78 | 275 | 67/100 | 358 | 181 |
| BCL2/A43G: MND | White | 0.72 (0.54, 0.97) | | 93/140 | 345 | 84/139 | 483 | 279 |
| BCL2/E29K: MND | White | 0.70 (0.51, 0.96) | | 85/129 | 345 | 77/127 | 506 | 282 |
| BCL2/P46L: MD | White | 0.38 (0.16, 0.88) | | 18/21 | 346 | 8/16 | 512 | 279 |
| BCL2/P46S: MND | White | 0.69 (0.51, 0.94) | | 87/130 | 334 | 79/131 | 463 | 275 |
| BCL2/P59L: MND | White | 0.73 (0.53, 0.99) | | 85/129 | 334 | 74/123 | 431 | 278 |

APPENDIX 2, TABLE 2.6-continued

TTP by somatic mutation and by covariate, IRC review
(Significant [p ≤ 0.05], Frequency of ≥10% and Higher)

| Marker: Level | Subgroup | HR (log scale) | HR (95% CI) | R Evt/N | R Median | Vc – R Evt/N | Vc – R Median | Marker: Subgroup N Total |
|---|---|---|---|---|---|---|---|---|
| BCL2/P59S: MND | White | | 0.69 (0.51, 0.94) | 87/128 | 334 | 80/130 | 463 | 274 |
| BCL2/Q52P: MND | White | | 0.69 (0.51, 0.93) | 91/135 | 334 | 83/137 | 463 | 272 |
| NOTCH/P2515FS4: MND | White | | 0.75 (0.57, 1.00) | 102/154 | 348 | 91/148 | 431 | 304 |
| NOTCH/X28INS: MND | White | | 0.75 (0.57, 0.97) | 119/174 | 345 | 107/171 | 422 | 352 |
| NOTCH/P2513L: MD | Ann Arbor Stage III | | 0.40 (0.17, 0.95) | 13/15 | 345 | 12/14 | 414 | 116 |
| BCL2/A43G: MND | Ann Arbor Stage IV | | 0.61 (0.41, 0.89) | 57/71 | 275 | 52/83 | 414 | 154 |
| BCL2/C.-11C > T: MND | Ann Arbor Stage IV | | 0.66 (0.47, 0.94) | 66/84 | 277 | 64/100 | 358 | 193 |
| BCL2/E29K: MND | Ann Arbor Stage IV | | 0.58 (0.39, 0.87) | 53/67 | 275 | 44/73 | 415 | 154 |
| BCL2/P46L: MND | Ann Arbor Stage IV | | 0.59 (0.38, 0.91) | 40/52 | 253 | 47/74 | 360 | 148 |
| BCL2/P46S: MND | Ann Arbor Stage IV | | 0.62 (0.42, 0.93) | 48/61 | 253 | 53/81 | 358 | 147 |
| BCL2/P59L: MND | Ann Arbor Stage IV | | 0.63 (0.42, 0.96) | 46/59 | 273 | 45/73 | 352 | 149 |
| BCL2/P59S: MND | Ann Arbor Stage IV | | 0.64 (0.43, 0.97) | 45/58 | 273 | 51/79 | 360 | 147 |
| BCL2/Q52P: MND | Ann Arbor Stage IV | | 0.60 (0.41, 0.90) | 49/62 | 273 | 53/83 | 360 | 145 |
| BCL2/R106H: MND | Ann Arbor Stage IV | | 0.57 (0.39, 0.84) | 57/72 | 274 | 51/83 | 414 | 186 |

APPENDIX 2, TABLE 2.6-continued

TTP by somatic mutation and by covariate, IRC review
(Significant [p ≤ 0.05], Frequency of ≥10% and Higher)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| NOTCH/F1593S: MND | Ann Arbor Stage IV | 0.64 (0.43, 0.95) | ⊢┼⊣ | 50/64 | 253 | 52/79 | 360 | 143 |
| NOTCH/G_A1702P: MND | Ann Arbor Stage IV | 0.61 (0.42, 0.88) | ⊢┼⊣ | 59/75 | 273 | 57/87 | 360 | 163 |
| NOTCH/I1681N: MND | Ann Arbor Stage IV | 0.62 (0.43, 0.89) | ⊢┼⊣ | 59/75 | 273 | 58/88 | 358 | 163 |
| NOTCH/L1575P: MND | Ann Arbor Stage IV | 0.64 (0.43, 0.95) | ⊢┼⊣ | 50/64 | 253 | 52/79 | 360 | 143 |
| NOTCH/L1586P: MND | Ann Arbor Stage IV | 0.64 (0.43, 0.95) | ⊢┼⊣ | 50/64 | 253 | 52/79 | 360 | 143 |
| NOTCH/L1586Q: MND | Ann Arbor Stage IV | 0.64 (0.44, 0.94) | ⊢┼⊣ | 52/67 | 273 | 55/83 | 360 | 150 |
| NOTCH/L1594P: MND | Ann Arbor Stage IV | 0.64 (0.43, 0.95) | ⊢┼⊣ | 50/64 | 253 | 52/79 | 360 | 143 |
| NOTCH/L1597H: MND | Ann Arbor Stage IV | 0.64 (0.44, 0.94) | ⊢┼⊣ | 52/67 | 273 | 55/83 | 360 | 150 |
| NOTCH/L1597_S1598INSG: MND | Ann Arbor Stage IV | 0.64 (0.43, 0.95) | ⊢┼⊣ | 50/64 | 253 | 52/79 | 360 | 143 |
| NOTCH/L1601P: MND | Ann Arbor Stage IV | 0.64 (0.43, 0.95) | ⊢┼⊣ | 50/64 | 253 | 52/79 | 360 | 143 |
| NOTCH/L1679P: MND | Ann Arbor Stage IV | 0.62 (0.43, 0.89) | ⊢┼⊣ | 59/75 | 273 | 58/88 | 358 | 163 |
| NOTCH/L1679Q: MND | Ann Arbor Stage IV | 0.62 (0.43, 0.89) | ⊢┼⊣ | 59/75 | 273 | 58/88 | 358 | 163 |
| NOTCH/L2458V: MND | Ann Arbor Stage IV | 0.61 (0.42, 0.90) | ⊢┼⊣ | 53/68 | 273 | 56/86 | 360 | 154 |
| NOTCH/P2513L: MND | Ann Arbor Stage IV | 0.55 (0.36, 0.84) | ⊢┼⊣ | 48/61 | 273 | 41/69 | 414 | 176 |

APPENDIX 2, TABLE 2.6-continued

TTP by somatic mutation and by covariate, IRC review
(Significant [p ≤ 0.05], Frequency of ≥10% and Higher)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| NOTCH/P2515FS4: MND | Ann Arbor Stage IV | 0.61 (0.42, 0.88) | | 58/74 | 273 | 58/91 | 366 | 167 |
| NOTCH/Q2441X: MND | Ann Arbor Stage IV | 0.61 (0.42, 0.90) | | 53/68 | 273 | 56/85 | 360 | 154 |
| NOTCH/Q2460X: MND | Ann Arbor Stage IV | 0.57 (0.38, 0.86) | | 49/64 | 273 | 49/79 | 414 | 156 |
| NOTCH/R1599 > QS: MND | Ann Arbor Stage IV | 0.64 (0.43, 0.95) | | 50/64 | 253 | 52/79 | 360 | 143 |
| NOTCH/R1599P: MND | Ann Arbor Stage IV | 0.64 (0.44, 0.94) | | 52/67 | 273 | 55/83 | 360 | 150 |
| NOTCH/V1579DEL: MND | Ann Arbor Stage IV | 0.64 (0.43, 0.95) | | 50/64 | 253 | 52/79 | 360 | 143 |
| NOTCH/V1579E: MND | Ann Arbor Stage IV | 0.64 (0.44, 0.94) | | 52/67 | 273 | 55/83 | 360 | 150 |
| NOTCH/V1579G: MND | Ann Arbor Stage IV | 0.64 (0.43, 0.95) | | 50/64 | 253 | 52/79 | 360 | 143 |
| NOTCH/X26DEL: MND | Ann Arbor Stage IV | 0.65 (0.45, 0.92) | | 61/76 | 275 | 66/101 | 360 | 180 |
| NOTCH/X26INS: MND | Ann Arbor Stage IV | 0.64 (0.45, 0.91) | | 62/79 | 275 | 66/101 | 360 | 180 |
| NOTCH/X28DEL: MND | Ann Arbor Stage IV | 0.64 (0.46, 0.91) | | 67/85 | 275 | 65/103 | 358 | 195 |
| NOTCH/X28INS: MND | Ann Arbor Stage IV | 0.60 (0.42, 0.84) | | 70/87 | 274 | 66/105 | 358 | 196 |

APPENDIX 2, TABLE 2.7

Duration of response by protein expression and by covariate, IRC review. *
(All reported groups are significant (p ≤ 0.05) and with a frequency ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| CD68 OVERALL POSITIVE: 0-25 | High FLIPI Score | 3.66 (1.10, 12.16) | | 7/11 | 423 | 7/8 | 202 | 91 |
| P27 % NUCLEI POSITIVE: 60-70 | High FLIPI Score | 0.14 (0.03, 0.74) | | 7/9 | 337 | 3/6 | 1162 | 96 |
| 20S INTENSITY CYTOPLASMIC SIGNAL: ≤2+ | Intermediate FLIPI Score | 2.39 (1.08, 5.26) | | 9/25 | 554 | 20/26 | 264 | 99 |
| 20S INTENSITY CYTOPLASMIC SIGNAL: ≥3+ | Intermediate FLIPI Score | 0.38 (0.17, 0.84) | | 17/25 | 352 | 10/23 | 813 | 99 |
| 20S INTENSITY CYTOPLASMIC SIGNAL: ≥3+ | No Prior Rituximab Therapy | 0.53 (0.29, 0.97) | | 22/32 | 427 | 20/43 | 638 | 155 |
| 20S % NUCLEAR STAINING: 30-50 | Prior Rituximab Therapy | 2.39 (0.97, 5.86) | | 9/13 | 356 | 13/14 | 245 | 97 |
| CD68 OVERALL POSITIVE: 0-25 | ≤1 year since last anti-lymphoma treatment | 9.97 (1.13, 88.13) | | 5/7 | 354 | 5/5 | 145 | 79 |
| 20S INTENSITY CYTOPLASMIC SIGNAL: ≥3+ | ≤65 years old | 0.55 (0.31, 0.98) | | 28/39 | 417 | 20/44 | 654 | 177 |
| CD68 POSITIVE FOLLICULAR: 0-25 | Female | 0.38 (0.15, 1.01) | | 12/20 | 354 | 8/15 | 648 | 131 |
| CD68 OVERALL POSITIVE: 51-75 | Male | 0.27 (0.07, 1.03) | | 5/7 | 279 | 6/12 | 784 | 98 |
| CD68 OVERALL POSITIVE: >75 | Male | 0.10 (0.01, 1.02) | | 3/3 | 284 | 2/7 | — | 98 |
| CD68 POSITIVE PERIFOLLICULAR: >75 | Male | 0.11 (0.01, 1.11) | | 3/3 | 284 | 2/7 | — | 86 |
| P27 % NUCLEI POSITIVE: 60-70 | Male | 0.29 (0.08, 1.08) | | 5/6 | 281 | 7/9 | 502 | 99 |
| P65 INTENSITY CYTOPLASMIC SIGNAL: ≤1+ | Ann Arbor Stage III | 0.16 (0.02, 1.19) | | 2/4 | 173 | 5/8 | 474 | 87 |

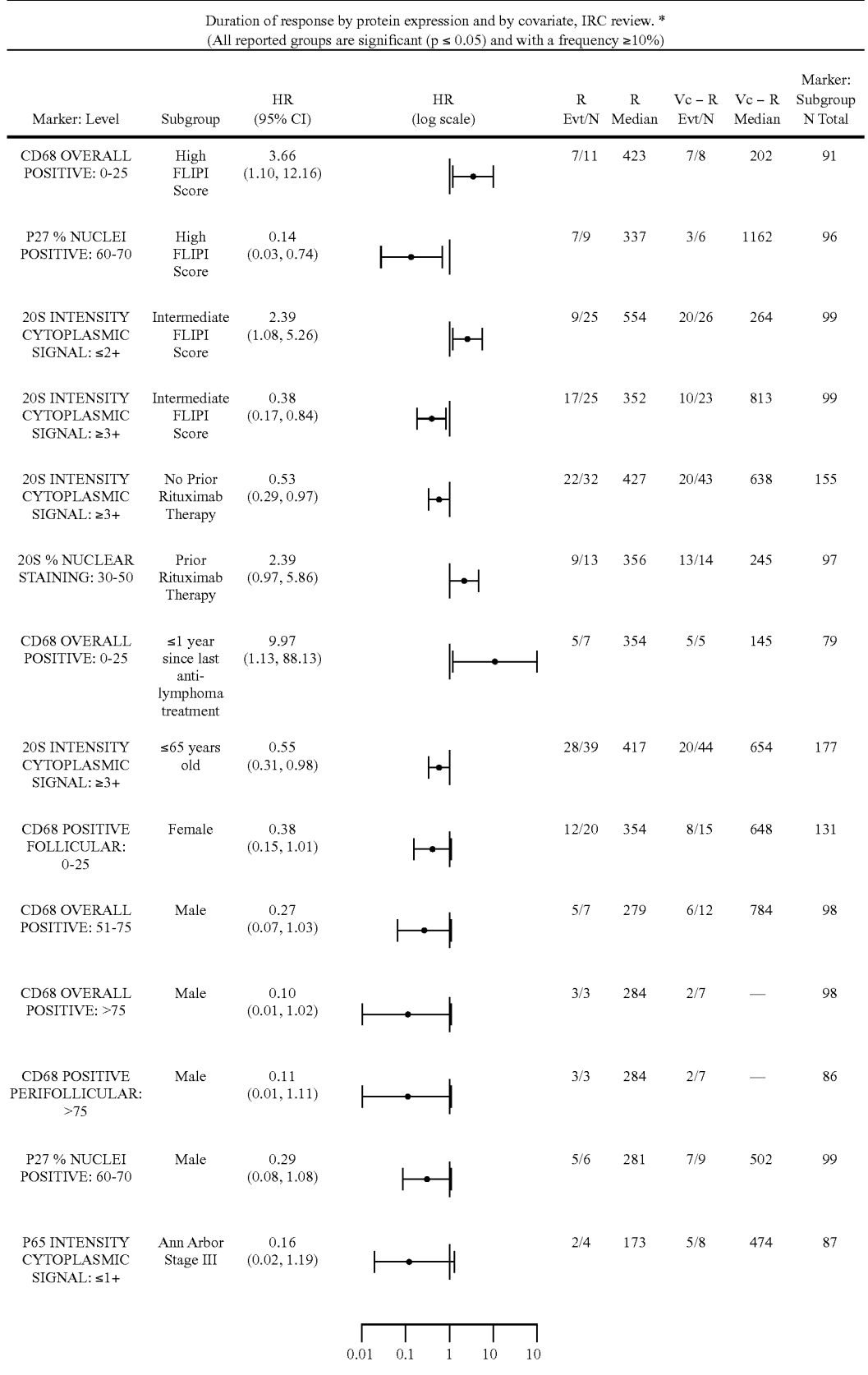

0.01  0.1  1  10  10

APPENDIX 2, TABLE 2.8

Duration of Response by Germline Genetic Variant and by Covariate, IRC Review.
(All Reported Groups are Significant (p ≤ 1.05) and at a Frequency ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| PSMB9/R60H: A/G | Male | 0.42 (0.19, 0.94) | | 10/11 | 211 | 19/28 | 351 | 120 |
| PSMB5/R24C: C/C | Ann Arbor Stage II | 3.29 (1.07, 10.09) | | 4/18 | — | 13/20 | 438 | 43 |

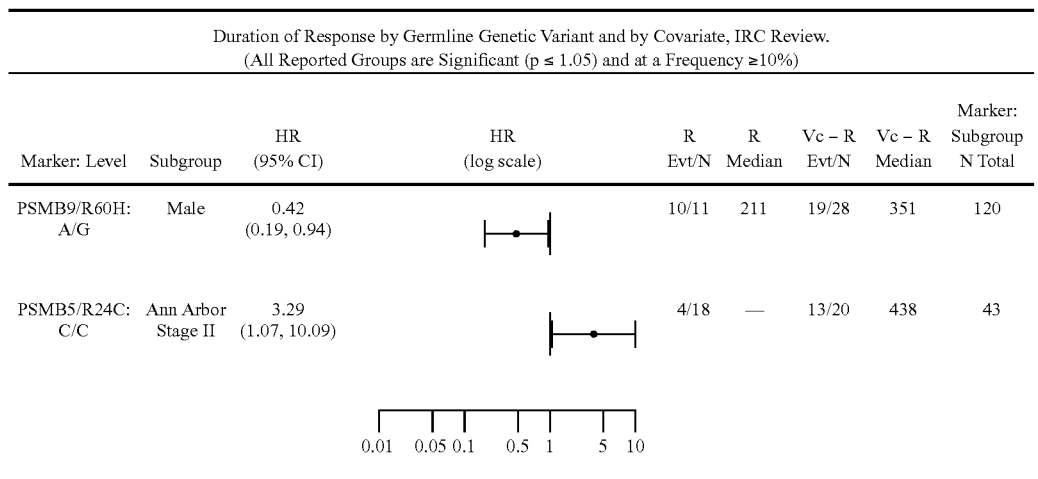

APPENDIX 2, TABLE 2.9

Duration of Response by Somatic Mutation and by Covariate, IRC Review.
(All Reported Groups are Significant (P ≤ 0.05) and at a Frequency ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| BCL2/ P59L: MD | No Subgroup | 0.15 (0.03, 0.71) | | 4/5 | 343 | 9/15 | 488 | 177 |
| BCL2/ P59L: MD | 1 Prior Line of Therapy | 0.11 (0.01, 1.21) | | 2/2 | 345 | 5/10 | 488 | 82 |
| BCL2/ P59L: MD | Prior Rituximab Therapy | 0.14 (0.01, 1.33) | | 3/3 | 330 | 4/5 | 372 | 68 |
| BCL2/ P46L: MD | >1 year since last anti-lymphoma treatment | 0.26 (0.06, 1.09) | | 5/5 | 356 | 4/8 | 502 | 115 |
| BCL2/ P59L: MD | >1 year since last anti-lymphoma treatment | 0.13 (0.02, 0.82) | | 3/4 | 330 | 6/10 | 502 | 116 |
| BCL2/ E29K: MND | ≤65 years old | 0.61 (0.37, 1.00) | | 32/49 | 353 | 32/66 | 648 | 128 |
| NOTCH/ X28INS: MND | ≤65 years old | 0.66 (0.43, 1.00) | | 44/64 | 369 | 45/84 | 490 | 152 |
| NOTCH/ P2513L: MND | >65 years old | 2.28 (1.02, 5.09) | | 10/23 | 948 | 18/22 | 356 | 62 |
| BCL2/ P59L: MD | White | 0.10 (0.02, 0.57) | | 4/5 | 343 | 8/14 | 488 | 163 |
| BCL2/ A43G: MND | Ann Arbor Stage IV | 0.57 (0.33, 1.00) | | 23/28 | 353 | 29/50 | 488 | 78 |

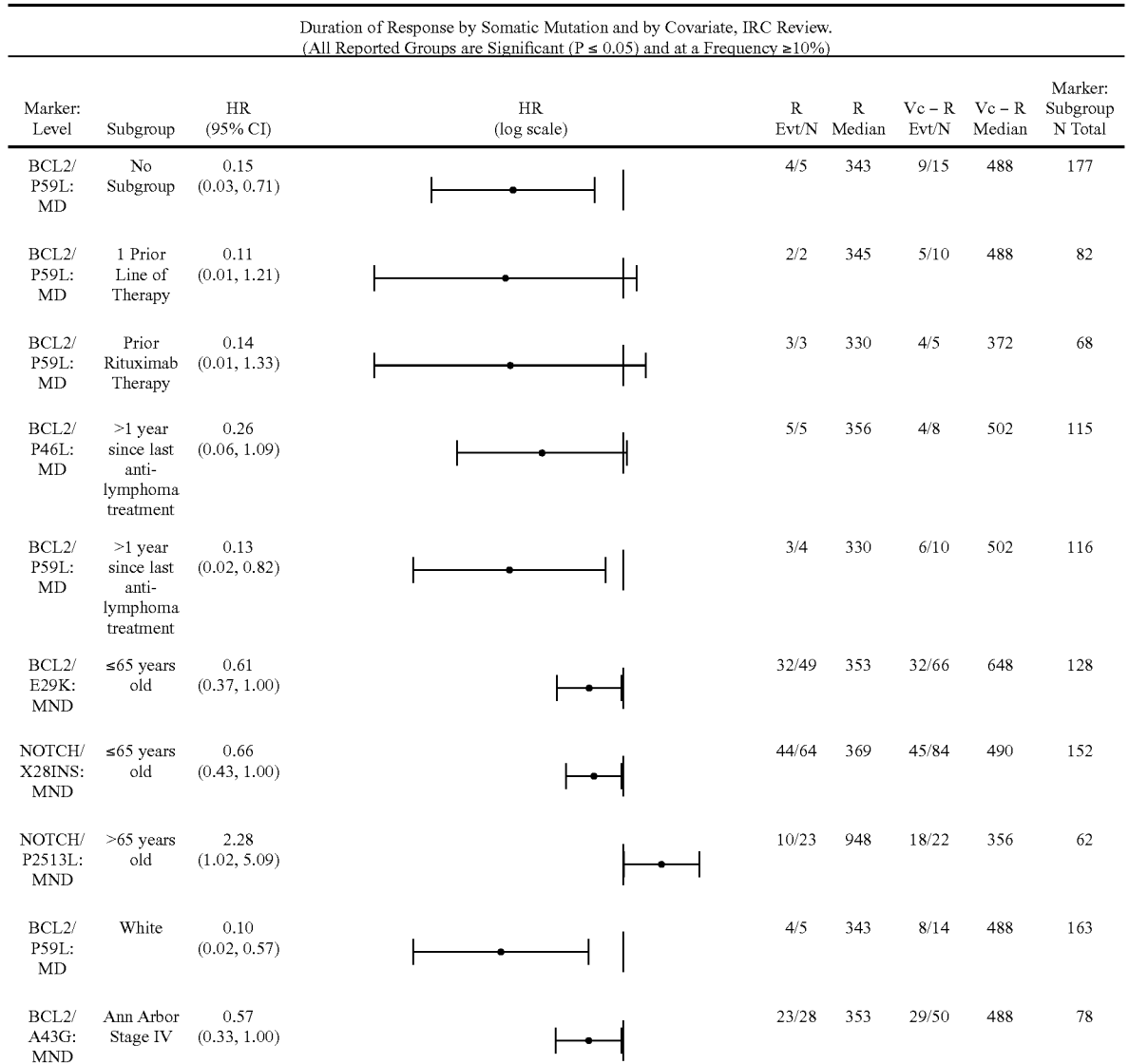

APPENDIX 2, TABLE 2.9-continued

Duration of Response by Somatic Mutation and by Covariate, IRC Review.
(All Reported Groups are Significant (P ≤ 0.05) and at a Frequency ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| BCL2/ E29K: MND | Ann Arbor Stage IV | 0.51 (0.28, 0.93) | | 21/26 | 344 | 23/43 | 490 | 78 |
| BCL2/ R106H: MND | Ann Arbor Stage IV | 0.54 (0.30, 0.96) | | 21/26 | 352 | 27/48 | 423 | 90 |
| NOTCH/ X28INS: MND | Ann Arbor Stage IV | 0.58 (0.35, 0.98) | | 26/31 | 353 | 35/58 | 423 | 91 |

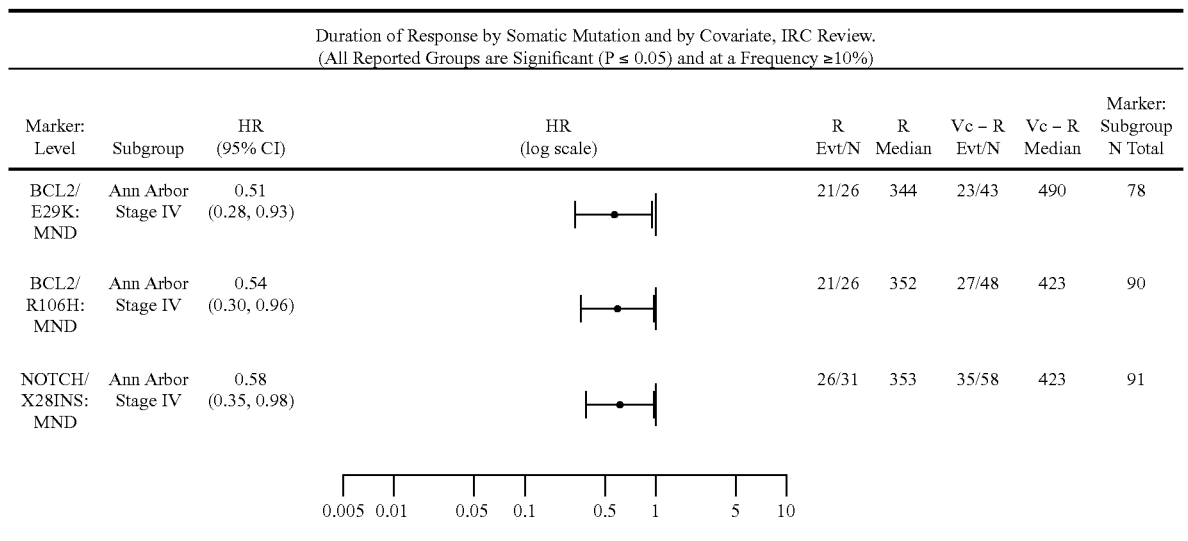

APPENDIX 2, TABLE 2.10

Time to Next Anti-Lymphoma Therapy by Protein Expression and by Covariate, IRC Review.
(All Reported Groups are Significant (p ≤ 0.05) and at a Frequency ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| CD68 OVERALL POSITIVE: 0-25 | No Subgroup | 0.41 (0.23, 0.73) | | 30/44 | 409 | 19/41 | 1047 | 442 |
| CD68 POSITIVE FOLLICULAR: 0-25 | No Subgroup | 0.54 (0.33, 0.88) | | 40/60 | 462 | 29/51 | 834 | 387 |
| CD68 POSITIVE PERIFOLLICULAR: 0-25 | No Subgroup | 0.48 (0.27, 0.87) | | 26/39 | 374 | 20/41 | 1103 | 384 |
| P27 SIGNAL TENSITY: ≥2+ | No Subgroup | 0.77 (0.60, 0.99) | | 127/199 | 533 | 114/196 | 700 | 463 |
| P65 % POSITIVE CYTOPLASMIC SIGNAL: >90% | No Subgroup | 0.75 (0.58, 0.96) | | 129/204 | 505 | 108/186 | 726 | 470 |
| CD68 POSITIVE PERIFOLLICULAR: >75 | 1 Prior Line of Therapy | 0.43 (0.19, 0.97) | | 15/18 | 437 | 10/16 | 744 | 174 |
| P27 % NUCLEI POSITIVE: 0-20 | 1 Prior Line of Therapy | 0.38 (0.15, 0.97) | | 19/26 | 434 | 6/16 | 1047 | 204 |
| P65 % NUCLEAR STAINING: 0 | 1 Prior Line of Therapy | 0.63 (0.41, 0.95) | | 54/79 | 546 | 39/73 | 841 | 203 |
| P65 % POSITIVE CYTOPLASMIC SIGNAL: >90% | 1 Prior Line of Therapy | 0.61 (0.42, 0.90) | | 59/89 | 550 | 47/88 | 841 | 203 |
| P65 INTENSITY CYTOPLASMIC SIGNAL: ≥2+ | 1 Prior Line of Therapy | 0.64 (0.43, 0.95) | | 54/85 | 568 | 47/91 | 841 | 203 |

APPENDIX 2, TABLE 2.10-continued

Time to Next Anti-Lymphoma Therapy by Protein Expression and by Covariate, IRC Review.
(All Reported Groups are Significant (p ≤ 0.05) and at a Frequency ≥ 10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| CD68 OVERALL POSITIVE: 0-25 | 2 Prior Lines of Therapy | 0.20 (0.04, 1.04) | | 6/8 | 204 | 2/7 | 1005 | 111 |
| CD68 POSITIVE PERIFOLLICULAR: 0-25 | 2 Prior Lines of Therapy | 0.09 (0.01, 0.81) | | 6/8 | 171 | 1/7 | — | 98 |
| P65 % NUCLEAR STAINING: ≤5% | 2 Prior Lines of Therapy | 0.31 (0.10, 0.92) | | 7/9 | 225 | 7/12 | 705 | 125 |
| P27 % NUCLEI POSITIVE: 60-70 | 3 Prior Lines of Therapy | 8.15 (0.93, 71.30) | | 1/6 | — | 5/5 | 227 | 74 |
| P27 SIGNAL INTENSITY: ≥2+ | 5 Prior Lines of Therapy | 0.20 (0.04, 1.02) | | 5/6 | 228 | 3/8 | 939 | 16 |
| P65 % NUCLEAR STAINING: ≤5% | 5 Prior Lines of Therapy | 0.13 (0.01, 1.34) | | 3/3 | 235 | 2/4 | 1235 | 16 |
| CD68 OVERALL POSITIVE: 0-25 | No High Tumor Burden | 0.23 (0.07, 0.79) | | 8/14 | 552 | 5/19 | 1235 | 204 |
| CD68 OVERALL POSITIVE: 51-75 | No High Tumor Burden | 2.27 (0.98, 5.28) | | 10/25 | — | 12/18 | 511 | 204 |
| CD68 POSITIVE FOLLICULAR: 0-25 | No High Tumor Burden | 0.38 (0.17, 0.87) | | 14/22 | 573 | 12/25 | 939 | 182 |
| CD68 POSITIVE PERIFOLLICULAR: 0-25 | No High Tumor Burden | 0.22 (0.06, 0.74) | | 8/13 | 501 | 5/16 | 1235 | 182 |
| P27 % NUCLEI POSITIVE: 0-20 | High Tumor Burden | 0.54 (0.30, 0.98) | | 23/27 | 220 | 23/31 | 503 | 248 |
| P27 % NUCLEI POSITIVE: 30-50 | High Tumor Burden | 0.45 (0.22, 0.93) | | 17/22 | 421 | 13/25 | 599 | 248 |
| P27 SIGNAL INTENSITY: ≤1+ | High Tumor Burden | 0.42 (0.19, 0.93) | | 16/18 | 220 | 11/17 | 975 | 248 |
| CD68 OVERALL POSITIVE: 0-25 | Intermediate FLIPI Score | 0.27 (0.08, 0.96) | | 7/11 | 485 | 5/15 | 1235 | 159 |
| CD68 POSITIVE FOLLICULAR: 0-25 | Intermediate FLIPI Score | 0.44 (0.19, 1.01) | | 14/20 | 421 | 11/20 | 939 | 141 |
| CD68 POSITIVE PERIFOLLICULAR: 0-25 | Intermediate FLIPI Score | 0.27 (0.08, 0.95) | | 7/13 | 501 | 5/17 | 1235 | 139 |
| CD68 OVERALL POSITIVE: 0-25 | Low FLIPI Score | 0.32 (0.10, 0.99) | | 8/10 | 422 | 5/11 | 1075 | 102 |

APPENDIX 2, TABLE 2.10-continued

Time to Next Anti-Lymphoma Therapy by Protein Expression and by Covariate, IRC Review.
(All Reported Groups are Significant (p ≤ 0.05) and at a Frequency ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| CD68 OVERALL POSITIVE: 0-25 | No Prior Rituximab Therapy | 0.36 (0.14, 0.93) | | 12/19 | 533 | 7/21 | 1103 | 241 |
| CD68 POSITIVE FOLLICULAR: 0-25 | No Prior Rituximab Therapy | 0.40 (0.19, 0.84) | | 23/36 | 485 | 10/25 | 1103 | 210 |
| CD68 POSITIVE PERIFOLLICULAR: 0-25 | No Prior Rituximab Therapy | 0.33 (0.11, 0.95) | | 12/18 | 533 | 5/15 | — | 208 |
| 20S % NUCLEAR STAINING: 60-70 | Prior Rituximab Therapy | 0.39 (0.15, 1.00) | | 17/21 | 343 | 6/12 | 1075 | 212 |
| CD68 OVERALL POSITIVE: 0-25 | Prior Rituximab Therapy | 0.41 (0.19, 0.89) | | 18/25 | 235 | 12/20 | 834 | 201 |
| P27 SIGNAL INTENSITY: ≥2+ | Prior Rituximab Therapy | 0.64 (0.44, 0.94) | | 60/88 | 421 | 48/85 | 718 | 210 |
| P65 % NUCLEAR STAINING: ≤5% | Prior Rituximab Therapy | 0.29 (0.14, 0.64) | | 16/21 | 232 | 13/27 | 975 | 215 |
| CD68 OVERALL POSITIVE: 0-25 | >1 year since last anti-lymphoma treatment | 0.26 (0.11, 0.60) | | 17/26 | 409 | 9/28 | 1235 | 269 |
| CD68 POSITIVE FOLLICULAR: 0-25 | >1 year since last anti-lymphoma treatment | 0.48 (0.25, 0.93) | | 22/34 | 550 | 16/33 | 1005 | 235 |
| CD68 POSITIVE PERIFOLLICULAR: 0-25 | >1 year since last anti-lymphoma treatment | 0.40 (0.18, 0.88) | | 15/24 | 533 | 11/27 | 1235 | 234 |
| P65 % POSITIVE CYTOPLASMIC SIGNAL: >90% | >1 year since last anti-lymphoma treatment | 0.68 (0.48, 0.98) | | 69/117 | 593 | 54/112 | 983 | 288 |
| 20S INTENSITY CYTOPLASMIC SIGNAL: ≥3+ | European Union | 0.58 (0.34, 0.97) | | 34/52 | 533 | 25/52 | 1075 | 214 |
| CD68 OVERALL POSITIVE: 0-25 | European Union | 0.40 (0.18, 0.90) | | 14/22 | 374 | 11/25 | 1103 | 211 |
| CD68 POSITIVE PERIFOLLICULAR: >75 | European Union | 0.35 (0.13, 0.96) | | 13/17 | 675 | 7/14 | 1185 | 185 |
| P27 % NUCLEI POSITIVE: 80-100 | European Union | 0.59 (0.35, 1.00) | | 29/41 | 655 | 27/51 | 939 | 214 |

APPENDIX 2, TABLE 2.10-continued

Time to Next Anti-Lymphoma Therapy by Protein Expression and by Covariate, IRC Review.
(All Reported Groups are Significant (p ≤ 0.05) and at a Frequency ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| P27 SIGNAL INTENSITY: ≥2+ | European Union | 0.67 (0.46, 0.99) | | 57/89 | 649 | 49/91 | 939 | 214 |
| P65 % POSITIVE CYTOPLASMIC SIGNAL: >90% | European Union | 0.67 (0.46, 0.99) | | 57/92 | 552 | 48/87 | 975 | 216 |
| P65 INTENSITY CYTOPLASMIC SIGNAL: ≤1+ | European Union | 0.45 (0.19, 1.02) | | 13/18 | 409 | 11/21 | 1005 | 216 |
| CD68 OVERALL POSITIVE: 0-25 | ≤65 years old | 0.38 (0.20, 0.73) | | 24/34 | 374 | 15/32 | 1005 | 329 |
| CD68 POSITIVE FOLLICULAR: 0-25 | ≤65 years old | 0.45 (0.26, 0.77) | | 33/46 | 332 | 24/41 | 764 | 292 |
| CD68 POSITIVE PERIFOLLICULAR: 0-25 | ≤65 years old | 0.48 (0.24, 0.98) | | 20/31 | 332 | 13/29 | 1075 | 289 |
| CD68 POSITIVE PERIFOLLICULAR: >75 | ≤65 years old | 0.45 (0.22, 0.91) | | 19/23 | 437 | 13/23 | 726 | 289 |
| P27 % NUCLEI POSITIVE: 0-20 | ≤65 years old | 0.52 (0.29, 0.96) | | 26/34 | 327 | 19/32 | 834 | 344 |
| P27 SIGNAL INTENSITY: ≥2+ | ≤65 years old | 0.74 (0.56, 0.98) | | 103/153 | 484 | 90/149 | 672 | 344 |
| P65 % NUCLEAR STAINING: ≤5% | ≤65 years old | 0.54 (0.29, 1.00) | | 19/29 | 374 | 22/43 | 975 | 349 |
| P65 % POSITIVE CYTOPLASMIC SIGNAL: >90% | ≤65 years old | 0.71 (0.53, 0.94) | | 103/154 | 484 | 84/142 | 719 | 349 |
| P65 INTENSITY CYTOPLASMIC SIGNAL: ≥2+ | ≤65 years old | 0.72 (0.54, 0.96) | | 101/152 | 484 | 82/139 | 718 | 349 |
| 20S % NUCLEAR STAINING: 0-20 | Female | 0.53 (0.30, 0.93) | | 35/61 | 568 | 19/49 | — | 259 |
| CD68 OVERALL POSITIVE: 0-25 | Female | 0.27 (0.10, 0.76) | | 16/26 | 434 | 5/18 | 1103 | 242 |
| CD68 POSITIVE FOLLICULAR: 0-25 | Female | 0.45 (0.21, 0.96) | | 23/37 | 462 | 10/22 | 1103 | 217 |
| CD68 POSITIVE PERIFOLLICULAR: 0-25 | Female | 0.29 (0.11, 0.79) | | 19/28 | 374 | 5/17 | 1107 | 215 |
| P65 INTENSITY CYTOPLASMIC SIGNAL: ≥2+ | Female | 0.68 (0.46, 1.00) | | 74/129 | 537 | 41/87 | 1047 | 263 |

APPENDIX 2, TABLE 2.10-continued

Time to Next Anti-Lymphoma Therapy by Protein Expression and by Covariate, IRC Review.
(All Reported Groups are Significant (p ≤ 0.05) and at a Frequency ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| 20S % NUCLEAR STAINING: 60-70 | Male | 0.42 (0.19, 0.93) | | 14/16 | 247 | 12/20 | 518 | 204 |
| 20S INTENSITY CYTOPLASMIC SIGNAL: ≥3+ | Male | 0.58 (0.34, 1.00) | | 20/27 | 421 | 37/62 | 764 | 204 |
| CD68 OVERALL POSITIVE: 0-25 | Male | 0.46 (0.22, 0.99) | | 14/18 | 251 | 14/23 | 975 | 200 |
| CD68 OVERALL POSITIVE: >75 | Male | 0.23 (0.07, 0.79) | | 8/9 | 427 | 4/11 | — | 200 |
| P65 % POSITIVE CYTOPLASMIC SIGNAL: >90% | Male | 0.68 (0.47, 0.98) | | 51/72 | 427 | 62/97 | 726 | 207 |
| CD68 POSITIVE FOLLICULAR: 0-25 | Asian | 0.13 (0.01, 1.09) | | 5/6 | 220 | 2/6 | — | 30 |
| CD68 POSITIVE PERIFOLLICULAR: 26-50 | Other | 0.14 (0.01, 1.31) | | 4/4 | 341 | 4/5 | 658 | 22 |
| CD68 OVERALL POSITIVE: 0-25 | White | 0.38 (0.20, 0.72) | | 24/35 | 409 | 16/35 | 1075 | 385 |
| CD68 POSITIVE FOLLICULAR: 0-25 | White | 0.57 (0.34, 0.98) | | 32/48 | 462 | 25/42 | 834 | 335 |
| CD68 POSITIVE PERIFOLLICULAR: 0-25 | White | 0.43 (0.22, 0.82) | | 19/27 | 501 | 19/39 | 1103 | 332 |
| P27 SIGNAL INTENSITY: ≥2+ | White | 0.75 (0.57, 0.98) | | 113/177 | 533 | 99/170 | 718 | 403 |
| P65 % POSITIVE CYTOPLASMIC SIGNAL: >90% | White | 0.73 (0.56, 0.96) | | 113/179 | 505 | 95/162 | 744 | 406 |
| P65 INTENSITY CYTOPLASMIC SIGNAL: ≥2+ | White | 0.75 (0.57, 0.99) | | 109/176 | 533 | 94/165 | 744 | 406 |
| CD68 OVERALL POSITIVE: 0-25 | Ann Arbor Stage III | 0.35 (0.14, 0.92) | | 12/16 | 276 | 9/12 | 905 | 144 |
| CD68 POSITIVE FOLLICULAR: 0-25 | Ann Arbor Stage III | 0.40 (0.19, 0.83) | | 19/24 | 332 | 13/18 | 764 | 135 |
| P27 % NUCLEI POSITIVE: 0-20 | Ann Arbor Stage III | 0.42 (0.17, 1.00) | | 14/16 | 418 | 12/15 | 613 | 149 |
| P65 INTENSITY CYTOPLASMIC SIGNAL: ≤1+ | Ann Arbor Stage III | 0.36 (0.13, 0.99) | | 10/11 | 261 | 7/11 | 834 | 151 |

APPENDIX 2, TABLE 2.10-continued

Time to Next Anti-Lymphoma Therapy by Protein Expression and by Covariate, IRC Review.
(All Reported Groups are Significant (p ≤ 0.05) and at a Frequency ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| CD68 OVERALL POSITIVE: 0-25 | Ann Arbor Stage IV | 0.37 (0.15, 0.92) | | 15/22 | 434 | 8/23 | 1047 | 222 |
| CD68 POSITIVE PERIFOLLICULAR: 0-25 | Ann Arbor Stage IV | 0.37 (0.14, 0.96) | | 11/15 | 374 | 8/22 | 1107 | 183 |

APPENDIX 2, TABLE 2.11

Time to Next Anti-Lymphoma Therapy by Germline Genetic Variant and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| PSMB1/A171S: G/G | No Subgroup | 0.78 (0.63, 0.97) | | 173/276 | 546 | 152/266 | 719 | 542 |
| PSMB1/I208N: T/T | No Subgroup | 0.78 (0.63, 0.97) | | 173/276 | 546 | 152/266 | 719 | 542 |
| PSMB1/P11A: C/G | No Subgroup | 0.68 (0.48, 0.94) | | 78/127 | 550 | 63/115 | 939 | 542 |
| PSMB1/P11A: G/G | No Subgroup | 0.57 (0.34, 0.97) | | 30/37 | 436 | 26/43 | 613 | 542 |
| PSMB1/P193L: C/C | No Subgroup | 0.78 (0.63, 0.97) | | 173/276 | 546 | 152/266 | 719 | 542 |
| PSMB2/E49X: G/G | No Subgroup | 0.78 (0.63, 0.97) | | 173/276 | 546 | 152/266 | 719 | 542 |
| PSMB2/G187V: G/G | No Subgroup | 0.78 (0.63, 0.97) | | 173/276 | 546 | 152/266 | 719 | 542 |
| PSMB2/L159F: C/C | No Subgroup | 0.78 (0.63, 0.97) | | 173/276 | 546 | 152/266 | 719 | 542 |
| PSMB5/L206M: C/C | No Subgroup | 0.78 (0.63, 0.97) | | 173/276 | 546 | 152/266 | 719 | 542 |
| PSMB5/R24C: C/C | No Subgroup | 0.78 (0.62, 0.99) | | 147/235 | 546 | 127/223 | 719 | 542 |
| PSMB6/A234D: C/C | No Subgroup | 0.78 (0.63, 0.97) | | 173/276 | 546 | 152/266 | 719 | 542 |

APPENDIX 2, TABLE 2.11-continued

Time to Next Anti-Lymphoma Therapy by Germline Genetic Variant and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| PSMB6/P107A: C/C | No Subgroup | 0.79 (0.63, 0.98) | | 167/265 | 550 | 150/261 | 717 | 542 |
| PSMB8/G8R: G/G | No Subgroup | 0.77 (0.61, 0.96) | | 165/264 | 537 | 144/256 | 719 | 542 |
| PSMB8/R141C: C/C | No Subgroup | 0.78 (0.63, 0.97) | | 173/276 | 546 | 152/266 | 719 | 542 |
| PSMB8/V182M: G/G | No Subgroup | 0.78 (0.63, 0.97) | | 173/276 | 546 | 152/266 | 719 | 542 |
| PSMB9/G9E: G/G | No Subgroup | 0.78 (0.63, 0.97) | | 172/274 | 546 | 152/265 | 718 | 542 |
| PSMB9/V32I: C/C | No Subgroup | 0.79 (0.63, 0.99) | | 167/266 | 546 | 146/254 | 717 | 542 |
| PSMB1/A171S: G/G | 1 Prior Line of Therapy | 0.70 (0.50, 0.98) | | 72/113 | 673 | 61/118 | 841 | 231 |
| PSMB1/I208N: T/T | 1 Prior Line of Therapy | 0.70 (0.50, 0.98) | | 72/113 | 673 | 61/118 | 841 | 231 |
| PSMB1/P11A: C/G | 1 Prior Line of Therapy | 0.56 (0.34, 0.95) | | 32/51 | 621 | 27/55 | 1047 | 231 |
| PSMBI/P11A: G/G | 1 Prior Line of Therapy | 0.35 (0.13, 0.93) | | 11/11 | 443 | 7/14 | 700 | 231 |
| PSMB1/P193L: C/C | 1 Prior Line of Therapy | 0.70 (0.50, 0.98) | | 72/113 | 673 | 61/118 | 841 | 231 |
| PSMB2/E49X: G/G | 1 Prior Line of Therapy | 0.70 (0.50, 0.98) | | 72/113 | 673 | 61/118 | 841 | 231 |
| PSMB2/G187V: G/G | 1 Prior Line of Therapy | 0.70 (0.50, 0.98) | | 72/113 | 673 | 61/118 | 841 | 231 |
| PSMB2/L159F: C/C | 1 Prior Line of Therapy | 0.70 (0.50, 0.98) | | 72/113 | 673 | 61/118 | 841 | 231 |
| PSMB5/L206M: C/C | 1 Prior Line of Therapy | 0.70 (0.50, 0.98) | | 72/113 | 673 | 61/118 | 841 | 231 |
| PSMB6/A234D: C/C | 1 Prior Line of Therapy | 0.70 (0.50, 0.98) | | 72/113 | 673 | 61/118 | 841 | 231 |
| PSMB6/P107A: C/C | 1 Prior Line of Therapy | 0.70 (0.49, 0.99) | | 70/108 | 673 | 60/116 | 841 | 231 |

APPENDIX 2, TABLE 2.11-continued

Time to Next Anti-Lymphoma Therapy by Germline Genetic Variant and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| PSMB8/G8R: G/G | 1 Prior Line of Therapy | 0.68 (0.47, 0.97) | | 69/109 | 673 | 55/111 | 852 | 231 |
| PSMB8/R141C: C/C | 1 Prior Line of Therapy | 0.70 (0.50, 0.98) | | 72/113 | 673 | 61/118 | 841 | 231 |
| PSMB8/V182M: G/G | 1 Prior Line of Therapy | 0.70 (0.50, 0.98) | | 72/113 | 673 | 61/118 | 841 | 231 |
| PSMB9/G9E: G/G | 1 Prior Line of Therapy | 0.71 (0.50, 1.00) | | 71/112 | 673 | 61/118 | 841 | 231 |
| PSMB1/A171S: G/G | 5 Prior Lines of Therapy | 0.29 (0.08, 0.99) | | 7/9 | 235 | 6/12 | 939 | 21 |
| PSMB1/I208N: T/T | 5 Prior Lines of Therapy | 0.29 (0.08, 0.99) | | 7/9 | 235 | 6/12 | 939 | 21 |
| PSMB1/P193L: C/C | 5 Prior Lines of Therapy | 0.29 (0.08, 0.99) | | 7/9 | 235 | 6/12 | 939 | 21 |
| PSMB2/E49X: G/G | 5 Prior Lines of Therapy | 0.29 (0.08, 0.99) | | 7/9 | 235 | 6/12 | 939 | 21 |
| PSMB2/G187V: G/G | 5 Prior Lines of Therapy | 0.29 (0.08, 0.99) | | 7/9 | 235 | 6/12 | 939 | 21 |
| PSMB2/L159F: C/C | 5 Prior Lines of Therapy | 0.29 (0.08, 0.99) | | 7/9 | 235 | 6/12 | 939 | 21 |
| PSMB5/L206M: C/C | 5 Prior Lines of Therapy | 0.29 (0.08, 0.99) | | 7/9 | 235 | 6/12 | 939 | 21 |
| PSMB5/R24C: C/C | 5 Prior Lines of Therapy | 0.16 (0.03, 0.79) | | 6/7 | 235 | 4/9 | 1235 | 21 |
| PSMB6/A234D: C/C | 5 Prior Lines of Therapy | 0.29 (0.08, 0.99) | | 7/9 | 235 | 6/12 | 939 | 21 |
| PSMB6/P107A: C/C | 5 Prior Lines of Therapy | 0.29 (0.08, 0.99) | | 7/9 | 235 | 6/12 | 939 | 21 |
| PSMB8/G8R: G/G | 5 Prior Lines of Therapy | 0.29 (0.08, 1.00) | | 7/9 | 235 | 6/11 | 939 | 21 |
| PSMB8/R141C: C/C | 5 Prior Lines of Therapy | 0.29 (0.08, 0.99) | | 7/9 | 235 | 6/12 | 939 | 21 |
| PSMB8/V182M: G/G | 5 Prior Lines of Therapy | 0.29 (0.08, 0.99) | | 7/9 | 235 | 6/12 | 939 | 21 |

APPENDIX 2, TABLE 2.11-continued

Time to Next Anti-Lymphoma Therapy by Germline Genetic Variant and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| PSMB9/G9E: G/G | 5 Prior Lines of Therapy | 0.29 (0.08, 0.99) | | 7/9 | 235 | 6/12 | 939 | 21 |
| PSMB9/V32I: C/C | 5 Prior Lines of Therapy | 0.25 (0.07, 0.86) | | 7/8 | 228 | 5/11 | 1235 | 21 |
| PSMB1/A171S: G/G | High Tumor Burden | 0.72 (0.55, 0.95) | | 108/147 | 396 | 98/149 | 521 | 296 |
| PSMB1/I208N: T/T | High Tumor Burden | 0.72 (0.55, 0.95) | | 108/147 | 396 | 98/149 | 521 | 296 |
| PSMB1/P11A: C/G | High Tumor Burden | 0.63 (0.41, 0.96) | | 49/72 | 358 | 38/65 | 675 | 296 |
| PSMB1/P193L: C/C | High Tumor Burden | 0.72 (0.55, 0.95) | | 108/147 | 396 | 98/149 | 521 | 296 |
| PSMB2/E49X: G/G | High Tumor Burden | 0.72 (0.55, 0.95) | | 108/147 | 396 | 98/149 | 521 | 296 |
| PSMB2/G187V: G/G | High Tumor Burden | 0.72 (0.55, 0.95) | | 108/147 | 396 | 98/149 | 521 | 296 |
| PSMB2/L159F: C/C | High Tumor Burden | 0.72 (0.55, 0.95) | | 108/147 | 396 | 98/149 | 521 | 296 |
| PSMB5/L206M: C/C | High Tumor Burden | 0.72 (0.55, 0.95) | | 108/147 | 396 | 98/149 | 521 | 296 |
| PSMB5/R24C: C/T | High Tumor Burden | 0.46 (0.24, 0.89) | | 19/21 | 317 | 18/24 | 536 | 296 |
| PSMB6/A234D: C/C | High Tumor Burden | 0.72 (0.55, 0.95) | | 108/147 | 396 | 98/149 | 521 | 296 |
| PSMB6/P107A: C/C | High Tumor Burden | 0.73 (0.55, 0.96) | | 104/140 | 380 | 97/146 | 518 | 296 |
| PSMB8/G8R: G/G | High Tumor Burden | 0.69 (0.52, 0.91) | | 104/140 | 374 | 94/145 | 521 | 296 |
| PSMB8/R141C: C/C | High Tumor Burden | 0.72 (0.55, 0.95) | | 108/147 | 396 | 98/149 | 521 | 296 |
| PSMB8/V182M: G/G | High Tumor Burden | 0.72 (0.55, 0.95) | | 108/147 | 396 | 98/149 | 521 | 296 |
| PSMB9/G9E: G/G | High Tumor Burden | 0.72 (0.55, 0.95) | | 107/145 | 396 | 98/148 | 518 | 296 |

APPENDIX 2, TABLE 2.11-continued

Time to Next Anti-Lymphoma Therapy by Germline Genetic Variant and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| PSMB9/V32I: C/C | High Tumor Burden | 0.71 (0.54, 0.94) | | 106/142 | 396 | 94/142 | 521 | 296 |
| PSMB1/A171S: G/G | >1 year since last anti-lymphoma treatment | 0.69 (0.51, 0.93) | | 98/165 | 688 | 80/166 | 969 | 331 |
| PSMB1/I208N: T/T | >1 year since last anti-lymphoma treatment | 0.69 (0.51, 0.93) | | 98/165 | 688 | 80/166 | 969 | 331 |
| PSMB1/P11A: G/G | >1 year since last anti-lymphoma treatment | 0.47 (0.23, 0.97) | | 17/20 | 429 | 13/25 | 872 | 331 |
| PSMB1/P193L: C/C | >1 year since last anti-lymphoma treatment | 0.69 (0.51, 0.93) | | 98/165 | 688 | 80/166 | 969 | 331 |
| PSMB2/E49X: G/G | >1 year since last anti-lymphoma treatment | 0.69 (0.51, 0.93) | | 98/165 | 688 | 80/166 | 969 | 331 |
| PSMB2/G187V: G/G | >1 year since last anti-lymphoma treatment | 0.69 (0.51, 0.93) | | 98/165 | 688 | 80/166 | 969 | 331 |
| PSMB2/L159F: C/C | >1 year since last anti-lymphoma treatment | 0.69 (0.51, 0.93) | | 98/165 | 688 | 80/166 | 969 | 331 |
| PSMB5/L206M: C/C | >1 year since last anti-lymphoma treatment | 0.69 (0.51, 0.93) | | 98/165 | 688 | 80/166 | 969 | 331 |
| PSMB5/R24C: C/C | >1 year since last anti-lymphoma treatment | 0.70 (0.51, 0.97) | | 81/137 | 649 | 68/141 | 983 | 331 |
| PSMB6/A234D: C/C | >1 year since last anti-lymphoma treatment | 0.69 (0.51, 0.93) | | 98/165 | 688 | 80/166 | 969 | 331 |
| PSMB6/P107A: C/C | >1 year since last anti-lymphoma treatment | 0.70 (0.52, 0.94) | | 95/159 | 702 | 79/162 | 969 | 331 |

APPENDIX 2, TABLE 2.11-continued

Time to Next Anti-Lymphoma Therapy by Germline Genetic Variant and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| PSMB8/G8R: G/G | >1 year since last anti-lymphoma treatment | 0.69 (0.51, 0.93) | | 91/155 | 702 | 74/159 | 1005 | 331 |
| PSMB8/R141C: C/C | >1 year since last anti-lymphoma treatment | 0.69 (0.51, 0.93) | | 98/165 | 688 | 80/166 | 969 | 331 |
| PSMB8/V182M: G/G | >1 year since last anti-lymphoma treatment | 0.69 (0.51, 0.93) | | 98/165 | 688 | 80/166 | 969 | 331 |
| PSMB9/G9E: G/G | >1 year since last anti-lymphoma treatment | 0.69 (0.51, 0.93) | | 97/163 | 688 | 80/165 | 969 | 331 |
| PSMB9/V32I: C/C | >1 year since last anti-lymphoma treatment | 0.68 (0.50, 0.91) | | 96/160 | 649 | 76/158 | 969 | 331 |
| PSMB1/A171S: G/G | European Union | 0.71 (0.51, 0.99) | | 75/119 | 675 | 66/122 | 939 | 241 |
| PSMB1/I208N: T/T | European Union | 0.71 (0.51, 0.99) | | 75/119 | 675 | 66/122 | 939 | 241 |
| PSMB1/P11A: C/G | European Union | 0.56 (0.34, 0.92) | | 34/49 | 462 | 29/51 | 1005 | 241 |
| PSMB1/P193L: C/C | European Union | 0.71 (0.51, 0.99) | | 75/119 | 675 | 66/122 | 939 | 241 |
| PSMB2/E49X: G/G | European Union | 0.71 (0.51, 0.99) | | 75/119 | 675 | 66/122 | 939 | 241 |
| PSMB2/G187V: G/G | European Union | 0.71 (0.51, 0.99) | | 75/119 | 675 | 66/122 | 939 | 241 |
| PSMB2/L159F: C/C | European Union | 0.71 (0.51, 0.99) | | 75/119 | 675 | 66/122 | 939 | 241 |
| PSMB5/L206M: C/C | European Union | 0.71 (0.51, 0.99) | | 75/119 | 675 | 66/122 | 939 | 241 |
| PSMB6/A234D: C/C | European Union | 0.71 (0.51, 0.99) | | 75/119 | 675 | 66/122 | 939 | 241 |
| PSMB8/G8R: G/G | European Union | 0.71 (0.50, 1.00) | | 70/111 | 649 | 62/117 | 939 | 241 |

APPENDIX 2, TABLE 2.11-continued

Time to Next Anti-Lymphoma Therapy by Germline Genetic Variant and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| PSMB8/R141C: C/C | European Union | 0.71 (0.51, 0.99) | | 75/119 | 675 | 66/122 | 939 | 241 |
| PSMB8/V182M: G/G | European Union | 0.71 (0.51, 0.99) | | 75/119 | 675 | 66/122 | 939 | 241 |
| PSMB9/G9E: G/G | European Union | 0.71 (0.51, 0.99) | | 75/119 | 675 | 66/122 | 939 | 241 |
| PSMB1/A171S: G/G | ≤65 years old | 0.72 (0.56, 0.92) | | 130/198 | 489 | 112/194 | 719 | 392 |
| PSMB1/I208N: T/T | ≤65 years old | 0.72 (0.56, 0.92) | | 130/198 | 489 | 112/194 | 719 | 392 |
| PSMB1/P11A: C/G | ≤65 years old | 0.62 (0.42, 0.91) | | 63/96 | 546 | 47/86 | 764 | 392 |
| PSMB1/P11A: G/G | ≤65 years old | 0.40 (0.21, 0.78) | | 21/25 | 409 | 16/30 | 834 | 392 |
| PSMB1/P193L: C/C | ≤65 years old | 0.72 (0.56, 0.92) | | 130/198 | 489 | 112/194 | 719 | 392 |
| PSMB2/E49X: G/G | ≤65 years old | 0.72 (0.56, 0.92) | | 130/198 | 489 | 112/194 | 719 | 392 |
| PSMB2/G187V: G/G | ≤65 years old | 0.72 (0.56, 0.92) | | 130/198 | 489 | 112/194 | 719 | 392 |
| PSMB2/L159F: C/C | ≤65 years old | 0.72 (0.56, 0.92) | | 130/198 | 489 | 112/194 | 719 | 392 |
| PSMB5/L206M: C/C | ≤65 years old | 0.72 (0.56, 0.92) | | 130/198 | 489 | 112/194 | 719 | 392 |
| PSMB5/R24C: C/C | ≤65 years old | 0.71 (0.54, 0.93) | | 113/170 | 489 | 97/167 | 719 | 392 |
| PSMB6/A234D: C/C | ≤65 years old | 0.72 (0.56, 0.92) | | 130/198 | 489 | 112/194 | 719 | 392 |
| PSMB6/P107A: C/C | ≤65 years old | 0.72 (0.56, 0.93) | | 125/189 | 504 | 110/190 | 718 | 392 |
| PSMB8/G8R: G/G | ≤65 years old | 0.72 (0.55, 0.93) | | 123/189 | 504 | 106/186 | 719 | 392 |
| PSMB8/R141C: C/C | ≤65 years old | 0.72 (0.56, 0.92) | | 130/198 | 489 | 112/194 | 719 | 392 |

APPENDIX 2, TABLE 2.11-continued

Time to Next Anti-Lymphoma Therapy by Germline Genetic Variant and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| PSMB8/V182M: G/G | ≤65 years old | 0.72 (0.56, 0.92) | | 130/198 | 489 | 112/194 | 719 | 392 |
| PSMB9/G9E: G/G | ≤65 years old | 0.72 (0.56, 0.93) | | 129/196 | 489 | 112/193 | 719 | 392 |
| PSMB9/V32I: C/C | ≤65 years old | 0.72 (0.56, 0.93) | | 127/192 | 489 | 107/186 | 718 | 392 |
| PSMB1/P11A: C/G | Female | 0.58 (0.36, 0.93) | | 42/75 | 546 | 30/66 | 1103 | 301 |
| PSMB8/G8R: G/G | Female | 0.72 (0.52, 0.98) | | 94/160 | 649 | 65/131 | 939 | 301 |
| PSMB1/P11A: G/G | Male | 0.50 (0.25, 1.01) | | 17/19 | 421 | 15/25 | 631 | 241 |
| PSMB9/R60H: A/G | Male | 0.43 (0.24, 0.76) | | 22/28 | 380 | 30/48 | 764 | 241 |
| PSMB1/P11A: C/G | Other | 0.07 (0.01, 0.81) | | 2/3 | 164 | 6/9 | 557 | 27 |
| PSMB1/P11A: C/G | White | 0.68 (0.47, 0.97) | | 67/111 | 581 | 54/97 | 975 | 473 |
| PSMB1/P11A: G/G | White | 0.54 (0.31, 0.94) | | 27/32 | 421 | 25/39 | 599 | 473 |
| PSMB1/A171S: G/G | Ann Arbor Stage IV | 0.72 (0.53, 0.97) | | 86/127 | 457 | 78/143 | 639 | 270 |
| PSMB1/I208N: T/T | Ann Arbor Stage IV | 0.72 (0.53, 0.97) | | 86/127 | 457 | 78/143 | 639 | 270 |
| PSMB1/P193L: C/C | Ann Arbor Stage IV | 0.72 (0.53, 0.97) | | 86/127 | 457 | 78/143 | 639 | 270 |
| PSMB2/E49X: G/G | Ann Arbor Stage IV | 0.72 (0.53, 0.97) | | 86/127 | 457 | 78/143 | 639 | 270 |
| PSMB2/G187V: G/G | Ann Arbor Stage IV | 0.72 (0.53, 0.97) | | 86/127 | 457 | 78/143 | 639 | 270 |
| PSMB2/L159F: C/C | Ann Arbor Stage IV | 0.72 (0.53, 0.97) | | 86/127 | 457 | 78/143 | 639 | 270 |
| PSMB5/L206M: C/C | Ann Arbor Stage IV | 0.72 (0.53, 0.97) | | 86/127 | 457 | 78/143 | 639 | 270 |

APPENDIX 2, TABLE 2.11-continued

Time to Next Anti-Lymphoma Therapy by Germline Genetic Variant and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| PSMB5/R24C: C/T | Ann Arbor Stage IV | 0.45 (0.20, 1.01) | | 11/15 | 421 | 13/28 | 991 | 270 |
| PSMB6/A234D: C/C | Ann Arbor Stage IV | 0.72 (0.53, 0.97) | | 86/127 | 457 | 78/143 | 639 | 270 |
| PSMB6/P107A: C/C | Ann Arbor Stage IV | 0.72 (0.53, 0.98) | | 84/124 | 485 | 77/140 | 602 | 270 |
| PSMB8/G8R: G/G | Ann Arbor Stage IV | 0.73 (0.53, 1.00) | | 80/120 | 457 | 74/138 | 602 | 270 |
| PSMB8/R141C: C/C | Ann Arbor Stage IV | 0.72 (0.53, 0.97) | | 86/127 | 457 | 78/143 | 639 | 270 |
| PSMB8/V182M: G/G | Ann Arbor Stage IV | 0.72 (0.53, 0.97) | | 86/127 | 457 | 78/143 | 639 | 270 |
| PSMB9/G9E: G/G | Ann Arbor Stage IV | 0.71 (0.52, 0.97) | | 86/126 | 457 | 78/142 | 602 | 270 |
| PSMB9/V32I: C/C | Ann Arbor Stage IV | 0.72 (0.53, 0.98) | | 84/123 | 457 | 76/138 | 639 | 270 |

APPENDIX 2, TABLE 2.12

Time to Next Anti-Lymphoma Therapy by Somatic Mutation and by Covariate, IRC review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| BCL2/A43G: MND | No Subgroup | 0.66 (0.49, 0.88) | | 104/161 | 501 | 84/154 | 791 | 315 |
| BCL2/C.-11C > T: MND | No Subgroup | 0.71 (0.54, 0.92) | | 127/192 | 501 | 102/179 | 719 | 390 |
| BCL2/E29K: MND | No Subgroup | 0.64 (0.47, 0.86) | | 98/150 | 484 | 77/139 | 791 | 318 |
| BCL2/P46L: MND | No Subgroup | 0.70 (0.51, 0.95) | | 86/135 | 504 | 77/139 | 743 | 314 |
| BCL2/P46S: MND | No Subgroup | 0.73 (0.54, 0.98) | | 92/147 | 504 | 84/147 | 751 | 310 |

APPENDIX 2, TABLE 2.12-continued

Time to Next Anti-Lymphoma Therapy by Somatic Mutation and by Covariate, IRC review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| BCL2/P59S: MND | No Subgroup | 0.72 (0.53, 0.96) | | 92/145 | 504 | 84/147 | 751 | 309 |
| BCL2/Q52P: MND | No Subgroup | 0.71 (0.53, 0.95) | | 97/153 | 501 | 88/154 | 751 | 307 |
| BCL2/R106H: MND | No Subgroup | 0.66 (0.50, 0.88) | | 108/162 | 489 | 84/151 | 751 | 372 |
| NOTCH/G_A1702P: MND | No Subgroup | 0.73 (0.55, 0.96) | | 113/175 | 501 | 93/161 | 726 | 337 |
| NOTCH/I1681N: MND | No Subgroup | 0.73 (0.56, 0.97) | | 113/175 | 501 | 94/162 | 719 | 337 |
| NOTCH/L1679P: MND | No Subgroup | 0.73 (0.56, 0.97) | | 113/175 | 501 | 94/162 | 719 | 337 |
| NOTCH/L1679Q: MND | No Subgroup | 0.73 (0.56, 0.97) | | 113/175 | 501 | 94/162 | 719 | 337 |
| NOTCH/L2458V: MND | No Subgroup | 0.75 (0.56, 0.99) | | 104/162 | 501 | 92/157 | 719 | 319 |
| NOTCH/P2513L: MND | No Subgroup | 0.69 (0.50, 0.95) | | 90/140 | 501 | 67/123 | 791 | 361 |
| NOTCH/P2515FS4: MND | No Subgroup | 0.70 (0.53, 0.92) | | 114/176 | 501 | 92/166 | 751 | 344 |
| NOTCH/Q2441X: MND | No Subgroup | 0.75 (0.57, 1.00) | | 103/161 | 501 | 92/155 | 719 | 319 |
| NOTCH/Q2460X: MND | No Subgroup | 0.72 (0.53, 0.96) | | 98/151 | 489 | 82/143 | 726 | 324 |
| NOTCH/X26DEL: MND | No Subgroup | 0.74 (0.57, 0.97) | | 112/175 | 505 | 102/178 | 744 | 361 |
| NOTCH/X26INS: MND | No Subgroup | 0.74 (0.56, 0.96) | | 114/179 | 505 | 103/180 | 744 | 361 |
| NOTCH/X28DEL: MND | No Subgroup | 0.72 (0.56, 0.93) | | 128/194 | 503 | 109/189 | 719 | 400 |
| NOTCH/X28INS: MND | No Subgroup | 0.70 (0.55, 0.90) | | 132/198 | 501 | 112/195 | 719 | 401 |
| BCL2/A43G: MND | 1 Prior Line of Therapy | 0.54 (0.34, 0.86) | | 46/72 | 550 | 30/67 | 991 | 139 |

APPENDIX 2, TABLE 2.12-continued

Time to Next Anti-Lymphoma Therapy by Somatic Mutation and by Covariate, IRC review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| BCL2/C.-11C > T: MND | 1 Prior Line of Therapy | 0.61 (0.40, 0.92) | | 57/86 | 568 | 38/78 | 988 | 170 |
| BCL2/E29K: MND | 1 Prior Line of Therapy | 0.54 (0.34, 0.88) | | 41/64 | 546 | 29/62 | 991 | 139 |
| BCL2/P46L: MND | 1 Prior Line of Therapy | 0.59 (0.37, 0.97) | | 37/58 | 589 | 30/63 | 991 | 140 |
| BCL2/P46S: MND | 1 Prior Line of Therapy | 0.61 (0.38, 0.97) | | 40/64 | 550 | 33/68 | 991 | 138 |
| BCL2/P59S: MND | 1 Prior Line of Therapy | 0.62 (0.39, 0.99) | | 41/66 | 573 | 32/66 | 988 | 138 |
| BCL2/Q52P: MND | 1 Prior Line of Therapy | 0.62 (0.39, 0.97) | | 42/67 | 550 | 35/71 | 988 | 138 |
| BCL2/R106H: MND | 1 Prior Line of Therapy | 0.58 (0.37, 0.90) | | 49/73 | 550 | 33/68 | 991 | 162 |
| NOTCH/P2515FS4: MND | 1 Prior Line of Therapy | 0.62 (0.40, 0.97) | | 48/75 | 573 | 35/72 | 988 | 149 |
| NOTCH/X28DEL: MND | 1 Prior Line of Therapy | 0.67 (0.45, 1.00) | | 56/85 | 568 | 44/84 | 756 | 177 |
| NOTCH/X28INS: MND | 1 Prior Line of Therapy | 0.63 (0.42, 0.93) | | 56/84 | 568 | 45/88 | 841 | 178 |
| BCL2/C.-11C > T: MND | 5 Prior Lines of Therapy | 0.17 (0.03, 1.05) | | 3/3 | 221 | 3/7 | 939 | 11 |
| NOTCH/X28DEL: MND | 5 Prior Lines of Therapy | 0.20 (0.04, 1.12) | | 4/4 | 342 | 3/7 | 939 | 11 |
| BCL2/A43G: MND | No High Tumor Burden | 0.61 (0.37, 0.98) | | 42/78 | 774 | 27/64 | — | 142 |
| BCL2/R106H: MND | No High Tumor Burden | 0.60 (0.37, 0.98) | | 46/79 | 690 | 26/58 | 1185 | 163 |
| NOTCH/P2513L: MD | No High Tumor Burden | 0.44 (0.19, 0.99) | | 17/26 | 593 | 9/21 | — | 163 |
| NOTCH/X28INS: MND | No High Tumor Burden | 0.63 (0.41, 0.96) | | 55/98 | 734 | 37/82 | 1107 | 184 |
| BCL2/A43G: MND | High Tumor Burden | 0.60 (0.42, 0.86) | | 62/83 | 380 | 57/90 | 534 | 173 |

APPENDIX 2, TABLE 2.12-continued

Time to Next Anti-Lymphoma Therapy by Somatic Mutation and by Covariate, IRC review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| BCL2/C.-11C > T: MND | High Tumor Burden | 0.65 (0.47, 0.90) | | 76/101 | 380 | 69/107 | 484 | 217 |
| BCL2/E29K: MND | High Tumor Burden | 0.56 (0.38, 0.81) | | 60/79 | 374 | 52/82 | 542 | 174 |
| BCL2/P46L: MND | High Tumor Burden | 0.57 (0.38, 0.84) | | 51/67 | 374 | 51/83 | 534 | 173 |
| BCL2/P46S: MND | High Tumor Burden | 0.63 (0.43, 0.92) | | 52/73 | 374 | 56/89 | 488 | 170 |
| BCL2/P59L: MND | High Tumor Burden | 0.66 (0.44, 0.97) | | 52/72 | 396 | 50/80 | 455 | 172 |
| BCL2/P59S: MND | High Tumor Burden | 0.62 (0.42, 0.90) | | 53/73 | 396 | 54/87 | 534 | 170 |
| BCL2/Q52P: MND | High Tumor Burden | 0.62 (0.42, 0.89) | | 55/76 | 374 | 58/92 | 534 | 168 |
| BCL2/R106H: MND | High Tumor Burden | 0.59 (0.41, 0.84) | | 62/83 | 380 | 58/93 | 542 | 209 |
| NOTCH/F1593S: MND | High Tumor Burden | 0.69 (0.48, 1.00) | | 55/77 | 410 | 60/91 | 488 | 168 |
| NOTCH/G_A1702P: MND | High Tumor Burden | 0.62 (0.44, 0.88) | | 67/90 | 374 | 62/96 | 534 | 187 |
| NOTCH/I1681N: MND | High Tumor Burden | 0.63 (0.45, 0.89) | | 67/90 | 374 | 63/97 | 534 | 187 |
| NOTCH/L1586P: MND | High Tumor Burden | 0.69 (0.48, 1.00) | | 55/77 | 410 | 60/91 | 488 | 168 |
| NOTCH/L1586Q: MND | High Tumor Burden | 0.65 (0.45, 0.94) | | 56/78 | 396 | 60/94 | 534 | 172 |
| NOTCH/L1594P: MND | High Tumor Burden | 0.69 (0.48, 1.00) | | 55/77 | 410 | 60/91 | 488 | 168 |
| NOTCH/L1597H: MND | High Tumor Burden | 0.65 (0.45, 0.94) | | 56/78 | 396 | 60/94 | 534 | 172 |
| NOTCH/L1597_S1598INSG: MND | High Tumor Burden | 0.69 (0.48, 1.00) | | 55/77 | 410 | 60/91 | 488 | 168 |
| NOTCH/L1601P: MND | High Tumor Burden | 0.68 (0.47, 0.98) | | 55/77 | 410 | 59/90 | 488 | 168 |

APPENDIX 2, TABLE 2.12-continued

Time to Next Anti-Lymphoma Therapy by Somatic Mutation and by Covariate, IRC review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| NOTCH/L1679P: MND | High Tumor Burden | 0.63 (0.45, 0.89) | | 67/90 | 374 | 63/97 | 534 | 187 |
| NOTCH/L1679Q: MND | High Tumor Burden | 0.63 (0.45, 0.89) | | 67/90 | 374 | 63/97 | 534 | 187 |
| NOTCH/L2458V: MND | High Tumor Burden | 0.64 (0.45, 0.91) | | 61/83 | 380 | 61/95 | 534 | 178 |
| NOTCH/P2513L: MND | High Tumor Burden | 0.54 (0.36, 0.80) | | 58/76 | 380 | 43/71 | 542 | 198 |
| NOTCH/P2515FS4: MND | High Tumor Burden | 0.61 (0.43, 0.87) | | 67/90 | 380 | 61/98 | 534 | 189 |
| NOTCH/Q2441X: MND | High Tumor Burden | 0.64 (0.45, 0.91) | | 61/83 | 380 | 61/95 | 534 | 178 |
| NOTCH/Q2460X: MND | High Tumor Burden | 0.61 (0.42, 0.88) | | 59/79 | 380 | 54/87 | 542 | 181 |
| NOTCH/R1599 > QS: MND | High Tumor Burden | 0.69 (0.48, 1.00) | | 55/77 | 410 | 60/91 | 488 | 168 |
| NOTCH/R1599P: MND | High Tumor Burden | 0.65 (0.45, 0.94) | | 56/78 | 396 | 60/94 | 534 | 172 |
| NOTCH/V1579DEL: MND | High Tumor Burden | 0.69 (0.48, 1.00) | | 55/77 | 410 | 60/91 | 488 | 168 |
| NOTCH/V1579E: MND | High Tumor Burden | 0.65 (0.45, 0.94) | | 56/78 | 396 | 60/94 | 534 | 172 |
| NOTCH/V1579G: MND | High Tumor Burden | 0.69 (0.48, 1.00) | | 55/77 | 410 | 60/91 | 488 | 168 |
| NOTCH/X26DEL: MND | High Tumor Burden | 0.67 (0.47, 0.94) | | 63/88 | 396 | 68/107 | 518 | 198 |
| NOTCH/X26INS: MND | High Tumor Burden | 0.66 (0.47, 0.93) | | 64/89 | 396 | 68/107 | 518 | 198 |
| NOTCH/X28DEL: MND | High Tumor Burden | 0.64 (0.46, 0.89) | | 74/99 | 374 | 72/111 | 488 | 216 |
| NOTCH/X28INS: MND | High Tumor Burden | 0.64 (0.47, 0.88) | | 77/100 | 343 | 75/113 | 474 | 217 |
| BCL2/P59L: MD | High FLIPI Score | 0.18 (0.03, 1.06) | | 4/6 | 211 | 6/7 | 658 | 125 |

APPENDIX 2, TABLE 2.12-continued

Time to Next Anti-Lymphoma Therapy by Somatic Mutation and by Covariate, IRC review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| BCL2/A43G: MND | Intermediate FLIPI Score | 0.60 (0.36, 1.00) | | 34/53 | 504 | 26/52 | 939 | 105 |
| BCL2/C.-11C > T: MND | Intermediate FLIPI Score | 0.59 (0.38, 0.93) | | 44/66 | 504 | 33/63 | 939 | 136 |
| BCL2/P46S: MND | Intermediate FLIPI Score | 0.59 (0.35, 1.00) | | 31/50 | 505 | 26/52 | 988 | 105 |
| BCL2/P59S: MND | Intermediate FLIPI Score | 0.60 (0.35, 1.00) | | 31/48 | 505 | 27/52 | 939 | 105 |
| BCL2/Q52P: MND | Intermediate FLIPI Score | 0.60 (0.36, 0.99) | | 32/51 | 505 | 28/54 | 988 | 105 |
| BCL2/R106H: MND | Intermediate FLIPI Score | 0.51 (0.31, 0.82) | | 40/55 | 501 | 28/54 | 988 | 130 |
| NOTCH/X28DEL: MND | Intermediate FLIPI Score | 0.65 (0.42, 1.00) | | 44/65 | 505 | 38/70 | 756 | 143 |
| BCL2/E29K: MND | No Prior Rituximab Therapy | 0.65 (0.43, 0.97) | | 57/93 | 534 | 41/76 | 883 | 186 |
| BCL2/P59L: MD | No Prior Rituximab Therapy | 0.15 (0.03, 0.80) | | 3/5 | 211 | 7/13 | 947 | 178 |
| BCL2/A43G: MND | Prior Rituximab Therapy | 0.59 (0.38, 0.92) | | 44/63 | 428 | 37/69 | 719 | 132 |
| BCL2/C.-11C > T: MND | Prior Rituximab Therapy | 0.58 (0.39, 0.86) | | 57/78 | 396 | 43/77 | 718 | 165 |
| BCL2/E29K: MND | Prior Rituximab Therapy | 0.59 (0.37, 0.92) | | 41/57 | 428 | 36/63 | 719 | 132 |
| BCL2/P59S: MND | Prior Rituximab Therapy | 0.60 (0.38, 0.95) | | 39/56 | 450 | 37/69 | 719 | 133 |
| BCL2/R106H: MND | Prior Rituximab Therapy | 0.54 (0.36, 0.83) | | 50/67 | 421 | 39/72 | 719 | 159 |
| NOTCH/G_A1702P: MND | Prior Rituximab Therapy | 0.60 (0.40, 0.91) | | 51/72 | 434 | 41/74 | 719 | 147 |
| NOTCH/I1681N: MND | Prior Rituximab Therapy | 0.61 (0.41, 0.93) | | 51/72 | 434 | 42/75 | 719 | 147 |
| NOTCH/L1586Q: MND | Prior Rituximab Therapy | 0.63 (0.41, 0.97) | | 44/63 | 443 | 41/73 | 719 | 136 |

APPENDIX 2, TABLE 2.12-continued

Time to Next Anti-Lymphoma Therapy by Somatic Mutation and by Covariate, IRC review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| NOTCH/L1597H: MND | Prior Rituximab Therapy | 0.63 (0.41, 0.97) | | 44/63 | 443 | 41/73 | 719 | 136 |
| NOTCH/L1679P: MND | Prior Rituximab Therapy | 0.61 (0.41, 0.93) | | 51/72 | 434 | 42/75 | 719 | 147 |
| NOTCH/L1679Q: MND | Prior Rituximab Therapy | 0.61 (0.41, 0.93) | | 51/72 | 434 | 42/75 | 719 | 147 |
| NOTCH/L2458V: MND | Prior Rituximab Therapy | 0.61 (0.40, 0.93) | | 47/66 | 443 | 42/75 | 719 | 141 |
| NOTCH/P2513L: MND | Prior Rituximab Therapy | 0.57 (0.35, 0.95) | | 39/57 | 450 | 25/51 | 751 | 154 |
| NOTCH/P2515FS4: MND | Prior Rituximab Therapy | 0.61 (0.41, 0.92) | | 51/72 | 434 | 42/77 | 719 | 149 |
| NOTCH/Q2441X: MND | Prior Rituximab Therapy | 0.61 (0.40, 0.93) | | 47/66 | 443 | 42/73 | 719 | 141 |
| NOTCH/Q2460X: MND | Prior Rituximab Therapy | 0.58 (0.37, 0.90) | | 45/62 | 434 | 36/66 | 719 | 143 |
| NOTCH/R1599P: MND | Prior Rituximab Therapy | 0.63 (0.41, 0.97) | | 44/63 | 443 | 41/73 | 719 | 136 |
| NOTCH/V1579E: MND | Prior Rituximab Therapy | 0.63 (0.41, 0.97) | | 44/63 | 443 | 41/73 | 719 | 136 |
| NOTCH/X26DEL: MND | Prior Rituximab Therapy | 0.65 (0.44, 0.98) | | 50/70 | 434 | 46/82 | 718 | 158 |
| NOTCH/X26INS: MND | Prior Rituximab Therapy | 0.64 (0.43, 0.94) | | 52/74 | 434 | 47/84 | 719 | 158 |
| NOTCH/X28DEL: MND | Prior Rituximab Therapy | 0.61 (0.42, 0.89) | | 60/83 | 427 | 49/86 | 672 | 175 |
| NOTCH/X28INS: MND | Prior Rituximab Therapy | 0.60 (0.41, 0.87) | | 62/86 | 427 | 50/88 | 672 | 175 |
| BCL2/A43G: MND | >1 year since last anti-lymphoma treatment | 0.63 (0.43, 0.94) | | 57/91 | 589 | 44/94 | 878 | 185 |
| BCL2/C.-11C > T: MND | >1 year since last anti-lymphoma treatment | 0.62 (0.44, 0.88) | | 73/112 | 560 | 55/112 | 878 | 233 |

APPENDIX 2, TABLE 2.12-continued

Time to Next Anti-Lymphoma Therapy by Somatic Mutation and by Covariate, IRC review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| BCL2/E29K: MND | >1 year since last anti-lymphoma treatment | 0.59 (0.39, 0.90) | | 52/82 | 550 | 39/83 | 883 | 185 |
| BCL2/R106H: MND | >1 year since last anti-lymphoma treatment | 0.57 (0.39, 0.83) | | 65/96 | 534 | 45/94 | 878 | 217 |
| NOTCH/P2513L: MND | >1 year since last anti-lymphoma treatment | 0.60 (0.39, 0.92) | | 50/78 | 560 | 37/81 | 878 | 213 |
| NOTCH/P2515FS4: MND | >1 year since last anti-lymphoma treatment | 0.65 (0.44, 0.94) | | 64/102 | 593 | 48/102 | 878 | 205 |
| NOTCH/Q2460X: MND | >1 year since last anti-lymphoma treatment | 0.66 (0.44, 0.99) | | 53/84 | 573 | 43/86 | 841 | 185 |
| NOTCH/X26INS: MND | >1 year since last anti-lymphoma treatment | 0.69 (0.48, 1.00) | | 62/102 | 643 | 54/110 | 883 | 212 |
| NOTCH/X28DEL: MND | >1 year since last anti-lymphoma treatment | 0.70 (0.49, 0.99) | | 70/112 | 589 | 58/116 | 872 | 236 |
| NOTCH/X28INS: MND | >1 year since last anti-lymphoma treatment | 0.64 (0.45, 0.90) | | 73/113 | 573 | 59/119 | 872 | 237 |
| BCL2/A43G: MND | European Union | 0.53 (0.33, 0.84) | | 41/66 | 649 | 32/72 | 1103 | 138 |
| BCL2/C.-11C > T: MND | European Union | 0.57 (0.38, 0.86) | | 53/79 | 505 | 41/83 | 983 | 169 |
| BCL2/E29K: MND | European Union | 0.58 (0.36, 0.94) | | 37/61 | 533 | 32/67 | 1075 | 138 |
| BCL2/P46L: MND | European Union | 0.58 (0.35, 0.96) | | 34/56 | 533 | 29/64 | 1185 | 139 |
| BCL2/P46S: MND | European Union | 0.59 (0.37, 0.94) | | 37/61 | 504 | 33/68 | 1075 | 136 |
| BCL2/P59S: MND | European Union | 0.60 (0.37, 0.96) | | 36/60 | 505 | 34/69 | 983 | 136 |

APPENDIX 2, TABLE 2.12-continued

Time to Next Anti-Lymphoma Therapy by Somatic Mutation and by Covariate, IRC review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| BCL2/Q52P: MND | European Union | 0.60 (0.38, 0.94) | | 38/63 | 504 | 36/73 | 983 | 136 |
| BCL2/R106H: MND | European Union | 0.57 (0.36, 0.89) | | 44/65 | 533 | 35/70 | 1005 | 160 |
| NOTCH/G_A1702P: MND | European Union | 0.61 (0.39, 0.95) | | 44/72 | 533 | 36/74 | 983 | 147 |
| NOTCH/I1681N: MND | European Union | 0.63 (0.40, 0.97) | | 44/72 | 533 | 37/75 | 983 | 147 |
| NOTCH/L1586Q: MND | European Union | 0.63 (0.40, 0.99) | | 40/66 | 505 | 36/72 | 983 | 138 |
| NOTCH/L1597H: MND | European Union | 0.63 (0.40, 0.99) | | 40/66 | 505 | 36/72 | 983 | 138 |
| NOTCH/L1679P: MND | European Union | 0.63 (0.40, 0.97) | | 44/72 | 533 | 37/75 | 983 | 147 |
| NOTCH/L1679Q: MND | European Union | 0.63 (0.40, 0.97) | | 44/72 | 533 | 37/75 | 983 | 147 |
| NOTCH/P2513L: MND | European Union | 0.47 (0.28, 0.80) | | 39/59 | 504 | 22/52 | — | 159 |
| NOTCH/P2515FS4: MND | European Union | 0.58 (0.38, 0.90) | | 48/77 | 533 | 36/77 | 1075 | 155 |
| NOTCH/R1599P: MND | European Union | 0.63 (0.40, 0.99) | | 40/66 | 505 | 36/72 | 983 | 138 |
| NOTCH/V1579E: MND | European Union | 0.63 (0.40, 0.99) | | 40/66 | 505 | 36/72 | 983 | 138 |
| NOTCH/X26DEL: MND | European Union | 0.64 (0.42, 0.99) | | 44/72 | 552 | 42/84 | 1005 | 159 |
| NOTCH/X26INS: MND | European Union | 0.63 (0.42, 0.96) | | 46/74 | 552 | 42/84 | 1005 | 159 |
| NOTCH/X28DEL: MND | European Union | 0.62 (0.41, 0.92) | | 53/82 | 533 | 45/87 | 983 | 177 |
| NOTCH/X28INS: MND | European Union | 0.61 (0.41, 0.90) | | 56/85 | 533 | 46/89 | 983 | 177 |
| BCL2/A43G: MND | ≤65 years old | 0.66 (0.48, 0.91) | | 84/124 | 484 | 65/115 | 743 | 239 |

APPENDIX 2, TABLE 2.12-continued

Time to Next Anti-Lymphoma Therapy by Somatic Mutation and by Covariate, IRC review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| BCL2/C.-11C > T: MND | ≤65 years old | 0.70 (0.52, 0.94) | | 101/147 | 484 | 81/135 | 718 | 296 |
| BCL2/E29K: MND | ≤65 years old | 0.60 (0.43, 0.85) | | 81/117 | 450 | 58/103 | 751 | 241 |
| BCL2/P46L: MND | ≤65 years old | 0.69 (0.48, 0.97) | | 71/105 | 485 | 59/104 | 743 | 238 |
| BCL2/P46S: MND | ≤65 years old | 0.71 (0.51, 0.99) | | 73/111 | 489 | 66/113 | 726 | 236 |
| BCL2/P59S: MND | ≤65 years old | 0.71 (0.51, 0.99) | | 74/110 | 489 | 68/114 | 726 | 235 |
| BCL2/Q52P: MND | ≤65 years old | 0.71 (0.51, 0.98) | | 78/117 | 485 | 69/117 | 726 | 234 |
| BCL2/R106H: MND | ≤65 years old | 0.61 (0.44, 0.84) | | 86/124 | 450 | 61/112 | 751 | 281 |
| NOTCH/G_A1702P: MND | ≤65 years old | 0.69 (0.51, 0.95) | | 91/133 | 462 | 71/121 | 719 | 255 |
| NOTCH/I1681N: MND | ≤65 years old | 0.70 (0.51, 0.96) | | 91/133 | 462 | 72/122 | 719 | 255 |
| NOTCH/L1679P: MND | ≤65 years old | 0.70 (0.51, 0.96) | | 91/133 | 462 | 72/122 | 719 | 255 |
| NOTCH/L1679Q: MND | ≤65 years old | 0.70 (0.51, 0.96) | | 91/133 | 462 | 72/122 | 719 | 255 |
| NOTCH/L2458V: MND | ≤65 years old | 0.71 (0.52, 0.98) | | 82/120 | 462 | 70/117 | 719 | 237 |
| NOTCH/P2513L: MND | ≤65 years old | 0.62 (0.43, 0.89) | | 74/107 | 462 | 50/90 | 751 | 269 |
| NOTCH/P2515FS4: MND | ≤65 years old | 0.67 (0.49, 0.92) | | 92/134 | 484 | 70/123 | 726 | 259 |
| NOTCH/Q2441X: MND | ≤65 years old | 0.72 (0.52, 0.99) | | 82/120 | 462 | 70/115 | 719 | 237 |
| NOTCH/Q2460X: MND | ≤65 years old | 0.68 (0.48, 0.95) | | 77/110 | 449 | 61/104 | 719 | 239 |
| NOTCH/X26DEL: MND | ≤65 years old | 0.70 (0.52, 0.95) | | 92/137 | 489 | 76/132 | 726 | 273 |

APPENDIX 2, TABLE 2.12-continued

Time to Next Anti-Lymphoma Therapy by Somatic Mutation and by Covariate, IRC review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| NOTCH/X26INS: MND | ≤65 years old | 0.70 (0.52, 0.95) | | 93/138 | 501 | 77/133 | 726 | 273 |
| NOTCH/X28DEL: MND | ≤65 years old | 0.68 (0.51, 0.90) | | 104/149 | 462 | 83/140 | 719 | 298 |
| NOTCH/X28INS: MND | ≤65 years old | 0.67 (0.50, 0.89) | | 106/149 | 462 | 85/143 | 718 | 298 |
| BCL2/P46L: MND | Female | 0.61 (0.39, 0.96) | | 51/86 | 535 | 31/68 | 1185 | 180 |
| BCL2/P59S: MND | Female | 0.65 (0.43, 1.00) | | 57/97 | 533 | 36/73 | 947 | 178 |
| BCL2/R106H: MND | Female | 0.65 (0.42, 0.99) | | 58/96 | 534 | 35/70 | 883 | 203 |
| BCL2/A43G: MND | Male | 0.55 (0.36, 0.82) | | 45/59 | 343 | 47/76 | 743 | 135 |
| BCL2/C.-11C > T: MND | Male | 0.62 (0.43, 0.90) | | 57/77 | 380 | 58/93 | 651 | 182 |
| BCL2/E29K: MND | Male | 0.51 (0.33, 0.77) | | 43/55 | 337 | 43/68 | 743 | 138 |
| BCL2/P46L: MD | Male | 0.11 (0.02, 0.63) | | 4/4 | 382 | 6/10 | 878 | 134 |
| BCL2/P46S: MND | Male | 0.64 (0.42, 0.99) | | 38/52 | 396 | 49/75 | 695 | 133 |
| BCL2/Q52P: MND | Male | 0.62 (0.41, 0.95) | | 39/53 | 396 | 50/78 | 695 | 131 |
| BCL2/R106H: MND | Male | 0.61 (0.41, 0.90) | | 50/66 | 396 | 49/81 | 695 | 169 |
| NOTCH/G_A1702P: MND | Male | 0.60 (0.40, 0.89) | | 47/63 | 337 | 51/81 | 726 | 145 |
| NOTCH/I1681N: MND | Male | 0.61 (0.41, 0.90) | | 47/63 | 337 | 52/82 | 695 | 145 |
| NOTCH/L1586Q: MND | Male | 0.65 (0.43, 0.98) | | 41/56 | 396 | 51/79 | 695 | 135 |
| NOTCH/L1597H: MND | Male | 0.65 (0.43, 0.98) | | 41/56 | 396 | 51/79 | 695 | 135 |

APPENDIX 2, TABLE 2.12-continued

Time to Next Anti-Lymphoma Therapy by Somatic Mutation and by Covariate, IRC review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| NOTCH/L1679P: MND | Male | 0.61 (0.41, 0.90) | | 47/63 | 337 | 52/82 | 695 | 145 |
| NOTCH/L1679Q: MND | Male | 0.61 (0.41, 0.90) | | 47/63 | 337 | 52/82 | 695 | 145 |
| NOTCH/L2458V: MND | Male | 0.60 (0.40, 0.91) | | 44/59 | 337 | 51/80 | 695 | 139 |
| NOTCH/P2513L: MND | Male | 0.52 (0.33, 0.82) | | 41/54 | 343 | 37/63 | 791 | 155 |
| NOTCH/P2515FS4: MND | Male | 0.57 (0.38, 0.85) | | 47/62 | 380 | 51/84 | 743 | 148 |
| NOTCH/Q2441X: MND | Male | 0.61 (0.40, 0.91) | | 44/59 | 337 | 51/79 | 695 | 139 |
| NOTCH/Q2460X: MD | Male | 0.14 (0.03, 0.71) | | 3/3 | 127 | 8/12 | 645 | 142 |
| NOTCH/Q2460X: MND | Male | 0.60 (0.39, 0.93) | | 42/57 | 343 | 43/70 | 726 | 142 |
| NOTCH/R1599P: MND | Male | 0.65 (0.43, 0.98) | | 41/56 | 396 | 51/79 | 695 | 135 |
| NOTCH/V1579E: MND | Male | 0.65 (0.43, 0.98) | | 41/56 | 396 | 51/79 | 695 | 135 |
| NOTCH/X26DEL: MND | Male | 0.58 (0.39, 0.85) | | 49/65 | 396 | 58/95 | 726 | 162 |
| NOTCH/X26INS: MND | Male | 0.56 (0.38, 0.82) | | 50/66 | 396 | 58/95 | 743 | 162 |
| NOTCH/X28DEL: MND | Male | 0.63 (0.44, 0.91) | | 56/75 | 396 | 61/97 | 695 | 180 |
| NOTCH/X28INS: MND | Male | 0.62 (0.44, 0.89) | | 59/78 | 396 | 63/100 | 651 | 181 |
| BCL2/A43G: MND | White | 0.67 (0.49, 0.91) | | 89/140 | 504 | 76/139 | 834 | 279 |
| BCL2/C.-11C > T: MND | White | 0.70 (0.53, 0.93) | | 110/168 | 504 | 90/158 | 726 | 342 |
| BCL2/E29K: MND | White | 0.63 (0.46, 0.87) | | 83/129 | 485 | 70/127 | 834 | 282 |

APPENDIX 2, TABLE 2.12-continued

Time to Next Anti-Lymphoma Therapy by Somatic Mutation and by Covariate, IRC review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| BCL2/P46L: MND | White | 0.68 (0.49, 0.95) | | 74/117 | 505 | 68/125 | 791 | 279 |
| BCL2/P46S: MND | White | 0.70 (0.51, 0.96) | | 81/130 | 505 | 74/131 | 834 | 275 |
| BCL2/P59L: MND | White | 0.72 (0.52, 0.99) | | 80/129 | 533 | 69/123 | 791 | 278 |
| BCL2/P59S: MND | White | 0.68 (0.50, 0.94) | | 81/128 | 505 | 73/130 | 834 | 274 |
| BCL2/Q52P: MND | White | 0.69 (0.50, 0.94) | | 85/135 | 504 | 77/137 | 834 | 272 |
| BCL2/R106H: MND | White | 0.68 (0.50, 0.92) | | 93/140 | 501 | 77/135 | 743 | 327 |
| NOTCH/G_A1702P: MND | White | 0.72 (0.54, 0.97) | | 97/152 | 504 | 82/143 | 743 | 295 |
| NOTCH/I1681N: MND | White | 0.72 (0.54, 0.97) | | 97/152 | 504 | 82/143 | 743 | 295 |
| NOTCH/L1679P: MND | White | 0.72 (0.54, 0.97) | | 97/152 | 504 | 82/143 | 743 | 295 |
| NOTCH/L1679Q: MND | White | 0.72 (0.54, 0.97) | | 97/152 | 504 | 82/143 | 743 | 295 |
| NOTCH/L2458V: MND | White | 0.73 (0.54, 0.99) | | 89/140 | 504 | 81/139 | 743 | 279 |
| NOTCH/P2513L: MND | White | 0.67 (0.48, 0.94) | | 78/122 | 504 | 59/108 | 841 | 319 |
| NOTCH/P2515FS4: MND | White | 0.68 (0.50, 0.91) | | 99/154 | 505 | 81/148 | 834 | 304 |
| NOTCH/Q2441X: MND | White | 0.74 (0.54, 1.00) | | 88/139 | 501 | 81/137 | 726 | 279 |
| NOTCH/Q2460X: MND | White | 0.70 (0.51, 0.96) | | 85/131 | 501 | 73/127 | 743 | 284 |
| NOTCH/X26DEL: MND | White | 0.73 (0.55, 0.97) | | 99/155 | 505 | 91/158 | 751 | 321 |
| NOTCH/X26INS: MND | White | 0.72 (0.54, 0.96) | | 101/159 | 533 | 92/160 | 751 | 321 |

APPENDIX 2, TABLE 2.12-continued

Time to Next Anti-Lymphoma Therapy by Somatic Mutation and by Covariate, IRC review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| NOTCH/X28DEL: MND | White | 0.73 (0.55, 0.95) | | 111/169 | 504 | 98/167 | 726 | 351 |
| NOTCH/X28INS: MND | White | 0.70 (0.53, 0.92) | | 115/174 | 504 | 99/171 | 743 | 352 |
| BCL2/A43G: MND | Ann Arbor Stage IV | 0.60 (0.40, 0.91) | | 48/71 | 450 | 42/83 | 658 | 154 |
| BCL2/C.-11C > T: MND | Ann Arbor Stage IV | 0.64 (0.44, 0.93) | | 60/84 | 450 | 54/100 | 639 | 193 |
| BCL2/E29K: MND | Ann Arbor Stage IV | 0.59 (0.38, 0.91) | | 46/67 | 450 | 37/73 | 651 | 154 |
| BCL2/P46L: MND | Ann Arbor Stage IV | 0.62 (0.39, 0.99) | | 35/52 | 449 | 38/74 | 651 | 148 |
| BCL2/P59L: MD | Ann Arbor Stage IV | 0.17 (0.03, 0.88) | | 3/5 | 182 | 8/12 | 725 | 149 |
| BCL2/R106H: MND | Ann Arbor Stage IV | 0.59 (0.39, 0.89) | | 50/72 | 449 | 42/83 | 651 | 186 |
| NOTCH/G_A1702P: MND | Ann Arbor Stage IV | 0.61 (0.41, 0.90) | | 52/75 | 428 | 47/87 | 649 | 163 |
| NOTCH/I1681N: MND | Ann Arbor Stage IV | 0.62 (0.42, 0.92) | | 52/75 | 428 | 48/88 | 649 | 163 |
| NOTCH/L1679P: MND | Ann Arbor Stage IV | 0.62 (0.42, 0.92) | | 52/75 | 428 | 48/88 | 649 | 163 |
| NOTCH/L1679Q: MND | Ann Arbor Stage IV | 0.62 (0.42, 0.92) | | 52/75 | 428 | 48/88 | 649 | 163 |
| NOTCH/L2458V: MND | Ann Arbor Stage IV | 0.63 (0.42, 0.95) | | 46/68 | 434 | 46/86 | 651 | 154 |
| NOTCH/P2513L: MND | Ann Arbor Stage IV | 0.55 (0.35, 0.87) | | 42/61 | 449 | 34/69 | 791 | 176 |
| NOTCH/P2515FS4: MND | Ann Arbor Stage IV | 0.59 (0.39, 0.87) | | 51/74 | 434 | 46/91 | 658 | 167 |
| NOTCH/Q2441X: MND | Ann Arbor Stage IV | 0.63 (0.42, 0.95) | | 46/68 | 434 | 46/85 | 651 | 154 |
| NOTCH/Q2460X: MND | Ann Arbor Stage IV | 0.61 (0.39, 0.93) | | 43/64 | 449 | 41/79 | 658 | 156 |

APPENDIX 2, TABLE 2.12-continued

Time to Next Anti-Lymphoma Therapy by Somatic Mutation and by Covariate, IRC review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| NOTCH/X26DEL: MND | Ann Arbor Stage IV | 0.63 (0.43, 0.93) | | 53/76 | 457 | 54/101 | 651 | 180 |
| NOTCH/X26INS: MND | Ann Arbor Stage IV | 0.63 (0.43, 0.91) | | 54/79 | 450 | 54/101 | 651 | 180 |
| NOTCH/X28DEL: MND | Ann Arbor Stage IV | 0.63 (0.44, 0.91) | | 61/85 | 449 | 56/103 | 644 | 195 |
| NOTCH/X28INS: MND | Ann Arbor Stage IV | 0.60 (0.42, 0.86) | | 64/87 | 434 | 57/105 | 644 | 196 |

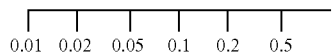

0.01  0.02  0.05  0.1  0.2  0.5

APPENDIX 2, TABLE 2.13

Treatment Free Interval by Protein Expression and by Covariate, IRC Review.
(All Reported Groups are Significant ( p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| CD68 OVERALL POSITIVE: 0-25 | No Subgroup | 0.42 (0.23, 0.75) | | 30/44 | 269 | 19/41 | 883 | 442 |
| CD68 POSITIVE FOLLICULAR: 0-25 | No Subgroup | 0.56 (0.34, 0.90) | | 40/60 | 307 | 29/51 | 671 | 387 |
| CD68 POSITIVE PERIFOLLICULAR: 0-25 | No Subgroup | 0.49 (0.27, 0.89) | | 26/39 | 234 | 20/41 | 924 | 384 |
| P65 % POSITIVE CYTOPLASMIC SIGNAL: >90% | No Subgroup | 0.77 (0.60, 1.00) | | 129/204 | 363 | 108/186 | 581 | 470 |
| CD68 POSITIVE PERIFOLLICULAR: >75 | 1 Prior Line of Therapy | 0.45 (0.20, 1.01) | | 15/18 | 297 | 10/16 | 587 | 174 |
| P27 % NUCLEI POSITIVE: 0-20 | 1 Prior Line of Therapy | 0.40 (0.16, 1.01) | | 19/26 | 293 | 6/16 | 883 | 204 |
| P65 % NUCLEAR STAINING: 0 | 1 Prior Line of Therapy | 0.66 (0.43, 0.99) | | 54/79 | 406 | 39/73 | 673 | 203 |
| P65 % POSITIVE CYTOPLASMIC SIGNAL: >90% | 1 Prior Line of Therapy | 0.63 (0.43, 0.93) | | 59/89 | 409 | 47/88 | 673 | 203 |
| P65 INTENSITY CYTOPLASMIC SIGNAL: ≥2+ | 1 Prior Line of Therapy | 0.66 (0.45, 0.98) | | 54/85 | 427 | 47/91 | 673 | 203 |
| CD68 OVERALL POSITIVE: 0-25 | 2 Prior Lines of Therapy | 0.20 (0.04, 1.02) | | 6/8 | 80 | 2/7 | 844 | 111 |

APPENDIX 2, TABLE 2.13-continued

Treatment Free Interval by Protein Expression and by Covariate, IRC Review.
(All Reported Groups are Significant ( p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| CD68 POSITIVE PERIFOLLICULAR: 0-25 | 2 Prior Lines of Therapy | 0.09 (0.01, 0.81) | | 6/8 | 64 | 1/7 | — | 98 |
| P65 % NUCLEAR STAINING: ≤5% | 2 Prior Lines of Therapy | 0.32 (0.11, 0.96) | | 7/9 | 85 | 7/12 | 542 | 125 |
| P27 % NUCLEI POSITIVE: 60-70 | 3 Prior Lines of Therapy | 8.31 (0.95, 72.50) | | 1/6 | — | 5/5 | 65 | 74 |
| P27 SIGNAL INTENSITY: ≥2+ | 5 Prior Lines of Therapy | 0.22 (0.04, 1.13) | | 5/6 | 88 | 3/8 | 778 | 16 |
| P65 % NUCLEAR STAINING: ≤5% | 5 Prior Lines of Therapy | 0.13 (0.01, 1.34) | | 3/3 | 95 | 2/4 | 1058 | 16 |
| CD68 OVERALL POSITIVE: 0-25 | No High Tumor Burden | 0.23 (0.07, 0.80) | | 8/14 | 411 | 5/19 | — | 204 |
| CD68 OVERALL POSITIVE: 51-75 | No High Tumor Burden | 2.33 (1.00, 5.41) | | 10/25 | — | 12/18 | 349 | 204 |
| CD68 POSITIVE FOLLICULAR: 0-25 | No High Tumor Burden | 0.40 (0.18, 0.91) | | 14/22 | 432 | 12/15 | 1058 | 182 |
| CD68 POSITIVE PERIFOLLICULAR: 0-25 | No High Tumor Burden | 0.23 (0.07, 0.78) | | 8/13 | 361 | 5/16 | 1058 | 182 |
| P27 % NUCLEI POSITIVE: 30-50 | High Tumor Burden | 0.49 (0.24, 1.01) | | 17/22 | 280 | 13/25 | 483 | 248 |
| P27 SIGNAL INTENSITY: ≤1+ | High Tumor Burden | 0.45 (0.20, 1.00) | | 16/18 | 122 | 11/17 | 818 | 248 |
| CD68 OVERALL POSITIVE: 0-25 | Intermediate FLIPI Score | 0.27 (0.08, 0.98) | | 7/11 | 343 | 5/15 | 1058 | 159 |
| CD68 POSITIVE PERIFOLLICULAR: 0-25 | Intermediate FLIPI Score | 0.27 (0.08, 0.95) | | 7/13 | 361 | 5/17 | 1058 | 139 |
| CD68 OVERALL POSITIVE: 0-25 | Low FLIPI Score | 0.32 (0.10, 1.01) | | 8/10 | 281 | 5/11 | 907 | 102 |
| CD68 OVERALL POSITIVE: 0-25 | No Prior Rituximab Therapy | 0.38 (0.15, 0.99) | | 12/19 | 393 | 7/21 | 942 | 241 |
| CD68 POSITIVE FOLLICULAR: 0-25 | No Prior Rituximab Therapy | 0.41 (0.19, 0.87) | | 23/36 | 344 | 10/25 | 942 | 210 |
| CD68 POSITIVE PERIFOLLICULAR: 0-25 | No Prior Rituximab Therapy | 0.33 (0.12, 0.97) | | 12/18 | 393 | 5/15 | — | 208 |
| 20S % NUCLEAR STAINING 60-70 | Prior Rituximab Therapy | 0.40 (0.16, 1.02) | | 17/21 | 190 | 6/12 | 907 | 212 |

APPENDIX 2, TABLE 2.13-continued

Treatment Free Interval by Protein Expression and by Covariate, IRC Review.
(All Reported Groups are Significant ( p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| CD68 OVERALL POSITIVE: 0-25 | Prior Rituximab Therapy | 0.42 (0.20, 0.90) | | 18/25 | 115 | 12/20 | 671 | 201 |
| P27 SIGNAL INTENSITY: ≥2+ | Prior Rituximab Therapy | 0.67 (0.46, 0.98) | | 60/88 | 272 | 48/85 | 554 | 210 |
| P65 % NUCLEAR STAINING: ≤5% | Prior Rituximab Therapy | 0.31 (0.14, 0.67) | | 16/21 | 93 | 13/27 | 818 | 215 |
| CD68 OVERALL POSITIVE: 0-25 | >1 year since last anti-lymphoma treatment | 0.27 (0.12, 0.63) | | 17/26 | 269 | 9/28 | 1058 | 269 |
| CD68 POSITIVE FOLLICULAR: 0-25 | >1 year since last anti-lymphoma treatment | 0.50 (0.26, 0.97) | | 22/34 | 409 | 16/33 | 907 | 235 |
| CD68 POSITIVE PERIFOLLICULAR: 0-25 | >1 year since last anti-lymphoma treatment | 0.42 (0.19, 0.92) | | 15/24 | 393 | 11/27 | 1058 | 234 |
| 20S INTENSITY CYTOPLASMIC SIGNAL: ≥3+ | European Union | 0.59 (0.35, 0.99) | | 34/52 | 393 | 25/52 | 907 | 214 |
| CD68 OVERALL POSITIVE: 0-25 | European Union | 0.41 (0.18, 0.92) | | 14/22 | 234 | 11/25 | 942 | 211 |
| CD68 POSITIVE PERIFOLLICULAR: >75 | European Union | 0.37 (0.14, 1.00) | | 13/17 | 533 | 7/14 | 1023 | 185 |
| CD68 OVERALL POSITIVE: 0-25 | ≤65 years old | 0.39 (0.20, 0.76) | | 24/34 | 234 | 15/32 | 844 | 329 |
| CD68 POSITIVE FOLLICULAR: 0-25 | ≤65 years old | 0.46 (0.27, 0.78) | | 33/46 | 190 | 24/41 | 603 | 292 |
| CD68 POSITIVE PERIFOLLICULAR: 0-25 | ≤65 years old | 0.50 (0.24, 1.01) | | 20/31 | 143 | 13/29 | 907 | 289 |
| CD68 POSITIVE PERIFOLLICULAR: >75 | ≤65 years old | 0.46 (0.22, 0.94) | | 19/23 | 297 | 13/23 | 587 | 289 |
| P27 % NUCLEI POSITIVE: 0-20 | ≤65 years old | 0.53 (0.29, 0.97) | | 26/34 | 187 | 19/32 | 671 | 344 |
| P65 % NUCLEAR STAINING: ≤5% | ≤65 years old | 0.54 (0.29, 1.00) | | 19/29 | 234 | 22/43 | 818 | 349 |
| P65 % POSITIVE CYTOPLASMIC SIGNAL: >90% | ≤65 years old | 0.73 (0.55, 0.97) | | 103/154 | 343 | 84/142 | 557 | 349 |
| P65 INTENSITY CYTOPLASMIC SIGNAL: ≥2+ | ≤65 years old | 0.74 (0.55, 0.99) | | 101/152 | 343 | 82/139 | 554 | 349 |

APPENDIX 2, TABLE 2.13-continued

Treatment Free Interval by Protein Expression and by Covariate, IRC Review.
(All Reported Groups are Significant ( p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| 20S % NUCLEAR STAINING 0-20 | Female | 0.55 (0.32, 0.97) | ⊢•⊣ | 35/61 | 427 | 19/49 | — | 259 |
| CD68 OVERALL POSITIVE: 0-25 | Female | 0.28 (0.10, 0.76) | ⊢•⊣ | 16/26 | 293 | 5/18 | 942 | 242 |
| CD68 POSITIVE FOLLICULAR: 0-25 | Female | 0.46 (0.22, 0.96) | ⊢•⊣ | 23/37 | 307 | 10/22 | 942 | 217 |
| CD68 POSITIVE PERIFOLLICULAR: 0-25 | Female | 0.28 (0.10, 0.77) | ⊢•⊣ | 19/28 | 234 | 5/17 | 942 | 215 |
| 20S % NUCLEAR STAINING 60-70 | Male | 0.43 (0.20, 0.95) | ⊢•⊣ | 14/16 | 110 | 12/20 | 390 | 204 |
| CD68 OVERALL POSITIVE: >75 | Male | 0.25 (0.07, 0.87) | ⊢•⊣ | 8/9 | 272 | 4/11 | — | 200 |
| CD68 POSITIVE FOLLICULAR: 0-25 | Asian | 0.13 (0.02, 1.17) | ⊢•⊣ | 5/6 | 148 | 2/6 | — | 30 |
| CD68 POSITIVE PERIFOLLICULAR: 26-50 | Other | 0.14 (0.01, 1.31) | ⊢—•—⊣ | 4/4 | 217 | 4/5 | 495 | 22 |
| CD68 OVERALL POSITIVE: 0-25 | White | 0.38 (0.20, 0.73) | ⊢•⊣ | 24/35 | 269 | 16/35 | 907 | 385 |
| CD68 POSITIVE FOLLICULAR: 0-25 | White | 0.59 (0.35, 1.00) | ⊢•⊣ | 32/48 | 307 | 25/42 | 671 | 335 |
| CD68 POSITIVE PERIFOLLICULAR: 0-25 | White | 0.43 (0.23, 0.83) | ⊢•⊣ | 19/27 | 361 | 19/39 | 924 | 332 |
| P65 % POSITIVE CYTOPLASMIC SIGNAL: >90% | White | 0.76 (0.58, 1.00) | ⊢•⊣ | 113/179 | 363 | 95/162 | 587 | 406 |
| CD68 OVERALL POSITIVE: 0-25 | Ann Arbor Stage III | 0.36 (0.14, 0.92) | ⊢•⊣ | 12/16 | 135 | 9/12 | 745 | 144 |
| CD68 POSITIVE FOLLICULAR: 0-25 | Ann Arbor Stage III | 0.44 (0.21, 0.90) | ⊢•⊣ | 19/24 | 190 | 13/18 | 603 | 135 |
| P27 % NUCLEI POSITIVE: 0-20 | Ann Arbor Stage III | 0.42 (0.17, 1.00) | ⊢•⊣ | 14/16 | 275 | 12/15 | 449 | 149 |
| P65 INTENSITY CYTOPLASMIC SIGNAL: ≤1+ | Ann Arbor Stage III | 0.38 (0.14, 1.02) | ⊢•⊣ | 10/11 | 119 | 7/11 | 671 | 151 |
| CD68 OVERALL POSITIVE: 0-25 | Ann Arbor Stage IV | 0.39 (0.16, 0.97) | ⊢•⊣ | 15/22 | 293 | 8/23 | 883 | 222 |
| CD68 POSITIVE PERIFOLLICULAR: 0-25 | Ann Arbor Stage IV | 0.37 (0.14, 0.96) | ⊢•⊣ | 11/15 | 234 | 8/22 | 924 | 183 |

APPENDIX 2, TABLE 2.13-continued

Treatment Free Interval by Protein Expression and by Covariate, IRC Review.
(All Reported Groups are Significant ( p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| | | | 0.01  0.1  1  10 | | | | | |

APPENDIX 2, TABLE 2.14

Treatment Free Interval by Germline Genetic Variant and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| PSMB1/A171S: G/G | No Subgroup | 0.80 (0.65, 1.00) | | 173/276 | 406 | 152/266 | 581 | 542 |
| PSMB1/I208N: T/T | No Subgroup | 0.80 (0.65, 1.00) | | 173/276 | 406 | 152/266 | 581 | 542 |
| PSMB1/P11A: C/G | No Subgroup | 0.69 (0.50, 0.97) | | 78/127 | 409 | 63/115 | 778 | 542 |
| PSMB1/P193L: C/C | No Subgroup | 0.80 (0.65, 1.00) | | 173/276 | 406 | 152/266 | 581 | 542 |
| PSMB2/E49X: G/G | No Subgroup | 0.80 (0.65, 1.00) | | 173/276 | 406 | 152/266 | 581 | 542 |
| PSMB2/G187V: G/G | No Subgroup | 0.80 (0.65, 1.00) | | 173/276 | 406 | 152/266 | 581 | 542 |
| PSMB2/L159F: C/C | No Subgroup | 0.80 (0.65, 1.00) | | 173/276 | 406 | 152/266 | 581 | 542 |
| PSMB5/L206M: C/C | No Subgroup | 0.80 (0.65, 1.00) | | 173/276 | 406 | 152/266 | 581 | 542 |
| PSMB6/A234D: C/C | No Subgroup | 0.80 (0.65, 1.00) | | 173/276 | 406 | 152/266 | 581 | 542 |
| PSMB8/G8R: G/G | No Subgroup | 0.79 (0.63, 0.99) | | 165/264 | 396 | 144/256 | 581 | 542 |
| PSMB8/R141C: C/C | No Subgroup | 0.80 (0.65, 1.00) | | 173/276 | 406 | 152/266 | 581 | 542 |
| PSMB8/V182M: G/G | No Subgroup | 0.80 (0.65, 1.00) | | 173/276 | 406 | 152/266 | 581 | 542 |
| PSMB1/P11A: C/G | 1 Prior Line of Therapy | 0.58 (0.35, 0.97) | | 32/51 | 480 | 27/55 | 883 | 231 |
| PSMB1/P11A: G/G | 1 Prior Line of Therapy | 0.37 (0.14, 0.98) | | 11/11 | 302 | 7/14 | 522 | 231 |

APPENDIX 2, TABLE 2.14-continued

Treatment Free Interval by Germline Genetic Variant and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| PSMB8/G8R: G/G | 1 Prior Line of Therapy | 0.70 (0.49, 0.99) | | 69/109 | 533 | 55/111 | 690 | 231 |
| PSMB1/A171S: G/G | 5 Prior Lines of Therapy | 0.29 (0.08, 1.01) | | 7/9 | 95 | 6/12 | 778 | 21 |
| PSMB1/I208N: T/T | 5 Prior Lines of Therapy | 0.29 (0.08, 1.01) | | 7/9 | 95 | 6/12 | 778 | 21 |
| PSMB1/P193L: C/C | 5 Prior Lines of Therapy | 0.29 (0.08, 1.01) | | 7/9 | 95 | 6/12 | 778 | 21 |
| PSMB2/E49X: G/G | 5 Prior Lines of Therapy | 0.29 (0.08, 1.01) | | 7/9 | 95 | 6/12 | 778 | 21 |
| PSMB2/G187V: G/G | 5 Prior Lines of Therapy | 0.29 (0.08, 1.01) | | 7/9 | 95 | 6/12 | 778 | 21 |
| PSMB2/L159F: C/C | 5 Prior Lines of Therapy | 0.29 (0.08, 1.01) | | 7/9 | 95 | 6/12 | 778 | 21 |
| PSMB5/L206M: C/C | 5 Prior Lines of Therapy | 0.29 (0.08, 1.01) | | 7/9 | 95 | 6/12 | 778 | 21 |
| PSMB5/R24C: C/C | 5 Prior Lines of Therapy | 0.17 (0.03, 0.86) | | 6/7 | 95 | 4/9 | 1058 | 21 |
| PSMB6/A234D: C/C | 5 Prior Lines of Therapy | 0.29 (0.08, 1.01) | | 7/9 | 95 | 6/12 | 778 | 21 |
| PSMB6/P107A: C/C | 5 Prior Lines of Therapy | 0.29 (0.08, 1.01) | | 7/9 | 95 | 6/12 | 778 | 21 |
| PSMB8/G8R: G/G | 5 Prior Lines of Therapy | 0.29 (0.08, 1.01) | | 7/9 | 95 | 6/11 | 778 | 21 |
| PSMB8/R141C: C/C | 5 Prior Lines of Therapy | 0.29 (0.08, 1.01) | | 7/9 | 95 | 6/12 | 778 | 21 |
| PSMB8/V182M: G/G | 5 Prior Lines of Therapy | 0.29 (0.08, 1.01) | | 7/9 | 95 | 6/12 | 778 | 21 |
| PSMB9/G9E: G/G | 5 Prior Lines of Therapy | 0.29 (0.08, 1.01) | | 7/9 | 95 | 6/12 | 778 | 21 |
| PSMB9/V32I: C/C | 5 Prior Lines of Therapy | 0.25 (0.07, 0.87) | | 7/8 | 88 | 5/11 | 1058 | 21 |
| PSMB1/A171S: G/G | High Tumor Burden | 0.75 (0.57, 0.99) | | 108/147 | 234 | 98/149 | 366 | 296 |
| PSMB1/I208N: T/T | High Tumor Burden | 0.75 (0.57, 0.99) | | 108/147 | 234 | 98/149 | 366 | 296 |

APPENDIX 2, TABLE 2.14-continued

Treatment Free Interval by Germline Genetic Variant and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| PSMB1/P11A: C/G | High Tumor Burden | 0.65 (0.42, 1.00) | ⊢•⊣ | 49/72 | 218 | 38/65 | 499 | 296 |
| PSMB1/P193L: C/C | High Tumor Burden | 0.75 (0.57, 0.99) | ⊢•⊣ | 108/147 | 234 | 98/149 | 366 | 296 |
| PSMB2/E49X: G/G | High Tumor Burden | 0.75 (0.57, 0.99) | ⊢•⊣ | 108/147 | 234 | 98/149 | 366 | 296 |
| PSMB2/G187V: G/G | High Tumor Burden | 0.75 (0.57, 0.99) | ⊢•⊣ | 108/147 | 234 | 98/149 | 366 | 296 |
| PSMB2/L159F: C/C | High Tumor Burden | 0.75 (0.57, 0.99) | ⊢•⊣ | 108/147 | 234 | 98/149 | 366 | 296 |
| PSMB5/L206M: C/C | High Tumor Burden | 0.75 (0.57, 0.99) | ⊢•⊣ | 108/147 | 234 | 98/149 | 366 | 296 |
| PSMB5/R24C: C/T | High Tumor Burden | 0.48 (0.25, 0.93) | ⊢•⊣ | 19/21 | 148 | 18/24 | 391 | 296 |
| PSMB6/A234D: C/C | High Tumor Burden | 0.75 (0.57, 0.99) | ⊢•⊣ | 108/147 | 234 | 98/149 | 366 | 296 |
| PSMB6/P107A: C/C | High Tumor Burden | 0.76 (0.57, 1.00) | ⊢•⊣ | 104/140 | 234 | 97/146 | 365 | 296 |
| PSMB8/G8R: G/G | High Tumor Burden | 0.71 (0.54, 0.94) | ⊢•⊣ | 104/140 | 218 | 94/145 | 390 | 296 |
| PSMB8/R141C: C/C | High Tumor Burden | 0.75 (0.57, 0.99) | ⊢•⊣ | 108/147 | 234 | 98/149 | 366 | 296 |
| PSMB8/V182M: G/G | High Tumor Burden | 0.75 (0.57, 0.99) | ⊢•⊣ | 108/147 | 234 | 98/149 | 366 | 296 |
| PSMB9/G9E: G/G | High Tumor Burden | 0.75 (0.57, 0.99) | ⊢•⊣ | 107/147 | 234 | 98/148 | 365 | 296 |
| PSMB9/V32I: C/C | High Tumor Burden | 0.74 (0.56, 0.98) | ⊢•⊣ | 106/142 | 234 | 94/142 | 366 | 296 |
| PSMB1/A171S: G/G | >1 year since last anti-lymphoma treatment | 0.71 (0.53, 0.95) | ⊢•⊣ | 98/165 | 547 | 80/166 | 800 | 331 |
| PSMB1/I208N: T/T | >1 year since last anti-lymphoma treatment | 0.71 (0.53, 0.95) | ⊢•⊣ | 98/165 | 547 | 80/166 | 800 | 331 |
| PSMB1/P193L: C/C | >1 year since last anti-lymphoma treatment | 0.71 (0.53, 0.95) | ⊢•⊣ | 98/165 | 547 | 80/166 | 800 | 331 |

APPENDIX 2, TABLE 2.14-continued

Treatment Free Interval by Germline Genetic Variant and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc − R Evt/N | Vc − R Median | Marker: Subgroup N Total |
|---|---|---|---|---|---|---|---|---|
| PSMB2/E49X: G/G | >1 year since last anti-lymphoma treatment | 0.71 (0.53, 0.95) | | 98/165 | 547 | 80/166 | 800 | 331 |
| PSMB2/G187V: G/G | >1 year since last anti-lymphoma treatment | 0.71 (0.53, 0.95) | | 98/165 | 547 | 80/166 | 800 | 331 |
| PSMB2/L159F: C/C | >1 year since last anti-lymphoma treatment | 0.71 (0.53, 0.95) | | 98/165 | 547 | 80/166 | 800 | 331 |
| PSMB5/L206M: C/C | >1 year since last anti-lymphoma treatment | 0.71 (0.53, 0.95) | | 98/165 | 547 | 80/166 | 800 | 331 |
| PSMB5/R24C: C/C | >1 year since last anti-lymphoma treatment | 0.72 (0.52, 1.00) | | 81/137 | 507 | 68/141 | 843 | 331 |
| PSMB6/A234D: C/C | >1 year since last anti-lymphoma treatment | 0.71 (0.53, 0.95) | | 98/165 | 547 | 80/166 | 800 | 331 |
| PSMB6/P107A: C/C | >1 year since last anti-lymphoma treatment | 0.72 (0.53, 0.97) | | 95/159 | 561 | 79/162 | 800 | 331 |
| PSMB8/G8R: G/G | >1 year since last anti-lymphoma treatment | 0.71 (0.52, 0.96) | | 91/155 | 562 | 74/159 | 843 | 331 |
| PSMB8/R141C: C/C | >1 year since last anti-lymphoma treatment | 0.71 (0.53, 0.95) | | 98/165 | 547 | 80/166 | 800 | 331 |
| PSMB8/V182M: G/G | >1 year since last anti-lymphoma treatment | 0.71 (0.53, 0.95) | | 98/165 | 547 | 80/166 | 800 | 331 |
| PSMB9/G9E: G/G | >1 year since last anti-lymphoma treatment | 0.71 (0.53, 0.95) | | 97/163 | 547 | 80/165 | 800 | 331 |
| PSMB9/V32I: C/C | >1 year since last anti-lymphoma treatment | 0.70 (0.51, 0.94) | | 96/160 | 507 | 76/158 | 800 | 331 |
| PSMB1/P11A: C/G | European Union | 0.56 (0.34, 0.93) | | 34/49 | 309 | 29/51 | 844 | 241 |
| PSMB1/A171S: G/G | ≤65 years old | 0.74 (0.57, 0.95) | | 130/198 | 344 | 112/194 | 557 | 392 |
| PSMB1/I208N: T/T | ≤65 years old | 0.74 (0.57, 0.95) | | 130/198 | 344 | 112/194 | 557 | 392 |

APPENDIX 2, TABLE 2.14-continued

Treatment Free Interval by Germline Genetic Variant and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| PSMB1/P11A: C/G | ≤65 years old | 0.63 (0.43, 0.92) | | 63/96 | 406 | 47/86 | 603 | 392 |
| PSMB1/P11A: G/G | ≤65 years old | 0.42 (0.22, 0.81) | | 21/25 | 269 | 16/30 | 671 | 392 |
| PSMB1/P193L: C/C | ≤65 years old | 0.74 (0.57, 0.95) | | 130/198 | 344 | 112/194 | 557 | 392 |
| PSMB2/E49X: G/G | ≤65 years old | 0.74 (0.57, 0.95) | | 130/198 | 344 | 112/194 | 557 | 392 |
| PSMB2/G187V: G/G | ≤65 years old | 0.74 (0.57, 0.95) | | 130/198 | 344 | 112/194 | 557 | 392 |
| PSMB2/L159F: C/C | ≤65 years old | 0.74 (0.57, 0.95) | | 130/198 | 344 | 112/194 | 557 | 392 |
| PSMB5/L206M: C/C | ≤65 years old | 0.74 (0.57, 0.95) | | 130/198 | 344 | 112/194 | 557 | 392 |
| PSMB5/R24C: C/C | ≤65 years old | 0.73 (0.56, 0.96) | | 113/170 | 344 | 97/167 | 581 | 392 |
| PSMB6/A234D: C/C | ≤65 years old | 0.74 (0.57, 0.95) | | 130/198 | 344 | 112/194 | 557 | 392 |
| PSMB6/P107A: C/C | ≤65 years old | 0.74 (0.57, 0.96) | | 125/189 | 363 | 110/190 | 554 | 392 |
| PSMB8/G8R: G/G | ≤65 years old | 0.74 (0.57, 0.96) | | 123/189 | 344 | 106/186 | 581 | 392 |
| PSMB8/R141C: C/C | ≤65 years old | 0.74 (0.57, 0.95) | | 130/198 | 344 | 112/194 | 557 | 392 |
| PSMB8/V182M: G/G | ≤65 years old | 0.74 (0.57, 0.95) | | 130/198 | 344 | 112/194 | 557 | 392 |
| PSMB9/G9E: G/G | ≤65 years old | 0.74 (0.57, 0.95) | | 129/196 | 344 | 112/193 | 557 | 392 |
| PSMB9/V32I: C/C | ≤65 years old | 0.74 (0.57, 0.96) | | 127/192 | 344 | 107/186 | 554 | 392 |
| PSMB1/P11A: C/G | Female | 0.59 (0.37, 0.95) | | 42/75 | 406 | 30/66 | 924 | 301 |
| PSMB9/R60H: A/G | Male | 0.45 (0.25, 0.79) | | 22/28 | 234 | 30/48 | 603 | 241 |
| PSMB1/P11A: C/G | Other | 0.09 (0.01, 1.06) | | 2/3 | 76 | 6/9 | 394 | 27 |

APPENDIX 2, TABLE 2.14-continued

Treatment Free Interval by Germline Genetic Variant and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| PSMB1/P11A: C/G | White | 0.69 (0.48, 0.99) | | 67/111 | 432 | 54/97 | 818 | 473 |
| PSMB1/P11A: G/G | White | 0.57 (0.33, 0.98) | | 27/32 | 272 | 25/39 | 449 | 473 |
| PSMB1/P11A: C/G | Ann Arbor Stage III | 0.53 (0.28, 0.98) | | 29/44 | 206 | 16/28 | 818 | 172 |

APPENDIX 2, TABLE 2.15

Treatment-Free Interval by Somatic Mutation and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| BCL2/A43G: MND | No Subgroup | 0.67 (0.50, 0.90) | | 104/161 | 344 | 84/154 | 649 | 315 |
| BCL2/C.-11C > T: MND | No Subgroup | 0.72 (0.56, 0.94) | | 127/192 | 361 | 102/179 | 587 | 390 |
| BCL2/E29K: MND | No Subgroup | 0.65 (0.48, 0.87) | | 98/150 | 343 | 77/139 | 649 | 318 |
| BCL2/P46L: MND | No Subgroup | 0.72 (0.53, 0.98) | | 86/135 | 362 | 77/139 | 595 | 314 |
| BCL2/P59S: MND | No Subgroup | 0.73 (0.54, 0.99) | | 92/145 | 362 | 84/147 | 629 | 309 |
| BCL2/Q52P: MND | No Subgroup | 0.73 (0.55, 0.97) | | 97/153 | 361 | 88/154 | 629 | 307 |
| BCL2/R106H: MND | No Subgroup | 0.68 (0.51, 0.90) | | 108/162 | 344 | 84/151 | 629 | 372 |
| NOTCH/G_A1702P: MND | No Subgroup | 0.74 (0.57, 0.98) | | 113/175 | 361 | 93/161 | 589 | 337 |
| NOTCH/I1681N: MND | No Subgroup | 0.75 (0.57, 0.99) | | 113/175 | 361 | 94/162 | 587 | 337 |
| NOTCH/L1679P: MND | No Subgroup | 0.75 (0.57, 0.99) | | 113/175 | 361 | 94/162 | 587 | 337 |
| NOTCH/L1679Q: MND | No Subgroup | 0.75 (0.57, 0.99) | | 113/175 | 361 | 94/162 | 587 | 337 |

APPENDIX 2, TABLE 2.15-continued

Treatment-Free Interval by Somatic Mutation and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| NOTCH/P2513L: MND | No Subgroup | 0.71 (0.52, 0.97) | | 90/140 | 360 | 67/123 | 649 | 361 |
| NOTCH/P2515FS4: MND | No Subgroup | 0.71 (0.54, 0.94) | | 114/176 | 361 | 92/166 | 629 | 344 |
| NOTCH/Q2460X: MND | No Subgroup | 0.74 (0.55, 0.99) | | 98/151 | 344 | 82/143 | 589 | 324 |
| NOTCH/X26DEL: MND | No Subgroup | 0.76 (0.58, 0.99) | | 112/175 | 363 | 102/178 | 595 | 361 |
| NOTCH/X26INS: MND | No Subgroup | 0.75 (0.58, 0.99) | | 114/179 | 363 | 103/180 | 595 | 361 |
| NOTCH/X28DEL: MND | No Subgroup | 0.74 (0.57, 0.96) | | 128/194 | 361 | 109/189 | 583 | 400 |
| NOTCH/X28INS: MND | No Subgroup | 0.72 (0.56, 0.93) | | 132/198 | 361 | 112/195 | 583 | 401 |
| BCL2/A43G: MND | 1 Prior Line of Therapy | 0.55 (0.35, 0.88) | | 46/72 | 409 | 30/67 | 907 | 139 |
| BCL2/C.-11C > T: MND | 1 Prior Line of Therapy | 0.63 (0.42, 0.95) | | 57/86 | 427 | 38/78 | 827 | 170 |
| BCL2/E29K: MND | 1 Prior Line of Therapy | 0.56 (0.34, 0.90) | | 41/64 | 406 | 29/62 | 828 | 139 |
| BCL2/P46L: MND | 1 Prior Line of Therapy | 0.61 (0.38, 1.00) | | 37/58 | 449 | 30/63 | 828 | 140 |
| BCL2/P46S: MND | 1 Prior Line of Therapy | 0.62 (0.39, 0.99) | | 40/64 | 409 | 33/68 | 828 | 138 |
| BCL2/Q52P: MND | 1 Prior Line of Therapy | 0.63 (0.40, 0.99) | | 42/67 | 409 | 35/71 | 827 | 138 |
| BCL2/R106H: MND | 1 Prior Line of Therapy | 0.59 (0.38, 0.92) | | 49/73 | 409 | 33/68 | 828 | 162 |
| NOTCH/P2515FS4: MND | 1 Prior Line of Therapy | 0.64 (0.41, 0.99) | | 48/75 | 432 | 35/72 | 827 | 149 |
| NOTCH/X28INS: MND | 1 Prior Line of Therapy | 0.65 (0.44, 0.96) | | 56/84 | 427 | 45/88 | 673 | 178 |
| BCL2/A43G: MND | No High Tumor Burden | 0.61 (0.38, 1.00) | | 42/78 | 632 | 27/64 | — | 142 |
| BCL2/R106H: MND | No High Tumor Burden | 0.61 (0.38, 0.99) | | 46/79 | 549 | 26/58 | 1023 | 163 |
| NOTCH/P2513L: MD | No High Tumor Burden | 0.45 (0.20, 1.01) | | 17/26 | 452 | 9/21 | — | 163 |

APPENDIX 2, TABLE 2.15-continued

Treatment-Free Interval by Somatic Mutation and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| NOTCH/X28INS: MND | No High Tumor Burden | 0.64 (0.42, 0.98) | | 55/98 | 592 | 37/82 | 924 | 184 |
| BCL2/A43G: MND | High Tumor Burden | 0.62 (0.43, 0.89) | | 62/83 | 234 | 57/90 | 379 | 173 |
| BCL2/C.-11C > T: MND | High Tumor Burden | 0.68 (0.49, 0.94) | | 76/101 | 234 | 69/107 | 326 | 217 |
| BCL2/E29K: MND | High Tumor Burden | 0.57 (0.40, 0.84) | | 60/79 | 234 | 52/82 | 392 | 174 |
| BCL2/P46L: MND | High Tumor Burden | 0.59 (0.40, 0.87) | | 51/67 | 234 | 51/83 | 379 | 173 |
| BCL2/P46S: MND | High Tumor Burden | 0.64 (0.44, 0.94) | | 52/73 | 234 | 56/89 | 337 | 170 |
| BCL2/P59L: MND | High Tumor Burden | 0.67 (0.45, 0.99) | | 52/72 | 254 | 50/80 | 318 | 172 |
| BCL2/P59S: MND | High Tumor Burden | 0.63 (0.43, 0.93) | | 53/73 | 254 | 54/87 | 379 | 170 |
| BCL2/Q52P: MND | High Tumor Burden | 0.63 (0.44, 0.92) | | 55/76 | 234 | 58/92 | 379 | 168 |
| BCL2/R106H: MND | High Tumor Burden | 0.61 (0.43, 0.88) | | 62/83 | 234 | 58/93 | 392 | 209 |
| NOTCH/G_A1702P: MND | High Tumor Burden | 0.64 (0.45, 0.91) | | 67/90 | 234 | 62/96 | 379 | 187 |
| NOTCH/I1681N: MND | High Tumor Burden | 0.65 (0.46, 0.92) | | 67/90 | 234 | 63/97 | 379 | 187 |
| NOTCH/L1586Q: MND | High Tumor Burden | 0.67 (0.47, 0.97) | | 56/78 | 254 | 60/94 | 379 | 172 |
| NOTCH/L1597H: MND | High Tumor Burden | 0.67 (0.47, 0.97) | | 56/78 | 254 | 60/94 | 379 | 172 |
| NOTCH/L1679P: MND | High Tumor Burden | 0.65 (0.46, 0.92) | | 67/90 | 234 | 63/97 | 379 | 187 |
| NOTCH/L1679Q: MND | High Tumor Burden | 0.65 (0.46, 0.92) | | 67/90 | 234 | 63/97 | 379 | 187 |
| NOTCH/L2458V: MND | High Tumor Burden | 0.66 (0.46, 0.94) | | 61/83 | 234 | 61/95 | 379 | 178 |
| NOTCH/P2513L: MND | High Tumor Burden | 0.56 (0.37, 0.83) | | 58/76 | 234 | 43/71 | 392 | 198 |

APPENDIX 2, TABLE 2.15-continued

Treatment-Free Interval by Somatic Mutation and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| NOTCH/P2515FS4: MND | High Tumor Burden | 0.63 (0.45, 0.90) | | 67/90 | 234 | 61/98 | 379 | 189 |
| NOTCH/Q2441X: MND | High Tumor Burden | 0.66 (0.46, 0.94) | | 61/83 | 234 | 61/95 | 379 | 178 |
| NOTCH/Q2460X: MND | High Tumor Burden | 0.63 (0.43, 0.91) | | 59/79 | 234 | 54/87 | 392 | 181 |
| NOTCH/R1599P: MND | High Tumor Burden | 0.67 (0.47, 0.97) | | 56/78 | 254 | 60/94 | 379 | 172 |
| NOTCH/V1579E: MND | High Tumor Burden | 0.67 (0.47, 0.97) | | 56/78 | 254 | 60/94 | 379 | 172 |
| NOTCH/X26DEL: MND | High Tumor Burden | 0.69 (0.49, 0.98 | | 63/88 | 254 | 68/107 | 379 | 198 |
| NOTCH/X26INS: MND | High Tumor Burden | 0.68 (0.49, 0.96) | | 64/89 | 254 | 68/107 | 379 | 198 |
| NOTCH/X28DEL: MND | High Tumor Burden | 0.67 (0.48, 0.92) | | 74/99 | 234 | 72/111 | 326 | 216 |
| NOTCH/X28INS: MND | High Tumor Burden | 0.67 (0.49, 0.92) | | 77/100 | 190 | 75/113 | 318 | 217 |
| BCL2/A43G: MND | Intermediate FLIPI Score | 0.60 (0.36, 1.00) | | 34/53 | 362 | 26/52 | 778 | 105 |
| BCL2/C.-11C > T: MND | Intermediate FLIPI Score | 0.60 (0.38, 0.95) | | 44/66 | 362 | 33/63 | 778 | 136 |
| BCL2/R106H: MND | Intermediate FLIPI Score | 0.52 (0.32, 0.84) | | 40/55 | 361 | 28/54 | 671 | 130 |
| BCL2/E29K: MND | No Prior Rituximab Therapy | 0.66 (0.44, 0.98) | | 57/93 | 393 | 41/76 | 718 | 186 |
| BCL2/P59L: MD | No Prior Rituximab Therapy | 0.17 (0.03, 0.91) | | 3/5 | 217 | 7/13 | 779 | 178 |
| BCL2/A43G: MND | Prior Rituximab Therapy | 0.62 (0.40, 0.96) | | 44/63 | 287 | 37/69 | 589 | 132 |
| BCL2/C.-11C > T: MND | Prior Rituximab Therapy | 0.60 (0.40, 0.89) | | 57/78 | 254 | 43/77 | 554 | 165 |
| BCL2/E29K: MND | Prior Rituximab Therapy | 0.62 (0.39, 0.97) | | 41/57 | 287 | 36/63 | 581 | 132 |
| BCL2/P59S: MND | Prior Rituximab Therapy | 0.63 (0.40, 0.98) | | 39/56 | 307 | 37/69 | 589 | 133 |
| BCL2/R106H: MND | Prior Rituximab Therapy | 0.57 (0.38, 0.88) | | 50/67 | 272 | 39/72 | 581 | 159 |

APPENDIX 2, TABLE 2.15-continued

Treatment-Free Interval by Somatic Mutation and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| NOTCH/G_A1702P: MND | Prior Rituximab Therapy | 0.62 (0.41, 0.94) | | 51/72 | 288 | 41/74 | 589 | 147 |
| NOTCH/I1681N: MND | Prior Rituximab Therapy | 0.64 (0.42, 0.96) | | 51/72 | 288 | 42/75 | 581 | 147 |
| NOTCH/L1679P: MND | Prior Rituximab Therapy | 0.64 (0.42, 0.96) | | 51/72 | 288 | 42/75 | 581 | 147 |
| NOTCH/L1679Q: MND | Prior Rituximab Therapy | 0.64 (0.42, 0.96) | | 51/72 | 288 | 42/75 | 581 | 147 |
| NOTCH/L2458V: MND | Prior Rituximab Therapy | 0.63 (0.41, 0.96) | | 47/66 | 302 | 42/75 | 581 | 141 |
| NOTCH/P2513L: MND | Prior Rituximab Therapy | 0.59 (0.36, 0.98) | | 39/57 | 307 | 25/51 | 649 | 154 |
| NOTCH/P2515FS4: MND | Prior Rituximab Therapy | 0.63 (0.42, 0.96) | | 51/72 | 288 | 42/77 | 581 | 149 |
| NOTCH/Q2441X: MND | Prior Rituximab Therapy | 0.63 (0.42, 0.97) | | 47/66 | 302 | 42/73 | 581 | 141 |
| NOTCH/Q2460X: MND | Prior Rituximab Therapy | 0.60 (0.39, 0.93) | | 45/62 | 288 | 36/66 | 589 | 143 |
| NOTCH/X26INS: MND | Prior Rituximab Therapy | 0.66 (0.45, 0.98) | | 52/74 | 288 | 47/84 | 581 | 158 |
| NOTCH/X28DEL: MND | Prior Rituximab Therapy | 0.64 (0.43, 0.93) | | 60/83 | 280 | 49/86 | 554 | 175 |
| NOTCH/X28INS: MND | Prior Rituximab Therapy | 0.62 (0.43, 0.91) | | 62/86 | 280 | 50/88 | 554 | 175 |
| BCL2/A43G: MND | >1 year since last anti-lymphoma treatment | 0.65 (0.44, 0.96) | | 57/91 | 449 | 44/94 | 716 | 185 |
| BCL2/C.-11C > T: MND | >1 year since last anti-lymphoma treatment | 0.64 (0.45, 0.90) | | 73/112 | 419 | 55/112 | 716 | 233 |
| BCL2/E29K: MND | >1 year since last anti-lymphoma treatment | 0.60 (0.40, 0.91) | | 52/82 | 409 | 39/83 | 718 | 185 |
| BCL2/R106H: MND | >1 year since last anti-lymphoma treatment | 0.58 (0.40, 0.85) | | 65/96 | 392 | 45/94 | 716 | 217 |
| NOTCH/P2513L: MND | >1 year since last anti-lymphoma treatment | 0.61 (0.40, 0.94) | | 50/78 | 419 | 37/81 | 716 | 213 |

APPENDIX 2, TABLE 2.15-continued

Treatment-Free Interval by Somatic Mutation and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| NOTCH/P2515FS4: MND | >1 year since last anti-lymphoma treatment | 0.66 (0.45, 0.96) | | 64/102 | 452 | 48/102 | 716 | 205 |
| NOTCH/X28INS: MND | >1 year since last anti-lymphoma treatment | 0.66 (0.47, 0.93) | | 73/113 | 432 | 59/119 | 709 | 237 |
| BCL2/A43G: MND | European Union | 0.54 (0.34, 0.86) | | 41/66 | 507 | 32/72 | 942 | 138 |
| BCL2/C.-11C > T: MND | European Union | 0.58 (0.38, 0.87) | | 53/79 | 363 | 41/83 | 843 | 169 |
| BCL2/E29K: MND | European Union | 0.60 (0.37, 0.96) | | 37/61 | 393 | 32/67 | 907 | 138 |
| BCL2/P46L: MND | European Union | 0.59 (0.36, 0.97) | | 34/56 | 393 | 29/64 | 1023 | 139 |
| BCL2/P46S: MND | European Union | 0.60 (0.37, 0.96) | | 37/61 | 362 | 33/68 | 907 | 136 |
| BCL2/P59S: MND | European Union | 0.61 (0.38, 0.97) | | 36/60 | 363 | 34/69 | 843 | 136 |
| BCL2/Q52P: MND | European Union | 0.61 (0.38, 0.96) | | 38/63 | 362 | 36/73 | 843 | 136 |
| BCL2/R106H: MND | European Union | 0.58 (0.37, 0.90) | | 44/65 | 393 | 35/70 | 844 | 160 |
| NOTCH/G_A1702P: MND | European Union | 0.62 (0.40, 0.96) | | 44/72 | 393 | 36/74 | 843 | 147 |
| NOTCH/I1681N: MND | European Union | 0.64 (0.41, 0.99) | | 44/72 | 393 | 37/75 | 843 | 147 |
| NOTCH/L1679P: MND | European Union | 0.64 (0.41, 0.99) | | 44/72 | 393 | 37/75 | 843 | 147 |
| NOTCH/L1679Q: MND | European Union | 0.64 (0.41, 0.99) | | 44/72 | 393 | 37/75 | 843 | 147 |
| NOTCH/P2513L: MND | European Union | 0.48 (0.28, 0.81) | | 39/59 | 362 | 22/52 | 942 | 159 |
| NOTCH/P2515FS4: MND | European Union | 0.59 (0.38, 0.91) | | 48/77 | 393 | 36/77 | 907 | 155 |
| NOTCH/X26INS: MND | European Union | 0.64 (0.42, 0.98) | | 46/74 | 411 | 42/84 | 844 | 159 |
| NOTCH/X28DEL: MND | European Union | 0.63 (0.42, 0.94) | | 53/82 | 393 | 45/87 | 843 | 177 |

APPENDIX 2, TABLE 2.15-continued

Treatment-Free Interval by Somatic Mutation and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| NOTCH/X28INS: MND | European Union | 0.62 (0.42, 0.91) | | 56/85 | 393 | 46/89 | 843 | 177 |
| BCL2/A43G: MND | ≤65 years old | 0.67 (0.48, 0.93) | | 84/124 | 343 | 65/115 | 595 | 239 |
| BCL2/C.-11C > T: MND | ≤65 years old | 0.72 (0.54, 0.96) | | 101/147 | 341 | 81/135 | 554 | 296 |
| BCLW/E29K: MND | ≤65 years old | 0.61 (0.44, 0.86) | | 81/117 | 307 | 58/103 | 649 | 241 |
| BCL2/P46L: MND | ≤65 years old | 0.70 (0.49, 0.99) | | 71/105 | 344 | 59/104 | 589 | 238 |
| BCL2/Q52P: MND | ≤65 years old | 0.72 (0.52, 1.00) | | 78/117 | 344 | 69/117 | 589 | 234 |
| BCL2/R106H: MND | ≤65 years old | 0.62 (0.44, 0.86) | | 86/124 | 309 | 61/112 | 649 | 281 |
| NOTCH/G_A1702P: MND | ≤65 years old | 0.71 (0.52, 0.96) | | 91/133 | 309 | 71/121 | 587 | 255 |
| NOTCH/I1681N: MND | ≤65 years old | 0.72 (0.52, 0.98) | | 91/133 | 309 | 72/122 | 581 | 255 |
| NOTCH/L1679P: MND | ≤65 years old | 0.72 (0.52, 0.98) | | 91/133 | 309 | 72/122 | 581 | 255 |
| NOTCH/L1679Q: MND | ≤65 years old | 0.72 (0.52, 0.98) | | 91/133 | 309 | 72/122 | 581 | 255 |
| NOTCH/L2458V: MND | ≤65 years old | 0.73 (0.53, 1.00) | | 82/120 | 309 | 70/117 | 581 | 237 |
| NOTCH/P2513L: MND | ≤65 years old | 0.63 (0.44, 0.91) | | 74/107 | 309 | 50/90 | 649 | 269 |
| NOTCH/P2515FS4: MND | ≤65 years old | 0.68 (0.50, 0.93) | | 92/134 | 341 | 70/123 | 589 | 259 |
| NOTCH/Q2460X: MND | ≤65 years old | 0.69 (0.49, 0.96) | | 77/110 | 307 | 61/104 | 581 | 239 |
| NOTCH/X26DEL: MND | ≤65 years old | 0.71 (0.53, 0.97) | | 92/137 | 344 | 76/132 | 595 | 273 |
| NOTCH/X26INS: MND | ≤65 years old | 0.72 (0.53, 0.97) | | 93/138 | 344 | 77/133 | 589 | 273 |
| NOTCH/X28DEL: MND | ≤65 years old | 0.69 0.52, 0.93) | | 104/149 | 309 | 83/140 | 581 | 298 |
| NOTCH/X28INS: MND | ≤65 years old | 0.68 (0.51, 0.91) | | 106/149 | 309 | 85/143 | 554 | 298 |

APPENDIX 2, TABLE 2.15-continued

Treatment-Free Interval by Somatic Mutation and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| BCL2/P46L: MND | Female | 0.62 (0.40, 0.98) | | 51/86 | 393 | 31/68 | 1023 | 180 |
| BCL2/A43G: MND | Male | 0.56 (0.37, 0.84) | | 45/59 | 215 | 47/76 | 587 | 135 |
| BCL2/C.-11C > T: MND | Male | 0.63 (0.44, 0.92) | | 57/77 | 234 | 58/93 | 534 | 182 |
| BCL2/E29K: MND | Male | 0.52 (0.34, 0.79) | | 43/55 | 190 | 43/68 | 587 | 138 |
| BCL2/P46L: MD | Male | 0.11 (0.02, 0.63) | | 4/4 | 244 | 6/10 | 716 | 134 |
| BCL2/Q52P: MND | Male | 0.64 (0.42, 0.98) | | 39/53 | 254 | 50/78 | 543 | 131 |
| BCL2/R106H: MND | Male | 0.62 (0.42, 0.93) | | 50/66 | 254 | 49/81 | 543 | 169 |
| NOTCH/G_A1702P: MND | Male | 0.61 (0.41, 0.91) | | 47/63 | 190 | 51/81 | 581 | 145 |
| NOTCH/I1681N: MND | Male | 0.62 (0.42, 0.92) | | 47/63 | 190 | 52/82 | 543 | 145 |
| NOTCH/L1679P: MND | Male | 0.62 (0.42, 0.92) | | 47/63 | 190 | 52/82 | 543 | 145 |
| NOTCH/L1679Q: MND | Male | 0.62 (0.42, 0.92) | | 47/63 | 190 | 52/82 | 543 | 145 |
| NOTCH/L2458V: MND | Male | 0.62 (0.41, 0.93) | | 44/59 | 190 | 51/80 | 543 | 139 |
| NOTCH/P2513L: MND | Male | 0.54 (0.35, 0.85) | | 41/54 | 190 | 37/63 | 629 | 155 |
| NOTCH/P2515FS4: MND | Male | 0.58 (0.39, 0.87) | | 47/62 | 234 | 51/84 | 587 | 148 |
| NOTCH/Q2441X: MND | Male | 0.62 (0.41, 0.93) | | 44/59 | 190 | 51/79 | 543 | 139 |
| NOTCH/Q2460X: MD | Male | 0.14 (0.03, 0.71) | | 3/3 | 55 | 8/12 | 504 | 142 |

APPENDIX 2, TABLE 2.15-continued

Treatment-Free Interval by Somatic Mutation and by Covariate, IRC Review.
(All Reported Groups are Significant (p ≤ 0.05) and at a Frequency of ≥ 10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| NOTCH/Q2460X: MND | Male | 0.62 (0.40, 0.95) | | 42/57 | 190 | 43/70 | 581 | 142 |
| NOTCH/X26DEL: MND | Male | 0.59 (0.40, 0.87) | | 49/65 | 254 | 58/95 | 583 | 162 |
| NOTCH/X26INS: MND | Male | 0.57 (0.39, 0.84) | | 50/66 | 234 | 58/95 | 583 | 162 |
| NOTCH/X28DEL: MND | Male | 0.65 (0.45, 0.94) | | 56/75 | 254 | 61/97 | 543 | 180 |
| NOTCH/X28INS: MND | Male | 0.64 (0.45, 0.91) | | 59/78 | 234 | 63/100 | 534 | 181 |
| BCL2/A43G: MND | White | 0.68 (0.50, 0.93) | | 89/140 | 361 | 76/139 | 671 | 279 |
| BCL2/C.-11C > T: MND | White | 0.72 (0.54, 0.95) | | 110/168 | 362 | 90/158 | 589 | 342 |
| BCL2/E29K: MND | White | 0.64 (0.47, 0.88) | | 83/129 | 344 | 70/127 | 671 | 282 |
| BCL2/P46L: MND | White | 0.70 (0.50, 0.97) | | 74/117 | 363 | 68/125 | 649 | 279 |
| BCL2/P46S: MND | White | 0.71 (0.52, 0.98) | | 81/130 | 363 | 74/131 | 671 | 275 |
| BCL2/P59S: MND | White | 0.70 (0.51, 0.96) | | 81/128 | 363 | 73/130 | 671 | 274 |
| BCL2/Q52P: MND | White | 0.70 (0.51, 0.96) | | 85/135 | 362 | 77/137 | 671 | 272 |
| BCL2/R106H: MND | White | 0.70 (0.51, 0.94) | | 93/140 | 361 | 77/135 | 629 | 327 |
| NOTCH/G_A1702P: MND | White | 0.73 (0.55, 0.99) | | 97/152 | 362 | 82/143 | 629 | 295 |
| NOTCH/I1681N: MND | White | 0.73 (0.55, 0.99) | | 97/152 | 362 | 82/143 | 629 | 295 |
| NOTCH/L1679P: MND | White | 0.73 (0.55, 0.99) | | 97/152 | 362 | 82/143 | 629 | 295 |
| NOTCH/L1679Q: MND | White | 0.73 (0.55, 0.99) | | 97/152 | 362 | 82/143 | 629 | 295 |

APPENDIX 2, TABLE 2.15-continued

Treatment-Free Interval by Somatic Mutation and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| NOTCH/P2513L: MND | White | 0.69 (0.49, 0.96) | | 78/122 | 362 | 59/108 | 673 | 319 |
| NOTCH/P2515FS4: MND | White | 0.69 (0.51, 0.93) | | 99/154 | 363 | 81/148 | 671 | 304 |
| NOTCH/Q2460X: MND | White | 0.71 (0.52, 0.98) | | 85/131 | 361 | 73/127 | 589 | 284 |
| NOTCH/X26DEL: MND | White | 0.75 (0.56, 0.99) | | 99/155 | 363 | 91/158 | 649 | 321 |
| NOTCH/X26INS: MND | White | 0.74 (0.56, 0.98) | | 101/159 | 392 | 92/160 | 649 | 321 |
| NOTCH/X28DEL: MND | White | 0.75 (0.57, 0.98) | | 111/169 | 362 | 98/167 | 587 | 351 |
| NOTCH/X28INS: MND | White | 0.72 (0.55, 0.94) | | 115/174 | 362 | 99/171 | 589 | 352 |
| BCL2/A43G: MND | Ann Arbor Stage IV | 0.62 (0.41, 0.93) | | 48/71 | 309 | 42/83 | 495 | 154 |
| BCL2/C.-11C > T: MND | Ann Arbor Stage IV | 0.66 (0.46, 0.95) | | 60/84 | 309 | 54/100 | 471 | 193 |
| BCL2/E29K: MND | Ann Arbor Stage IV | 0.60 (0.39, 0.93) | | 46/67 | 307 | 37/73 | 490 | 154 |
| BCL2/P59L: MD | Ann Arbor Stage IV | 0.19 (0.03, 1.00) | | 3/5 | 145 | 8/12 | 562 | 149 |
| BCL2/R106H: MND | Ann Arbor Stage IV | 0.60 (0.40, 0.91) | | 50/72 | 307 | 42/83 | 490 | 186 |
| NOTCH/G_A1702P: MND | Ann Arbor Stage IV | 0.62 (0.42, 0.93) | | 52/75 | 287 | 47/87 | 487 | 163 |
| NOTCH/I1681N: MND | Ann Arbor Stage IV | 0.64 (0.43, 0.94) | | 52/75 | 287 | 48/88 | 487 | 163 |
| NOTCH/L1679P: MND | Ann Arbor Stage IV | 0.64 (0.43, 0.94) | | 52/75 | 287 | 48/88 | 487 | 163 |
| NOTCH/L1679Q: MND | Ann Arbor Stage IV | 0.64 (0.43, 0.94) | | 52/75 | 287 | 48/88 | 487 | 163 |

APPENDIX 2, TABLE 2.15-continued

Treatment-Free Interval by Somatic Mutation and by Covariate, IRC Review.
(All Reported Groups are Significant (p ≤ 0.05) and at a Frequency of ≥10%)

| Marker: Level | Subgroup | HR (95% CI) | HR (log scale) | R Evt/N | R Median | Vc – R Evt/N | Vc – R Median | Marker: Subgroup N Total |
|---|---|---|---|---|---|---|---|---|
| NOTCH/L2458V: MND | Ann Arbor Stage IV | 0.65 (0.43, 0.98) | | 46/68 | 293 | 46/86 | 490 | 154 |
| NOTCH/P2513L: MND | Ann Arbor Stage IV | 0.57 (0.36, 0.90) | | 42/61 | 307 | 34/69 | 629 | 176 |
| NOTCH/P2515FS4: MND | Ann Arbor Stage IV | 0.60 (0.40, 0.90) | | 51/74 | 293 | 46/91 | 495 | 167 |
| NOTCH/Q2441X: MND | Ann Arbor Stage IV | 0.65 (0.43, 0.98) | | 46/68 | 293 | 46/85 | 490 | 154 |
| NOTCH/Q2460X: MND | Ann Arbor Stage IV | 0.63 (0.41, 0.96) | | 43/64 | 307 | 41/79 | 495 | 156 |
| NOTCH/X26DEL: MND | Ann Arbor Stage IV | 0.65 (0.45, 0.95) | | 53/76 | 317 | 54/101 | 490 | 180 |
| NOTCH/X26INS: MND | Ann Arbor Stage IV | 0.65 (0.44, 0.94) | | 54/79 | 309 | 54/101 | 490 | 180 |
| NOTCH/X28DEL: MND | Ann Arbor Stage IV | 0.66 (0.46, 0.94) | | 61/85 | 307 | 56/103 | 483 | 195 |
| NOTCH/X28INS: MND | Ann Arbor Stage IV | 0.62 (0.43, 0.89) | | 64/87 | 293 | 57/105 | 183 | 196 |

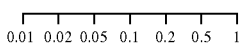

0.01 0.02 0.05 0.1 0.2 0.5 1

APPENDIX 3

Pair-Wise Combinations of Markers

The following table outlines the data for all significant pair-wise combinations.

Note: Selected=Biomarker positive, Not Selected=Biomarker negative

APPENDIX 3, TABLE 3.1

Significant Pair-Wise Combinations

| Marker A Type | Marker A | Marker A Level | Marker B Type | Marker B | Marker B Level | Combination | N Selected | N Excluded | N Unevaluable | N (Vc-R vs R) | % of ITT | Median PFS (Vc-R vs R) | PFS Difference | % PFS Difference | PFS Logrank P-value | PFS HR | Median OS (Vc-R vs R) | Median OS Logrank P-value | OS HR |
|---|---|---|---|---|---|---|---|---|---|---|---|---|---|---|---|---|---|---|---|
| B_D NA | PSMB1/P11A | C/G | Protein | CD68 POSITIVE FOLLICULAR | 0-50 | Selected | 118 | 238 | 319 | N: 57 vs 61 | % in ITT: 17.5% | 506d vs 277d | 229 | (82.7% improvement) | P-value = 1e-04 | HR = 0.407 (0.266-0.639) | NAd vs NAd | 0.0550 | 0.426 (0.174-1.046) |
| B_D NA | PSMB1/P11A | C/G | Protein | CD68 POSITIVE FOLLICULAR | 0-50 | Excluded | 118 | 238 | 319 | N: 118 vs 120 | % in ITT: 35.3% | 380d vs 381d | -1 | (-0.3% improvement) | P-value = 0.8097 | HR = 1.04 (0.759-1.425) | NAd vs NAd | 0.9645 | 1.011 (0.617-1.658) |
| B_D NA | PSMB1/P11A | C/G | Protein | CD68 POSITIVE FOLLICULAR | 0-50 | Total | 118 | 238 | 319 | N: 175 vs 181 | % in ITT: 52.7% | 414d vs 345d | 69 | (20% improvement) | P-value = 0.0855 | HR = 0.801 (0.621-1.032) | NAd vs NAd | 0.3270 | 0.808 (0.527-1.239) |
| B_D NA | PSMB5/R24C | C/T | Protein | P65 INTENSITY CYTOPLASMIC SIGNAL | ≤1+ | Selected | 12 | 425 | 238 | N: 5 vs 7 | % in ITT: 1.8% | 827d vs 314.5d | 512.5 | (163% improvement) | P-value = 0.0439 | HR = 0.149 (0.018-1.253) | NAd vs 717d | 0.3026 | 0.333 (0.037-2.994) |
| B_D NA | PSMB5/R24C | C/T | Protein | P65 INTENSITY CYTOPLASMIC SIGNAL | ≤1+ | Excluded | 12 | 425 | 238 | N: 208 vs 217 | % in ITT: 63% | 406d vs 338d | 68 | (20.1% improvement) | P-value = 0.0641 | HR = 0.803 (0.637-1.013) | NAd vs NAd | 0.9151 | 0.979 (0.663-1.446) |
| B_D NA | PSMB5/R24C | C/T | Protein | P65 INTENSITY CYTOPLASMIC SIGNAL | ≤1+ | Total | 12 | 425 | 238 | N: 213 vs 224 | % in ITT: 64.7% | 414d vs 338d | 76 | (22.5% improvement) | P-value = 0.0354 | HR = 0.782 (0.622-0.984) | NAd vs Nad | 0.7048 | 0.929 (0.634-1.36) |
| B_D NA | PSMB1/P11A | C/G | Protein | 20S % POSITIVE CYTOPLASMIC SIGNAL | 95-100 | Selected | 100 | 330 | 245 | N: 50 vs 50 | % in ITT: 14.8% | 576d vs 288d | 288 | (100% improvement) | P-value = 0.0145 | HR = 0.543 (0.33-0.894) | NAd vs NAd | 0.0949 | 0.516 (0.234-1.138) |
| B_D NA | PSMB1/P11A | C/G | Protein | 20S % POSITIVE CYTOPLASMIC SIGNAL | 95-100 | Excluded | 100 | 330 | 245 | N: 159 vs 171 | % in ITT: 48.9% | 355d vs 346d | 9 | (2.6% improvement) | P-value = 0.3458 | HR= 0.882 (0.679-1.145) | NAd vs NAd | 0.5966 | 1.127 (0.723-1.758) |
| B_D NA | PSMB1/P11A | C/G | Protein | 20S % POSITIVE CYTOPLASMIC SIGNAL | 95-100 | Total | 100 | 330 | 245 | N: 209 vs 221 | % in ITT: 63.7% | 406d vs 345d | 61 | (17.7% improvement) | P-value = 0.0397 | HR= 0.785 (0.624-0.989) | NAd vs NAd | 0.7080 | 0.929 (0.632-1.365) |
| Clinical | PRIORITX | 1 | Protein | CD68 POSITIVE FOLLICULAR | 0-50 | Selected | 132 | 254 | 289 | N: 63 vs 69 | % in ITT: 19.6% | 553d vs 282d | 271 | (96.1% improvement) | P-value = 0.0129 | HR= 0.567 (0.36-0.893) | NAd vs NAd | 0.3616 | 0.675 (0.288-1.58) |
| Clinical | PRIORITX | 1 | Protein | CD68 POSITIVE FOLLICULAR | 0-50 | Excluded | 132 | 254 | 289 | N: 127 vs | % in ITT: 37.6% | 346d vs 348d | -2 | (-0.6% improvement) | P-value = 0.9957 | HR = 1 (0.746- | NAd vs NAd | 0.6993 | 0.91 (0.566-1.466) |

APPENDIX 3, TABLE 3.1-continued

Significant Pair-Wise Combinations

| Marker A Type | Marker A | Marker A Level | Marker B Type | Marker B | Marker B Level | Combination | N Selected | N Excluded | N Un-evaluable | N (Vc-R vs R) | % of ITT | Median PFS (Vc-R vs R) | PFS Difference | % PFS Difference | PFS Logrank P-value | PFS HR | Median OS (Vc-R vs R) | OS Log-rank P-value | OS HR |
|---|---|---|---|---|---|---|---|---|---|---|---|---|---|---|---|---|---|---|---|
| Clinical | PRIORTX | 1 | Protein | CD68 POSITIVE FOLLICULAR | 0-50 | Total | 132 | 254 | 289 | N: 127 190 vs 196 | % in ITT: 57.2% | 396d vs 346d | 50 | (14.5% improvement) | P-value = 0.1781 | HR = 0.846 (0.663-1.08) 1.339) | NAd vs NAd | 0.4068 | 0.839 (0.554-1.27) |
| B_D NA | PSMB1/P11A | C/G | Clinical | TLAST | >1 year | Selected | 146 | 396 | 133 | N: 72 vs 74 | % in ITT: 21.6% | 554d vs 322d | 232 | (72% improvement) | P-value = 0.0198 | HR = 0.615 (0.407-0.929) | NAd vs NAd | 0.8289 | 1.091 (0.498-2.391) |
| B_D NA | PSMB1/P11A | C/G | Clinical | TLAST | >1 year | Excluded | 146 | 396 | 133 | N: 194 vs 202 | % in ITT: 58.7% | 352d vs 345d | 7 | (2% improvement) | P-value = 0.512 | HR = 0.923 (0.726-1.174) | NAd vs NAd | 0.9430 | 1.014 (0.694-1.482) |
| B_D NA | PSMB1/P11A | C/G | Clinical | TLAST | >1 year | Total | 146 | 396 | 133 | N: 266 vs 276 | % in ITT: 80.3% | 414d vs 345d | 69 | (20% improvement) | P-value = 0.0744 | HR = 0.828 (0.673-1.019) | NAd vs NAd | 0.8540 | 1.033 (0.734-1.453) |
| Clinical | RACEGRP | OTHER | Protein | 20S % NUCLEAR STAINING | 30-90 | Selected | 18 | 445 | 212 | N: 11 vs 7 | % in ITT: 2.7% | 346d vs 114d | 232 | (203.5% improvement) | P-value = 0.032 | HR = 0.272 (0.077-0.963) | 928d vs NAd | 0.7517 | 1.309 (0.246-6.958) |
| Clinical | RACEGRP | OTHER | Protein | 20S % NUCLEAR STAINING | 30-90 | Excluded | 18 | 445 | 212 | N: 214 vs 231 | % in ITT: 65.9% | 396d vs 347d | 49 | (14.1% improvement) | P-value = 0.1229 | HR = 0.836 (0.665-1.05) | NAd vs NAd | 0.5139 | 0.879 (0.598-1.293) |
| Clinical | RACEGRP | OTHER | Protein | 20S % NUCLEAR STAINING | 30-90 | Total | 18 | 445 | 212 | N: 225 vs 238 | % in ITT: 68.6% | 367d vs 345d | 22 | (6.4% improvement) | P-value = 0.1 | HR = 0.83 (0.665-1.037) | NAd vs NAd | 0.6640 | 0.921 (0.634-1.336) |
| B_D NA | PSMB1/P11A | C/G | Protein | CD68 POSITIVE PERI-FOLLICULAR | >50 | Selected | 52 | 302 | 321 | N: 24 vs 28 | % in ITT: 7.7% | 506d vs 280d | 226 | (80.7% improvement) | P-value = 0.0365 | HR = 0.484 (0.241-0.971) | NAd vs 1175d | 0.3998 | 0.648 (0.235-1.791) |
| B_D NA | PSMB1/P11A | C/G | Protein | CD68 POSITIVE PERI-FOLLICULAR | >50 | Excluded | 52 | 302 | 321 | N: 150 vs 152 | % in ITT: 44.7% | 414d vs 347d | 67 | (19.3% improvement) | P-value = 0.2937 | HR = 0.862 (0.653-1.138) | NAd vs NAd | 0.5170 | 0.855 (0.533-1.373) |
| B_D NA | PSMB1/P11A | C/G | Protein | CD68 POSITIVE PERI-FOLLICULAR | >50 | Total | 52 | 302 | 321 | N: 174 vs 180 | % in ITT: 52.4% | 417d vs 345d | 72 | (20.9% improvement) | P-value = 0.0849 | HR = 0.8 (0.619-1.032) | NAd vs NAd | 0.3311 | 0.809 (0.528-1.241) |
| Clinical | HITUBD | NO | Protein | CD68 OVERALL POSITIVE | 0-50 | Selected | 132 | 309 | 234 | N: 64 vs 68 | % in ITT: 19.6% | 693d vs 486d | 207 | (42.6% improvement) | P-value = 0.0177 | HR = 0.576 (0.363-0.915) | NAd vs NAd | 0.0204 | 0.316 (0.113-0.882) |

APPENDIX 3, TABLE 3.1-continued

Significant Pair-Wise Combinations

| Marker A Type | Marker A | Marker A Level | Marker B Type | Marker B | Marker B Level | Combination | N Selected | N Excluded | N Uneval-uable | N (Vc-R vs R) | % of ITT | Median PFS (Vc-R vs R) | PFS Difference | % PFS Difference | PFS Logrank P-value | PFS HR | Median OS (Vc-R vs R) | OS Logrank P-value | OS HR |
|---|---|---|---|---|---|---|---|---|---|---|---|---|---|---|---|---|---|---|---|
| Clinical | HITUBD | NO | Protein | CD68 OVERALL POSITIVE | 0-50 | Excluded | 132 | 309 | 234 | N: 153 vs 156 | % in ITT: 45.8% | 346d vs 287d | 59 | (20.6% improvement) | P-value = 0.5759 | HR = 0.927 (0.712-1.207) | NAd vs NAd | 0.6702 | 1.096 (0.718-1.674) |
| Clinical | HITUBD | NO | Protein | CD68 OVERALL POSITIVE | 0-50 | Total | 132 | 309 | 234 | N: 217 vs 224 | % in ITT: 65.3% | 360d vs 345d | 15 | (4.2999-999999-9999% improvement) | P-value = 0.0864 | HR = 0.819 (0.652-1.029) | NAd vs NAd | 0.5387 | 0.887 (0.604-1.301) |
| B_D NA | PSMB9/R60H | G/G | Protein | P65 % NUCLEAR STAINING | >0 | Selected | 63 | 374 | 238 | N: 35 vs 28 | % in ITT: 9.3% | 491d vs 288d | 203 | (70.5% improvement) | P-value = 0.0303 | HR = 0.511 (0.275-0.952) | NAd vs NAd | 0.3042 | 0.578 (0.2-1.667) |
| B_D NA | PSMB9/R60H | G/G | Protein | P65 % NUCLEAR STAINING | >0 | Excluded | 63 | 374 | 238 | N: 178 vs 196 | % in ITT: 55.4% | 367d vs 345d | 22 | (6.4% improvement) | P-value = 0.1982 | HR = 0.85 (0.664-1.088) | NAd vs NAd | 0.9516 | 1.013 (0.673-1.525) |
| B_D NA | PSMB9/R60H | G/G | Protein | P65 % NUCLEAR STAINING | >0 | Total | 63 | 374 | 238 | N: 213 vs 224 | % in ITT: 64.7% | 414d vs 338d | 76 | (22.5% improvement) | P-value = 0.0354 | HR = 0.782 (0.622-0.984) | NAd vs NAd | 0.7048 | 0.929 (0.634-1.36) |
| Clinical | HITUBD | NO | Protein | CD68 POSITIVE FOLLICULAR | 0-50 | Selected | 130 | 256 | 289 | N: 64 vs 66 | % in ITT: 19.3% | 624d vs 421d | 203 | (48.2% improvement) | P-value = 0.031 | HR = 0.604 (0.38-096) | NAd vs NAd | 0.0222 | 0.288 (0.092-0.896) |
| Clinical | HITUBD | NO | Protein | CD68 POSITIVE FOLLICULAR | 0-50 | Excluded | 130 | 256 | 289 | N: 126 vs 130 | % in ITT: 37.9% | 346d vs 283d | 63 | (22.3% improvement) | P-value = 0.8569 | HR = 0.974 (0.729-1.3) | NAd vs NAd | 0.8758 | 1.037 (0.657-1.636) |
| Clinical | HITUBD | NO | Protein | CD68 POSITIVE FOLLICULAR | 0-50 | Total | 130 | 256 | 289 | N: 190 vs 196 | % in ITT: 57.2% | 396d vs 346d | 50 | (14.5% improvement) | P-value = 0.1781 | HR = 0.846 (0.663-1.08) | NAd vs NAd | 0.4068 | 0.839 (0.554-127) |
| Clinical | PRITUX | NO | Protein | CD68 POSITIVE FOLLICULAR | 0-50 | Selected | 159 | 227 | 289 | N: 73 vs 86 | % in ITT: 23.6% | 483d vs 281d | 202 | (71.9% improvement) | P-value = 0.0066 | HR = 0.586 (0.397-0.866) | NAd vs NAd | 0.0713 | 0.53 (0.262-1.069) |
| Clinical | PRITUX | NO | Protein | CD68 POSITIVE FOLLICULAR | 0-50 | Excluded | 159 | 227 | 289 | N: 117 vs 110 | % in ITT: 33.6% | 346d vs 349d | -3 | (-0.9% improvement) | P-value = 0.6451 | HR = 1.079 (0.782-1.487) | NAd vs NAd | 0.6426 | 1.134 (0.667-1.928) |
| Clinical | PRITUX | NO | Protein | CD68 POSITIVE FOLLICULAR | 0-50 | Total | 159 | 227 | 289 | N: 190 vs 196 | % in ITT: 57.2% | 396d vs 346d | 50 | (14.5% improvement) | P-value = 0.1781 | HR = 0.846 (0.663-1.08) | NAd vs NAd | 0.4068 | 0.839 (0.554-1.27) |

APPENDIX 3, TABLE 3.1-continued

Significant Pair-Wise Combinations

| Marker A Type | Marker A | Marker A Level | Marker B Type | Marker B | Marker B Level | Combination | N Selected | N Excluded | N Uneval-uable | N (Vc-R vs R) | % of ITT | Median PFS (Vc-R vs R) | PFS Difference | % PFS Difference | PFS Logrank P-value | PFS HR | Median OS OS (Vc-R vs R) | Log-rank P-value | OS HR |
|---|---|---|---|---|---|---|---|---|---|---|---|---|---|---|---|---|---|---|---|
| B_D NA | PSMB5/ R24C | C/T | Protein | CD68 POSITIVE FOLLICULAR | 0-50 | Selected | 39 | 317 | 319 | N: 18 vs 21 | % in ITT: 5.8% | 417d vs 220d | 197 | (89.5% improve-ment) | P-value = 0.022 | HR = 0.415 (0.19-0.903) | NAd vs NAd | 0.0557 | 0.247 (0.052-1.165) |
| B_D NA | PSMB5/ R24C | C/T | Protein | CD68 POSITIVE FOLLICULAR | 0-50 | Excluded | 39 | 317 | 319 | N: 157 vs 160 | % in ITT: 47% | 414d vs 348d | 66 | (19% improve-ment) | P-value = 0.2328 | HR = 0.849 (0.648-1.112) | NAd vs NAd | 0.7320 | 0.924 (0.587-1.454) |
| B_D NA | PSMB5/ R24C | C/T | Protein | CD68 POSITIVE FOLLICULAR | 0-50 | Total | 39 | 317 | 319 | N: 175 vs 181 | % in ITT: 52.7% | 414d vs 345d | 69 | (20% improve-ment) | P-value = 0.0855 | HR = 0.801 (0.621-1.032) | NAd vs NAd | 0.3270 | 0.808 (0.527-1.239) |
| B_D NA | PSMB1/ P11A | C/G | Clinical | AGEGRP | <=65 | Selected | 182 | 360 | 133 | N: 86 vs 96 | % in ITT: 27% | 464d vs 279d | 185 | (66.3% improve-ment) | P-value = 0.0071 | HR = 0.605 (0.418-0.875) | NAd vs NAd | 0.5650 | 0.822 (0.421-1.605) |
| B_D NA | PSMB1/ P11A | C/G | Clinical | AGEGRP | <=65 | Excluded | 182 | 360 | 133 | N: 180 vs 180 | % in ITT: 53.3% | 355d vs 348d | 7 | (2% improve-ment) | P-value = 0.766 | HR = 0.962 (0.748-1.238) | NAd vs NAd | 0.6392 | 1.1 (0.738-1.64) |
| B_D NA | PSMB1/ P11A | C/G | Clinical | AGEGRP | <=65 | Total | 182 | 360 | 133 | N: 266 vs 276 | % in ITT: 80.3% | 414d vs 345d | 69 | (20% improve-ment) | P-value = 0.0744 | HR = 0.828 (0.673-1.019) | NAd vs NAd | 0.8540 | 1.033 (0.734-1.453) |
| Clinical | SEX | MALE | Protein | 20S % NUCLEAR STAINING | 30-90 | Selected | 111 | 352 | 212 | N: 63 vs 48 | % in ITT: 16.4% | 415d vs 235d | 180 | (76.6% improve-ment) | P-value = 0.005 | HR = 0.534 (0.342-0.832) | NAd vs 1263d | 0.0324 | 0.482 (0.243-0.955) |
| Clinical | SEX | MALE | Protein | 20S % NUCLEAR STAINING | 30-90 | Excluded | 111 | 352 | 212 | N: 162 vs 190 | % in ITT: 52.1% | 360d vs 357d | 3 | (0.8% improve-ment) | P-value = 0.4394 | HR = 0.903 (0.697-1.169) | NAd vs NAd | 0.5157 | 1.16 (0.742-1.813) |
| Clinical | SEX | MALE | Protein | 20S % NUCLEAR STAINING | 30-90 | Total | 111 | 352 | 212 | N: 225 vs 238 | % in ITT: 68.6% | 367d vs 345d | 22 | (6.4% improve-ment) | P-value = 0.1 | HR = 0.83 (0.665-1.037) | NAd vs NAd | 0.6640 | 0.921 (0.634-1336) |
| B_D NA | PSMB1/ P11A | G/G | B_D NA | PSMB5/ R24C | C/T | Selected | 14 | 528 | 133 | N: 7 vs 7 | % in ITT: 2.1% | 417d vs 237.5d | 179.5 | (75.6% improve-ment) | P-value = 0.0221 | HR = 0.18 (0.035-0.921) | 1037d vs NAd | 0.6740 | 0.6 (0.054-6.662) |
| B_D NA | PSMB1/ P11A | G/G | B_D NA | PSMB5/ R24C | C/T | Excluded | 14 | 528 | 133 | N: 259 vs 269 | % in ITT: 78.2% | 414d vs 345d | 69 | (20% improve-ment) | P-value = 0.1175 | HR = 0.845 (0.685-1.043) | NAd vs NAd | 0.7952 | 1.047 (0.741-1.479) |

APPENDIX 3, TABLE 3.1-continued

Significant Pair-Wise Combinations

| Marker A Type | Marker A | Marker A Level | Marker B Type | Marker B | Marker B Level | Combination | N Selected | N Excluded | N Un-evaluable | N (Vc-R vs R) | % of ITT | Median PFS (Vc-R vs R) | PFS Difference | % PFS Difference | PFS Logrank P-value | PFS HR | Median OS (Vc-R vs R) | Median OS Log-rank P-value | OS HR |
|---|---|---|---|---|---|---|---|---|---|---|---|---|---|---|---|---|---|---|---|
| B_D NA | PSMB1/P11A | G/G | B_D NA | PSMB5/R24C | C/T | Total | 14 | 528 | 133 | N: 266 vs 276 | % in ITT: 80.3% | 414d vs 345d | 69 | (20% improvement) | P-value = 0.0744 | HR = 0.828 (0.673-1.019) | NAd vs NAd | 0.8540 | 1.033 (0.734-1.453) |
| B_D NA | PSMB1/P11A | C/G | Protein | P27 % NUCLEI POSITIVE | 0-70 | Selected | 110 | 320 | 245 | N: 53 vs 57 | % in ITT: 16.3% | 444d vs 277d | 167 | (60.3% improvement) | P-value = 7e-04 | HR = 0.456 (0.286-0.727) | NAd vs NAd | 0.3082 | 0.67 (0.307-1.459) |
| B_D NA | PSMB1/P11A | C/G | Protein | P27 % NUCLEI POSITIVE | 0-70 | Excluded | 110 | 320 | 245 | N: 158 vs 162 | % in ITT: 47.4% | 360d vs 348d | 12 | (3.4% improvement) | P-value = 0.4399 | HR = 0.9 (0.689-1.176) | NAd vs NAd | 0.9580 | 0.988 (0.637-1.532) |
| B_D NA | PSMB1/P11A | C/G | Protein | P27 % NUCLEI POSITIVE | 0-70 | Total | 110 | 320 | 245 | N: 211 vs 219 | % in ITT: 63.7% | 396d vs 338d | 58 | (17.2% improvement) | P-value = 0.0319 | HR = 0.777 (0.617-0.979) | NAd vs NAd | 0.5987 | 0.903 (0.617-1.322) |
| B_D NA | PSMB1/P11A | C/G | Protein | P27 SIGNAL INTENSITY | >=2+ | Selected | 155 | 275 | 245 | N: 75 vs 80 | % in ITT: 23% | 444d vs 280d | 164 | (58.6% improvement) | P-value = 0.0085 | HR = 0.593 (0.4-0.879) | NAd vs NAd | 0.3831 | 0.749 (0.391-1.436) |
| B_D NA | PSMB1/P11A | C/G | Protein | P27 SIGNAL INTENSITY | >=2+ | Excluded | 155 | 275 | 245 | N: 136 vs 139 | % in ITT: 40.7% | 352d vs 346d | 6 | (1.6999-999999-999999% improvement) | P-value = 0.4562 | HR = 0.897 (0.674-1.194) | NAd vs NAd | 0.9691 | 0.991 (0.618-1.589) |
| B_D NA | PSMB1/P11A | C/G | Protein | P27 SIGNAL INTENSITY | >=2+ | Total | 155 | 275 | 245 | N: 211 vs 219 | % in ITT: 63.7% | 396d vs 338d | 58 | (17.2% improvement) | P-value = 0.0319 | HR = 0.777 (0.617-0.979) | NAd vs NAd | 0.5987 | 0.903 (0.617-1.322) |
| Clinical | TLAST | >1 year | Protein | CD68 POSITIVE FOLLICULAR | 0-50 | Selected | 176 | 210 | 289 | N: 86 vs 90 | % in ITT: 26.1% | 519d vs 357d | 162 | (45.4% improvement) | P-value = 0.0185 | HR = 0.633 (0.431-0.929) | NAd vs NAd | 0.2048 | 0.587 (0.256-1.35) |
| Clinical | TLAST | >1 year | Protein | CD68 POSITIVE FOLLICULAR | 0-50 | Excluded | 176 | 210 | 289 | N: 104 vs 106 | % in ITT: 31.1% | 346d vs 288d | 58 | (20.1% improvement) | P-value = 0.8222 | HR = 1.038 (0.755-1.428) | NAd vs NAd | 0.7189 | 0.915 (0.565-1.483) |
| Clinical | TLAST | >1 year | Protein | CD68 POSITIVE FOLLICULAR | 0-50 | Total | 176 | 210 | 289 | N: 190 vs 196 | % in ITT: 57.2% | 396d vs 346d | 50 | (14.5% improvement) | P-value = 0.1781 | HR = 0.846 (0.663-1.08) | NAd vs NAd | 0.4068 | 0.839 (0.554-1.27) |
| B_D NA | PSMB1/P11A | C/G | Protein | 20S % NUCLEAR STAINING | 30-90 | Selected | 108 | 322 | 245 | N: 45 vs 63 | % in ITT: 16% | 431d vs 275d | 156 | (56.7% improvement) | P-value = 0.0428 | HR = 0.621 (0.39-0.989) | NAd vs NAd | 0.1377 | 0.54 (0.236-1.234) |

APPENDIX 3, TABLE 3.1-continued

Significant Pair-Wise Combinations

| Marker A Type | Marker A | Marker A Level | Marker B Type | Marker B | Marker B Level | Combination | N Selected | N Excluded | N Uneval-uable | N (Vc-R vs R) | % of ITT | Median PFS (Vc-R vs R) | PFS Difference | % PFS Difference | PFS Logrank P-value | PFS HR | Median OS (Vc-R vs R) | OS Log-rank P-value | OS HR |
|---|---|---|---|---|---|---|---|---|---|---|---|---|---|---|---|---|---|---|---|
| B_D NA | PSMB1/ P11A | C/G | Protein | 20S % NUCLEAR STAINING | 30-90 | Excluded | 108 | 322 | 245 | N: 164 vs 158 | % in ITT: 47.7% | 380d vs 346d | 34 | (9.8% improvement) | P-value = 0.231 | HR = 0.849 (0.65-1.11) | NAd vs NAd | 0.6667 | 1.104 (0.704-1.729) |
| B_D NA | PSMB1/ P11A | C/G | Protein | 20S % NUCLEAR STAINING | 30-90 | Total | 108 | 322 | 245 | N: 209 vs 221 | % in ITT: 63.7% | 406d vs 345d | 61 | (17.7% improvement) | P-value = 0.0397 | HR = 0.785 (0.624-0.989) | NAd vs NAd | 0.7080 | 0.929 (0.632-1.365) |
| Clinical | AGEGRP | <=65 | Protein | CD68 POSITIVE FOLLICULAR | 0-50 | Selected | 215 | 171 | 289 | N: 102 vs 113 | % in ITT: 31.9% | 429d vs 275d | 154 | (56% improvement) | P-value = 8e-04 | HR = 0.57 (0.408-0.797) | NAd vs NAd | 0.1020 | 0.62 (0.348-1.105) |
| Clinical | AGEGRP | <=65 | Protein | CD68 POSITIVE FOLLICULAR | 0-50 | Excluded | 215 | 171 | 289 | N: 88 vs 83 | % in ITT: 25.3% | 348d vs 427d | -79 | (-18.5% improvement) | P-value = 0.0837 | HR = 1.383 (0.955-2.003) | NAd vs NAd | 0.5681 | 1.196 (0.646-2.217) |
| Clinical | AGEGRP | <=65 | Protein | CD68 POSITIVE FOLLICULAR | 0-50 | Total | 215 | 171 | 289 | N: 190 vs 196 | % in ITT: 57.2% | 396d vs 346d | 50 | (14.5% improvement) | P-value = 0.1781 | HR = 0.846 (0.663-1.08) | NAd vs NAd | 0.4068 | 0.839 (0.554-1.27) |
| B_D NA | PSMB1/ P11A | C/G | Protein | P65 % POSITIVE CYTOPLASMIC SIGNAL | >90% | Selected | 157 | 280 | 238 | N: 75 vs 82 | % in ITT: 23.3% | 431d vs 278d | 153 | (55% improvement) | P-value = 0.0048 | HR = 0.574 (0.389-0.848) | NAd vs NAd | 0.2892 | 0.7 (0.361-1.358) |
| B_D NA | PSMB1/ P11A | C/G | Protein | P65 % POSITIVE CYTOPLASMIC SIGNAL | >90% | Excluded | 157 | 280 | 238 | N: 138 vs 142 | % in ITT: 41.5% | 355d vs 348d | 7 | (2% improvement) | P-value = 0.513 | HR = 0.909 (0.684-1.209) | NAd vs NAd | 0.7743 | 1.071 (0.67-1.712) |
| B_D NA | PSMB1/ P11A | C/G | Protein | P65 % POSITIVE CYTOPLASMIC SIGNAL | >90% | Total | 157 | 280 | 238 | N: 213 vs 224 | % in ITT: 64.7% | 414d vs 338d | 76 | (22.5% improvement) | P-value = 0.0354 | HR = 0.782 (0.622-0.984) | NAd vs NAd | 0.7048 | 0.929 (0.634-1.36) |
| B_D NA | PSMB9/ R60H | A/G | Protein | 20S % POSITIVE CYTOPLASMIC SIGNAL | 95-100 | Selected | 89 | 341 | 245 | N: 45 vs 44 | % in ITT: 13.2% | 426d vs 273d | 153 | (56% improvement) | P-value = 0.0222 | HR = 0.544 (0.32-0.925) | NAd vs NAd | 0.2901 | 0.659 (0.302-1.436) |
| B_D NA | PSMB9/ R60H | A/G | Protein | 20S % POSITIVE CYTOPLASMIC SIGNAL | 95-100 | Excluded | 89 | 341 | 245 | N: 164 vs 177 | % in ITT: 50.5% | 396d vs 347d | 49 | (14.1% improvement) | P-value = 0.2336 | HR = 0.855 (0.661-1.106) | NAd vs NAd | 0.9020 | 1.028 (0.659-1.603) |
| B_D NA | PSMB9/ R60H | A/G | Protein | 20S % POSITIVE CYTOPLASMIC SIGNAL | 95-100 | Total | 89 | 341 | 245 | N: 209 vs 221 | % in ITT: 63.7% | 406d vs 345d | 61 | (17.7% improvement) | P-value = 0.0397 | HR = 0.785 (0.624-0.989) | NAd vs NAd | 0.7080 | 0.929 (0.632-1.365) |

APPENDIX 3, TABLE 3.1-continued

Significant Pair-Wise Combinations

| Marker A Type | Marker A | Marker A Level | Marker B Type | Marker B | Marker B Level | Combination | N Selected | N Excluded | N Un-evaluable | N (Vc-R vs R) | % of ITT | Median PFS (Vc-R vs R) | PFS Difference | % PFS Difference | PFS Logrank P-value | PFS HR | Median OS (Vc-R vs R) | Log-rank P-value | OS HR |
|---|---|---|---|---|---|---|---|---|---|---|---|---|---|---|---|---|---|---|---|
| B_D NA | PSMB1/P11A | C/G | Protein | 20S INTENSITY CYTOPLASMIC SIGNAL | <=2+ | Selected | 108 | 322 | 245 | N: 55 vs 53 | % in ITT: 16% | 431d vs 278d | 153 | (55% improvement) | P-value = 0.0269 | HR = 0.601 (0.381-0.948) | NAd vs NAd | 0.4710 | 0.724 (0.3-1.749) |
| B_D NA | PSMB1/P11A | C/G | Protein | 20S INTENSITY CYTOPLASMIC SIGNAL | <=2+ | Excluded | 108 | 322 | 245 | N: 154 vs 168 | % in ITT: 47.7% | 380d vs 345d | 35 | (10.1% improvement) | P-value = 0.2403 | HR = 0.852 (0.651-1.114) | NAd vs NAd | 0.9958 | 0.999 (0.651-1.533) |
| B_D NA | PSMB1/P11A | C/G | Protein | 20S INTENSITY CYTOPLASMIC SIGNAL | <=2+ | Total | 108 | 322 | 245 | N: 209 vs 221 | % in ITT: 63.7% | 406d vs 345d | 61 | (17.7% improvement) | P-value = 0.0397 | HR = 0.785 (0.624-0.989) | NAd vs NAd | 0.7080 | 0.929 (0.632-1.365) |
| B_D NA | PSMB9/R60H | A/G | Protein | CD68 POSITIVE FOLLICULAR | 0-50 | Selected | 104 | 252 | 319 | N: 51 vs 53 | % in ITT: 15.4% | 426d vs 273d | 153 | (56% improvement) | P-value = 0.0339 | HR = 0.592 (0.362-0.968) | NAd vs NAd | 0.1848 | 0.537 (0.211-1.366) |
| B_D NA | PSMB9/R60H | A/G | Protein | CD68 POSITIVE FOLLICULAR | 0-50 | Excluded | 104 | 252 | 319 | N: 124 vs 128 | % in ITT: 37.3% | 414d vs 349d | 65 | (18.6% improvement) | P-value = 0.435 | HR = 0.888 (0.659-1.197) | NAd vs NAd | 0.7690 | 0.93 (0.574-1.508) |
| B_D NA | PSMB9/R60H | A/G | Protein | CD68 POSITIVE FOLLICULAR | 0-50 | Total | 104 | 252 | 319 | N: 175 vs 181 | % in ITT: 52.7% | 414d vs 345d | 69 | (20% improvement) | P-value = 0.0855 | HR = 0.801 (0.621-1.032) | NAd vs NAd | 0.3270 | 0.808 (0.527-1.239) |
| B_D NA | PSMB9/R60H | G/G | Protein | 20S % NUCLEAR STAINING | 30-90 | Selected | 145 | 285 | 245 | N: 74 vs 71 | % in ITT: 21.5% | 431d vs 280d | 151 | (53.9% improvement) | P-value = 0.0262 | HR = 0.647 (0.439-0.953) | NAd vs NAd | 0.2782 | 0.702 (0.368-1.336) |
| B_D NA | PSMB9/R60H | G/G | Protein | 20S % NUCLEAR STAINING | 30-90 | Excluded | 145 | 285 | 245 | N: 135 vs 150 | % in ITT: 42.2% | 360d vs 345d | 15 | (4.2999-999999999% improvement) | P-value = 0.3045 | HR = 0.86 (0.644-1.148) | NAd vs NAd | 0.7758 | 1.073 (0.661-1.741) |
| B_D NA | PSMB9/R60H | G/G | Protein | 20S % NUCLEAR STAINING | 30-90 | Total | 145 | 285 | 245 | N: 209 vs 221 | % in ITT: 63.7% | 406d vs 345d | 61 | (17.7% improvement) | P-value = 0.0397 | HR = 0.785 (0.624-0.989) | NAd vs NAd | 0.7080 | 0.929 (0.632-1.365) |
| Protein | CD68 POSITIVE FOLLICULAR | 0-50 | Protein | P65 % POSITIVE CYTOPLASMIC SIGNAL | >90% | Selected | 250 | 136 | 289 | N: 114 vs 136 | % in ITT: 37% | 429d vs 279d | 150 | (53.8% improvement) | P-value = 0.0019 | HR = 0.616 (0.452-0.839) | NAd vs NAd | 0.0605 | 0.593 (0.342-1.029) |
| Protein | CD68 POSITIVE FOLLICULAR | 0-50 | Protein | P65 % POSITIVE CYTOPLASMIC SIGNAL | >90% | Excluded | 250 | 136 | 289 | N: 76 vs 60 | % in ITT: 20.1% | 324d vs 486d | -162 | (-33.3% improvement) | P-value = 0.0545 | HR = 1.52 (0.989-2.335) | NAd vs NAd | 0.3261 | 1.408 (0.709-2.795) |

APPENDIX 3, TABLE 3.1-continued

Significant Pair-Wise Combinations

| Marker A Type | Marker A | Marker A Level | Marker B | Marker B Level | Marker B Type | Combination | N Selected | N Excluded | N Un-evaluable | N (Vc-R vs R) | % of ITT | Median PFS (Vc-R vs R) | PFS Difference | % PFS Difference | PFS Logrank P-value | PFS HR | Median OS OS (Vc-R vs R) | Log-rank P-value | OS HR |
|---|---|---|---|---|---|---|---|---|---|---|---|---|---|---|---|---|---|---|---|
| Protein | CD68 POSITIVE FOLLICULAR | 0-50 | P65 % POSITIVE CYTOPLASMIC SIGNAL | >90% | Protein | Total | 250 | 136 | 289 | N: 190 vs 196 | % in ITT: 57.2% | 396d vs 346d | 50 | (14.5% improvement) | P-value = 0.1781 | HR = 0.846 (0.663-1.08) | NAd vs NAd | 0.4068 | 0.839 (0.554-1.27) |
| Clinical | AGEGRP | <=65 | CD68 POSITIVE PERI-FOLLICULAR | 0-50 | Protein | Selected | 177 | 207 | 291 | N: 89 vs 88 | % in ITT: 26.2% | 431d vs 281d | 150 | (53.4% improvement) | P-value = 0.0274 | HR = 0.663 (0.458-0.959) | NAd vs NAd | 0.7612 | 0.91 (0.496-1.67) |
| Clinical | AGEGRP | <=65 | CD68 POSITIVE PERI-FOLLICULAR | 0-50 | Protein | Excluded | 177 | 207 | 291 | N: 100 vs 107 | % in ITT: 30.7% | 348d vs 351d | -3 | (-0.9% improvement) | P-value = 0.874 | HR = 1.027 (0.739-1.428) | NAd vs NAd | 0.3903 | 0.779 (0.44-1.379) |
| Clinical | AGEGRP | <=65 | CD68 POSITIVE PERI-FOLLICULAR | 0-50 | Protein | Total | 177 | 207 | 291 | N: 189 vs 195 | % in ITT: 56.9% | 406d vs 346d | 60 | (17.3% improvement) | P-value = 0.1772 | HR = 0.845 (0.662-1.08) | NAd vs NAd | 0.4116 | 0.841 (0.555-1.273) |
| Clinical | TLAST | >1 year | P65 % POSITIVE CYTOPLASMIC SIGNAL | >90% | Protein | Selected | 229 | 241 | 205 | N: 112 vs 117 | % in ITT: 33.9% | 506d vs 357d | 149 | (41.7% improvement) | P-value = 0.0331 | HR = 0.698 (0.5-0.973) | NAd vs NAd | 0.3300 | 0.713 (0.36-1.413) |
| Clinical | TLAST | >1 year | P65 % POSITIVE CYTOPLASMIC SIGNAL | >90% | Protein | Excluded | 229 | 241 | 205 | N: 117 vs 124 | % in ITT: 35.7% | 345d vs 280d | 65 | (23.2% improvement) | P-value = 0.6849 | HR = 0.941 (0.699-1.266) | NAd vs NAd | 0.9927 | 1.002 (0.644-1.557) |
| Clinical | TLAST | >1 year | P65 % POSITIVE CYTOPLASMIC SIGNAL | >90% | Protein | Total | 229 | 241 | 205 | N: 229 vs 241 | % in ITT: 69.6% | 367d vs 345d | 22 | (6.4% improvement) | P-value = 0.0902 | HR = 0.826 (0.663-1.03) | NAd vs NAd | 0.6612 | 0.921 (0.636-1.332) |
| B_D NA | PSMB1/ P11A | C/G | CD68 OVERALL POSITIVE | 0-50 | Protein | Selected | 129 | 280 | 266 | N: 64 vs 65 | % in ITT: 19.1% | 426d vs 278d | 148 | (53.2% improvement) | P-value = 0.0025 | HR = 0.525 (0.343-0.804) | NAd vs NAd | 0.2690 | 0.647 (0.297-1.409) |
| B_D NA | PSMB1/ P11A | C/G | CD68 OVERALL POSITIVE | 0-50 | Protein | Excluded | 129 | 280 | 266 | N: 137 vs 143 | % in ITT: 41.5% | 355d vs 348d | 7 | (2% improvement) | P-value = 0.4433 | HR = 0.894 (0.672-1.191) | NAd vs NAd | 0.9914 | 1.002 (0.633-1.587) |
| B_D NA | PSMB1/ P11A | C/G | CD68 OVERALL POSITIVE | 0-50 | Protein | Total | 129 | 280 | 266 | N: 201 vs 208 | % in ITT: 60.6% | 399d vs 345d | 51 | (14.8% improvement) | P-value = 0.0281 | HR = 0.768 (0.606-0.973) | NAd vs NAd | 0.5159 | 0.877 (0.591-1.302) |
| Protein | CD68 POSITIVE FOLLICULAR | 0-50 | CD68 POSITIVE PERI-FOLLICULAR | 0-50 | Protein | Selected | 193 | 191 | 291 | N: 94 vs 99 | % in ITT: 28.6% | 429d vs 282d | 147 | (52.1% improvement) | P-value = 0.0075 | HR = 0.625 (0.441-0.885) | NAd vs NAd | 0.0947 | 0.596 (0.323-1.101) |

APPENDIX 3, TABLE 3.1-continued

Significant Pair-Wise Combinations

| Marker A Type | Marker A | Marker A Level | Marker B Type | Marker B | Marker B Level | Combination | N Selected | N Excluded | N Uneval-uable | N (Vc-R vs R) | % of ITT | Median PFS (Vc-R vs R) | PFS Difference | % PFS Difference | PFS Logrank P-value | PFS HR | Median OS (Vc-R vs R) | Log-rank P-value | OS HR |
|---|---|---|---|---|---|---|---|---|---|---|---|---|---|---|---|---|---|---|---|
| Protein | CD68 POSITIVE FOLLICULAR | 0-50 | Protein | CD68 POSITIVE PERI-FOLLICULAR | 0-50 | Excluded | 193 | 191 | 291 | N: 95 vs 96 | % in ITT: 28.3% | 344d vs 351d | -7 | (-2% improve-ment) | P-value = 0.5972 | HR = 1.098 (0.775-1.556) | NAd vs NAd | 0.6374 | 1.148 (0.647-2.036) |
| Protein | CD68 POSITIVE FOLLICULAR | 0-50 | Protein | CD68 POSITIVE PERI-FOLLICULAR | 0-50 | Total | 193 | 191 | 291 | N: 189 vs 195 | % in ITT: 56.9% | 406d vs 346d | 60 | (17.3% improve-ment) | P-value = 0.1772 | HR = 0.845 (0.662-1.08) | NAd vs NAd | 0.4116 | 0.841 (0.555-1.273) |
| Clinical | FLIPI | High | Protein | P27 % NUCLEI POSITIVE | 0-70 | Selected | 113 | 350 | 212 | N: 53 vs 60 | % in ITT: 16.7% | 358d vs 212d | 146 | (68.9% improve-ment) | P-value = 0.0156 | HR = 0.588 (0.381-0.908) | 1103d vs 1111d | 0.8099 | 0.934 (0.539-1.619) |
| Clinical | FLIPI | High | Protein | P27 % NUCLEI POSITIVE | 0-70 | Excluded | 113 | 350 | 212 | N: 174 vs 176 | % in ITT: 51.9% | 406d vs 351d | 55 | (15.7% improve-ment) | P-value = 0.4522 | HR = 0.905 (0.698-1.174) | NAd vs NAd | 0.5519 | 0.859 (0.522-1.416) |
| Clinical | FLIPI | High | Protein | P27 % NUCLEI POSITIVE | 0-70 | Total | 113 | 350 | 212 | N: 227 vs 236 | % in ITT: 68.6% | 366d vs 345d | 21 | (6.1% improve-ment) | P-value = 0.0844 | HR = 0.822 (0.659-1.027) | NAd vs NAd | 0.5615 | 0.896 (0.62-1.297) |
| Clinical | SEX | MALE | Protein | P65 % POSITIVE CYTOPLASMIC SIGNAL | >90% | Selected | 169 | 301 | 205 | N: 97 vs 72 | % in ITT: 25% | 414d vs 271d | 143 | (52.8% improve-ment) | P-value = 0.0094 | HR = 0.622 (0.433-0.894) | NAd vs NAd | 0.0574 | 0.571 (0.317-1.025) |
| Clinical | SEX | MALE | Protein | P65 % POSITIVE CYTOPLASMIC SIGNAL | >90% | Excluded | 169 | 301 | 205 | N: 132 vs 169 | % in ITT: 44.6% | 355d vs 375d | -20 | (-5.3% improve-ment) | P-value = 0.4653 | HR = 0.9 (0.678-1.194) | NAd vs NAd | 0.4521 | 1.2 (0.746-1.931) |
| Clinical | SEX | MALE | Protein | P65 % POSITIVE CYTOPLASMIC SIGNAL | >90% | Total | 169 | 301 | 205 | N: 229 vs 241 | % in ITT: 69.6% | 367d vs 345d | 22 | (6.4% improve-ment) | P-value = 0.0902 | HR = 0.826 (0.663-1.03) | NAd vs NAd | 0.6612 | 0.921 (0.636-1.332) |
| B_D NA | PSMB1/P11A | C/G | B_D NA | PSMB9/R60H | G/G | Selected | 150 | 392 | 133 | N: 66 vs 84 | % in ITT: 22.2% | 431d vs 288d | 143 | (49.7% improve-ment) | P-value = 0.0335 | HR = 0.65 (0.436-0.97) | NAd vs NAd | 0.7239 | 0.888 (0.458-1.722) |
| B_D NA | PSMB1/P11A | C/G | B_D NA | PSMB9/R60H | G/G | Excluded | 150 | 392 | 133 | N: 200 vs 192 | % in ITT: 58.1% | 380d vs 346d | 34 | (9.8% improve-ment) | P-value = 0.4293 | HR = 0.906 (0.71-1.157) | NAd vs NAd | 0.6731 | 1.09 (0.73-1.629) |
| B_D NA | PSMB1/P11A | C/G | B_D NA | PSMB9/R60H | G/G | Total | 150 | 392 | 133 | N: 266 vs 276 | % in ITT: 80.3% | 414d vs 345d | 69 | (20% improve-ment) | P-value = 0.0744 | HR = 0.828 (0.673-1.019) | NAd vs NAd | 0.8540 | 1.033 (0.734-1.453) |

APPENDIX 3, TABLE 3.1-continued

Significant Pair-Wise Combinations

| Marker A Type | Marker A | Marker A Level | Marker B | Marker B Type | Marker B Level | Combination | N Selected | N Excluded | N Unevaluable | N (Vc-R vs R) | % of ITT | Median PFS (Vc-R vs R) | PFS Difference | % PFS Difference | PFS Logrank P-value | PFS HR | Median OS OS (Vc-R vs R) | Log-rank P-value | OS HR |
|---|---|---|---|---|---|---|---|---|---|---|---|---|---|---|---|---|---|---|---|
| Clinical | AGEGRP | <=65 | P27 % NUCLEI POSITIVE | Protein | 0-70 | Selected | 194 | 269 | 212 | N: 93 vs 101 | % in ITT: 28.7% | 422d vs 279d | 143 | (51.3% improvement) | P-value = 0.0458 | HR = 0.7 (0.493-0.996) | NAd vs NAd | 0.8473 | 0.946 (0.54-1.658) |
| Clinical | AGEGRP | <=65 | P27 % NUCLEI POSITIVE | Protein | 0-70 | Excluded | 194 | 269 | 212 | N: 134 vs 135 | % in ITT: 39.9% | 352d vs 348d | 4 | (1.0999-9999999999% improvement) | P-value = 0.5904 | HR = 0.923 (0.693-1.231) | NAd vs NAd | 0.5476 | 0.86 (0.526-1.406) |
| Clinical | AGEGRP | <=65 | P27 % NUCLEI POSITIVE | Protein | 0-70 | Total | 194 | 269 | 212 | N: 227 vs 236 | % in ITT: 68.6% | 366d vs 345d | 21 | (6.1% improvement) | P-value = 0.0844 | HR = 0.822 (0.659-1.027) | NAd vs NAd | 0.5615 | 0.896 (0.62-1.297) |
| Protein | 20S % NUCLEAR STAINING | 30-90 | 20S INTENSITY CYTOPLASMIC SIGNAL | Protein | >=3+ | Selected | 153 | 310 | 212 | N: 79 vs 74 | % in ITT: 22.7% | 422d vs 280d | 142 | (50.7% improvement) | P-value = 0.0462 | HR = 0.681 (0.467-0.994) | NAd vs NAd | 0.0906 | 0.568 (0.292-1.103) |
| Protein | 20S % NUCLEAR STAINING | 30-90 | 20S INTENSITY CYTOPLASMIC SIGNAL | Protein | >=3+ | Excluded | 153 | 310 | 212 | N: 146 vs 164 | % in ITT: 45.9% | 351d vs 347d | 4 | (1.2% improvement) | P-value = 0.5581 | HR = 0.921 (0.7-1.213) | NAd vs NAd | 0.5534 | 1.148 (0.727-1.815) |
| Protein | 20S % NUCLEAR STAINING | 30-90 | 20S INTENSITY CYTOPLASMIC SIGNAL | Protein | >=3+ | Total | 153 | 310 | 212 | N: 225 vs 238 | % in ITT: 68.6% | 367d vs 345d | 22 | (6.4% improvement) | P-value = 0.1 | HR = 0.83 (0.665-1.037) | NAd vs NAd | 0.6640 | 0.921 (0.634-1.336) |
| B_D NA | PSMB9/ R60H | A/G | CD68 OVERALL POSITIVE | Protein | 0-50 | Selected | 112 | 297 | 266 | N: 56 vs 56 | % in ITT: 16.6% | 414d vs 273d | 141 | (51.6% improvement) | P-value = 0.0031 | HR = 0.501 (0.313-0.8) | NAd vs NAd | 0.2509 | 0.61 (0.26-1.43) |
| B_D NA | PSMB9/ R60H | A/G | CD68 OVERALL POSITIVE | Protein | 0-50 | Excluded | 112 | 297 | 266 | N: 145 vs 152 | % in ITT: 44% | 358d vs 349d | 9 | (2.6% improvement) | P-value = 0.3488 | HR = 0.876 (0.665-1.155) | NAd vs NAd | 0.9776 | 1.006 (0.644-1.573) |
| B_D NA | PSMB9/ R60H | A/G | CD68 OVERALL POSITIVE | Protein | 0-50 | Total | 112 | 297 | 266 | N: 201 vs 208 | % in ITT: 60.6% | 396d vs 345d | 51 | (14.8% improvement) | P-value = 0.0281 | HR = 0.768 (0.606-0.973) | NAd vs NAd | 0.5159 | 0.877 (0.591-1.302) |
| B_D NA | PSMB5/ R24C | C/C | 20S % NUCLEAR STAINING | Protein | 30-90 | Selected | 199 | 231 | 245 | N: 95 vs 104 | % in ITT: 29.5% | 422d vs 281d | 141 | (50.2% improvement) | P-value = 0.0385 | HR = 0.701 (0.5-0.983) | NAd vs NAd | 0.6988 | 0.896 (0.513-1.563) |
| B_D NA | PSMB5/ R24AC | C/C | 20S % NUCLEAR STAINING | Protein | 30-90 | Excluded | 199 | 231 | 245 | N: 114 vs 117 | % in ITT: 34.2% | 355d vs 346d | 9 | (2.6% improvement) | P-value = 0.384 | HR = 0.869 (0.633-1.193) | NAd vs NAd | 0.8760 | 0.958 (0.562-1.635) |

APPENDIX 3, TABLE 3.1-continued

Significant Pair-Wise Combinations

| Marker A Type | Marker A | Marker A Level | Marker B Type | Marker B | Marker B Level | Combination | N Selected | N Excluded | N Uneval-uable | N (Vc-R vs R) | % of ITT | Median PFS (Vc-R vs R) | PFS Difference | % PFS Difference | PFS Logrank P-value | PFS HR | Median OS (Vc-R vs R) | OS Log-rank P-value | OS HR |
|---|---|---|---|---|---|---|---|---|---|---|---|---|---|---|---|---|---|---|---|
| B_D NA | PSMB5/R24C | C/C | Protein | 20S % NUCLEAR STAINING | 30-90 | Total | 199 | 231 | 245 | N: 209 vs 221 | % in ITT: 63.7% | 406d vs 345d | 61 | (17.7% improvement) | P-value = 0.0397 | HR = 0.785 (0.624-0.989) | NAd vs NAd | 0.7080 | 0.929 (0.632-1.365) |
| B_D NA | PSMB1/P11A | C/G | Clinical | ANNARBOR | >=III | Selected | 199 | 343 | 133 | N: 96 vs 103 | % in ITT: 29.5% | 415d vs 275d | 140 | (50.9% improvement) | P-value = 0.0076 | HR = 0.639 (0.459-0.89) | NAd vs NAd | 0.7606 | 0.92 (0.536-1.577) |
| B_D NA | PSMB1/P11A | C/G | Clinical | ANNARBOR | >=III | Excluded | 199 | 343 | 133 | N: 170 vs 173 | % in ITT: 50.8% | 414d vs 375d | 39 | (10.4% improvement) | P-value = 0.6023 | HR = 0.931 (0.712-1.218) | NAd vs NAd | 0.6663 | 1.102 (0.708-1.716) |
| B_D NA | PSMB1/P11A | C/G | Clinical | ANNARBOR | >=III | Total | 199 | 343 | 133 | N: 266 vs 276 | % in ITT: 80.3% | 414d vs 345d | 69 | (20% improvement) | P-value = 0.0744 | HR = 0.828 (0.673-1.019) | NAd vs NAd | 0.8540 | 1.033 (0.734-1.453) |
| Clinical | FLIPI | High | Protein | P65 % POSITIVE CYTOPLASMIC SIGNAL | >90% | Selected | 160 | 310 | 205 | N: 77 vs 83 | % in ITT: 23.7% | 352d vs 212d | 140 | (66% improvement) | P-value = 0.0168 | HR = 0.644 (0.448-0.926) | 1343d vs 1263d | 0.4043 | 0.808 (0.49-1.333) |
| Clinical | FLIPI | High | Protein | P65 % POSITIVE CYTOPLASMIC SIGNAL | >90% | Excluded | 160 | 310 | 205 | N: 152 vs 158 | % in ITT: 45.9% | 429d vs 378d | 51 | (13.5% improvement) | P-value = 0.5531 | HR = 0.919 (0.695-1.215) | NAd vs NAd | 0.8360 | 1.06 (0.612-1.836) |
| Clinical | FLIPI | High | Protein | P65 % POSITIVE CYTOPLASMIC SIGNAL | >90% | Total | 160 | 310 | 205 | N: 229 vs 241 | % in ITT: 69.6% | 367d vs 345d | 22 | (6.4% improvement) | P-value = 0.0902 | HR = 0.826 (0.663-1.03) | NAd vs NAd | 0.6612 | 0.921 (0.636-1.332) |
| Clinical | AGEGRP | <=65 | Protein | P65 % POSITIVE CYTOPLASMIC SIGNAL | >90% | Selected | 296 | 174 | 205 | N: 142 vs 154 | % in ITT: 43.9% | 415d vs 277d | 138 | (49.8% improvement) | P-value = 0.0078 | HR = 0.684 (0.515-0.906) | NAd vs NAd | 0.6825 | 0.907 (0.569-1.447) |
| Clinical | AGEGRP | <=65 | Protein | P65 % POSITIVE CYTOPLASMIC SIGNAL | >90% | Excluded | 296 | 174 | 205 | N: 87 vs 87 | % in ITT: 25.8% | 352d vs 414d | -62 | (-15% improvement) | P-value = 0.4179 | HR = 1.159 (0.809-1.66) | NAd vs NAd | 0.8391 | 0.94 (0.513-1.721) |
| Clinical | AGEGRP | <=65 | Protein | P65 % POSITIVE CYTOPLASMIC SIGNAL | >90% | Total | 296 | 174 | 205 | N: 229 vs 241 | % in ITT: 69.6% | 367d vs 345d | 22 | (6.4% improvement) | P-value = 0.0902 | HR = 0.826 (0.663-1.03) | NAd vs NAd | 0.6612 | 0.921 (0.636-1.332) |
| Protein | 20S % NUCLEAR STAINING | 30-90 | Protein | P65 % POSITIVE CYTOPLASMIC SIGNAL | >90% | Selected | 232 | 231 | 212 | N: 109 vs 123 | % in ITT: 34.4% | 414d vs 277d | 137 | (49.5% improvement) | P-value = 0.0249 | HR = 0.7 (0.512-0.957) | NAd vs NAd | 0.5718 | 0.86 (0.509-1.451) |

APPENDIX 3, TABLE 3.1-continued

Significant Pair-Wise Combinations

| Marker A Type | Marker A | Marker A Level | Marker B Type | Marker B | Marker B Level | Combination | N Selected | N Excluded | N Unevaluable | N (Vc-R vs R) | % of ITT | Median PFS (Vc-R vs R) | PFS Difference | % PFS Difference | PFS Logrank P-value | PFS HR | Median OS (Vc-R vs R) | OS Logrank P-value | OS HR |
|---|---|---|---|---|---|---|---|---|---|---|---|---|---|---|---|---|---|---|---|
| Protein | 20S % NUCLEAR STAINING | 30-90 | Protein | P65 % POSITIVE CYTOPLASMIC SIGNAL | >90% | Excluded | 232 | 231 | 212 | N: 116 vs 115 | % in ITT: 34.2% | 351d vs 419d | -68 | (-16.2% improvement) | P-value = 0.9146 | HR = 0.983 (0.714-1.353) | NAd vs NAd | 0.9292 | 0.976 (0.571-1.668) |
| Protein | 20S % NUCLEAR STAINING | 30-90 | Protein | P65 % POSITIVE CYTOPLASMIC SIGNAL | >90% | Total | 232 | 231 | 212 | N: 225 vs 238 | % in ITT: 68.6% | 367d vs 345d | 22 | (6.4% improvement) | P-value = 0.1 | HR = 0.83 (0.665-1.037) | NAd vs NAd | 0.6640 | 0.921 (0.634-1.336) |
| B_D NA | PSMB1/P11A | C/G | Protein | P65 % NUCLEAR STAINING | 0 | Selected | 144 | 293 | 238 | N: 70 vs 74 | % in ITT: 21.3% | 415d vs 279d | 136 | (48.7% improvement) | P-value = 0.0243 | HR = 0.641 (0.434-0.947) | NAd vs NAd | 0.5700 | 0.825 (0.424-1.605) |
| B_D NA | PSMB1/P11A | C/G | Protein | P65 % NUCLEAR STAINING | 0 | Excluded | 144 | 293 | 238 | N: 143 vs 150 | % in ITT: 43.4% | 406d vs 346d | 60 | (17.3% improvement) | P-value = 0.2722 | HR = 0.853 (0.642-1.133) | NAd vs NAd | 0.9159 | 0.975 (0.612-1.554) |
| B_D NA | PSMB1/P11A | C/G | Protein | P65 % NUCLEAR STAINING | 0 | Total | 144 | 293 | 238 | N: 213 vs 224 | % in ITT: 64.7% | 414d vs 338d | 76 | (22.5% improvement) | P-value = 0.0354 | HR = 0.782 (0.622-0.984) | NAd vs NAd | 0.7048 | 0.929 (0.634-1.36) |
| Protein | CD68 OVERALL POSITIVE | 0-50 | Protein | P65 % POSITIVE CYTOPLASMIC SIGNAL | >90% | Selected | 255 | 185 | 235 | N: 126 vs 129 | % in ITT: 37.8% | 414d vs 279d | 135 | (48.4% improvement) | P-value = 0.0086 | HR = 0.671 (0.498-0.906) | NAd vs NAd | 0.3681 | 0.798 (0.488-1.305) |
| Protein | CD68 OVERALL POSITIVE | 0-50 | Protein | P65 % POSITIVE CYTOPLASMIC SIGNAL | >90% | Excluded | 255 | 185 | 235 | N: 90 vs 95 | % in ITT: 27.4% | 352d vs 375d | -23 | (-6.1% improvement) | P-value = 0.7752 | HR = 1.052 (0.736-1.503) | NAd vs NAd | 0.8468 | 1.062 (0.575-1.96) |
| Protein | CD68 OVERALL POSITIVE | 0-50 | Protein | P65 % POSITIVE CYTOPLASMIC SIGNAL | >90% | Total | 255 | 185 | 235 | N: 216 vs 224 | % in ITT: 65.2% | 366d vs 345d | 21 | (6.1% improvement) | P-value = 0.0769 | HR = 0.814 (0.648-1.023) | NAd vs NAd | 0.5608 | 0.892 (0.608-1.309) |
| Clinical | AGEGRP | <=65 | Protein | CD68 OVERALL POSITIVE | 0-50 | Selected | 226 | 215 | 234 | N: 115 vs 111 | % in ITT: 33.5% | 414d vs 279d | 135 | (48.4% improvement) | P-value = 0.0104 | HR = 0.658 (0.476-0.909) | NAd vs NAd | 0.7470 | 0.915 (0.533-1.569) |
| Clinical | AGEGRP | <=65 | Protein | CD68 OVERALL POSITIVE | 0-50 | Excluded | 226 | 215 | 234 | N: 102 vs 113 | % in ITT: 31.9% | 352d vs 351d | 1 | (0.2999-9999999-9989% improvement) | P-value = 0.8542 | HR = 1.03 (0.745-1.424) | NAd vs NAd | 0.5974 | 0.863 (0.499-1.492) |
| Clinical | AGEGRP | <=65 | Protein | CD68 OVERALL POSITIVE | 0-50 | Total | 226 | 215 | 234 | N: 217 | % in ITT: | 360d vs | 15 | (4.2999-999999- | P-value = 0.5387 | HR = 0.819 | NAd vs | 0.5387 | 0.887 (0.604- |

APPENDIX 3, TABLE 3.1-continued

Significant Pair-Wise Combinations

| Marker A Type | Marker A | Marker A Level | Marker B Type | Marker B | Marker B Level | Combination | N Selected | N Excluded | N Uneval-uable | N (Vc-R vs R) | % of ITT | Median PFS (Vc-R vs R) | PFS Difference | % PFS Difference | PFS Logrank P-value | PFS HR | Median OS (Vc-R vs R) | OS Logrank P-value | OS HR |
|---|---|---|---|---|---|---|---|---|---|---|---|---|---|---|---|---|---|---|---|
| Clinical | PRITUX | | | POSITIVE | | | | | | vs 224 | 65.3% | 345d | | 9999% improvement | 0.0864 | (0.652-1.029) | NAd | | 1.301) |
| Clinical | PRITUX | NO | Protein | P65 % NUCLEAR STAINING | 0 | Selected | 194 | 276 | 205 | N: 92 vs 102 | % in ITT: 28.7% | 422d vs 287d | 135 | (47% improvement) | P-value = 0.0407 | HR = 0.702 (0.5-0.987) | NAd vs NAd | 0.6357 | 0.877 (0.511-1.508) |
| Clinical | PRITUX | NO | Protein | P65 % NUCLEAR STAINING | 0 | Excluded | 194 | 276 | 205 | N: 137 vs 139 | % in ITT: 40.9% | 351d vs 346d | 5 | (1.4% improvement) | P-value = 0.6871 | HR = 0.942 (0.703-1.262) | NAd vs NAd | 0.9900 | 0.997 (0.601-1.653) |
| Clinical | PRITUX | NO | Protein | P65 % NUCLEAR STAINING | 0 | Total | 194 | 276 | 205 | N: 229 vs 241 | % in ITT: 69.6% | 367d vs 345d | 22 | (6.4% improvement) | P-value = 0.0902 | HR = 0.826 (0.663-1.03) | NAd vs NAd | 0.6612 | 0.921 (0.636-1.332) |
| Clinical | TLAST | >1 year | Protein | CD68 OVERALL POSITIVE | 0-50 | Selected | 189 | 252 | 234 | N: 99 vs 90 | % in ITT: 28% | 483d vs 348d | 135 | (38.8% improvement) | P-value = 0.0451 | HR = 0.695 (0.486-0.994) | NAd vs NAd | 0.4895 | 0.789 (0.402-1.549) |
| Clinical | TLAST | >1 year | Protein | CD68 OVERALL POSITIVE | 0-50 | Excluded | 189 | 252 | 234 | N: 118 vs 134 | % in ITT: 37.3% | 347d vs 288d | 59 | (20.5% improvement) | P-value = 0.7048 | HR = 0.944 (0.702-1.27) | NAd vs NAd | 0.8742 | 0.963 (0.604-1.534) |
| Clinical | TLAST | >1 year | Protein | CD68 OVERALL POSITIVE | 0-50 | Total | 189 | 252 | 234 | N: 217 vs 224 | % in ITT: 65.3% | 360d vs 345d | 15 | (4.2999999999% improvement) | P-value = 0.0864 | HR = 0.819 (0.652-1.029) | NAd vs NAd | 0.5387 | 0.887 (0.604-1.301) |
| Protein | CD68 OVERALL POSITIVE | 0-50 | Protein | CD68 POSITIVE FOLLICULAR | 0-50 | Selected | 231 | 155 | 289 | N: 113 vs 118 | % in ITT: 34.2% | 414d vs 281d | 133 | (47.3% improvement) | P-value = 0.0037 | HR = 0.63 (0.459-0.863) | NAd vs NAd | 0.0725 | 0.604 (0.346-1.053) |
| Protein | CD68 OVERALL POSITIVE | 0-50 | Protein | CD68 POSITIVE FOLLICULAR | 0-50 | Excluded | 231 | 155 | 289 | N: 77 vs 78 | % in ITT: 23% | 380d vs 381d | −1 | (−0.3% improvement) | P-value = 0.257 | HR = 1.254 (0.846-1.858) | NAd vs NAd | 0.3788 | 1.331 (0.702-2.524) |
| Protein | CD68 OVERALL POSITIVE | 0-50 | Protein | CD68 POSITIVE FOLLICULAR | 0-50 | Total | 231 | 155 | 289 | N: 190 vs 196 | % in ITT: 57.2% | 396d vs 346d | 50 | (14.5% improvement) | P-value = 0.1781 | HR = 0.846 (0.663-1.08) | NAd vs NAd | 0.4068 | 0.839 (0.554-1.27) |
| Protein | CD68 POSITIVE FOLLICULAR | 0-50 | Protein | P65 INTENSITY CYTOPLASMIC SIGNAL | >=2+ | Selected | 242 | 144 | 289 | N: 114 vs 128 | % in ITT: 35.9% | 414d vs 281d | 133 | (47.3% improvement) | P-value = 0.0064 | HR = 0.653 (0.48-0.89) | NAd vs NAd | 0.0511 | 0.58 (0.333-1.009) |

APPENDIX 3, TABLE 3.1-continued

Significant Pair-Wise Combinations

| Marker A Type | Marker A | Marker A Level | Marker B Type | Marker B | Marker B Level | Combination | N Selected | N Excluded | N Unevaluable | N (Vc-R vs R) | % of ITT | Median PFS (Vc-R vs R) | PFS Difference | % PFS Difference | PFS Logrank P-value | PFS HR | Median OS OS (Vc-R vs R) | Log-rank P-value | OS HR |
|---|---|---|---|---|---|---|---|---|---|---|---|---|---|---|---|---|---|---|---|
| Protein | CD68 POSITIVE FOLLICULAR | 0-50 | Protein | P65 INTENSITY CYTOPLASMIC SIGNAL | >=2+ | Excluded | 242 | 144 | 289 | N: 76 vs 68 | % in ITT: 21.3% | 351d vs 439d | -88 | (-20% improvement) | P-value = 0.1744 | HR = 1.334 (0.879-2.024) | NAd vs NAd | 0.2917 | 1.432 (0.732-2.8) |
| Protein | CD68 POSITIVE FOLLICULAR | 0-50 | Protein | P65 INTENSITY CYTOPLASMIC SIGNAL | >=2+ | Total | 242 | 144 | 289 | N: 190 vs 196 | % in ITT: 57.2% | 396d vs 346d | 50 | (14.5% improvement) | P-value = 0.1781 | HR = 0.846 (0.663-1.08) | NAd vs NAd | 0.4068 | 0.839 (0.554-1.27) |
| B_D NA | PSMB9/ R60H | A/G | Protein | P65 % POSITIVE CYTOPLASMIC SIGNAL | >90% | Selected | 130 | 307 | 238 | N: 64 vs 66 | % in ITT: 19.3% | 406d vs 273d | 133 | (48.7% improvement) | P-value = 0.0268 | HR = 0.616 (0.4-0.95) | NAd vs NAd | 0.1673 | 0.589 (0.275-1.26) |
| B_D NA | PSMB9/ R60H | A/G | Protein | P65 % POSITIVE CYTOPLASMIC SIGNAL | >90% | Excluded | 130 | 307 | 238 | N: 149 vs 158 | % in ITT: 45.5% | 414d vs 348d | 66 | (19% improvement) | P-value = 0.2491 | HR = 0.853 (0.65-1.118) | NAd vs NAd | 0.6468 | 1.11 (0.711-1.73) |
| B_D NA | PSMB9/ R60H | A/G | Protein | P65 % POSITIVE CYTOPLASMIC SIGNAL | >90% | Total | 130 | 307 | 238 | N: 213 vs 224 | % in ITT: 64.7% | 414d vs 338d | 76 | (22.5% improvement) | P-value = 0.0354 | HR = 0.782 (0.622-0.984) | NAd vs NAd | 0.7048 | 0.929 (0.634-1.36) |
| Protein | CD68 POSITIVE FOLLICULAR | 0-50 | Protein | P27 SIGNAL INTENSITY | >=2+ | Selected | 251 | 135 | 289 | N: 121 vs 130 | % in ITT: 37.2% | 414d vs 282d | 132 | (46.8% improvement) | P-value = 0.0058 | HR = 0.651 (0.479-0.885) | NAd vs NAd | 0.0695 | 0.612 (0.359-1.045) |
| Protein | CD68 POSITIVE FOLLICULAR | 0-50 | Protein | P27 SIGNAL INTENSITY | >=2+ | Excluded | 251 | 135 | 289 | N: 69 vs 66 | % in ITT: 20% | 351d vs 465d | -114 | (-24.5% improvement) | P-value = 0.1445 | HR = 1.363 (0.898-2.07) | NAd vs NAd | 0.2852 | 1.46 (0.726-2.936) |
| Protein | CD68 POSITIVE FOLLICULAR | 0-50 | Protein | P27 SIGNAL INTENSITY | >=2+ | Total | 251 | 135 | 289 | N: 190 vs 196 | % in ITT: 57.2% | 396d vs 346d | 50 | (14.5% improvement) | P-value = 0.1781 | HR = 0.846 (0.663-1.08) | NAd vs NAd | 0.4068 | 0.839 (0.554-1.27) |
| Clinical | FLIPI | High | Protein | CD68 POSITIVE FOLLICULAR | 0-50 | Selected | 119 | 267 | 289 | N: 53 vs 66 | % in ITT: 17.6% | 347d vs 220d | 127 | (57.7% improvement) | P-value = 0.0481 | HR = 0.655 (0.429-1) | NAd vs 1263d | 0.2401 | 0.692 (0.374-1.282) |
| Clinical | FLIPI | High | Protein | CD68 POSITIVE FOLLICULAR | 0-50 | Excluded | 119 | 267 | 289 | N: 137 vs 130 | % in ITT: 39.6% | 431d vs 381d | 50 | (13.1% improvement) | P-value = 0.8607 | HR = 0.974 (0.72-1.318) | NAd vs NAd | 0.8997 | 1.038 (0.585-1.841) |
| Clinical | FLIPI | High | Protein | CD68 POSITIVE FOLLICULAR | 0-50 | Total | 119 | 267 | 289 | N: 190 vs 196 | % in ITT: 57.2% | 396d vs 346d | 50 | (14.5% improvement) | P-value = 0.1781 | HR = 0.846 (0.663-1.08) | NAd vs NAd | 0.4068 | 0.839 (0.554-1.27) |

APPENDIX 3, TABLE 3.1-continued

Significant Pair-Wise Combinations

| Marker A Type | Marker A | Marker A Level | Marker B Type | Marker B | Marker B Level | Combination | N Selected | N Excluded | N Unevaluable | N (Vc-R vs R) | % of ITT | Median PFS (Vc-R vs R) | PFS Difference | % PFS Difference | PFS Logrank P-value | PFS HR | Median OS (Vc-R vs R) | OS Log-rank P-value | OS HR |
|---|---|---|---|---|---|---|---|---|---|---|---|---|---|---|---|---|---|---|---|
| B_D NA | PSMB9/ R60H | G/G | Clinical | AGEGRP | <=65 | Selected | 232 | 310 | 133 | N: 113 vs 119 | % in ITT: 34.4% | 456d vs 330d | 126 | (38.2% improvement) | P-value = 0.032 | HR = 0.706 (0.513-0.972) | NAd vs NAd | 0.9809 | 0.993 (0.574-1.72) |
| B_D NA | PSMB9/ R60H | G/G | Clinical | AGEGRP | <=65 | Excluded | 232 | 310 | 133 | N: 153 vs 157 | % in ITT: 45.9% | 355d vs 345d | 10 | (2.8999-999999-9999% improvement) | P-value = 0.6085 | HR = 0.931 (0.708-1.223) | NAd vs NAd | 0.8407 | 1.046 (0.676-1.618) |
| B_D NA | PSMB9/ R60H | G/G | Clinical | AGEGRP | <=65 | Total | 232 | 310 | 133 | N: 266 vs 276 | % in ITT: 80.3% | 414d vs 345d | 69 | (20% improvement) | P-value = 0.0744 | HR = 0.828 (0.673-1.019) | NAd vs NAd | 0.8540 | 1.033 (0.734-1.453) |
| Protein | CD68 POSITIVE FOLLICULAR | 0-50 | Protein | P27 % NUCLEI POSITIVE | 0-70 | Selected | 156 | 230 | 289 | N: 66 vs 90 | % in ITT: 23.1% | 406d vs 281d | 125 | (44.5% improvement) | P-value = 0.034 | HR = 0.655 (0.44-0.973) | NAd vs NAd | 0.4918 | 0.796 (0.415-1.527) |
| Protein | CD68 POSITIVE FOLLICULAR | 0-50 | Protein | P27 % NUCLEI POSITIVE | 0-70 | Excluded | 156 | 230 | 289 | N: 124 vs 106 | % in ITT: 34.1% | 367d vs 365d | 2 | (0.49999-999999-9989% improvement) | P-value = 0.9376 | HR = 1.013 (0.738-1.39) | NAd vs NAd | 0.6162 | 0.87 (0.505-1.499) |
| Protein | CD68 POSITIVE FOLLICULAR | 0-50 | Protein | P27 % NUCLEI POSITIVE | 0-70 | Total | 156 | 230 | 289 | N: 190 vs 196 | % in ITT: 57.2% | 396d vs 346d | 50 | (14.5% improvement) | P-value = 0.1781 | HR = 0.846 (0.663-1.08) | NAd vs NAd | 0.4068 | 0.839 (0.554-1.27) |
| B_D NA | PSMB1/ P11A | C/G | Clinical | RACEGRP | WHITE | Selected | 208 | 334 | 133 | N: 97 vs 111 | % in ITT: 30.8% | 444d vs 326d | 118 | (36.2% improvement) | P-value = 0.0499 | HR = 0.714 (0.509-1.001) | NAd vs NAd | 0.6910 | 0.889 (0.498-1.589) |
| B_D NA | PSMB1/ P11A | C/G | Clinical | RACEGRP | WHITE | Excluded | 208 | 334 | 133 | N: 169 vs 165 | % in ITT: 49.5% | 360d vs 345d | 15 | (4.2999-999999-9999% improvement) | P-value = 0.3716 | HR = 0.887 (0.68-1.155) | NAd vs NAd | 0.6309 | 1.109 (0.726-1.695) |
| B_D NA | PSMB1/ P11A | C/G | Clinical | RACEGRP | WHITE | Total | 208 | 334 | 133 | N: 266 vs 276 | % in ITT: 80.3% | 414d vs 345d | 69 | (20% improvement) | P-value = 0.0744 | HR = 0.828 (0.673-1.019) | NAd vs NAd | 0.8540 | 1.033 (0.734-1.453) |
| Clinical | AGEGRP | <=65 | Protein | P27 SIGNAL INTENSITY | >=2+ | Selected | 302 | 161 | 212 | N: 149 vs 153 | % in ITT: 44.7% | 396d vs 279d | 117 | (41.9% improvement) | P-value = 0.0348 | HR = 0.742 (0.561-0.98) | NAd vs NAd | 0.4996 | 0.855 (0.543-1.347) |

APPENDIX 3, TABLE 3.1-continued

Significant Pair-Wise Combinations

| Marker A Type | Marker A | Marker A Level | Marker B Type | Marker B | Marker B Level | Combination | N Selected | N Excluded | N Unevaluable | N (Vc-R vs R) | % of ITT | Median PFS (Vc-R vs R) | PFS Difference | % PFS Difference | PFS Logrank P-value | PFS HR | Median OS OS (Vc-R vs R) | Log-rank P-value | OS HR |
|---|---|---|---|---|---|---|---|---|---|---|---|---|---|---|---|---|---|---|---|
| Clinical | AGEGRP | <=65 | Protein | P27 SIGNAL INTENSITY | >=2+ | Excluded | 302 | 161 | 212 | N: 78 vs 83 | % in ITT: 23.9% | 355d vs 349d | 6 | (1.6999-999999-9999% improvement) | P-value = 0.9982 | HR = 1 (0.691-1.446) | NAd vs NAd | 0.9211 | 0.968 (0.512-1.831) |
| Clinical | AGEGRP | <=65 | Protein | P27 SIGNAL INTENSITY | >=2+ | Total | 302 | 161 | 212 | N: 227 vs 236 | % in ITT: 68.6% | 366d vs 345d | 21 | (6.1% improvement) | P-value = 0.0844 | HR = 0.822 (0.659-1.027) | NAd vs NAd | 0.5615 | 0.896 (0.62-1.297) |
| Clinical | SEX | MALE | Protein | P27 % NUCLEI POSITIVE | 0-70 | Selected | 120 | 343 | 212 | N: 64 vs 56 | % in ITT: 17.8% | 351d vs 235d | 116 | (49.4% improvement) | P-value = 0.0331 | HR = 0.639 (0.423-0.967) | NAd vs NAd | 0.2905 | 0.703 (0.365-1.355) |
| Clinical | SEX | MALE | Protein | P27 % NUCLEI POSITIVE | 0-70 | Excluded | 120 | 343 | 212 | N: 163 vs 180 | % in ITT: 50.8% | 380d vs 351d | 29 | (8.3% improvement) | P-value = 0.2275 | HR = 0.849 (0.651-1.107) | NAd vs NAd | 0.8108 | 0.947 (0.605-1.482) |
| Clinical | SEX | MALE | Protein | P27 % NUCLEI POSITIVE | 0-70 | Total | 120 | 343 | 212 | N: 227 vs 236 | % in ITT: 68.6% | 366d vs 345d | 21 | (6.1% improvement) | P-value = 0.0844 | HR = 0.822 (0.659-1.027) | NAd vs NAd | 0.5615 | 0.896 (0.62-1.297) |
| Clinical | AGEGRP | <=65 | Protein | P65 INTENSITY CYTOPLASMIC SIGNAL | >=2+ | Selected | 291 | 179 | 205 | N: 139 vs 152 | % in ITT: 43.1% | 396d vs 281d | 115 | (40.9% improvement) | P-value = 0.0438 | HR = 0.749 (0.564-0.993) | NAd vs NAd | 0.6033 | 0.883 (0.551-1.413) |
| Clinical | AGEGRP | <=65 | Protein | P65 INTENSITY CYTOPLASMIC SIGNAL | >=2+ | Excluded | 291 | 179 | 205 | N: 90 vs 89 | % in ITT: 26.5% | 360d vs 349d | 11 | (3.2% improvement) | P-value = 0.9045 | HR = 0.978 (0.685-1.395) | NAd vs NAd | 0.9236 | 0.971 (0.534-1.767) |
| Clinical | AGEGRP | <=65 | Protein | P65 INTENSITY CYTOPLASMIC SIGNAL | >=2+ | Total | 291 | 179 | 205 | N: 229 vs 241 | % in ITT: 69.6% | 367d vs 345d | 22 | (6.4% improvement) | P-value = 0.0902 | HR = 0.826 (0.663-1.03) | NAd vs NAd | 0.6612 | 0.921 (0.636-1.332) |
| Protein | CD68 POSITIVE FOLLICULAR | 0-50 | Protein | P65 % NUCLEAR STAINING | 0 | Selected | 208 | 178 | 289 | N: 94 vs 114 | % in ITT: 30.8% | 396d vs 282d | 114 | (40.4% improvement) | P-value = 0.0366 | HR = 0.699 (0.499-0.98) | NAd vs NAd | 0.3965 | 0.78 (0.439-1.387) |
| Protein | CD68 POSITIVE FOLLICULAR | 0-50 | Protein | P65 % NUCLEAR STAINING | 0 | Excluded | 208 | 178 | 289 | N: 96 vs 82 | % in ITT: 26.4% | 406d vs 379d | 27 | (7.1% improvement) | P-value = 0.6341 | HR = 1.094 (0.757-1.581) | NAd vs NAd | 0.8015 | 0.925 (0.505-1.695) |
| Protein | CD68 POSITIVE FOLLICULAR | 0-50 | Protein | P65 % NUCLEAR STAINING | 0 | Total | 208 | 178 | 289 | N: 190 vs 196 | % in ITT: 57.2% | 396d vs 346d | 50 | (14.5% improvement) | P-value = 0.1781 | HR = 0.846 (0.663-1.08) | NAd vs NAd | 0.4068 | 0.839 (0.554-1.27) |

APPENDIX 3, TABLE 3.1-continued

Significant Pair-Wise Combinations

| Marker A Type | Marker A | Marker A Level | Marker B Type | Marker B | Marker B Level | Combination | N Selected | N Excluded | N Uneval- uable | N (Vc-R vs R) | % of ITT | Median PFS (Vc-R vs R) | PFS Difference | % PFS Difference | PFS Logrank P-value | PFS HR | Median OS (Vc-R vs R) | OS Log-rank P-value | OS HR |
|---|---|---|---|---|---|---|---|---|---|---|---|---|---|---|---|---|---|---|---|
| Clinical | FLIPI | High | Protein | P65 INTENSITY CYTOPLASMIC SIGNAL | >=2+ | Selected | 156 | 314 | 205 | N: 76 vs 80 | % in ITT: 23.1% | 352d vs 239d | 113 | (47.3% improvement) | P-value = 0.0229 | HR = 0.653 (0.451-0.945) | 1343d vs NAd | 0.5476 | 0.856 (0.515-1.421) |
| Clinical | FLIPI | High | Protein | P65 INTENSITY CYTOPLASMIC SIGNAL | >=2+ | Excluded | 156 | 314 | 205 | N: 153 vs 161 | % in ITT: 46.5% | 429d vs 348d | 81 | (23.3% improvement) | P-value = 0.5476 | HR = 0.919 (0.697-1.211) | NAd vs NAd | 0.9311 | 0.977 (0.57-1.674) |
| Clinical | FLIPI | High | Protein | P65 INTENSITY CYTOPLASMIC SIGNAL | >=2+ | Total | 156 | 314 | 205 | N: 229 vs 241 | % in ITT: 69.6% | 367d vs 345d | 22 | (6.4% improvement) | P-value = 0.0902 | HR = 0.826 (0.663-1.03) | NAd vs NAd | 0.6612 | 0.921 (0.636-1.332) |
| B_D_NA | PSMB1/P11A | C/G | Clinical | HITUBD | YES | Selected | 137 | 405 | 133 | N: 65 vs 72 | % in ITT: 20.3% | 351d vs 241d | 110 | (45.6% improvement) | P-value = 0.0273 | HR = 0.643 (0.433-0.955) | NAd vs NAd | 0.8487 | 0.942 (0.514-1.728) |
| B_D_NA | PSMB1/P11A | C/G | Clinical | HITUBD | YES | Excluded | 137 | 405 | 133 | N: 201 vs 204 | % in ITT: 60% | 429d vs 375d | 54 | (14.4% improvement) | P-value = 0.3654 | HR = 0.893 (0.7-1.14) | NAd vs NAd | 0.7275 | 1.076 (0.711-1.629) |
| B_D_NA | PSMB1/P11A | C/G | Clinical | HITUBD | YES | Total | 137 | 405 | 133 | N: 266 vs 276 | % in ITT: 80.3% | 414d vs 345d | 69 | (20% improvement) | P-value = 0.0744 | HR = 0.828 (0.673-1.019) | NAd vs NAd | 0.8540 | 1.033 (0.734-1.453) |
| Protein | 20S INTENSITY CYTOPLASMIC SIGNAL | >=3+ | Protein | CD68 POSITIVE FOLLICULAR | 0-50 | Selected | 138 | 248 | 289 | N: 66 vs 72 | % in ITT: 20.4% | 435d vs 326d | 109 | (33.4% improvement) | P-value = 0.048 | HR = 0.657 (0.432-0.999) | NAd vs NAd | 0.1965 | 0.624 (0.302-1.285) |
| Protein | 20S INTENSITY CYTOPLASMIC SIGNAL | >=3+ | Protein | CD68 POSITIVE FOLLICULAR | 0-50 | Excluded | 138 | 248 | 289 | N: 124 vs 124 | % in ITT: 36.7% | 352d vs 348d | 4 | (1.0999-999999-9999% improvement) | P-value = 0.8748 | HR = 0.976 (0.721-1.322) | NAd vs NAd | 0.9537 | 0.985 (0.591-1.641) |
| Protein | 20S INTENSITY CYTOPLASMIC SIGNAL | >=3+ | Protein | CD68 POSITIVE FOLLICULAR | 0-50 | Total | 138 | 248 | 289 | N: 190 vs 196 | % in ITT: 57.2% | 396d vs 346d | 50 | (14.5% improvement) | P-value = 0.1781 | HR = 0.846 (0.663-1.08) | NAd vs NAd | 0.4068 | 0.839 (0.554-1.27) |
| Clinical | FLIPI | High | Protein | P27 SIGNAL INTENSITY | >=2+ | Selected | 164 | 299 | 212 | N: 81 vs 83 | % in ITT: 24.3% | 346d vs 239d | 107 | (44.8% improvement) | P-value = 0.0449 | HR = 0.694 (0.485-0.993) | 1343d vs 1263d | 0.2893 | 0.761 (0.459-1.262) |
| Clinical | FLIPI | High | Protein | P27 SIGNAL INTENSITY | >=2+ | Excluded | 164 | 299 | 212 | N: 146 vs 153 | % in ITT: 44.3% | 429d vs 357d | 72 | (20.2% improvement) | P-value = 0.3899 | HR = 0.883 (0.665-1.173) | NAd vs NAd | 0.8014 | 1.072 (0.622-1.848) |

APPENDIX 3, TABLE 3.1-continued

Significant Pair-Wise Combinations

| Marker A Type | Marker A | Marker A Level | Marker B Type | Marker B | Marker B Level | Com-bination | N Se-lected | N Ex-cluded | N Un-eval-uable | N (Vc-R vs R) | % of ITT | Median PFS (Vc-R vs R) | PFS Differ-ence | % PFS Differ-ence | PFS Logrank P-value | PFS HR | Median OS (Vc-R vs R) | OS Log-rank P-value | OS HR |
|---|---|---|---|---|---|---|---|---|---|---|---|---|---|---|---|---|---|---|---|
| Clinical | FLIPI | High | Protein | P27 SIGNAL INTENSITY | >=2+ | Total | 164 | 299 | 212 | N: 227 vs 236 | % in ITT: 68.6% | 366d vs 345d | 21 | (6.1% improve-ment) | P-value = 0.0844 | HR = 0.822 (0.659-1.027) | NAd vs NAd | 0.5615 | 0.896 (0.62-1.297) |
| Clinical | PRITUX | NO | Protein | P65 % POSITIVE CYTOPLASMIC SIGNAL | >90% | Selected | 217 | 253 | 205 | N: 105 vs 112 | % in ITT: 32.1% | 426d vs 322d | 104 | (32.3% improve-ment) | P-value = 0.0193 | HR = 0.677 (0.488-0.94) | NAd vs NAd | 0.2559 | 0.732 (0.427-1.256) |
| Clinical | PRITUX | NO | Protein | P65 % POSITIVE CYTOPLASMIC SIGNAL | >90% | Excluded | 217 | 253 | 205 | N: 124 vs 129 | % in ITT: 37.5% | 345d vs 346d | −1 | (−0.3% improve-ment) | P-value = 0.9336 | HR = 0.987 (0.731-1.333) | NAd vs NAd | 0.5660 | 1.161 (0.697-1.936) |
| Clinical | PRITUX | NO | Protein | P65 % POSITIVE CYTOPLASMIC SIGNAL | >90% | Total | 217 | 253 | 205 | N: 229 vs 241 | % in ITT: 69.6% | 367d vs 345d | 22 | (6.4% improve-ment) | P-value = 0.0902 | HR = 0.826 (0.663-1.03) | NAd vs NAd | 0.6612 | 0.921 (0.636-1.332) |
| B_D NA | PSMB1/ P11A | C/G | Protein | P65 INTENSITY CYTOPLASMIC SIGNAL | >=2+ | Selected | 154 | 283 | 238 | N: 73 vs 81 | % in ITT: 22.8% | 426d vs 322d | 104 | (32.3% improve-ment) | P-value = 0.027 | HR = 0.645 (0.435-0.955) | NAd vs NAd | 0.3233 | 0.71 (0.358-1.406) |
| B_D NA | PSMB1/ P11A | C/G | Protein | P65 INTENSITY CYTOPLASMIC SIGNAL | >=2+ | Excluded | 154 | 283 | 238 | N: 140 vs 143 | % in ITT: 41.9% | 360d vs 346d | 14 | (4% improve-ment) | P-value = 0.2961 | HR = 0.86 (0.648-1.141) | NAd vs NAd | 0.8398 | 1.049 (0.66-1.666) |
| B_D NA | PSMB1/ P11A | C/G | Protein | P65 INTENSITY CYTOPLASMIC SIGNAL | >=2+ | Total | 154 | 283 | 238 | N: 213 vs 224 | % in ITT: 64.7% | 414d vs 338d | 76 | (22.5% improve-ment) | P-value = 0.0354 | HR = 0.782 (0.622-0.984) | NAd vs NAd | 0.7048 | 0.929 (0.634-1.36) |
| B_D NA | PSMB1/ P11A | C/G | Clinical | PRITUX | NO | Selected | 138 | 404 | 133 | N: 70 vs 68 | % in ITT: 20.4% | 426d vs 322d | 104 | (32.3% improve-ment) | P-value = 0.0388 | HR = 0.658 (0.44-0.982) | NAd vs NAd | 0.4750 | 0.786 (0.404-1.528) |
| B_D NA | PSMB1/ P11A | C/G | Clinical | PRITUX | NO | Excluded | 138 | 404 | 133 | N: 196 vs 208 | % in ITT: 59.9% | 363d vs 345d | 18 | (5.2% improve-ment) | P-value = 0.3874 | HR = 0.898 (0.705-1.145) | NAd vs NAd | 0.5551 | 1.127 (0.757-1.68) |
| B_D NA | PSMB1/ P11A | C/G | Clinical | PRITUX | NO | Total | 138 | 404 | 133 | N: 266 vs 276 | % in ITT: 80.3% | 414d vs 345d | 69 | (20% improve-ment) | P-value = 0.0744 | HR = 0.828 (0.673-1.019) | NAd vs NAd | 0.8540 | 1.033 (0.734-1.453) |
| B_D NA | PSMB9/ R60H | G/G | Protein | CD68 POSITIVE FOLLICULAR | 0-50 | Selected | 145 | 211 | 319 | N: 66 vs 79 | % in ITT: 21.5% | 429d vs 326d | 103 | (31.6% improve-ment) | P-value = 0.0269 | HR = 0.641 (0.43-0.954) | NAd vs NAd | 0.1089 | 0.565 (0.279-1.146) |

APPENDIX 3, TABLE 3.1-continued

Significant Pair-Wise Combinations

| Marker A Type | Marker A | Marker B | Marker B Type | Marker A Level | Marker B Level | Combination | N Selected | N Excluded | N Unevaluable | N (Vc-R vs R) | % of ITT | Median PFS (Vc-R vs R) | PFS Difference | % PFS Difference | PFS Logrank P-value | PFS HR | Median OS (Vc-R vs R) | OS Log-rank P-value | OS HR |
|---|---|---|---|---|---|---|---|---|---|---|---|---|---|---|---|---|---|---|---|
| B_D NA | PSMB9/ R60H | CD68 POSITIVE FOLLICULAR | Protein | G/G | 0-50 | Excluded | 145 | 211 | 319 | N: 109 vs 102 | % in ITT: 31.3% | 406d vs 347d | 59 | (17% improvement) | P-value = 0.7477 | HR = 0.947 (0.677-1.324) | NAd vs NAd | 0.9946 | 0.998 (0.576-1.731) |
| B_D NA | PSMB9/ R60H | CD68 POSITIVE FOLLICULAR | Protein | G/G | 0-50 | Total | 145 | 211 | 319 | N: 175 vs 181 | % in ITT: 52.7% | 414d vs 345d | 69 | (20% improvement) | P-value = 0.0855 | HR = 0.801 (0.621-1.032) | NAd vs NAd | 0.3270 | 0.808 (0.527-1.239) |
| Protein | 20S INTENSITY CYTOPLASMIC SIGNAL | P65 % POSITIVE CYTOPLASMIC SIGNAL | Protein | >=3+ | >90% | Selected | 195 | 268 | 212 | N: 95 vs 100 | % in ITT: 28.9% | 435d vs 334d | 101 | (30.2% improvement) | P-value = 0.0304 | HR = 0.681 (0.481-0.965) | NAd vs NAd | 0.1802 | 0.66 (0.358-1.217) |
| Protein | 20S INTENSITY CYTOPLASMIC SIGNAL | P65 % POSITIVE CYTOPLASMIC SIGNAL | Protein | >=3+ | >90% | Excluded | 195 | 268 | 212 | N: 130 vs 138 | % in ITT: 39.7% | 351d vs 345d | 6 | (1.6999999999% improvement) | P-value = 0.7745 | HR = 0.959 (0.718-1.28) | NAd vs NAd | 0.5860 | 1.141 (0.709-1.838) |
| Protein | 20S INTENSITY CYTOPLASMIC SIGNAL | P65 % POSITIVE CYTOPLASMIC SIGNAL | Protein | >=3+ | >90% | Total | 195 | 268 | 212 | N: 225 vs 238 | % in ITT: 68.6% | 367d vs 345d | 22 | (6.4% improvement) | P-value = 0.1 | HR = 0.83 (0.665-1.037) | NAd vs NAd | 0.6640 | 0.921 (0.634-1.336) |
| Clinical | RACEGRP | CD68 POSITIVE FOLLICULAR | Protein | WHITE | 0-50 | Selected | 239 | 147 | 289 | N: 114 vs 125 | % in ITT: 35.4% | 431d vs 334d | 97 | (29% improvement) | P-value = 0.0043 | HR = 0.63 (0.458-0.868) | NAd vs NAd | 0.0785 | 0.592 (0.328-1.069) |
| Clinical | RACEGRP | CD68 POSITIVE FOLLICULAR | Protein | WHITE | 0-50 | Excluded | 239 | 147 | 289 | N: 76 vs 71 | % in ITT: 21.8% | 324d vs 375d | -51 | (-13.6% improvement) | P-value = 0.1919 | HR = 1.294 (0.878-1.908) | NAd vs NAd | 0.5253 | 1.215 (0.665-2.219) |
| Clinical | RACEGRP | CD68 POSITIVE FOLLICULAR | Protein | WHITE | 0-50 | Total | 239 | 147 | 289 | N: 190 vs 196 | % in ITT: 57.2% | 396d vs 346d | 50 | (14.5% improvement) | P-value = 0.1781 | HR = 0.846 (0.663-1.08) | NAd vs NAd | 0.4068 | 0.839 (0.554-1.27) |
| Protein | 20S % NUCLEAR STAINING | CD68 OVERALL POSITIVE | Protein | 30-90 | 0-50 | Selected | 168 | 271 | 236 | N: 82 vs 86 | % in ITT: 24.9% | 367d vs 271d | 96 | (35.4% improvement) | P-value = 0.0181 | HR = 0.647 (0.45-0.931) | NAd vs NAd | 0.3345 | 0.753 (0.424-1.34) |
| Protein | 20S % NUCLEAR STAINING | CD68 OVERALL POSITIVE | Protein | 30-90 | 0-50 | Excluded | 168 | 271 | 236 | N: 134 vs 137 | % in ITT: 40.1% | 355d vs 365d | -10 | (-2.7% improvement) | P-value = 0.7301 | HR = 0.949 (0.706-1.276) | NAd vs NAd | 0.8394 | 1.055 (0.627-1.774) |
| Protein | 20S % NUCLEAR STAINING | CD68 OVERALL POSITIVE | Protein | 30-90 | 0-50 | Total | 168 | 271 | 236 | N: 216 vs 223 | % in ITT: 65% | 366d vs 345d | 21 | (6.1% improvement) | P-value = 0.0853 | HR = 0.818 (0.651-1.029) | NAd vs NAd | 0.6244 | 0.908 (0.618-1.335) |

APPENDIX 3, TABLE 3.1-continued

Significant Pair-Wise Combinations

| Marker A Type | Marker A | Marker A Level | Marker B Type | Marker B | Marker B Level | Combination | N Selected | N Excluded | N Unevaluable | N (Vc-R vs R) | % of ITT | Median PFS (Vc-R vs R) | PFS Difference | % PFS Difference | PFS Logrank P-value | PFS HR | Median OS (Vc-R vs R) | OS Logrank P-value | OS HR |
|---|---|---|---|---|---|---|---|---|---|---|---|---|---|---|---|---|---|---|---|
| Clinical | AGEGRP | <=65 | Protein | 20S % NUCLEAR STAINING | 30-90 | Selected | 193 | 270 | 212 | N: 96 vs 97 | % in ITT: 28.6% | 367d vs 271d | 96 | (35.4% improvement) | P-value = 0.0413 | HR = 0.703 (0.5-0.988) | NAd vs NAd | 0.6180 | 0.865 (0.49-1.527) |
| Clinical | AGEGRP | <=65 | Protein | 20S % NUCLEAR STAINING | 30-90 | Excluded | 193 | 270 | 212 | N: 129 vs 141 | % in ITT: 40% | 380d vs 357d | 23 | (6.4% improvement) | P-value = 0.6011 | HR = 0.925 (0.689-1.241) | NAd vs NAd | 0.8251 | 0.946 (0.576-1.552) |
| Clinical | AGEGRP | <=65 | Protein | 20S % NUCLEAR STAINING | 30-90 | Total | 193 | 270 | 212 | N: 225 vs 238 | % in ITT: 68.6% | 367d vs 345d | 22 | (6.4% improvement) | P-value = 0.1 | HR = 0.83 (0.665-1.037) | NAd vs NAd | 0.6640 | 0.921 (0.634-1.336) |
| Clinical | HITUBD | YES | Protein | P65 % POSITIVE CYTOPLASMIC SIGNAL | >90% | Selected | 202 | 268 | 205 | N: 100 vs 102 | % in ITT: 29.9% | 346d vs 253d | 93 | (36.8% improvement) | P-value = 0.0486 | HR = 0.728 (0.531-0.999) | 1343d vs NAd | 0.7230 | 0.917 (0.567-1.481) |
| Clinical | HITUBD | YES | Protein | P65 % POSITIVE CYTOPLASMIC SIGNAL | >90% | Excluded | 202 | 268 | 205 | N: 129 vs 139 | % in ITT: 39.7% | 487d vs 422d | 65 | (15.4% improvement) | P-value = 0.4198 | HR = 0.88 (0.646-1.199) | NAd vs NAd | 0.6827 | 0.886 (0.496-1.584) |
| Clinical | HITUBD | YES | Protein | P65 % POSITIVE CYTOPLASMIC SIGNAL | >90% | Total | 202 | 268 | 205 | N: 229 vs 241 | % in ITT: 69.6% | 367d vs 345d | 22 | (6.4% improvement) | P-value = 0.0902 | HR = 0.826 (0.663-1.03) | NAd vs NAd | 0.6612 | 0.921 (0.636-1.332) |
| Protein | 20S % NUCLEAR STAINING | 30-90 | Protein | CD68 POSITIVE FOLLICULAR | 0-50 | Selected | 164 | 222 | 289 | N: 75 vs 89 | % in ITT: 24.3% | 366d vs 274d | 92 | (33.6% improvement) | P-value = 0.0133 | HR = 0.631 (0.437-0.911) | NAd vs NAd | 0.2666 | 0.702 (0.374-1.315) |
| Protein | 20S % NUCLEAR STAINING | 30-90 | Protein | CD68 POSITIVE FOLLICULAR | 0-50 | Excluded | 164 | 222 | 289 | N: 115 vs 107 | % in ITT: 32.9% | 422d vs 427d | -5 | (-1.2% improvement) | P-value = 0.6841 | HR = 1.072 (0.769-1.494) | NAd vs NAd | 0.9562 | 0.984 (0.561-1.727) |
| Protein | 20S % NUCLEAR STAINING | 30-90 | Protein | CD68 POSITIVE FOLLICULAR | 0-50 | Total | 164 | 222 | 289 | N: 190 vs 196 | % in ITT: 57.2% | 396d vs 346d | 50 | (14.5% improvement) | P-value = 0.1781 | HR = 0.846 (0.663-1.08) | NAd vs NAd | 0.4068 | 0.839 (0.554-1.27) |
| B_D NA | PSMB5/R24C | C/C | Clinical | AGEGRP | <=65 | Selected | 337 | 205 | 133 | N: 167 vs 170 | % in ITT: 49.9% | 422d vs 330d | 92 | (27.9% improvement) | P-value = 0.0146 | HR = 0.722 (0.555-0.939) | NAd vs NAd | 0.9869 | 1.004 (0.638-1.579) |
| B_D NA | PSMB5/R24C | C/C | Clinical | AGEGRP | <=65 | Excluded | 337 | 205 | 133 | N: 99 vs 106 | % in ITT: 30.4% | 355d vs 348d | 7 | (2% improvement) | P-value = 0.8278 | HR = 1.037 (0.739-1.457) | NAd vs NAd | 0.7965 | 1.071 (0.636-1.801) |

APPENDIX 3, TABLE 3.1-continued

Significant Pair-Wise Combinations

| Marker A Type | Marker A | Marker A Level | Marker B Type | Marker B | Marker B Level | Combination | N Selected | N Excluded | N Unevaluable | N (Vc-R vs R) | % of ITT | Median PFS (Vc-R vs R) | PFS Difference | % PFS Difference | PFS Logrank P-value | PFS HR | Median OS (Vc-R vs R) | OS Logrank P-value | OS HR |
|---|---|---|---|---|---|---|---|---|---|---|---|---|---|---|---|---|---|---|---|
| B_D NA | PSMB5/R24C | C/C | Clinical | AGEGRP | <=65 | Total | 337 | 205 | 133 | N: 266 vs 276 | % in ITT: 80.3% | 414d vs 345d | 69 | (20% improvement) | P-value = 0.0744 | HR = 0.828 (0.673-1.019) | NAd vs NAd | 0.8540 | 1.033 (0.734-1.453) |
| B_D NA | PSMB5/R24C | C/C | Protein | CD68 POSITIVE FOLLICULAR | 0-50 | Selected | 225 | 131 | 319 | N: 104 vs 121 | % in ITT: 33.3% | 426d vs 334d | 92 | (27.5% improvement) | P-value = 0.0247 | HR = 0.691 (0.499-0.956) | NAd vs NAd | 0.2817 | 0.729 (0.41-1.298) |
| B_D NA | PSMB5/R24C | C/C | Protein | CD68 POSITIVE FOLLICULAR | 0-50 | Excluded | 225 | 131 | 319 | N: 71 vs 60 | % in ITT: 19.4% | 414d vs 348d | 66 | (19% improvement) | P-value = 0.8308 | HR = 1.046 (0.687-1.594) | NAd vs NAd | 0.7179 | 0.888 (0.466-1.692) |
| B_D NA | PSMB5/R24C | C/C | Protein | CD68 POSITIVE FOLLICULAR | 0-50 | Total | 225 | 131 | 319 | N: 175 vs 181 | % in ITT: 52.7% | 414d vs 345d | 69 | (20% improvement) | P-value = 0.0855 | HR = 0.801 (0.621-1.032) | NAd vs NAd | 0.3270 | 0.808 (0.527-1.239) |
| Clinical | SEX | FEMALE | Protein | CD68 POSITIVE FOLLICULAR | 0-50 | Selected | 163 | 223 | 239 | N: 69 vs 94 | % in ITT: 24.1% | 435d vs 345d | 90 | (26.1% improvement) | P-value = 0.015 | HR = 0.609 (0.406-0.913) | NAd vs NAd | 0.5324 | 0.794 (0.385-1.639) |
| Clinical | SEX | FEMALE | Protein | CD68 POSITIVE FOLLICULAR | 0-50 | Excluded | 163 | 223 | 239 | N: 121 vs 102 | % in ITT: 33% | 352d vs 347d | 5 | (1.4% improvement) | P-value = 0.854 | HR = 1.031 (0.75-1.416) | NAd vs NAd | 0.4476 | 0.821 (0.493-1.368) |
| Clinical | SEX | FEMALE | Protein | CD68 POSITIVE FOLLICULAR | 0-50 | Total | 163 | 223 | 289 | N: 190 vs 196 | % in ITT: 57.2% | 396d vs 346d | 50 | (14.5% improvement) | P-value = 0.1781 | HR = 0.846 (0.663-1.08) | NAd vs NAd | 0.4068 | 0.839 (0.554-1.27) |
| B_D NA | PSMB9/R60H | A/G | Protein | P65 % NUCLEAR STAINING | 0 | Selected | 120 | 317 | 238 | N: 60 vs 60 | % in ITT: 17.8% | 366d vs 277d | 89 | (32.1% improvement) | P-value = 0.0212 | HR = 0.6 (0.386-0.93) | NAd vs NAd | 0.2104 | 0.635 (0.31-1.3) |
| B_D NA | PSMB9/R60H | A/G | Protein | P65 % NUCLEAR STAINING | 0 | Excluded | 120 | 317 | 238 | N: 153 vs 164 | % in ITT: 47% | 415d vs 348d | 67 | (19.3% improvement) | P-value = 0.2428 | HR = 0.851 (0.65-1.115) | NAd vs NAd | 0.7295 | 1.083 (0.689-1.704) |
| B_D NA | PSMB9/R60H | A/G | Protein | P65 % NUCLEAR STAINING | 0 | Total | 120 | 317 | 238 | N: 213 vs 224 | % in ITT: 64.7% | 414d vs 338d | 76 | (22.5% improvement) | P-value = 0.0354 | HR = 0.782 (0.622-0.984) | NAd vs NAd | 0.7048 | 0.929 (0.634-1.36) |
| Protein | 20S % POSITIVE CYTOPLASMIC SIGNAL | 95-100 | Protein | CD68 POSITIVE FOLLICULAR | 0-50 | Selected | 183 | 203 | 289 | N: 90 vs 93 | % in ITT: 27.1% | 426d vs 338d | 88 | (26% improvement) | P-value = 0.0168 | HR = 0.646 (0.449-0.928) | NAd vs NAd | 0.0772 | 0.578 (0.313-1.069) |

APPENDIX 3, TABLE 3.1-continued

Significant Pair-Wise Combinations

| Marker A Type | Marker A | Marker A Level | Marker B Type | Marker B | Marker B Level | Combination | N Selected | N Excluded | N Unevaluable | N (Vc-R vs R) | % of ITT | Median PFS (Vc-R vs R) | PFS Difference | % PFS Difference | PFS Logrank P-value | PFS HR | Median OS (Vc-R vs R) | OS Logrank P-value | OS HR |
|---|---|---|---|---|---|---|---|---|---|---|---|---|---|---|---|---|---|---|---|
| Protein | 20S % POSITIVE CYTOPLASMIC SIGNAL | 95-100 | Protein | CD68 POSITIVE FOLLICULAR | 0-50 | Excluded | 183 | 203 | 289 | N: 100 vs 103 | % in ITT: 30.1% | 351d vs 347d | 4 | (1.2% improvement) | P-value = 0.7086 | HR = 1.066 (0.762-1.49) | NAd vs NAd | 0.5747 | 1.178 (0.664-2.09) |
| Protein | 20S % POSITIVE CYTOPLASMIC SIGNAL | 95-100 | Protein | CD68 POSITIVE FOLLICULAR | 0-50 | Total | 183 | 203 | 289 | N: 190 vs 196 | % in ITT: 57.2% | 396d vs 346d | 50 | (14.5% improvement) | P-value = 0.1781 | HR = 0.846 (0.663-1.08) | NAd vs NAd | 0.4068 | 0.839 (0.554-1.27) |
| B,D NA | PSMB5/ R24C | C/C | Protein | P65 % POSITIVE CYTOPLASMIC SIGNAL | >90% | Selected | 300 | 137 | 238 | N: 141 vs 159 | % in ITT: 44.4% | 422d vs 334d | 88 | (26.3% improvement) | P-value = 0.017 | HR = 0.713 (0.54-0.943) | NAd vs NAd | 0.6127 | 0.887 (0.558-1.411) |
| B,D NA | PSMB5/ R24C | C/C | Protein | P65 % POSITIVE CYTOPLASMIC SIGNAL | >90% | Excluded | 300 | 137 | 238 | N: 72 vs 65 | % in ITT: 20.3% | 352d vs 347d | 5 | (1.4% improvement) | P-value = 0.819 | HR = 0.953 (0.633-1.435) | NAd vs NAd | 0.9886 | 1.005 (0.513-1.972) |
| B,D NA | PSMB5/ R24C | C/C | Protein | P65 % POSITIVE CYTOPLASMIC SIGNAL | >90% | Total | 300 | 137 | 238 | N: 213 vs 224 | % in ITT: 64.7% | 414d vs 338d | 76 | (22.5% improvement) | P-value = 0.0354 | HR = 0.782 (0.622-0.984) | NAd vs NAd | 0.7048 | 0.929 (0.634-1.36) |
| Protein | P27 SIGNAL INTENSITY | >=2+ | Protein | P65 % POSITIVE CYTOPLASMIC SIGNAL | >90% | Selected | 348 | 114 | 213 | N: 168 vs 180 | % in ITT: 51.6% | 414d vs 326d | 88 | (27% improvement) | P-value = 0.0333 | HR = 0.755 (0.583-0.979) | NAd vs NAd | 0.2119 | 0.76 (0.493-1.171) |
| Protein | P27 SIGNAL INTENSITY | >=2+ | Protein | P65 % POSITIVE CYTOPLASMIC SIGNAL | >90% | Excluded | 348 | 114 | 213 | N: 58 vs 56 | % in ITT: 16.9% | 347d vs 347d | 0 | (0% improvement) | P-value = 0.8643 | HR = 1.04 (0.669-1.617) | NAd vs NAd | 0.3256 | 1.455 (0.686-3.086) |
| Protein | P27 SIGNAL INTENSITY | >=2+ | Protein | P65 % POSITIVE CYTOPLASMIC SIGNAL | >90% | Total | 348 | 114 | 213 | N: 226 vs 236 | % in ITT: 68.4% | 366d vs 345d | 21 | (6.1% improvement) | P-value = 0.0753 | HR = 0.817 (0.654-1.021) | NAd vs NAd | 0.5839 | 0.902 (0.623-1.305) |
| Clinical | HITUBD | YES | Protein | P27 NUCLEI POSITIVE | 0-70 | Selected | 148 | 315 | 212 | N: 75 vs 73 | % in ITT: 21.9% | 324d vs 239d | 85 | (35.6% improvement) | P-value = 0.0384 | HR = 0.677 (0.466-0.982) | 1343d vs NAd | 0.7672 | 0.918 (0.524-1.61) |
| Clinical | HITUBD | YES | Protein | P27 NUCLEI POSITIVE | 0-70 | Excluded | 148 | 315 | 212 | N: 152 vs 163 | % in ITT: 46.7% | 426d vs 357d | 69 | (19.3% improvement) | P-value = 0.2588 | HR = 0.852 (0.645-1.126) | NAd vs NAd | 0.4225 | 0.817 (0.498-1.34) |
| Clinical | HITUBD | YES | Protein | P27 NUCLEI POSITIVE | 0-70 | Total | 148 | 315 | 212 | N: 227 vs 236 | % in ITT: 68.6% | 366d vs 345d | 21 | (6.1% improvement) | P-value = 0.0844 | HR = 0.822 (0.659-1.027) | NAd vs NAd | 0.5615 | 0.896 (0.62-1.297) |

APPENDIX 3, TABLE 3.1-continued

Significant Pair-Wise Combinations

| Marker A Type | Marker A | Marker A Level | Marker B Type | Marker B | Marker B Level | Com-bination | N Se-lected | N Ex-cluded | N Un-eval-uable | N (Vc-R vs R) | % of ITT | Median PFS (Vc-R vs R) | PFS Differ-ence | % PFS Differ-ence | PFS Logrank P-value | PFS HR | Median OS (Vc-R vs R) | OS Log-rank P-value | OS HR |
|---|---|---|---|---|---|---|---|---|---|---|---|---|---|---|---|---|---|---|---|
| Clinical | RACEGRP | WHITE | Protein | P65 % POSITIVE CYTOPLASMIC SIGNAL | >90% | Selected | 341 | 129 | 205 | N: 162 vs 179 | % in ITT: 50.5% | 417d vs 334d | 83 | (24.9% improve-ment) | P-value = 0.0163 | HR = 0.725 (0.558-0.943) | NAd vs NAd | 0.2846 | 0.783 (0.501-1.226) |
| Clinical | RACEGRP | WHITE | Protein | P65 % POSITIVE CYTOPLASMIC SIGNAL | >90% | Excluded | 341 | 129 | 205 | N: 67 vs 62 | % in ITT: 19.1% | 346d vs 378d | -32 | (-8.5% improve-ment) | P-value = 0.4834 | HR = 1.159 (0.767-1.752) | NAd vs NAd | 0.5035 | 1.257 (0.643-2.455) |
| Clinical | RACEGRP | WHITE | Protein | P65 % POSITIVE CYTOPLASMIC SIGNAL | >90% | Total | 341 | 129 | 205 | N: 229 vs 241 | % in ITT: 69.6% | 367d vs 345d | 22 | (6.4% improve-ment) | P-value = 0.0902 | HR = 0.826 (0.663-1.03) | NAd vs NAd | 0.6612 | 0.921 (0.636-1.332) |
| Clinical | ANNARBOR | >=III | Protein | P65 % POSITIVE CYTOPLASMIC SIGNAL | >90% | Selected | 321 | 149 | 205 | N: 152 vs 169 | % in ITT: 47.6% | 360d vs 278d | 82 | (29.5% improve-ment) | P-value = 0.0306 | HR = 0.75 (0.578-0.974) | NAd vs NAd | 0.5983 | 0.891 (0.58-1.369) |
| Clinical | ANNARBOR | >=III | Protein | P65 % POSITIVE CYTOPLASMIC SIGNAL | >90% | Excluded | 321 | 149 | 205 | N: 77 vs 72 | % in ITT: 22.1% | 435d vs 432d | 3 | (0.6999-999999-9999% improve-ment) | P-value = 0.78 | HR = 1.063 (0.696-1.622) | NAd vs NAd | 0.8428 | 1.077 (0.518-2.242) |
| Clinical | ANNARBOR | >=III | Protein | P65 % POSITIVE CYTOPLASMIC SIGNAL | >90% | Total | 321 | 149 | 205 | N: 229 vs 241 | % in ITT: 69.6% | 367d vs 345d | 22 | (6.4% improve-ment) | P-value = 0.0902 | HR = 0.826 (0.663-1.03) | NAd vs NAd | 0.6612 | 0.921 (0.636-1.332) |
| Clinical | REGION | REST OF WORLD | Protein | CD68 OVERALL POSITIVE | 0-50 | Selected | 137 | 304 | 234 | N: 67 vs 70 | % in ITT: 20.3% | 358d vs 277d | 81 | (29.2% improve-ment) | P-value = 0.0407 | HR = 0.668 (0.452-0.987) | NAd vs NAd | 0.2957 | 0.716 (0.382-1.341) |
| Clinical | REGION | REST OF WORLD | Protein | CD68 OVERALL POSITIVE | 0-50 | Excluded | 137 | 304 | 234 | N: 150 vs 154 | % in ITT: 45% | 380d vs 351d | 29 | (8.3% improve-ment) | P-value = 0.552 | HR = 0.917 (0.691-1.217) | NAd vs NAd | 0.9650 | 1.011 (0.621-1.645) |
| Clinical | REGION | REST OF WORLD | Protein | CD68 OVERALL POSITIVE | 0-50 | Total | 137 | 304 | 234 | N: 217 vs 224 | % in ITT: 65.3% | 360d vs 345d | 15 | (4.2999-999999-9999% improve-ment) | P-value = 0.0864 | HR = 0.819 (0.652-1.029) | NAd vs NAd | 0.5387 | 0.887 (0.604-1.301) |
| Clinical | RACEGRP | WHITE | Protein | CD68 OVERALL POSITIVE | 0-50 | Selected | 260 | 181 | 234 | N: 132 vs 128 | % in ITT: 38.5% | 414d vs 334d | 80 | (24% improve-ment) | P-value = 0.0248 | HR = 0.71 (0.526-0.959) | NAd vs NAd | 0.1697 | 0.701 (0.421-1.167) |
| Clinical | RACEGRP | WHITE | Protein | CD68 OVERALL | 0-50 | Excluded | 260 | 181 | 234 | N: 85 | % in ITT: | 351d vs | 3 | (0.8999-999999- | P-value = | HR = 0.991 | NAd vs | 0.4069 | 1.28 (0.713- |

APPENDIX 3, TABLE 3.1-continued

Significant Pair-Wise Combinations

| Marker A Type | Marker A | Marker A Level | Marker B Type | Marker B | Marker B Level | Combination | N Selected | N Excluded | N Unevaluable | N (Vc-R vs R) | % of ITT | Median PFS (Vc-R vs R) | PFS Difference | % PFS Difference | PFS Logrank P-value | PFS HR | Median OS (Vc-R vs R) | Log-rank P-value | OS HR |
|---|---|---|---|---|---|---|---|---|---|---|---|---|---|---|---|---|---|---|---|
| Clinical | RACEGRP | WHITE | | | POSITIVE | | | | | vs 96 | 26.8% | 348d | | 9999% improvement) | 0.9662 | (0.696-1.411) | NAd | | 2.299 |
| Clinical | RACEGRP | WHITE | Protein | CD68 OVERALL POSITIVE | 0-50 | Total | 260 | 181 | 234 | N: 217 vs 224 | % in ITT: 65.3% | 360d vs 345d | 15 | (4.2999-999999-9999% improvement) | P-value = 0.0864 | HR = 0.819 (0.652-1.029) | NAd vs NAd | 0.5387 | 0.887 (0.604-1.301) |
| Clinical | FLIPI | High | Protein | CD68 OVERALL POSITIVE | 0-50 | Selected | 135 | 306 | 234 | N: 67 vs 68 | % in ITT: 20% | 352d vs 273d | 79 | (28.9% improvement) | P-value = 0.0339 | HR = 0.658 (0.446-0.971) | 1343d vs NAd | 0.2526 | 0.727 (0.421-1.257) |
| Clinical | FLIPI | High | Protein | CD68 OVERALL POSITIVE | 0-50 | Excluded | 135 | 306 | 234 | N: 150 vs 156 | % in ITT: 45.3% | 414d vs 357d | 57 | (16% improvement) | P-value = 0.4519 | HR = 0.898 (0.677-1.191) | NAd vs NAd | 0.9548 | 0.984 (0.574-1.687) |
| Clinical | FLIPI | High | Protein | CD68 OVERALL POSITIVE | 0-50 | Total | 135 | 306 | 234 | N: 217 vs 224 | % in ITT: 65.3% | 360d vs 345d | 15 | (4.2999-999999-9999% improvement) | P-value = 0.0864 | HR = 0.819 (0.652-1.029) | NAd vs NAd | 0.5387 | 0.887 (0.604-1.301) |
| B_D NA | PSMB5/ R24C | C/C | Clinical | ANNARBOR | >=III | Selected | 375 | 167 | 133 | N: 182 vs 193 | % in ITT: 55.6% | 360d vs 281d | 79 | (28.1% improvement) | P-value = 0.0395 | HR = 0.776 (0.61-0.989) | NAd vs NAd | 0.5509 | 1.127 (0.761-1.668) |
| B_D NA | PSMB5/ R24C | C/C | Clinical | ANNARBOR | >=III | Excluded | 375 | 167 | 133 | N: 84 vs 83 | % in ITT: 24.7% | 512d vs 422d | 90 | (21.3% improvement) | P-value = 0.9843 | HR = 0.996 (0.662-1.499) | NAd vs NAd | 0.5602 | 0.814 (0.406-1.631) |
| B_D NA | PSMB5/ R24C | C/C | Clinical | ANNARBOR | >=III | Total | 375 | 167 | 133 | N: 266 vs 276 | % in ITT: 80.3% | 414d vs 345d | 69 | (20% improvement) | P-value = 0.0744 | HR = 0.828 (0.673-1.019) | NAd vs NAd | 0.8540 | 1.033 (0.734-1.453) |
| B_D NA | PSMB5/ R24C | C/T | Clinical | HITUBD | YES | Selected | 45 | 497 | 133 | N: 24 vs 21 | % in ITT: 6.7% | 352d vs 275d | 77 | (28% improvement) | P-value = 0.0054 | HR = 0.383 (0.191-0.769) | NAd vs NAd | 0.1763 | 0.496 (0.176-1.399) |
| B_D NA | PSMB5/ R24C | C/T | Clinical | HITUBD | YES | Excluded | 45 | 497 | 133 | N: 242 vs 255 | % in ITT: 73.6% | 414d vs 347d | 67 | (19.3% improvement) | P-value = 0.1634 | HR = 0.856 (0.688-1.065) | NAd vs NAd | 0.5518 | 1.116 (0.777-1.605) |
| B_D NA | PSMB5/ R24C | C/T | Clinical | HITUBD | YES | Total | 45 | 497 | 133 | N: 266 vs 276 | % in ITT: 80.3% | 414d vs 345d | 69 | (20% improvement) | P-value = 0.0744 | HR = 0.828 (0.673-1.019) | NAd vs NAd | 0.8540 | 1.033 (0.734-1.453) |

APPENDIX 3, TABLE 3.1-continued

Significant Pair-Wise Combinations

| Marker A Type | Marker A | Marker A Level | Marker B Type | Marker B | Marker B Level | Combination | N Selected | N Excluded | N Unevaluable | N (Vc-R vs R) | % of ITT | Median PFS (Vc-R vs R) | PFS Difference | % PFS Difference | PFS Logrank P-value | PFS HR | Median OS (Vc-R vs R) | OS Log-rank P-value | OS HR |
|---|---|---|---|---|---|---|---|---|---|---|---|---|---|---|---|---|---|---|---|
| Protein | CD68 OVERALL POSITIVE | 0-50 | Protein | P27 % NUCLEI POSITIVE | 0-70 | Selected | 181 | 260 | 234 | N: 85 vs 96 | % in ITT: 26.8% | 358d vs 282d | 76 | (27% improvement) | P-value = 0.0484 | HR = 0.699 (0.488-1) | NAd vs NAd | 0.5757 | 0.851 (0.485-1.496) |
| Protein | CD68 OVERALL POSITIVE | 0-50 | Protein | P27 % NUCLEI POSITIVE | 0-70 | Excluded | 181 | 260 | 234 | N: 132 vs 128 | % in ITT: 38.5% | 367d vs 349d | 18 | (5.2% improvement) | P-value = 0.4931 | HR = 0.901 (0.669-1.213) | NAd vs NAd | 0.7267 | 0.911 (0.539-1.538) |
| Protein | CD68 OVERALL POSITIVE | 0-50 | Protein | P27 % NUCLEI POSITIVE | 0-70 | Total | 181 | 260 | 234 | N: 217 vs 224 | % in ITT: 65.3 | 360d vs 345d | 15 | (4.2999-999999-9999% improvement) | P-value = 0.0864 | HR = 0.819 (0.652-1.029) | NAd vs NAd | 0.5387 | 0.887 (0.604-1.301) |
| B_D NA | PSMB9/R60H | A/G | Clinical | SEX | MALE | Selected | 76 | 466 | 133 | N: 48 vs 28 | % in ITT: 11.3% | 348d vs 273d | 75 | (27.5% improvement) | P-value = 0.0491 | HR = 0.583 (0.337-1.008) | NAd vs NAd | 0.7868 | 0.879 (0.345-2.242) |
| B_D NA | PSMB9/R60H | A/G | Clinical | SEX | MALE | Excluded | 76 | 466 | 133 | N: 218 vs 248 | % in ITT: 69% | 422d vs 348d | 74 | (21.3% improvement) | P-value = 0.1201 | HR = 0.835 (0.666-1.048) | NAd vs NAd | 0.7578 | 1.06 (0.733-1.533) |
| B_D NA | PSMB9/R60H | A/G | Clinical | SEX | MALE | Total | 76 | 466 | 133 | N: 266 vs 276 | % in ITT: 80.3% | 414d vs 345d | 69 | (20% improvement) | P-value = 0.0744 | HR = 0.828 (0.673-1.019) | NAd vs NAd | 0.8540 | 1.033 (0.734-1.453) |
| Protein | CD68 OVERALL POSITIVE | 0-50 | Protein | P27 SIGNAL INTENSITY | >=2+ | Selected | 252 | 189 | 234 | N: 129 vs 231 | % in ITT: 37.3% | 396d vs 322d | 74 | (23% improvement) | P-value = 0.0434 | HR = 0.734 (0.543-0.992) | NAd vs NAd | 0.1214 | 0.676 (0.411-1.113) |
| Protein | CD68 OVERALL POSITIVE | 0-50 | Protein | P27 SIGNAL INTENSITY | >=2+ | Excluded | 252 | 189 | 234 | N: 88 vs 101 | % in ITT: 28% | 352d vs 348d | 4 | (1.0999999999% improvement) | P-value = 0.7527 | HR = 0.944 (0.665-1.34) | NAd vs NAd | 0.3802 | 1.31 (0.715-2.402) |
| Protein | CD68 OVERALL POSITIVE | 0-50 | Protein | P27 SIGNAL INTENSITY | >=2+ | Total | 252 | 189 | 234 | N: 217 vs 224 | % in ITT: 65.3% | 360d vs 345d | 15 | (4.2999-999999-9999% improvement) | P-value = 0.0864 | HR = 0.819 (0.652-1.029) | NAd vs NAd | 0.5387 | 0.887 (0.604-1.301) |
| Protein | CD68 OVERALL POSITIVE | >=III | Protein | CD68 POSITIVE FOLLICULAR | 0-50 | Selected | 239 | 147 | 289 | N: 110 vs 129 | % in ITT: 35.4% | 351d vs 278d | 73 | (26.3% improvement) | P-value = 0.0172 | HR = 0.693 (0.512-0.939) | NAd vs NAd | 0.2011 | 0.71 (0.419-1.203) |
| Clinical | ANNARBOR | >=III | Protein | CD68 POSITIVE | 0-50 | Excluded | 239 | 147 | 289 | N: 80 | % in ITT: | 435d vs | -57 | (-11.6% improve- | P-value = | HR = 1.29 | NAd vs | 0.6331 | 1.187 (0.586- |

APPENDIX 3, TABLE 3.1-continued

Significant Pair-Wise Combinations

| Marker A Type | Marker A | Marker A Level | Marker B Type | Marker B | Marker B Level | Combination | N Selected | N Excluded | N Un-evaluable | N (Vc-R vs R) | % of ITT | Median PFS (Vc-R vs R) | PFS Difference | % PFS Difference | PFS Logrank P-value | PFS HR | Median OS OS (Vc-R vs R) | Log-rank P-value | OS HR |
|---|---|---|---|---|---|---|---|---|---|---|---|---|---|---|---|---|---|---|---|
| Clinical | ANNARBOR | >=III | | FOLLICULAR | 0-50 | Total | 239 | 147 | 289 | N: vs 67 | 21.8% | 492d | 50 | (14.5% improve-ment) | 0.248 | (0.837-1.989) | NAd | 0.4068 | 2.406) |
| Clinical | ANNARBOR | >=III | Protein | CD68 POSITIVE FOLLICULAR | 0-50 | Total | 239 | 147 | 289 | N: 190 vs 196 | % in ITT: 57.2% | 396d vs 346d | 50 | (14.5% improve-ment) | P-value = 0.1781 | HR = 0.846 (0.663-1.08) | NAd vs NAd | 0.4068 | 0.839 (0.554-1.27) |
| Clinical | FLIPI | Inter-mediate | Protein | P65 % POSITIVE CYTOPLASMIC SIGNAL | <=90% | Selected | 35 | 435 | 205 | N: 19 vs 16 | % in ITT: 5.2% | 351d vs 567d | -216 | (-38.1% improve-ment) | P-value = 0.0277 | HR = 2.941 (1.075-8.05) | NAd vs NAd | 0.6255 | 1.524 (0.277-8.379) |
| Clinical | FLIPI | Inter-mediate | Protein | P65 % POSITIVE CYTOPLASMIC SIGNAL | <=90% | Excluded | 35 | 435 | 205 | N: 210 vs 225 | % in ITT: 64.4% | 396d vs 326d | 70 | (21.5% improve-ment) | P-value = 0.0193 | HR = 0.761 (0.605-0.957) | NAd vs NAd | 0.5888 | 0.9 (0.616-1.317) |
| Clinical | FLIPI | Inter-mediate | Protein | P65 % POSITIVE CYTOPLASMIC SIGNAL | <=90% | Total | 35 | 435 | 205 | N: 229 vs 241 | % in ITT: 69.6% | 367d vs 345d | 22 | (6.4% improve-ment) | P-value = 0.0902 | HR = 0.826 (0.663-1.03) | NAd vs NAd | 0.6612 | 0.921 (0.636-1.332) |
| B_D NA | PSMB9/ R60H | A/A | Clinical | ANNARBOR | <=II | Selected | 10 | 532 | 133 | N: 2 vs 8 | % in ITT: 1.5% | 87d vs 347d | -260 | (-74.9% improve-ment) | P-value = 0.01 | HR = 12.341 (1.094-139.179) | 140d vs NAd | 0.0009 | 8342757-52.139 (0-Inf) |
| B_D NA | PSMB9/ R60H | A/A | Clinical | ANNARBOR | <=II | Excluded | 10 | 532 | 133 | N: 264 vs 268 | % in ITT: 78.8% | 414d vs 334d | 80 | (24% improve-ment) | P-value = 0.0538 | HR = 0.814 (0.66-1.004) | NAd vs NAd | 0.9481 | 0.989 (0.7-1.396) |
| B_D NA | PSMB9/ R60H | A/A | Clinical | ANNARBOR | <=II | Total | 10 | 532 | 133 | N: 266 vs 276 | % in ITT: 80.3% | 414d vs 345d | 69 | (20% improve-ment) | P-value = 0.0744 | HR = 0.828 (0.673-1.019) | NAd vs NAd | 0.8540 | 1.033 (0.734-1.453) |
| Clinical | AGEGRP | >65 | Protein | CD68 POSITIVE FOLLICULAR | >50 | Selected | 25 | 361 | 239 | N: 13 vs 12 | % in ITT: 3.7% | 324d vs 708d | -384 | (-54.2% improve-ment) | P-value = 0.0252 | HR = 2.999 (1.095-8.21) | NAd vs 971d | 0.8613 | 0.895 (0.257-3.112) |
| Clinical | AGEGRP | >65 | Protein | CD68 POSITIVE FOLLICULAR | >50 | Excluded | 25 | 361 | 289 | N: 177 vs 184 | % in ITT: 53.5% | 414d vs 338d | 76 | (22.5% improve-ment) | P-value = 0.0595 | HR = 0.784 (0.608-1.011) | NAd vs NAd | 0.4138 | 0.833 (0.536-1.293) |
| Clinical | AGEGRP | >65 | Protein | CD68 POSITIVE FOLLICULAR | >50 | Total | 25 | 361 | 289 | N: 190 vs 196 | % in ITT: 57.2% | 396d vs 346d | 50 | (14.5% improve-ment) | P-value = 0.1781 | HR = 0.846 (0.663-1.08) | NAd vs NAd | 0.4068 | 0.839 (0.554-1.27) |
| Clinical | RACEGRP | OTHER | Protein | 20S % NUCLEAR STAINING | 0-20 | Selected | 7 | 456 | 212 | N: 2 vs | % in ITT: 1% | 351d vs 763d | -412 | (-54% improve-ment) | P-value = 0.0455 | HR = 1861675-64.897 | 371d vs NAd | 0.1573 | 281008-16.562 (0-Inf) |

APPENDIX 3, TABLE 3.1-continued

Significant Pair-Wise Combinations

| Marker A Type | Marker A | Marker A Level | Marker B | Marker B Type | Marker B Level | Combination | N Selected | N Excluded | N Uneval-uable | N (Vc-R vs R) | % of ITT | Median PFS (Vc-R vs R) | PFS Difference | % PFS Difference | PFS Logrank P-value | PFS HR | Median OS (Vc-R vs R) | OS Log-rank P-value | OS HR |
|---|---|---|---|---|---|---|---|---|---|---|---|---|---|---|---|---|---|---|---|
| Clinical | RACEGRP | OTHER | 20S % NUCLEAR STAINING | Protein | 0-20 | Excluded | 7 | 456 | 212 | N: 5 vs 233 | % in ITT: 67.6% | 367d vs 338d | 29 | (8.6% improvement) | P-value = 0.072 | HR = 0.815 (0.652-1.019) | NAd vs NAd | 0.5543 | 0.893 (0.614-1.299) |
| Clinical | RACEGRP | OTHER | 20S % NUCLEAR STAINING | Protein | 0-20 | Total | 7 | 456 | 212 | N: 225 vs 238 | % in ITT: 68.6% | 367d vs 343d | 22 | (6.4% improvement) | P-value = 0.1 | HR = 0.83 (0.665-1.037) | NAd vs NAd | 0.6640 | 0.921 (0.634-1.336) |
| Protein | 20S INTENSITY CYTOPLASMIC SIGNAL | >=3+ | P65 % POSITIVE CYTOPLASMIC SIGNAL | Protein | <=90% | Selected | 18 | 445 | 212 | N: 12 vs 6 | % in ITT: 2.7% | 191d vs 708d | -517 | (-73% improvement) | P-value = 0.0111 | HR = 9.726 (1.204-78.546) | NAd vs 717d | 0.3995 | 0.525 (0.114-2.411) |
| Protein | 20S INTENSITY CYTOPLASMIC SIGNAL | >=3+ | P65 % POSITIVE CYTOPLASMIC SIGNAL | Protein | <=90% | Excluded | 18 | 445 | 212 | N: 213 vs 232 | % in ITT: 65.9% | 396d vs 338d | 58 | (17.2% improvement) | P-value = 0.033 | HR = 0.781 (0.622-0.981) | NAd vs NAd | 0.7212 | 0.932 (0.634-1.37) |
| Protein | 20S INTENSITY CYTOPLASMIC SIGNAL | >=3+ | P65 % POSITIVE CYTOPLASMIC SIGNAL | Protein | <=90% | Total | 18 | 445 | 212 | N: 225 vs 238 | % in ITT: 68.6% | 367d vs 345d | 22 | (6.4% improvement) | P-value = 0.1 | HR = 0.83 (0.665-1.037) | NAd vs NAd | 0.6640 | 0.921 (0.634-1.336) |
| Clinical | SEX | FEMALE | CD68 POSITIVE FOLLICULAR | Protein | >50 | Selected | 54 | 332 | 289 | N: 22 vs 32 | % in ITT: 8% | 344d vs 889d | -545 | (-61.3% improvement) | P-value = 0.0156 | HR = 2.293 (1.149-4.575) | 1078d vs NAd | 0.0178 | 3.398 (1.16-9.958) |
| Clinical | SEX | FEMALE | CD68 POSITIVE FOLLICULAR | Protein | >50 | Excluded | 54 | 332 | 289 | N: 168 vs 164 | % in ITT: 49.2% | 414d vs 283d | 131 | (46.3% improvement) | P-value = 0.007 | HR = 0.698 (0.537-0.908) | NAd vs NAd | 0.0624 | 0.649 (0.41-1.026) |
| Clinical | SEX | FEMALE | CD68 POSITIVE FOLLICULAR | Protein | >50 | Total | 54 | 332 | 289 | N: 190 vs 196 | % in ITT: 57.2% | 396d vs 346d | 50 | (14.5% improvement) | P-value = 0.1781 | HR = 0.846 (0.663-1.08) | NAd vs NAd | 0.4068 | 0.839 (0.554-1.27) |
| Protein | CD68 POSITIVE FOLLICULAR | >50 | P65 % POSITIVE CYTOPLASMIC | Protein | <=90% | Selected | 8 | 378 | 289 | N: 5 vs | % in ITT: 1.2% | 487d vs 1083d | -596 | (-55% improvement) | P-value = 0.0136 | HR = 1558276-6.206 | NAd vs NAd | 0.1967 | 0 (0-Inf) |

APPENDIX 3, TABLE 3.1-continued

Significant Pair-Wise Combinations

| Marker A Type | Marker A | Marker A Level | Marker B Type | Marker B | Marker B Level | Combination | N Selected | N Excluded | N Unevaluable | N (Vc-R vs R) | % of ITT | Median PFS (Vc-R vs R) | PFS Difference | % PFS Difference | PFS Logrank P-value | PFS HR | Median OS (Vc-R vs R) | OS Log-rank P-value | OS HR |
|---|---|---|---|---|---|---|---|---|---|---|---|---|---|---|---|---|---|---|---|
| Protein | CD68 POSITIVE FOLLICULAR | >50 | Protein | P65 % POSITIVE CYTOPLASMIC SIGNAL | <=90% | Excluded | 8 | 378 | 289 | N: 185 vs 193 | % in ITT: 56% | 396d vs 345d | 51 | (14.8% improvement) | P-value = 0.1162 | HR = 0.821 (0.641-1.051) | NAd vs NAd | 0.5254 | 0.874 (0.576-1.325) |
| Protein | CD68 POSITIVE FOLLICULAR | >50 | Protein | P65 % POSITIVE CYTOPLASMIC SIGNAL | <=90% | Total | 8 | 378 | 289 | N: 190 vs 196 | % in ITT: 57.2% | 396d vs 346d | 50 | (14.5% improvement) | P-value = 0.1781 | HR = 0.846 (0.663-1.08) | NAd vs NAd | 0.4068 | 0.839 (0.554-1.27) |
| Protein | CD68 OVERALL POSITIVE | >50 | Protein | P65 % POSITIVE CYTOPLASMIC SIGNAL | <=90% | Selected | 8 | 432 | 235 | N: 5 vs 3 | % in ITT: 1.2% | 144d vs 751d | -607 | (-80.8% improvement) | P-value = 0.0434 | HR = 1217047-1.716 (0-Inf) | 887d vs NAd | 0.1970 | 704857-1.582 (0-Inf) |
| Protein | CD68 OVERALL POSITIVE | >50 | Protein | P65 % POSITIVE CYTOPLASMIC SIGNAL | <=90% | Excluded | 8 | 432 | 235 | N: 211 vs 221 | % in ITT: 64% | 380d vs 345d | 35 | (10.1% improvement) | P-value = 0.0487 | HR = 0.793 (0.63-0.999) | NAd vs NAd | 0.3832 | 0.841 (0.57-1.242) |
| Protein | CD68 OVERALL POSITIVE | >50 | Protein | P65 % POSITIVE CYTOPLASMIC SIGNAL | <=90% | Total | 8 | 432 | 235 | N: 216 vs 224 | % in ITT: 65.2% | 366d vs 345d | 21 | (6.1% improvement) | P-value = 0.0769 | HR = 0.814 (0.648-1.023) | NAd vs NAd | 0.5608 | 0.892 (0.608-1.309) |
| Protein | CD68 POSITIVE FOLLICULAR | >50 | Protein | CD68 POSITIVE PERI-FOLLICULAR | 0-50 | Selected | 45 | 339 | 291 | N: 26 vs 19 | % in ITT: 6.7% | 344d vs 1083d | -739 | (-68.2% improvement) | P-value = 0.0143 | HR = 2.642 (1.182-5.908) | NAd vs NAd | 0.3295 | 1.784 (0.548-5.8) |
| Protein | CD68 POSITIVE FOLLICULAR | >50 | Protein | CD68 POSITIVE PERI-FOLLICULAR | 0-50 | Excluded | 45 | 339 | 291 | N: 163 vs 176 | % in ITT: 50.2% | 414d vs 326d | 88 | (27% improvement) | P-value = 0.0227 | HR = 0.739 (0.569-0.96) | NAd vs NAd | 0.1951 | 0.743 (0.473-1.167) |
| Protein | CD68 POSITIVE FOLLICULAR | >50 | Protein | CD68 POSITIVE PERI-FOLLICULAR | 0-50 | Total | 45 | 339 | 291 | N: 189 vs 195 | % in ITT: 56.9% | 406d vs 346d | 60 | (17.3% improvement) | P-value = 0.1772 | HR = 0.845 (0.662-1.08) | NAd vs NAd | 0.4116 | 0.841 (0.555-1.273) |
| Protein | CD68 OVERALL | 0-50 | Protein | CD68 POSITIVE | >50 | Selected | 32 | 354 | 289 | N: 19 vs 19 | % in ITT: | 307d vs | NA | (NA% improvement) | P-value = | HR = 3.155 | NAd vs | 0.4981 | 1.592 (0.41- |

APPENDIX 3, TABLE 3.1-continued

Significant Pair-Wise Combinations

| Marker A Type | Marker A | Marker A Level | Marker B Type | Marker B | Marker B Level | Combination | N Selected | N Excluded | N Unevaluable | N (Vc-R vs R) | % of ITT | Median PFS (Vc-R vs R) | PFS Difference | % PFS Difference | PFS Logrank P-value | PFS HR | Median OS (Vc-R vs R) | OS Logrank P-value | OS HR |
|---|---|---|---|---|---|---|---|---|---|---|---|---|---|---|---|---|---|---|---|
| | POSITIVE | | | FOLLICULAR | | | | | | vs 13 | 4.7% | NAd | | ment) | 0.0127 | (1.22-8.164) | NAd | | 6.178) |
| Protein | CD68 OVERALL POSITIVE | 0-50 | Protein | CD68 POSITIVE FOLLICULAR | >50 | Excluded | 32 | 354 | 289 | N: 171 vs 183 | % in ITT: 52.4% | 406d vs 326d | 80 | (24.5% improvement) | P-value = 0.0309 | HR = 0.755 (0.585-0.976) | NAd vs NAd | 0.2670 | 0.779 (0.501-1.212) |
| Protein | CD68 OVERALL POSITIVE | 0-50 | Protein | CD68 POSITIVE FOLLICULAR | >50 | Total | 32 | 354 | 289 | N: 190 vs 196 | % in ITT: 57.2% | 396d vs 346d | 50 | (14.5% improvement) | P-value = 0.1781 | HR = 0.846 (0.663-1.08) | NAd vs NAd | 0.4068 | 0.839 (0.554-1.27) |
| B_DNA | PSMB9/R60H | A/A | Clinical | REGION | UNITED STATES/CANADA | Selected | 6 | 536 | 133 | N: 2 vs 4 | % in ITT: 0.9% | 75d vs 346d | -271 | (-78.3% improvement) | P-value = 0.0269 | HR = 432481-90.876 (0-Inf) | 211d vs NAd | 0.0177 | 6225219-0.678 (0-Inf) |
| B_DNA | PSMB9/R60H | A/A | Clinical | REGION | UNITED STATES/CANADA | Excluded | 6 | 536 | 133 | N: 264 vs 272 | % in ITT: 79.4% | 414d vs 338d | 76 | (22.5% improvement) | P-value = 0.052 | HR = 0.814 (0.661-1.002) | NAd vs NAd | 0.9831 | 1.004 (0.711-1.418) |
| B_DNA | PSMB9/R60H | A/A | Clinical | REGION | UNITED STATES/CANADA | Total | 6 | 536 | 133 | N: 266 vs 276 | % in ITT: 80.3% | 414d vs 345d | 69 | (20% improvement) | P-value = 0.0744 | HR = 0.828 (0.673-1.019) | NAd vs NAd | 0.8540 | 1.033 (0.734-1.453) |

The invention claimed is:

1. A method for predicting response to a cancer treatment comprising bortezomib and rituximab in a non-Hodgkin's lymphoma cancer patient, comprising:
   detecting the presence of a first predictor in a biological sample from said non-Hodgkin's lymphoma cancer patient, wherein said first predictor is low CD68;
   detecting the presence of a second predictor in said non-Hodgkin's lymphoma cancer patient, wherein said second predictor is a PSMB1 (P11A) polymorphism comprising a C/G heterozygote; wherein the presence of a biomarker pair comprising the low CD68 and the PSMB1 (P11A) polymorphism is correlated with at least one positive outcome; and
   selecting the non-Hodgkin's lymphoma cancer patients that have an increased chance for a favorable outcome to the cancer treatment comprising bortezomib and rituximab based on the presence of the biomarker pair comprising the first and second predictor; and
   treating the selected non-Hodgkin's lymphoma cancer patients with the cancer treatment comprising bortezomib and rituximab.

2. The method of claim 1, wherein low CD68 is 50% or less CD68-positive cells, as determined by immunohistochemistry.

3. The method of claim 1, wherein the non-Hodgkin lymphoma is follicular B-cell non-Hodgkin lymphoma.

* * * * *